US010544194B2

(12) United States Patent
Comstedt et al.

(10) Patent No.: US 10,544,194 B2
(45) Date of Patent: *Jan. 28, 2020

(54) MUTANT FRAGMENTS OF OSPA AND METHODS AND USES RELATING THERETO

(71) Applicant: Valneva Austria GmbH, Vienna (AT)

(72) Inventors: Pär Comstedt, Vienna (AT); Urban Lundberg, Pressbaum (AT); Andreas Meinke, Pressbaum (AT); Markus Hanner, Pressbaum (AT); Wolfgang Schüler, Vienna (AT); Benjamin Wizel, Hoeilaart (BE); Christoph Reinisch, Siegenfeld (AT); Brigitte Grohmann, Perchtoldsdorf (AT); Robert Schlegl, Siegenfeld (AT)

(73) Assignee: Valneva Austria GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 15/272,581

(22) Filed: Sep. 22, 2016

(65) Prior Publication Data

US 2017/0101446 A1   Apr. 13, 2017

Related U.S. Application Data

(63) Continuation of application No. 14/412,722, filed as application No. PCT/EP2013/064403 on Jul. 8, 2013, now abandoned, which is a continuation of application No. 13/802,991, filed on Mar. 14, 2013, now Pat. No. 8,986,704.

(60) Provisional application No. 61/668,627, filed on Jul. 6, 2012.

(51) Int. Cl.
| C07K 14/20 | (2006.01) |
| A61K 39/02 | (2006.01) |
| C12N 5/07 | (2010.01) |
| C12N 15/70 | (2006.01) |
| C07K 16/12 | (2006.01) |
| C12P 21/02 | (2006.01) |
| C12P 21/00 | (2006.01) |
| A61K 39/00 | (2006.01) |
| A61K 38/00 | (2006.01) |

(52) U.S. Cl.
CPC ............ *C07K 14/20* (2013.01); *A61K 39/02* (2013.01); *A61K 39/0225* (2013.01); *C07K 16/12* (2013.01); *C07K 16/1207* (2013.01); *C12N 5/06* (2013.01); *C12N 15/70* (2013.01); *C12P 21/00* (2013.01); *C12P 21/02* (2013.01); *A61K 38/00* (2013.01); *A61K 2039/55505* (2013.01); *A61K 2039/6018* (2013.01); *A61K 2039/6031* (2013.01); *C07K 2317/24* (2013.01); *C07K 2317/54* (2013.01); *C07K 2317/55* (2013.01); *C07K 2319/00* (2013.01); *Y02A 50/39* (2018.01); *Y02A 50/396* (2018.01); *Y02A 50/40* (2018.01); *Y02A 50/401* (2018.01); *Y02A 50/403* (2018.01)

(58) Field of Classification Search
None
See application file for complete search history.

(56) References Cited

U.S. PATENT DOCUMENTS

| 6,248,562 B1 | 6/2001 | Dunn et al. |
| 7,008,625 B2 | 3/2006 | Dattwyler et al. |
| 8,986,704 B2 * | 3/2015 | Comstedt ............... A61K 39/02 424/190.1 |
| 9,926,343 B2 | 3/2018 | Comstedt et al. |
| 9,975,927 B2 | 5/2018 | Lundberg et al. |
| 2004/0023325 A1 | 2/2004 | Luft et al. |
| 2011/0293652 A1 | 12/2011 | Crowe et al. |
| 2014/0010835 A1 | 1/2014 | Comstedt et al. |
| 2015/0232517 A1 | 8/2015 | Comstedt et al. |
| 2015/0250865 A1 | 9/2015 | Comstedt et al. |
| 2016/0333056 A1 | 11/2016 | Lundberg et al. |
| 2017/0107263 A1 | 4/2017 | Comstedt et al. |
| 2018/0327460 A1 | 11/2018 | Comstedt et al. |
| 2018/0362593 A1 | 12/2018 | Lundberg et al. |

FOREIGN PATENT DOCUMENTS

| CN | 103118701 A | 5/2013 |
| WO | WO 2008/031133 A2 | 3/2008 |
| WO | WO 2011/143617 A1 | 11/2011 |
| WO | WO 2011/143623 A1 | 11/2011 |
| WO | WO 2012/066420 A1 | 5/2012 |
| WO | WO 2012/066423 A1 | 5/2012 |
| WO | WO 2014/006226 A1 | 1/2014 |
| WO | WO 2015/104396 A1 | 7/2015 |

(Continued)

OTHER PUBLICATIONS

Greenspan et al., Defining epitopes: It's not as easy as it seems. Nat Biotechnol. Oct. 1999;17(10):936-7.

(Continued)

*Primary Examiner* — Patricia Duffy

(74) *Attorney, Agent, or Firm* — Wolf, Greenfield & Sacks, P.C.

(57) ABSTRACT

The present invention relates to a polypeptide comprising a mutant fragment of an outer surface protein A (OspA), a nucleic acid coding the same, a pharmaceutical composition (particularly for use as a medicament of in a method of treating or preventing a *Borrelia* infection) comprising the polypeptide and/or the nucleic acid, a method of treating or preventing a *Borrelia* infection and a method of immunizing a subject.

9 Claims, 5 Drawing Sheets

Specification includes a Sequence Listing.

(56) References Cited

FOREIGN PATENT DOCUMENTS

| WO | WO 2015/169271 A1 | 11/2015 |
|---|---|---|
| WO | WO 2018/189372 A1 | 10/2018 |

OTHER PUBLICATIONS

[No Author Listed] pET System Manual. 2006. Novagen.
Bessler et al. Synthetic lipopeptides as novel adjuvants. Res Immunol. Jun. 1992;143(5):548-53; discussion 579-80.
Betz, Disulfide bonds and the stability of globular proteins. Protein Sci. Oct. 1993;2(10):1551-8.
Bouchon et al., Analysis of the lipidated recombinant outer surface protein A from Borrelia burgdorferi by mass spectrometry. Anal Biochem. Mar. 1, 1997;246(1):52-61.
Comstedt et al., Efficacy testing of a novel OspA based Lyme borreliosis vaccine. Gordon Research Conference: "Biology of Spirochetes", Ventura, California. Jan. 19-24, 2014. Abstract.
Comstedt et al., Investigation of a vaccine targeting Lyme borreliosis in Europe. Gordon Research Conference: "Biology of Spirochetes". Ventura, California. Jan. 19-24, 2014. Abstract.
Creighton et al., Mechanisms and catalysts of disulfide bond formation in proteins. Trends Biotechnol. Jan. 1995;13(1):18-23.
Crowe, A Lyme borreliosis vaccine for Europe and beyond. Climate change impact on ticks and tick-borne diseases. Brussels. Feb. 6, 2009.
Ding et al., Structural identification of a key protective B-cell epitope in Lyme disease antigen OspA. J Mol Biol. Oct. 6, 2000;302(5):1153-64.
Erdile et al., Role of attached lipid in immunogenicity of Borrelia burgdorferi OspA. Infect Immun. Jan. 1993;61(1):81-90.
Fass, Disulfide bonding in protein biophysics. Annu Rev Biophys. 2012;41:63-79. doi: 10.1146/annurev-biophys-050511-102321. Epub Dec. 20, 2011.
Golde et al., Reactivity with a specific epitope of outer surface protein A predicts protection from infection with the Lyme disease spirochete, Borrelia burgdorferi. Infect Immun. Mar. 1997;65(3):882-9.
Hertadi et al., Unfolding mechanics of multiple OspA substructures investigated with single molecule force spectroscopy. J Mol Biol. Nov. 7, 2003;333(5):993-1002.
Koide et al., Multistep denaturation of Borrelia burgdorferi OspA, a protein containing a single-layer beta-sheet. Biochemistry. Apr. 13, 1999;38(15):4757-67.
Koide et al., Structure-based design of a second-generation Lyme disease vaccine based on a C-terminal fragment of Borrelia burgdorferi OspA. J Mol Biol. Jul. 8, 2005;350(2):290-9.
Li et al., Crystal structure of Lyme disease antigen outer surface protein A complexed with an Fab. Proc Natl Acad Sci U S A. Apr. 15, 1997;94(8):3584-9.
Liang et al., An immunodominant conserved region within the variable domain of VlsE, the variable surface antigen of Borrelia burgdorferi. J Immunol. Nov. 15, 1999;163(10):5566-73.
Lindgren et al., Lyme borreliosis in Europe: influences of climate and climate change, epidemiology, ecology and adaptation measures. World Health Organization. 2006. 34 pages.
Livey et al., Development of a novel Lyme disease vaccine. The International Conference on Lyme Borreliosis and other Tick Borne Diseases. 2010. Poster.
Marshall et al., Safety and immunogenicity of a meningococcal B bivalent rLP2086 vaccine in healthy toddlers aged 18-36 months: a phase 1 randomized-controlled clinical trial. Pediatr Infect Dis J. Oct. 2012;31(10):1061-8.
Nissen et al., A randomized, controlled, phase 1/2 trial of a Neisseria meningitidis serogroup B bivalent rLP2086 vaccine in healthy children and adolescents. Pediatr Infect Dis J. Apr. 2013;32(4):364-71. doi: 10.1097/INF.0b013e31827b0d24.
Pantoliano et al., High-density miniaturized thermal shift assays as a general strategy for drug discovery. J Biomol Screen. Dec. 2001;6(6):429-40.
Parmley, Uptick for Lyme vaccine. Biocentury innovations. Jan. 2015;15-16.
Pham et al., NMR studies of Borrelia burgdorferi OspA, a 28 kDa protein containing a single-layer beta-sheet. J Biomol NMR. May 1998;11(4):407-14.
Richmond et al., A bivalent Neisseria meningitidis recombinant lipidated factor H binding protein vaccine in young adults: results of a randomised, controlled, dose-escalation phase 1 trial. Vaccine. Sep. 21, 2012;30(43):6163-74. doi: 10.1016/j.vaccine.2012.07.065. Epub Aug. 5, 2012.
Richmond et al., Safety, immunogenicity, and tolerability of meningococcal serogroup B bivalent recombinant lipoprotein 2086 vaccine in healthy adolescents: a randomised, single-blind, placebo-controlled, phase 2 trial. Lancet Infect Dis. Aug. 2012;12(8):597-607. Epub May 7, 2012.
Steere et al., Vaccination against Lyme disease with recombinant Borrelia burgdorferi outer-surface lipoprotein A with adjuvant. Lyme Disease Vaccine Study Group. N Engl J Med. Jul. 23, 1998;339(4):209-15.
Van Hoecke et al., Evaluation of the safety, reactogenicity and immunogenicity of three recombinant outer surface protein (OspA) Lyme vaccines in healthy adults. Vaccine. Dec. 1996;14(17-18):1620-6.
Wilske et al., An OspA serotyping system for Borrelia burgdorferi based on reactivity with monoclonal antibodies and OspA sequence analysis. J Clin Microbiol. Feb. 1993;31(2):340-50.
Yoder et al., Tripalmitoyl-S-glyceryl-cysteine-dependent OspA vaccination of toll-like receptor 2-deficient mice results in effective protection from Borrelia burgdorferi challenge. Infect Immun. Jul. 2003;71(7):3894-900.
[No Author Listed] Valneva report positive phase I interim results for its lyme vaccine candidate VLA15. Valneva. Mar. 19, 2018.
Baker et al., Electrostatics of nanosystems: application to microtubules and the ribosome. Proc Natl Acad Sci U S A. Aug. 28, 2001;98(18):10037-41.
Bockenstedt et al., Identification of a Borrelia burgdorferi OspA T cell epitope that promotes anti-OspA IgG in mice. J Immunol. Dec. 15, 1996;157(12):5496-502.
Bockenstedt et al., Inability of truncated recombinant Osp A proteins to elicit protective immunity to Borrelia burgdorferi in mice. J Immunol. Jul. 15, 1993;151(2):900-6.
Caruthers et al., New chemical methods for synthesizing polynucleotides. Nucleic Acids Symp Ser. 1980;(7):215-23.
Clinical Trials Identifier: NCT3010228. Study assessing the safety, immunogenicity and dose response of VLA15, a new vaccine candidate against Lyme borreliosis. Jan. 4, 2017. retrieved Mar. 26, 2018 from https://clinicaltrials.gov/ct2/show/study/NCT03010228.
Comstedt et al., Design and development of a novel vaccine for protection against Lyme borreliosis. PLoS One. Nov. 19, 2014;9(11):e113294. doi: 10.1371/journal.pone.0113294.
Comstedt et al., The novel Lyme borreliosis vaccine VLA15 shows broad protection against Borrelia species expressing six different OspA serotypes. PLoS One. Sep. 1, 2017;12(9):e0184357. doi:10.1371/journal.pone.0184357. eCollection 2017.
Dolinsky et al., PDB2PQR: expanding and upgrading automated preparation of biomolecular structures for molecular simulations. Nucleic Acids Res. Jul. 2007;35(Web Server issue):W522-5.
Dykhuizen et al. 1993 (Borrelia burgdorferi is clonal: Implications for taxonomy and vaccine development; Proc. Natl. Acad. Sci. 90: 10163-10167).
Friguet et al., Measurements of the true affinity constant in solution of antigen-antibody complexes by enzyme-linked immunosorbent assay. J Immunol Methods. Mar. 18, 1985;77(2):305-19.
Gern et al., Immunization with a polyvalent OspA vaccine protects mice against Ixodes ricinus tick bites infected by Borrelia burgdorferi ss, Borrelia garinii and Borrelia afzelii. Vaccine. Oct. 1997;15(14):1551-7.
Horn et al., Synthesis of oligonucleotides on cellulose. Part II: Design and synthetic strategy to the synthesis of 22 oligodeoxynucleotides coding for gastric inhibitory polypeptide (GIP). Nucleic Acids Symp Ser. 1980;(7):225-32.

(56) References Cited

OTHER PUBLICATIONS

Kiefer et al., The SWISS-MODEL Repository and associated resources. Nucleic Acids Res. Jan. 2009;37(Database issue):D387-92. doi: 10.1093/nar/gkn750.

Lingelbach, Developing a vaccine against Lyme disease Progress update post Phase 1 interim results. World Vaccine Congress. Apr. 4, 2018. Valneva.

Livey et al., A new approach to a Lyme disease vaccine. Clin Infect Dis. Feb. 2011;52 Suppl 3:S266-70. doi: 10.1093/cid/ciq118.

Makabe et al., Atomic-resolution crystal structure of Borrelia burgdorferi outer surface protein A via surface engineering. Protein Sci. Aug. 2006;15(8):1907-14. Epub Jul. 5, 2006.

Nakagawa et al., Calorimetric dissection of thermal unfolding of OspA, a predominantly beta-sheet protein containing a single-layer beta-sheet. J Mol Biol. Nov. 1, 2002;323(4):751-62.

Pawley et al., Backbone dynamics and thermodynamics of Borrelia outer surface protein A. J Mol Biol. Dec. 13, 2002;324(5):991-1002.

Pronk et al., GROMACS 4.5: a high-throughput and highly parallel open source molecular simulation toolkit. Bioinformatics. Apr. 1, 2013;29(7):845-54. doi: 10.1093/bioinformatics/btt055.

Roberge et al., A strategy for a convergent synthesis of N-linked glycopeptides on a solid support. Science. Jul. 14, 1995;269(5221):202-4.

Schwendinger et al., Evaluation of OspA vaccination-induced serological correlates of protection against Lyme borreliosis in a mouse model. PLoS One. Nov. 18, 2013;8(11):e79022. doi: 10.1371/journal. pone.0079022.

[No Author Listed] ECDC; Meeting Report: Second expert consultation on tick-borne diseases with emphasis on Lyme borreliosis and tick-borne encephalitis, Stockholm, Sweden. Nov. 22-23, 2011.

[No Author Listed], Press release: Valneva Reports Positive Initial Booster Data and Final Phase 1 Data for its Lyme Disease Vaccine Candidate.

Altschul et al., Basic Local Alignment Search Tool (1990) J. Mol. Biol. 215:403-410.

Bunikis et al., A Surface-Exposed Region of a Novel Outer Membrane Protein (P66) of Borrelia spp . is Variable in Size and Sequence (1998) J Bacteriology 180(7):1618-1623.

Chakrabarti et al., Dissecting Protein—Protein Recognition Sites; Proteins: Structure, Function, and Genetics (2002) 47:334-343.

Compton et al., Introduction of a Disulfide Bond Leads to Stabilization and Crystallization of a Ricin Immunogen (2011) Proteins 79(4):1048-1060. doi:10.1002/prot.22933.

Comstedt et al., Characterization and optimization of a novel vaccine for protection against Lyme borreliosis (2015) Vaccine 33:5982-5988.

Cutler et al., Emerging borreliae—Expanding beyond Lyme borreliosis (2017) Molecular and Cellular Probes 31:22-27.

Davies and Cohen. Interactions of protein antigens with antibodies (1996) Proc. Natl. Acad. Sci. USA 93:7-12.

de Silva et al. Borrelia burgdorferi OspA Is an Arthropod-specific Transmission-blocking Lyme Disease Vaccine (1996) J. Exp. Med. 183:271-275.

Devereaux et al. A comprehensive set of sequence analysis programs for the VAX (1984) Nucleic Acids Research 12(1):387-395.

Embers et al., Vaccination against Lyme disease: past, present, and future (2013) Frontiers in Cellular and Infection Microbiology www.frontiersin.org 3(6): doi:10.3389/fcimb.2013.00006.

Fingerle et al., Epidemiological aspects and molecular characterization of Borrelia burgdorferi s.l. from southern Germany with special respect to the new species Borrelia spieltnanii sp. nov. (2008) International Journal of Medical Microbiology 298:279-290. doi:10.1016/j.ijmm.2007.05.002.

Grygorczuk et al., Assessment of the frequency of different Borrelia burgdorferi sensu lato species in patients with Lyme borreliosis from north-east Poland by studying preferential serologic response and DNA isolates (2013) Annals of Agricultural and Environmental Medicine 20(1):21-29.

Hinckley et al., Lyme Disease Testing by Large Commercial Laboratories in the United States (2014) Clin Infect Dis. 59(5):676-681. doi:10.1093/cid/ciu397.

Iyer et al., Stage-specific global alterations in the transcriptomes of Lyme disease spirochetes during tick feeding and following mammalian host adaptation (2015) Molecular Microbiology 95(3):509-538. doi:10.1111/mmi.12882 First published online Dec. 30, 2014.

Jiang et al., Purification of Borrelia burgdorferi Outer Surface Protein A (OspA) and Analysis of Antibody Binding Domains (1994) Clinical Diagnostic Laboratory Immunology. 1(4):406-412.

Legros et al., Characterization of an anti-Borrelia burgdorferi OspA conformational epitope by limited proteolysis of monoclonal antibody-bound antigen and mass spectrometric peptide mapping (2000) Protein Science 9:1002-1010.

Lingelbach, World Vaccine Congress presentation, Apr. 16, 2019 entitled: "Developing a vaccine against Lyme disease; Phase 1 results and next steps".

Lo Conte et al., The Atomic Structure of Protein-Protein Recognition Sites (1999) J. Mol. Biol. 285:2177-2198.

Montgomery RR, et al. Direct Demonstration of Antigenic Substitution of Borrelia burgdorferi Ex Vivo: Exploration of the Paradox of the Early Immune Response to Outer Surface Proteins A and C in Lyme Disease(1996) J. Exp. Med. 183:261-269.

Nelson et al., Incidence of Clinician-Diagnosed Lyme Disease, United States, 2005-2010 (2015) Emerging Infectious Diseases 21(9):1625-1631. DOI: http://dx.doi.org/10.3201/eid2109.150417.

Ornstein et al., Characterization of Lyme Borreliosis Isolates from Patients with Erythema Migrans and Neuroborreliosis in Southern Sweden (2001) J Clinical Microbiology 39(4):1294-1298. DOI: 10.1128/JCM.39.4.1294-1298.

Ornstein et al., Differential Immune Response to the Variable Surface Loop Antigen of P66 of Borrelia burgdorferi Sensu Lato Species in Geographically Diverse Populations of Lyme Borreliosis Patients (2002) Clinical Diagnostic Laboratory Immunology 9(6):1382-1384. DOI: 10.1128/CDLI.9.6.1382-1384.2002.

Pal et al., Attachment of Borrelia burgdorferi within Ixodes scapularis mediated by outer surface protein A (2000) J. Clin. Invest. 106:561-569.

Piesman et al., Lyme borreliosis in Europe and North America (2004) Parasitology 129, S191—S220. DOI: 10.1017/S0031182003004694.

Poland, Vaccines against Lyme Disease: What Happened and What Lessons Can We Learn? (2011) Clinical Infectious Diseases 52(S3):S253-S258. DOI: 10.1093/cid/ciq116.

Radolf et al., Of ticks, mice and men: understanding the dual-host lifestyle of Lyme disease spirochaetes (2012) Nat Rev Microbiol. 10(2): 87-99. doi:10.1038/nrmicro2714.

Rizzoli et al. Lyme borreliosis in Europe (2011) Euro Surveill. 16(27):pii=19906. Available online: http://www.eurosurveillance.org/ViewArticle.aspx?ArticleId=19906.

Scarselli et al. Rational Design of a Meningococcal Antigen Inducing Broad Protective Immunity (2011) www.ScienceTranslationalMedicine.org 3(91):91ra62.

Schaible et al. Monoclonal antibodies specific for the outer surface protein A (OspA) of Borrelia burgdoiferi prevent Lyme borreliosis in severe combined immunodeficiency (scid ) mice (1990) Proc. Nati. Acad. Sci. USA 87:3768-3772.

Schubach et al. Mapping Antibody-Binding Domains of the Major Outer Surface Membrane Protein (OspA) of Borrelia burgdorferi (1991) Infection Immunity 59(6):1911-1915.

Schuijt et al. Lyme borreliosis vaccination: the facts, the challenge, the future (2011) Trends in Parasitology 27(1):40-47. doi:10.1016/j.pt.2010.06.006.

Sears et al. Molecular Mapping of Osp-A Mediated Immunity Against Borrelia burgdoiferi , The Agent of Lyme Disease (1991) J Immunol. 147(6):1995-2000.

Sigal et al. A vaccine consisting of recombinant Borrelia burgdoiferi outer surface protein A to prevent lyme disease (1998) N Engl J Med 339:216-22.

Stanek et al. Lyme borreliosis (2012) Lancet 379:461-73 DOI:10.1016/S0140-6736(11)60103-7. Published Online Sep. 7, 2011.

Stupica et al. Correlation of Culture Positivity, PCR Positivity, and Burden of Borrelia burgdoiferi Sensu Lato in Skin Samples of

(56) References Cited

OTHER PUBLICATIONS

Erythema Migrans Patients with Clinical Findings (2015) PLoS ONE 10(9): e0136600. doi:10.1371/journal.pone.0136600.
Wressnig et al. Safety and immunogenicity of a novel multivalent OspA vaccine against Lyme borreliosis in healthy adults: a double-blind, randomised, dose-escalation phase 1/2 trial (2013) The Lancet http://dx.doi.org/10.1016/S1473-3099(13)70110-5.
Zhong et al. Plasmid DNA and protein vaccination of mice to the outer surface protein A of *Borrelia burgdorferi* leads to induction of T helper cells with specificity for a major epitope and augmentation of protective IgG antibodies in vivo (1996) Eur. J. Immunol. 26:2749-2757.

\* cited by examiner

Figure 1

SEQUENCE LISTING

<160> NUMBER OF SEQ ID NOS: 218

<210> SEQ ID NO 1
<211> LENGTH: 152
<212> TYPE: PRT
<213> ORGANISM: Artificial Sequence
<220> FEATURE:
<223> OTHER INFORMATION: S2D0-His

<400> SEQUENCE: 1

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys Gly
    130                 135                 140

Leu Glu His His His His His His
145                 150

<210> SEQ ID NO 2
<211> LENGTH: 152
<212> TYPE: PRT
<213> ORGANISM: Artificial Sequence
<220> FEATURE:
<223> OTHER INFORMATION: S2D1-His

<400> SEQUENCE: 2

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Cys Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Cys Asn Ala Leu Lys Gly
    130                 135                 140

```
Leu Glu His His His His His His
145                 150

<210> SEQ ID NO 3
<211> LENGTH: 152
<212> TYPE: PRT
<213> ORGANISM: Artificial Sequence
<220> FEATURE:
<223> OTHER INFORMATION: S2D2-His

<400> SEQUENCE: 3

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Cys Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Cys Lys Gly
    130                 135                 140

Leu Glu His His His His His His
145                 150

<210> SEQ ID NO 4
<211> LENGTH: 152
<212> TYPE: PRT
<213> ORGANISM: Artificial Sequence
<220> FEATURE:
<223> OTHER INFORMATION: S2D3-His

<400> SEQUENCE: 4

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Cys Val Gln Lys Tyr Asp Ser Ala Gly Thr Asn Leu Glu Gly Thr
        115                 120                 125

Cys Val Glu Ile Lys Thr Leu Asp Glu Leu Lys Asn Ala Leu Lys Gly
    130                 135                 140
```

```
Leu Glu His His His His His His
145                 150

<210> SEQ ID NO 5
<211> LENGTH: 152
<212> TYPE: PRT
<213> ORGANISM: Artificial Sequence
<220> FEATURE:
<223> OTHER INFORMATION: S2D4-His

<400> SEQUENCE: 5

Glu Leu Ser Ala Lys Thr Met Thr Arg Glu Cys Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Cys Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys Gly
    130                 135                 140

Leu Glu His His His His His His
145                 150

<210> SEQ ID NO 6
<211> LENGTH: 152
<212> TYPE: PRT
<213> ORGANISM: Artificial Sequence
<220> FEATURE:
<223> OTHER INFORMATION: S2D5-His

<400> SEQUENCE: 6

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Cys Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Cys Asp Glu Leu Lys Asn Ala Leu Lys Gly
```

Leu Glu His His His His His His
145                 150

<210> SEQ ID NO 7
<211> LENGTH: 152
<212> TYPE: PRT
<213> ORGANISM: Artificial Sequence
<220> FEATURE:
<223> OTHER INFORMATION: S2D6-His

<400> SEQUENCE: 7

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
                20                  25                  30

Lys Asn Phe Thr Leu Glu Gly Lys Val Ala Asn Asp Lys Val Thr Leu
            35                  40                  45

Glu Val Lys Glu Gly Thr Cys Thr Leu Ser Lys Glu Ile Ala Lys Ser
50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Cys Lys Gly
    130                 135                 140

Leu Glu His His His His His His
145                 150

<210> SEQ ID NO 8
<211> LENGTH: 152
<212> TYPE: PRT
<213> ORGANISM: Artificial Sequence
<220> FEATURE:
<223> OTHER INFORMATION: S2D7-His

<400> SEQUENCE: 8

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
                20                  25                  30

Lys Asn Phe Thr Leu Glu Gly Lys Val Ala Asn Asp Lys Val Thr Leu
            35                  40                  45

Glu Val Lys Glu Gly Thr Val Thr Leu Ser Lys Glu Ile Ala Lys Ser
50                  55                  60

Gly Glu Val Thr Cys Ala Leu Asn Asp Thr Asn Thr Thr Gln Ala Thr
65                  70                  75                  80

Lys Lys Thr Gly Ala Trp Asp Ser Lys Thr Ser Thr Cys Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys Gly
    130                 135                 140

Leu Glu His His His His His His
145                 150

<210> SEQ ID NO 9
<211> LENGTH: 152
<212> TYPE: PRT
<213> ORGANISM: Artificial Sequence
<220> FEATURE:
<223> OTHER INFORMATION: S2D8-His

<400> SEQUENCE: 9

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
                20                  25                  30

Lys Asn Phe Thr Leu Glu Gly Lys Val Ala Asn Asp Lys Val Thr Leu
            35                  40                  45

Glu Val Lys Glu Gly Thr Val Thr Leu Ser Lys Glu Ile Ala Lys Ser
50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Cys Thr Val Gln Lys Tyr Asp Ser Ala Gly Thr Asn Leu Glu Gly Thr
        115                 120                 125

Ala Val Glu Cys Lys Thr Leu Asp Glu Leu Lys Asn Ala Leu Lys Gly
    130                 135                 140

Leu Glu His His His His His His
145                 150

<210> SEQ ID NO 10
<211> LENGTH: 152
<212> TYPE: PRT
<213> ORGANISM: Artificial Sequence
<220> FEATURE:
<223> OTHER INFORMATION: S2D9-His

<400> SEQUENCE: 10

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
                20                  25                  30

Lys Asn Phe Thr Leu Glu Gly Lys Val Ala Asn Asp Lys Val Thr Leu
            35                  40                  45

Glu Val Lys Glu Gly Cys Val Thr Leu Ser Lys Glu Ile Ala Lys Ser
50                  55                  60

Gly Glu Val Thr Val Ala Leu Asn Asp Cys Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys Gly
            130                 135                 140

Leu Glu His His His His His His
145                 150

<210> SEQ ID NO 11
<211> LENGTH: 152
<212> TYPE: PRT
<213> ORGANISM: Artificial Sequence
<220> FEATURE:
<223> OTHER INFORMATION: S2D10-His

<400> SEQUENCE: 11

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
                20                  25                  30

Lys Asn Phe Thr Leu Glu Gly Lys Val Ala Asn Asp Lys Val Thr Leu
            35                  40                  45

Glu Val Lys Glu Gly Thr Val Thr Leu Ser Lys Glu Ile Ala Lys Ser
50                  55                  60

Gly Glu Val Thr Val Ala Cys Asn Asp Thr Asn Thr Gln Ala Thr
65                  70                  75                  80

Lys Lys Thr Cys Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys Gly
            130                 135                 140

Leu Glu His His His His His His
145                 150

<210> SEQ ID NO 12
<211> LENGTH: 152
<212> TYPE: PRT
<213> ORGANISM: Artificial Sequence
<220> FEATURE:
<223> OTHER INFORMATION: S2D11-His

<400> SEQUENCE: 12

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
                20                  25                  30

Lys Asn Phe Thr Leu Glu Gly Lys Val Ala Asn Asp Lys Val Thr Leu
            35                  40                  45

Glu Val Lys Glu Gly Thr Val Thr Leu Ser Lys Glu Ile Ala Lys Ser
        50                  55                  60

Gly Glu Val Thr Val Ala Leu Asn Asp Thr Asn Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Cys Lys Tyr Asp Ser Ala Gly Thr Asn Leu Glu Gly Thr

```
                    115                 120                 125
Cys Val Glu Ile Lys Thr Leu Asp Glu Leu Lys Asn Ala Leu Lys Gly
                130                 135                 140

Leu Glu His His His His His His
145                 150

<210> SEQ ID NO 13
<211> LENGTH: 152
<212> TYPE: PRT
<213> ORGANISM: Artificial Sequence
<220> FEATURE:
<223> OTHER INFORMATION: S2D12-His

<400> SEQUENCE: 13

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
                20                  25                  30

Lys Asn Phe Thr Cys Glu Gly Lys Val Ala Asn Asp Lys Val Thr Cys
            35                  40                  45

Glu Val Lys Glu Gly Thr Val Thr Leu Ser Lys Glu Ile Ala Lys Ser
50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Ser Thr Ser Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys Gly
    130                 135                 140

Leu Glu His His His His His His
145                 150

<210> SEQ ID NO 14
<211> LENGTH: 16
<212> TYPE: PRT
<213> ORGANISM: Borrelia burgdorferi

<400> SEQUENCE: 14

Met Lys Lys Tyr Leu Leu Gly Ile Gly Leu Ile Leu Ala Leu Ile Ala
1               5                   10                  15

<210> SEQ ID NO 15
<211> LENGTH: 15
<212> TYPE: PRT
<213> ORGANISM: Borrelia burgdorferi

<400> SEQUENCE: 15

Met Arg Leu Leu Ile Gly Phe Ala Leu Ala Leu Ala Leu Ile Gly
1               5                   10                  15

<210> SEQ ID NO 16
<211> LENGTH: 20
<212> TYPE: PRT
<213> ORGANISM: Escherichia coli

<400> SEQUENCE: 16

Met Lys Ala Thr Lys Leu Val Leu Gly Ala Val Ile Leu Gly Ser Thr
```

```
1               5                   10                  15
Leu Leu Ala Gly
            20

<210> SEQ ID NO 17

Ile Ser Val Asn Ser Lys Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
            245                 250                 255

Gly Thr Ala Val Glu Ile Lys Thr Leu Asp Glu Leu Lys Asn Ala Leu
        260                 265                 270

Lys

<210> SEQ ID NO 20
<211> LENGTH: 273
<212> TYPE: PRT
<213> ORGANISM: Borrelia burgdorferi

<400> SEQUENCE: 20

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys

<210> SEQ ID NO 21
<211> LENGTH: 274
<212> TYPE: PRT
<213> ORGANISM: Borrelia garinii

<400> SEQUENCE: 21

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Lys Val Leu Val Ser Lys Glu Lys Asp Lys
        35                  40                  45

Asp Gly Lys Tyr Ser Leu Met Ala Thr Val Glu Lys Leu Glu Leu Lys
    50                  55                  60

Gly Thr Ser Asp Lys Ser Asn Gly Ser Gly Val Leu Glu Gly Glu Lys
65                  70                  75                  80

Ala Asp Lys Ser Lys Ala Lys Leu Thr Ile Ser Gln Asp Leu Asn Gln
                85                  90                  95

Thr Thr Phe Glu Ile Phe Lys Glu Asp Gly Lys Thr Leu Val Ser Arg
            100                 105                 110

Lys Val Asn Ser Lys Asp Lys Ser Ser Thr Glu Glu Lys Phe Asn Asp
        115                 120                 125

Lys Gly Lys Leu Ser Glu Lys Val Val Thr Arg Ala Asn Gly Thr Arg
    130                 135                 140

Leu Glu Tyr Thr Glu Ile Lys Asn Asp Gly Ser Gly Lys Ala Lys Glu
145                 150                 155                 160

Val Leu Lys Gly Phe Ala Leu Glu Gly Thr Leu Thr Asp Gly Gly Glu
                165                 170                 175

Thr Lys Leu Thr Val Thr Glu Gly Thr Val Thr Leu Ser Lys Asn Ile
            180                 185                 190

Ser Lys Ser Gly Glu Ile Thr Val Ala Leu Asn Asp Thr Glu Thr Thr
        195                 200                 205

Pro Ala Asp Lys Lys Thr Gly Glu Trp Lys Ser Asp Thr Ser Thr Leu
    210                 215                 220

Thr Ile Ser Lys Asn Ser Gln Lys Pro Lys Gln Leu Val Phe Thr Lys
225                 230                 235                 240

Glu Asn Thr Ile Thr Val Gln Asn Tyr Asn Arg Ala Gly Asn Ala Leu
                245                 250                 255

Glu Gly Ser Pro Ala Glu Ile Lys Asp Leu Ala Glu Leu Lys Ala Ala
            260                 265                 270

Leu Lys
```

<210> SEQ ID NO 22
<211> LENGTH: 273
<212> TYPE: PRT
<213> ORGANISM: Borrelia bavariensis

<400> SEQUENCE: 22

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys

Ser Asp Lys Ser Lys Ala Lys Leu Thr Ile Ser Glu Asp Leu Ser Lys
            85                  90                  95

Thr Thr Phe Glu Ile Phe Lys Glu Asp Gly Lys Thr Leu Val Ser Lys
            100                 105                 110

Lys Val Asn Ser Lys Asp Lys Ser Ser Ile Glu Glu Lys Phe Asn Ala
            115                 120                 125

Lys Gly Glu Leu Ser Glu Lys Thr Ile Leu Arg Ala Asn Gly Thr Arg
            130                 135                 140

Leu Glu Tyr Thr Glu Ile Lys Ser Asp Gly Thr Gly Lys Ala Lys Glu
145                 150                 155                 160

Val Leu Lys Asp Phe Ala Leu Glu Gly Thr Leu Ala Ala Asp Lys Thr
            165                 170                 175

Thr Leu Lys Val Thr Glu Gly Thr Val Val Leu Ser Lys His Ile Pro
            180                 185                 190

Asn Ser Gly Glu Ile Thr Val Glu Leu Asn Asp Ser Asn Ser Thr Gln
            195                 200                 205

Ala Thr Lys Lys Thr Gly Lys Trp Asp Ser Asn Thr Ser Thr Leu Thr
            210                 215                 220

Ile Ser Val Asn Ser Lys Lys Thr Lys Asn Ile Val Phe Thr Lys Glu
225                 230                 235                 240

Asp Thr Ile Thr Val Gln Lys Tyr Asp Ser Ala Gly Thr Asn Leu Glu
            245                 250                 255

Gly Asn Ala Val Glu Ile Lys Thr Leu Asp Glu Leu Lys Asn Ala Leu
            260                 265                 270

Lys

<210> SEQ ID NO 23
<211> LENGTH: 273
<212> TYPE: PRT
<213> ORGANISM: Borrelia garinii

<400> SEQUENCE: 23

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Lys Val Leu Val Ser Lys Glu Lys Asp Lys
            35                  40                  45

Asp Gly Lys Tyr Ser Leu Met Ala Thr Val Glu Lys Leu Glu Leu Lys
        50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Glu Asp Leu Ser Lys
            85                  90                  95

Thr Thr Phe Glu Ile Phe Lys Glu Asp Gly Lys Thr Leu Val Ser Lys
            100                 105                 110

Lys Val Thr Leu Lys Asp Lys Ser Ser Thr Glu Glu Lys Phe Asn Glu
            115                 120                 125

Lys Gly Glu Ile Ser Glu Lys Thr Ile Val Arg Ala Asn Gly Thr Arg
            130                 135                 140

Leu Glu Tyr Thr Asp Ile Lys Ser Asp Lys Thr Gly Lys Ala Lys Glu
145                 150                 155                 160

Val Leu Lys Asp Phe Thr Leu Glu Gly Thr Leu Ala Ala Asp Gly Lys
            165                 170                 175

```
Thr Thr Leu Lys Val Thr Glu Gly Thr Val Thr Leu Ser Lys Asn Ile
            180                 185                 190
Ser Lys Ser Gly Glu Ile Thr Val Ala Leu Asp Asp Thr Asp Ser Ser
            195                 200                 205
Gly Asn Lys Lys Ser Gly Thr Trp Asp Ser Gly Thr Ser Thr Leu Thr
    210                 215                 220
Ile Ser Lys Asn Arg Thr Lys Thr Lys Gln Leu Val Phe Thr Lys Glu
225                 230                 235                 240
Asp Thr Ile Thr Val Gln Asn Tyr Asp Ser Ala Gly Thr Asn Leu Glu
                245                 250                 255
Gly Lys Ala Val Glu Ile Thr Thr Leu Lys Glu Leu Lys Asn Ala Leu
            260                 265                 270
Lys

<210> SEQ ID NO 24
<211> LENGTH: 274
<212> TYPE: PRT
<213> ORGANISM: Borrelia garinii

<400> SEQUENCE: 24

Met Lys Lys Tyr Leu Leu Gly Ile Gly Leu Ile Leu Ala Leu Ile Ala
1               5                   10                  15
Cys Lys Gln Asn Val Ser Ser Leu Asp Glu Lys Asn Ser Val Ser Val
            20                  25                  30
Asp Leu Pro Gly Gly Met Thr Val Leu Val Ser Lys Glu Lys Asp Lys
            35                  40                  45
Asp Gly Lys Tyr Ser Leu Glu Ala Thr Val Asp Lys Leu Glu Leu Lys
    50                  55                  60
Gly Thr Ser Asp Lys Asn Asn Gly Ser Gly Thr Leu Glu Gly Glu Lys
65                  70                  75                  80
Thr Asp Lys Ser Lys Val Lys Ser Thr Ile Ala Asp Asp Leu Ser Gln
            85                  90                  95
Thr Lys Phe Glu Ile Phe Lys Glu Asp Gly Lys Thr Leu Val Ser Lys
            100                 105                 110
Lys Val Thr Leu Lys Asp Lys Ser Ser Thr Glu Glu Lys Phe Asn Gly
            115                 120                 125
Lys Gly Glu Thr Ser Glu Lys Thr Ile Val Arg Ala Asn Gly Thr Arg
    130                 135                 140
Leu Glu Tyr Thr Asp Ile Lys Ser Asp Gly Ser Gly Lys Ala Lys Glu
145                 150                 155                 160
Val Leu Lys Asp Phe Thr Leu Glu Gly Thr Leu Ala Ala Asp Gly Lys
                165                 170                 175
Thr Thr Leu Lys Val Thr Glu Gly Thr Val Val Leu Ser Lys Asn Ile
            180                 185                 190
Leu Lys Ser Gly Glu Ile Thr Ala Ala Leu Asp Asp Ser Asp Thr Thr
            195                 200                 205
Arg Ala Thr Lys Lys Thr Gly Lys Trp Asp Ser Lys Thr Ser Thr Leu
    210                 215                 220
Thr Ile Ser Val Asn Ser Gln Lys Thr Lys Asn Leu Val Phe Thr Lys
225                 230                 235                 240
Glu Asp Thr Ile Thr Val Gln Arg Tyr Asp Ser Ala Gly Thr Asn Leu
                245                 250                 255
Glu Gly Lys Ala Val Glu Ile Thr Thr Leu Lys Glu Leu Lys Asn Ala
            260                 265                 270
```

Leu Lys

<210> SEQ ID NO 25
<211> LENGTH: 274
<212> TYPE: PRT
<213> ORGANISM: Borrelia garinii

<400> SEQUENCE: 25

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Ser Lys Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Ala Lys Ser Lys Ala Lys Leu Thr Ile Ala Asp Asp Leu Ser Gln
                85                  90                  95

Thr Lys Phe Glu Ile Phe Lys Gly Asp Gly Lys Thr Leu Val Ser Lys
            100                 105                 110

Lys Val Thr Leu Lys Asp Lys Ser Ser Thr Glu Glu Lys Phe Asn Asp
        115                 120                 125

Lys Gly Lys Leu Ser Glu Lys Val Val Thr Arg Ala Asn Gly Thr Arg
130                 135                 140

Leu Glu Tyr Thr Glu Ile Gln Asn Asp Gly Ser Gly Lys Ala Lys Glu
145                 150                 155                 160

Val Leu Lys Ser Leu Thr Leu Glu Gly Thr Leu Thr Ala Asp Gly Glu
                165                 170                 175

Thr Lys Leu Thr Val Glu Ala Gly Thr Val Thr Leu Ser Lys Asn Ile
            180                 185                 190

Ser Glu Ser Gly Glu Ile Thr Val Glu Leu Lys Asp Thr Glu Thr Thr
        195                 200                 205

Pro Ala Asp Lys Lys Ser Gly Thr Trp Asp Ser Lys Thr Ser Thr Leu
210                 215                 220

Thr Ile Ser Lys Asn Ser Gln Lys Thr Lys Gln Leu Val Phe Thr Lys
225                 230                 235                 240

Glu Asn Thr Ile Thr Val Gln Lys Tyr Asn Thr Ala Gly Thr Lys Leu
                245                 250                 255

Glu Gly Ser Pro Ala Glu Ile Lys Asp Leu Glu Ala Leu Lys Ala Ala
            260                 265                 270

Leu Lys

<210> SEQ ID NO 26
<211> LENGTH: 21
<212> TYPE: DNA
<213> ORGANISM: Artificial Sequence
<220> FEATURE:
<223> OTHER INFORMATION: pcr primer

<400> SEQUENCE: 26
gtatgtttag tgaggggggt g                                         21

<210> SEQ ID NO 27
<211> LENGTH: 22
<212> TYPE: DNA

```
<213> ORGANISM: Artificial Sequence
<220> FEATURE:
<223> OTHER INFORMATION: pcr primer

<400> SEQUENCE: 27
ggatcatagc tcaggtggtt ag                                              22

<210> SEQ ID NO 28
<211> LENGTH: 22
<212> TYPE: DNA
<213> ORGANISM: Artificial Sequence
<220> FEATURE:
<223> OTHER INFORMATION: pcr primer

<400> SEQUENCE: 28
aggggggtga agtcgtaaca ag                                              22

<210> SEQ ID NO 29
<211> LENGTH: 22
<212> TYPE: DNA
<213> ORGANISM: Artificial Sequence
<220> FEATURE:
<223> OTHER INFORMATION: pcr primer

<400> SEQUENCE: 29
gtctgataaa cctgaggtcg ga                                              22

<210> SEQ ID NO 30
<211> LENGTH: 25
<212> TYPE: PRT
<213> ORGANISM: Artificial Sequence
<220> FEATURE:
<223> OTHER INFORMATION: 25-mer peptide

<400> SEQUENCE: 30

Met Lys Lys Asp Asp Gln Ile Ala Ala Ala Met Val Leu Arg Gly Met
1               5                   10                  15

Ala Lys Asp Gly Gln Phe Ala Leu Lys
            20                  25

<210> SEQ ID NO 31
<211> LENGTH: 36
<212> TYPE: PRT
<213> ORGANISM: Mus musculus

<400> SEQUENCE: 31

Arg Leu Ala Gly Leu Leu Arg Lys Gly Gly Glu Lys Ile Gly Glu Lys
1               5                   10                  15

Leu Lys Lys Ile Gly Gln Lys Ile Lys Asn Phe Phe Gln Lys Leu Val
            20                  25                  30

Pro Gln Pro Glu
        35

<210> SEQ ID NO 32
<211> LENGTH: 26
<212> TYPE: DNA
<213> ORGANISM: Artificial sequence
<220> FEATURE:
<223> OTHER INFORMATION: immunostimulatory oligodeoxynucleotide
<220> FEATURE:
<221> NAME/KEY: misc_feature
<222> LOCATION: (1)..(26)
<223> OTHER INFORMATION: n=inosine

<400> SEQUENCE: 32
```

<210> SEQ ID NO 33
<211> LENGTH: 11
<212> TYPE: PRT
<213> ORGANISM: Artificial Sequence
<220> FEATURE:
<223> OTHER INFORMATION: immunostimulatory peptide

<400> SEQUENCE: 33

Lys Leu Lys Leu Leu Leu Leu Leu Lys Leu Lys
1               5                   10

<210> SEQ ID NO 34
<211> LENGTH: 148
<212> TYPE: PRT
<213> ORGANISM: Borrelia afzelii

<400> SEQUENCE: 34

Phe Asn Glu Lys Gly Glu Leu Ser Ala Lys Thr Met Thr Arg Glu Asn
1               5                   10 15

Gly Thr Lys Leu Glu Tyr Thr Glu Met Lys Ser Asp Gly Thr Gly Lys
20 25 30

Ala Lys Glu Val Leu Lys Asn Phe Thr Leu Glu Gly Lys Val Ala Asn
35 40 45

Asp Lys Val Thr Leu Glu Val Lys Glu Gly Thr Val Thr Leu Ser Lys
50 55 60

Glu Ile Ala Lys Ser Gly Glu Val Thr Val Ala Leu Asn Asp Thr Asn
65 70 75 80

Thr Thr Gln Ala Thr Lys Lys Thr Gly Ala Trp Asp Ser Lys Thr Ser
85 90 95

Thr Leu Thr Ile Ser Val Asn Ser Lys Lys Thr Thr Gln Leu Val Phe
100 105 110

Thr Lys Gln Asp Thr Ile Thr Val Gln Lys Tyr Asp Ser Ala Gly Thr
115 120 125

Asn Leu Glu Gly Thr Ala Val Glu Ile Lys Thr Leu Asp Glu Leu Lys
130 135 140

Asn Ala Leu Lys
145

<210> SEQ ID NO 35
<211> LENGTH: 143
<212> TYPE: PRT
<213> ORGANISM: Borrelia afzelii

<400> SEQUENCE: 35

Glu Leu Ser Ala Lys Thr Met Thr Arg Glu Asn Gly Thr Lys Leu Glu
1 5 10 15

Tyr Thr Glu Met Lys Ser Asp Gly Thr Gly Lys Ala Lys Glu Val Leu
20 25 30

Lys Asn Phe Thr Leu Glu Gly Lys Val Ala Asn Asp Lys Val Thr Leu
35 40 45

Glu Val Lys Glu Gly Thr Val Thr Leu Ser Lys Glu Ile Ala Lys Ser
50 55 60

Gly Glu Val Thr Val Ala Leu Asn Asp Thr Asn Thr Thr Gln Ala Thr
65 70 75 80

Lys Lys Thr Gly Ala Trp Asp Ser Lys Thr Ser Thr Leu Thr Ile Ser
85 90 95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys
    130                 135                 140

<210> SEQ ID NO 36
<211> LENGTH: 8
<212> TYPE: PRT
<213> ORGANISM: Artificial Sequence
<220> FEATURE:
<223> OTHER INFORMATION: peptide linker

<400> SEQUENCE: 36

Gly Gly Gly Gly Gly Gly Gly Gly
1               5

<210> SEQ ID NO 37
<211> LENGTH: 12
<212> TYPE: PRT
<213> ORGANISM: Artificial Sequence
<220> FEATURE:
<223> OTHER INFORMATION: peptide linker

<400> SEQUENCE: 37

Gly Gly Gly Gly Gly Gly Gly Gly Gly Gly Gly Gly
1               5                   10

<210> SEQ ID NO 38
<211> LENGTH: 4
<212> TYPE: PRT
<213> ORGANISM: Artificial Sequence
<220> FEATURE:
<223> OTHER INFORMATION: peptide linker

<400> SEQUENCE: 38

Gly Ala Gly Ala
1

<210> SEQ ID NO 39
<211> LENGTH: 8
<212> TYPE: PRT
<213> ORGANISM: Artificial Sequence
<220> FEATURE:
<223> OTHER INFORMATION: peptide linker

<400> SEQUENCE: 39

Gly Ala Gly Ala Gly Ala Gly Ala
1               5

<210> SEQ ID NO 40
<211> LENGTH: 12
<212> TYPE: PRT
<213> ORGANISM: Artificial Sequence
<220> FEATURE:
<223> OTHER INFORMATION: peptide linker

<400> SEQUENCE: 40

Gly Ala Gly Ala Gly Ala Gly Ala Gly Ala Gly Ala
1               5                   10

<210> SEQ ID NO 41
<211> LENGTH: 8
<212> TYPE: PRT
<213> ORGANISM: Artificial Sequence

```
<220> FEATURE:
<223> OTHER INFORMATION: peptide linker

<400> SEQUENCE: 41

Gly Gly Gly Ser Gly Gly Gly Ser
1               5

<210> SEQ ID NO 42
<211> LENGTH: 12
<212> TYPE: PRT
<213> ORGANISM: Artificial Sequence
<220> FEATURE:
<223> OTHER INFORMATION: peptide linker

<400> SEQUENCE: 42

Gly Gly Gly Ser Gly Gly Gly Ser Gly Gly Gly Ser
1               5                   10

<210> SEQ ID NO 43
<211> LENGTH: 317
<212> TYPE: PRT
<213> ORGANISM: Artificial Sequence
<220> FEATURE:
<223> OTHER INFORMATION: S1D4-S2D4_aa

<400> SEQUENCE: 43

Phe Asn Glu Lys Gly Glu Val Ser Glu Lys Ile Ile Thr Arg Ala Cys
1               5                   10                  15

Gly Thr Arg Leu Glu Tyr Thr Gly Ile Lys Ser Asp Gly Ser Gly Lys
                20                  25                  30

Ala Lys Glu Val Leu Lys Asn Phe Thr Leu Glu Gly Lys Val Ala Asn
            35                  40                  45

Asp Lys Thr Thr Leu Val Val Lys Glu Gly Thr Val Thr Leu Ser Lys
        50                  55                  60

Asn Ile Ser Lys Ser Gly Glu Val Ser Val Glu Leu Asn Asp Thr Asp
65                  70                  75                  80

Ser Ser Ala Ala Thr Lys Lys Thr Ala Ala Trp Asn Ser Gly Thr Ser
                85                  90                  95

Thr Leu Thr Ile Thr Val Asn Ser Lys Lys Thr Lys Asp Leu Val Phe
                100                 105                 110

Thr Lys Glu Cys Thr Ile Thr Val Gln Gln Tyr Asp Ser Asn Gly Thr
            115                 120                 125

Lys Leu Glu Gly Ser Ala Val Glu Ile Thr Lys Leu Asp Glu Ile Lys
        130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Glu Lys Gly Glu Leu
                165                 170                 175

Ser Ala Lys Thr Met Thr Arg Glu Cys Gly Thr Lys Leu Glu Tyr Thr
                180                 185                 190

Glu Met Lys Ser Asp Gly Thr Gly Lys Ala Lys Glu Val Leu Lys Asn
            195                 200                 205

Phe Thr Leu Glu Gly Lys Val Ala Asn Asp Lys Val Thr Leu Glu Val
        210                 215                 220

Lys Glu Gly Thr Val Thr Leu Ser Lys Glu Ile Ala Lys Ser Gly Glu
225                 230                 235                 240

Val Thr Val Ala Leu Asn Asp Thr Asn Thr Gln Ala Thr Lys Lys
                245                 250                 255
```

```
Thr Gly Ala Trp Asp Ser Lys Thr Ser Thr Leu Thr Ile Ser Val Asn
            260                 265                 270

Ser Lys Lys Thr Thr Gln Leu Val Phe Thr Lys Gln Cys Thr Ile Thr
        275                 280                 285

Val Gln Lys Tyr Asp Ser Ala Gly Thr Asn Leu Glu Gly Thr Ala Val
    290                 295                 300

Glu Ile Lys Thr Leu Asp Glu Leu Lys Asn Ala Leu Lys
305                 310                 315

<210> SEQ ID NO 44
<211> LENGTH: 1020
<212> TYPE: DNA
<213> ORGANISM: Artificial Sequence
<220> FEATURE:
<223> OTHER INFORMATION: Lip-S1D4-S2D4_nt

<400> SEQUENCE: 44
atgaaagcta ctaaactggt actgggcgcg gtaatcctgg gttctactct gctggcaggt      60
tgctcaagct tcaacgaaaa gggcgaagtc tcggaaaaaa tcattacccg tgcttgcggc     120
acccgtctgg aatacaccgg cattaaatcg gatggcagcg gcaaagcgaa ggaagttctg     180
aaaaacttta ccctggaagg caagtcgcaa atgataaga ccacccctggt ggtgaaagaa     240 ggcaccgtta cgctgagcaa aaacattagt aagtccggtg aagtctctgt ggaactgaat     300
gataccgaca gctctgcggc caccaaaaag acggcagctt ggaactcagg cacctcgacg     360
ctgaccatta cggttaattc caaaaagacc aaagatctgg tcttcacgaa agaatgcacc     420
atcacggtgc agcaatatga cagcaacggt accaaactgg aaggctctgc ggtggaaatc     480
acgaaactgg atgaaatcaa aaatgctctg aaaggtacta gtgacaaaaa caatggctct     540
ggtagcaaag agaaaaacaa agatggcaag tactcattca cgaaaaagg cgaactgtcg     600 gcgaaaacga tgacgcgtga atgcggcacc aaactggaat atacggaaat gaaaagcgat     660
ggcaccggta agcgaaaga agttctgaaa aactttaccc tggaaggcaa agtcgccaat     720
gacaaagtca ccctggaagt gaaagaaggc accgttacgc tgtcaaaaga aattgcaaaa     780
tcgggtgaag tgaccgttgc tctgaacgat acgaatacca cgcaagcgac caagaaaacc     840
ggcgcctggg acagcaaaac ctctacgctg accattagtg ttaacagcaa gaaaaccacg     900
cagctggtct tcaccaaaca atgtacgatc ccgtgcaga aatacgatag tgcgggtacc     960
aacctggaag gcaccgctgt tgaaatcaaa accctggacg aactgaaaaa cgccctgaaa    1020

<210> SEQ ID NO 45
<211> LENGTH: 329
<212> TYPE: PRT
<213> ORGANISM: Artificial Sequence
<220> FEATURE:
<223> OTHER INFORMATION: Lip-S1D4-S2D4_His_aa
<220> FEATURE:
<221> NAME/KEY: LIPID
<222> LOCATION: (1)..(1)
<223> OTHER INFORMATION: LIPIDATION

<400> SEQUENCE: 45

Cys Ser Ser Phe Asn Glu Lys Gly Glu Val Ser Glu Lys Ile Ile Thr
1               5                   10                  15

Arg Ala Cys Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45
```

Val Ala Asn Asp Lys Thr Thr Leu Val Val Lys Glu Gly Thr Val Thr
50              55                  60

Leu Ser Lys Asn Ile Ser Lys Ser Gly Glu Val Ser Val Glu Leu Asn
65              70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
                100                 105                 110

Leu Val Phe Thr Lys Glu Cys Thr Ile Thr Val Gln Gln Tyr Asp Ser
            115                 120                 125

Asn Gly Thr Lys Leu Glu Gly Ser Ala Val Glu Ile Thr Lys Leu Asp
130                 135                 140

Glu Ile Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Cys Gly Thr Lys Leu
                180                 185                 190

Glu Tyr Thr Glu Met Lys Ser Asp Gly Thr Gly Lys Ala Lys Glu Val
            195                 200                 205

Leu Lys Asn Phe Thr Leu Glu Gly Lys Val Ala Asn Asp Lys Val Thr
210                 215                 220

Leu Glu Val Lys Glu Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
                245                 250                 255

Thr Lys Lys Thr Gly Ala Trp Asp Ser Lys Thr Ser Thr Leu Thr Ile
                260                 265                 270

Ser Val Asn Ser Lys Lys Thr Thr Gln Leu Val Phe Thr Lys Gln Cys
            275                 280                 285

Thr Ile Thr Val Gln Lys Tyr Asp Ser Ala Gly Thr Asn Leu Glu Gly
290                 295                 300

Thr Ala Val Glu Ile Lys Thr Leu Asp Glu Leu Lys Asn Ala Leu Lys
305                 310                 315                 320

Gly Leu Glu His His His His His His
                325

<210> SEQ ID NO 46
<211> LENGTH: 1047
<212> TYPE: DNA
<213> ORGANISM: Artificial Sequence
<220> FEATURE:
<223> OTHER INFORMATION: Lip-S1D4-S2D4_His_nt

<400> SEQUENCE: 46
atgaaagcta ctaaactggt actgggcgcg gtaatcctgg gttctactct gctggcaggt      60
tgctcaagct tcaacgaaaa gggcgaagtc tcggaaaaaa tcattacccg tgcttgcggc     120
acccgtctgg aatacaccgg cattaaatcg gatggcagcg gcaaagcgaa ggaagttctg     180 aaaaactta ccctggaagg caaagtcgca atgataaga ccaccctggt ggtgaaagaa       240
ggcaccgtta cgctgagcaa aaacattagt aagtccggtg aagtctctgt ggaactgaat    300
gataccgaca gctctgcggc caccaaaaag acggcagctt ggaactcagg cacctcgacg    360
ctgaccatta cggttaattc caaaaagacc aaagatctgg tcttcacgaa agaatgcacc    420
atcacggtgc agcaatatga cagcaacggt accaaactgg aaggctctgc ggtggaaatc    480

-continued

```
acgaaactgg atgaaatcaa aaatgctctg aaaggtacta gtgacaaaaa caatggctct    540
ggtagcaaag agaaaaacaa agatggcaag tactcattca acgaaaaagg cgaactgtcg    600
gcgaaaacga tgacgcgtga atgcggcacc aaactggaat atacggaaat gaaaagcgat    660
ggcaccggta aagcgaaaga agttctgaaa aactttaccc tggaaggcaa agtcgccaat    720
gacaaagtca ccctggaagt gaaagaaggc accgttacgc tgtcaaaaga aattgcaaaa    780
tcgggtgaag tgaccgttgc tctgaacgat acgaatacca cgcaagcgac caagaaaacc    840
ggcgcctggg acagcaaaac ctctacgctg accattagtg ttaacagcaa gaaaaccacg    900
cagctggtct tcaccaaaca atgtacgatc accgtgcaga aatacgatag tgcgggtacc    960
aacctggaag gcaccgctgt tgaaatcaaa accctggacg aactgaaaaa cgccctgaaa   1020
ggcctcgagc accaccacca ccaccac                                       1047
```

<210> SEQ ID NO 47
<211> LENGTH: 317
<212> TYPE: PRT
<213> ORGANISM: Artificial Sequence
<220> FEATURE:
<223> OTHER INFORMATION: S1D1-S2D1_aa

<400> SEQUENCE: 47

```
Phe Asn Glu Lys Gly Glu Val Ser Glu Lys Ile Ile Thr Arg Ala Asp
1               5                   10                  15

Gly Thr Arg Leu Glu Tyr Thr Gly Ile Lys Ser Asp Gly Ser Gly Lys
            20                  25                  30

Ala Lys Glu Val Leu Lys Asn Phe Thr Leu Glu Gly Lys Val Ala Asn
        35                  40                  45

Asp Lys Thr Thr Leu Val Val Lys Cys Gly Thr Val Thr Leu Ser Lys
    50                  55                  60

Asn Ile Ser Lys Ser Gly Glu Val Ser Val Glu Leu Asn Asp Thr Asp
65                  70                  75                  80

Ser Ser Ala Ala Thr Lys Lys Thr Ala Ala Trp Asn Ser Gly Thr Ser
                85                  90                  95

Thr Leu Thr Ile Thr Val Asn Ser Lys Lys Thr Lys Asp Leu Val Phe
            100                 105                 110

Thr Lys Glu Asn Thr Ile Thr Val Gln Gln Tyr Asp Ser Asn Gly Thr
        115                 120                 125

Lys Leu Glu Gly Ser Ala Val Glu Ile Thr Lys Leu Asp Glu Ile Cys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Glu Lys Gly Glu Leu
                165                 170                 175

Ser Ala Lys Thr Met Thr Arg Glu Asn Gly Thr Lys Leu Glu Tyr Thr
            180                 185                 190

Glu Met Lys Ser Asp Gly Thr Gly Lys Ala Lys Glu Val Leu Lys Asn
        195                 200                 205

Phe Thr Leu Glu Gly Lys Val Ala Asn Asp Lys Val Thr Leu Glu Val
    210                 215                 220

Lys Cys Gly Thr Val Thr Leu Ser Lys Glu Ile Ala Lys Ser Gly Glu
225                 230                 235                 240

Val Thr Val Ala Leu Asn Asp Thr Asn Thr Thr Gln Ala Thr Lys Lys
                245                 250                 255
```

Thr Gly Ala Trp Asp Ser Lys Thr Ser Thr Leu Thr Ile Ser Val Asn
            260                 265                 270

Ser Lys Lys Thr Thr Gln Leu Val Phe Thr Lys Gln Asp Thr Ile Thr
        275                 280                 285

Val Gln Lys Tyr Asp Ser Ala Gly Thr Asn Leu Glu Gly Thr Ala Val
    290                 295                 300

Glu Ile Lys Thr Leu Asp Glu Leu Cys Asn Ala Leu Lys
305                 310                 315

<210> SEQ ID NO 48
<211> LENGTH: 1020
<212> TYPE: DNA
<213> ORGANISM: Artificial Sequence
<220> FEATURE:
<223> OTHER INFORMATION: Lip-S1D1-S2D1_nt

<400> SEQUENCE: 48
atgaaagcta ctaaactggt actgggcgcg gtaatcctgg gttctactct gctggcaggt      60
tgctcaagct tcaacgaaaa gggcgaagtc agcgaaaaaa tcattacccg cgcagacggc     120
acccgcctgg aatacaccgg catcaaatcg gacggcagcg gcaaagcgaa agaagttctg     180
aaaaacttta ccctggaagg caaagtcgca atgataaaa ccaccctggt ggtgaaatgc     240
ggcaccgtta cgctgagcaa aaacattagt aaatccggtg aagtctctgt ggaactgaat     300
gataccgaca gctctgcggc caccaagaaa ccgcagcttg gaactcagg cacctcgacg     360
ctgaccatta cggttaatag caagaaaacc aaagatctgg tcttcacgaa agaaaacacc     420
atcacggtgc agcaatatga cagcaatggt accaaactgg aaggctccgc tgtggaaatc     480
acgaaactgg atgaaatctg taatgctctg aaaggtacta gtgacaaaaa caatggctct     540
ggtagcaaag agaaaaacaa agatggcaag tactcattca cgaaaaaggg cgaactgtcg     600
gcgaaaacga tgacgcgtga aacggcacc aaactggaat atacggaaat gaaaagcgat     660
ggcaccggta agcgaaaga agttctgaaa aactttaccc tggaaggcaa agtcgccaat     720
gacaaagtca ccctggaagt gaaatgcggc accgttacgc tgtcaaaaga aattgcaaaa     780
tcgggtgaag tgaccgttgc tctgaacgat acgaatacca cgcaagcgac caagaaaacc     840
ggcgcctggg acagcaaaac ctctacgctg accattagtg ttaatagcaa gaaaaccacg     900
cagctggtct tcaccaaaca agatacgatc accgtgcaga atacgacag tgcgggtacc     960
aacctggaag gcacggctgt tgaaatcaaa accctggacg aactgtgtaa cgccctgaaa    1020

<210> SEQ ID NO 49
<211> LENGTH: 329
<212> TYPE: PRT
<213> ORGANISM: Artificial Sequence
<220> FEATURE:
<223> OTHER INFORMATION: Lip-S1D1-S2D1_His_aa
<220> FEATURE:
<221> NAME/KEY: LIPID
<222> LOCATION: (1)..(1)
<223> OTHER INFORMATION: LIPIDATION

<400> SEQUENCE: 49

Cys Ser Ser Phe Asn Glu Lys Gly Glu Val Ser Glu Lys Ile Ile Thr
1               5                   10                  15

Arg Ala Asp Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45

| | | | | | | | | | | | | |
|---|---|---|---|---|---|---|---|---|---|---|---|---|
|Val|Ala|Asn|Asp|Lys|Thr|Thr|Leu|Val|Val|Lys|Cys|Gly|Thr|Val|Thr|
|50| | | | |55| | | | |60| | | | |

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
               100                 105                 110

Leu Val Phe Thr Lys Glu Asn Thr Ile Thr Val Gln Gln Tyr Asp Ser
           115                 120                 125

Asn Gly Thr Lys Leu Glu Gly Ser Ala Val Glu Ile Thr Lys Leu Asp
130                 135                 140

Glu Ile Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Asn Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
210                 215                 220

Leu Glu Val Lys Cys Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
                245                 250                 255

Thr Lys Lys Thr Gly Ala Trp Asp Ser Lys Thr Ser Thr Leu Thr Ile
            260                 265                 270

Ser Val Asn Ser Lys Lys Thr Thr Gln Leu Val Phe Thr Lys Gln Asp
        275                 280                 285

Thr Ile Thr Val Gln Lys Tyr Asp Ser Ala Gly Thr Asn Leu Glu Gly
    290                 295                 300

Thr Ala Val Glu Ile Lys Thr Leu Asp Glu Leu Cys Asn Ala Leu Lys
305                 310                 315                 320

Gly Leu Glu His His His His His His
            325

<210> SEQ ID NO 50
<211> LENGTH: 1047
<212> TYPE: DNA
<213> ORGANISM: Artificial Sequence
<220> FEATURE:
<223> OTHER INFORMATION: Lip-S1D1-S2D1_His_nt

<400> SEQUENCE: 50

```
atgaaagcta ctaaactggt actgggcgcg gtaatcctgg ttctactct gctggcaggt      60 tgctcaagct tcaacgaaaa gggcgaagtc agcgaaaaaa tcattaccg cgcagacggc     120 acccgcctgg aatacaccgg catcaaatcg gacggcagcg gcaaagcgaa agaagttctg    180
aaaaacttta ccctggaagg caaagtcgca atgataaaaa ccaccctggt ggtgaaatgc    240
ggcaccgtta cgctgagcaa aaacattagt aaatccggtg aagtctctgt ggaactgaat    300
gataccgaca gctctgcggc caccaagaaa accgcagctt ggaactcagg cacctcgacg    360
ctgaccatta cggttaatag caagaaaacc aaagatctgg tcttcacgaa agaaaacacc    420
atcacggtgc agcaatatga cagcaatggt accaaactgg aaggctccgc tgtggaaatc    480
```

```
acgaaactgg atgaaatctg taatgctctg aaaggtacta gtgacaaaaa caatggctct    540
ggtagcaaag agaaaacaa agatggcaag tactcattca acgaaaaagg cgaactgtcg     600
gcgaaaacga tgacgcgtga aaacggcacc aaactggaat atacggaaat gaaaagcgat    660
ggcaccggta aagcgaaaga agttctgaaa aactttaccc tggaaggcaa agtcgccaat    720
gacaaagtca ccctggaagt gaaatgcggc accgttacgc tgtcaaaaga aattgcaaaa    780
tcgggtgaag tgaccgttgc tctgaacgat acgaatacca cgcaagcgac caagaaaacc    840
ggcgcctggg acagcaaaac ctctacgctg accattagtg ttaatagcaa gaaaaccacg    900
cagctggtct tcaccaaaca agatacgatc ccgtgcaga aatacgacag tgcgggtacc     960
aacctggaag gcacggctgt tgaaatcaaa accctggacg aactgtgtaa cgccctgaaa   1020
ggcctcgagc accaccacca ccaccac                                       1047
```

<210> SEQ ID NO 51
<211> LENGTH: 318
<212> TYPE: PRT
<213> ORGANISM: Artificial Sequence
<220> FEATURE:
<223> OTHER INFORMATION: S3D4-S4D4_aa

<400> SEQUENCE: 51

```
Phe Asn Glu Lys Gly Lys Leu Ser Glu Lys Val Val Thr Arg Ala Cys
1               5                   10                  15

Gly Thr Arg Leu Glu Tyr Thr Glu Ile Lys Asn Asp Gly Ser Gly Lys
                20                  25                  30

Ala Lys Glu Val Leu Lys Gly Phe Ala Leu Glu Gly Thr Leu Thr Asp
            35                  40                  45

Gly Gly Glu Thr Lys Leu Thr Val Thr Glu Gly Thr Val Thr Leu Ser
        50                  55                  60

Lys Asn Ile Ser Lys Ser Gly Glu Ile Thr Val Ala Leu Asn Asp Thr
65                  70                  75                  80

Glu Thr Thr Pro Ala Asp Lys Lys Thr Gly Glu Trp Lys Ser Asp Thr
                85                  90                  95

Ser Thr Leu Thr Ile Ser Lys Asn Ser Gln Lys Pro Lys Gln Leu Val
            100                 105                 110

Phe Thr Lys Glu Cys Thr Ile Thr Val Gln Asn Tyr Asn Arg Ala Gly
        115                 120                 125

Asn Ala Leu Glu Gly Ser Pro Ala Glu Ile Lys Asp Leu Ala Glu Leu
130                 135                 140

Lys Ala Ala Leu Lys Gly Thr Ser Asp Lys Asn Asn Gly Ser Gly Ser
145                 150                 155                 160

Lys Glu Lys Asn Lys Asp Gly Lys Tyr Ser Phe Asn Ala Lys Gly Glu
                165                 170                 175

Leu Ser Glu Lys Thr Ile Leu Arg Ala Cys Gly Thr Arg Leu Glu Tyr
            180                 185                 190

Thr Glu Ile Lys Ser Asp Gly Thr Gly Lys Ala Lys Glu Val Leu Lys
        195                 200                 205

Asp Phe Ala Leu Glu Gly Thr Leu Ala Ala Asp Lys Thr Thr Leu Lys
210                 215                 220

Val Thr Glu Gly Thr Val Val Leu Ser Lys His Ile Pro Asn Ser Gly
225                 230                 235                 240

Glu Ile Thr Val Glu Leu Asn Asp Ser Asn Ser Thr Gln Ala Thr Lys
                245                 250                 255
```

Lys Thr Gly Lys Trp Asp Ser Asn Thr Ser Thr Leu Thr Ile Ser Val
              260                 265                 270

Asn Ser Lys Lys Thr Lys Asn Ile Val Phe Thr Lys Glu Cys Thr Ile
        275                 280                 285

Thr Val Gln Lys Tyr Asp Ser Ala Gly Thr Asn Leu Glu Gly Asn Ala
        290                 295                 300

Val Glu Ile Lys Thr Leu Asp Glu Leu Lys Asn Ala Leu Lys
305                 310                 315

<210> SEQ ID NO 52
<211> LENGTH: 1023
<212> TYPE: DNA
<213> ORGANISM: Artificial Sequence
<220> FEATURE:
<223> OTHER INFORMATION: Lip-S3D4-S4D4_nt

<400> SEQUENCE: 52
atgaaagcta ctaaactggt actgggcgcg gtaatcctgg gttctactct gctggcaggt      60
tgctcaagct tcaacgaaaa gggcaaactg tcagaaaaag tggtcacccg cgcttgtggc     120
acccgcctgg aatacaccga atcaaaaac gacggctcgg gcaaagcgaa ggaagttctg     180
aaaggctttg ccctggaagg taccctgacg gatggcggtg aaaccaaact gaccgtgacg     240
gaaggcaccg ttacgctgtc taaaaacatt agcaagtctg gtgaaatcac ggtcgcactg     300
aatgataccg aaaccacgcc ggctgacaaa agaccggcg aatggaaaag tgacacctcc     360
acgctgacca tttcaaagaa ctcgcagaaa ccgaagcaac tggtcttcac caagaatgc     420
acgatcaccg tgcagaacta taatcgtgcc ggtaatgctc tggaaggctc cccggctgaa     480
atcaaggacc tggcggaact gaaggcggca ctgaaaggca ctagtgacaa aaacaatggc     540
tctggtagca agagaaaaa caagatggc aagtactcat tcaacgctaa aggtgaactg     600
tcggaaaaaa ccatcctgcg cgcctgtggc acccgcctgg aatacacgga atcaagtcg     660
gacggcacgg gcaaagcaaa ggaagtcctg aaagattttg ctctggaagg taccctggcg     720
gccgacaaaa ccacgctgaa ggtgacggaa ggcaccgtgg ttctgagcaa acatattccg     780
aactctggtg aaatcaccgt tgaactgaac gatagcaatt ctacgcaggc gaccaaaaag     840
acgggcaaat gggacagtaa tacctccacg ctgaccattt cagtcaactc gaaaaagacc     900
aaaaatattg tgttcacgaa ggaatgcacg atcaccgttc aaaaatatga ttccgcaggt     960
accaacctgg aaggcaacgc tgtggaaatc aaaaccctgg acgaactgaa aaatgctctg    1020
aag                                                                  1023

<210> SEQ ID NO 53
<211> LENGTH: 330
<212> TYPE: PRT
<213> ORGANISM: Artificial Sequence
<220> FEATURE:
<223> OTHER INFORMATION: Lip-S3D4-S4D4_His_aa
<220> FEATURE:
<221> NAME/KEY: LIPID
<222> LOCATION: (1)..(1)
<223> OTHER INFORMATION: LIPIDATION

<400> SEQUENCE: 53

Cys Ser Ser Phe Asn Glu Lys Gly Lys Leu Ser Glu Lys Val Val Thr
1               5                   10                  15

Arg Ala Cys Gly Thr Arg Leu Glu Tyr Thr Glu Ile Lys Asn Asp Gly
            20                  25                  30

Ser Gly Lys Ala Lys Glu Val Leu Lys Gly Phe Ala Leu Glu Gly Thr

|     |     |     | 35  |     |     |     | 40  |     |     |     | 45  |     |     |
| --- | --- | --- | --- | --- | --- | --- | --- | --- | --- | --- | --- | --- | --- |
Leu Thr Asp Gly Gly Glu Thr Lys Leu Thr Val Thr Glu Gly Thr Val
 50                      55                      60

Thr Leu Ser Lys Asn Ile Ser Lys Ser Gly Glu Ile Thr Val Ala Leu
 65                      70                      75                      80

Asn Asp Thr Glu Thr Thr Pro Ala Asp Lys Lys Thr Gly Glu Trp Lys
                         85                      90                      95

Ser Asp Thr Ser Thr Leu Thr Ile Ser Lys Asn Ser Gln Lys Pro Lys
                        100                     105                     110

Gln Leu Val Phe Thr Lys Glu Cys Thr Ile Thr Val Gln Asn Tyr Asn
                115                     120                     125

Arg Ala Gly Asn Ala Leu Glu Gly Ser Pro Ala Glu Ile Lys Asp Leu
            130                     135                     140

Ala Glu Leu Lys Ala Ala Leu Lys Gly Thr Ser Asp Lys Asn Asn Gly
145                     150                     155                     160

Ser Gly Ser Lys Glu Lys Asn Lys Asp Gly Lys Tyr Ser Phe Asn Ala
                165                     170                     175

Lys Gly Glu Leu Ser Glu Lys Thr Ile Leu Arg Ala Cys Gly Thr Arg
            180                     185                     190

Leu Glu Tyr Thr Glu Ile Lys Ser Asp Gly Thr Gly Lys Ala Lys Glu
        195                     200                     205

Val Leu Lys Asp Phe Ala Leu Glu Gly Thr Leu Ala Ala Asp Lys Thr
210                     215                     220

Thr Leu Lys Val Thr Glu Gly Thr Val Val Leu Ser Lys His Ile Pro
225                     230                     235                     240

Asn Ser Gly Glu Ile Thr Val Glu Leu Asn Asp Ser Asn Ser Thr Gln
                245                     250                     255

Ala Thr Lys Lys Thr Gly Lys Trp Asp Ser Asn Thr Ser Thr Leu Thr
                260                     265                     270

Ile Ser Val Asn Ser Lys Lys Thr Lys Asn Ile Val Phe Thr Lys Glu
            275                     280                     285

Cys Thr Ile Thr Val Gln Lys Tyr Asp Ser Ala Gly Thr Asn Leu Glu
290                     295                     300

Gly Asn Ala Val Glu Ile Lys Thr Leu Asp Glu Leu Lys Asn Ala Leu
305                     310                     315                     320

Lys Gly Leu Glu His His His His His His
                325                     330

<210> SEQ ID NO 54
<211> LENGTH: 1050
<212> TYPE: DNA
<213> ORGANISM: Artificial Sequence
<220> FEATURE:
<223> OTHER INFORMATION: Lip-S3D4-S4D4_His_nt

<400> SEQUENCE: 54
atgaaagcta ctaaactggt actgggcgcg gtaatcctgg ttctactctc gctggcaggt      60
tgctcaagct tcaacgaaaa gggcaaactg tcagaaaaag tggtcacccg cgcttgtggc     120
acccgcctgg aatacaccga atcaaaaac gacggctcgg caaagcgaa ggaagttctg      180 aaaggctttg ccctggaagg taccctgacg gatggcggtg aaaccaaact gaccgtgacg     240
gaaggcaccg ttacgctgtc taaaaacatt agcaagtctg gtgaaatcac ggtcgcactg     300 aatgatacccg aaaccacgcc ggctgacaaa aagaccggcg aatggaaaag tgacaccctcc    360 acgctgacca tttcaaagaa ctcgcagaaa ccgaagcaac tggtcttcac caaagaatgc     420

```
acgatcaccg tgcagaacta taatcgtgcc ggtaatgctc tggaaggctc cccggctgaa    480
atcaaggacc tggcggaact gaaggcggca ctgaaaggca ctagtgacaa aaacaatggc    540
tctggtagca aagagaaaaa caaagatggc aagtactcat tcaacgctaa aggtgaactg    600
tcggaaaaaa ccatcctgcg cgcctgtggc acccgcctgg aatacacgga aatcaagtcg    660
gacggcacgg gcaaagcaaa ggaagtcctg aaagattttg ctctggaagg taccctggcg    720
gccgacaaaa ccacgctgaa ggtgacggaa ggcaccgtgg ttctgagcaa acatattccg    780
aactctggtg aaatcaccgt tgaactgaac gatagcaatt ctacgcaggc gaccaaaaag    840
acgggcaaat gggacagtaa tacctccacg ctgaccattt cagtcaactc gaaaaagacc    900
aaaaatattg tgttcacgaa ggaatgcacg atcaccgttc aaaaatatga ttccgcaggt    960
accaacctgg aaggcaacgc tgtggaaatc aaaaccctgg acgaactgaa aaatgctctg   1020
aagggtctcg agcaccacca ccaccaccac                                    1050
```

<210> SEQ ID NO 55
<211> LENGTH: 318
<212> TYPE: PRT
<213> ORGANISM: Artificial Sequence
<220> FEATURE:
<223> OTHER INFORMATION: S3D1-S4D1_aa

<400> SEQUENCE: 55

```
Phe Asn Glu Lys Gly Lys Leu Ser Glu Lys Val Val Thr Arg Ala Asn
1               5                  10                  15

Gly Thr Arg Leu Glu Tyr Thr Glu Ile Lys Asn Asp Gly Ser Gly Lys
            20                  25                  30

Ala Lys Glu Val Leu Lys Gly Phe Ala Leu Glu Gly Thr Leu Thr Asp
        35                  40                  45

Gly Gly Glu Thr Lys Leu Thr Val Thr Cys Gly Thr Val Thr Leu Ser
    50                  55                  60

Lys Asn Ile Ser Lys Ser Gly Glu Ile Thr Val Ala Leu Asn Asp Thr
65                  70                  75                  80

Glu Thr Thr Pro Ala Asp Lys Lys Thr Gly Glu Trp Lys Ser Asp Thr
                85                  90                  95

Ser Thr Leu Thr Ile Ser Lys Asn Ser Gln Lys Pro Lys Gln Leu Val
            100                 105                 110

Phe Thr Lys Glu Asn Thr Ile Thr Val Gln Asn Tyr Asn Arg Ala Gly
        115                 120                 125

Asn Ala Leu Glu Gly Ser Pro Ala Glu Ile Lys Asp Leu Ala Glu Leu
    130                 135                 140

Cys Ala Ala Leu Lys Gly Thr Ser Asp Lys Asn Asn Gly Ser Gly Ser
145                 150                 155                 160

Lys Glu Lys Asn Lys Asp Gly Lys Tyr Ser Phe Asn Ala Lys Gly Glu
                165                 170                 175

Leu Ser Glu Lys Thr Ile Leu Arg Ala Asn Gly Thr Arg Leu Glu Tyr
            180                 185                 190

Thr Glu Ile Lys Ser Asp Gly Thr Gly Lys Ala Lys Glu Val Leu Lys
        195                 200                 205

Asp Phe Ala Leu Glu Gly Thr Leu Ala Ala Asp Lys Thr Thr Leu Lys
    210                 215                 220

Val Thr Cys Gly Thr Val Val Leu Ser Lys His Ile Pro Asn Ser Gly
225                 230                 235                 240

Glu Ile Thr Val Glu Leu Asn Asp Ser Asn Ser Thr Gln Ala Thr Lys
```

```
                    245                 250                 255
Lys Thr Gly Lys Trp Asp Ser Asn Thr Ser Thr Leu Thr Ile Ser Val
            260                 265                 270

Asn Ser Lys Lys Thr Lys Asn Ile Val Phe Thr Lys Glu Asp Thr Ile
        275                 280                 285

Thr Val Gln Lys Tyr Asp Ser Ala Gly Thr Asn Leu Glu Gly Asn Ala
    290                 295                 300

Val Glu Ile Lys Thr Leu Asp Glu Leu Cys Asn Ala Leu Lys
305                 310                 315
```

<210> SEQ ID NO 56
<211> LENGTH: 1023
<212> TYPE: DNA
<213> ORGANISM: Artificial Sequence
<220> FEATURE:
<223> OTHER INFORMATION: Lip-S3D1-S4D1_nt

<400> SEQUENCE: 56

```
atgaaagcta ctaaactggt actgggcgcg gtaatcctgg gttctactct gctggcaggt    60
tgctcaagct tcaacgaaaa gggcaaactg tcggaaaaag tggtcacccg cgcaaatggc   120
acccgcctgg aatacacgga atcaaaaac gatggtagcg gcaaagcgaa ggaagttctg   180
aaaggctttg ccctggaagg taccctgacg gatggcggtg aaaccaaact gaccgtgacg   240
tgcggcaccg ttacgctgtc taaaaacatt agcaagtctg gtgaaatcac ggtcgcactg   300
aatgataccg aaaccacgcc ggctgacaaa agaccggcg aatggaaaag tgacacctcc   360
acgctgacca tttcaaagaa ctcgcagaaa ccgaagcaac tggtcttcac caagaaaaac   420
acgatcaccg tgcagaacta taatcgtgcc ggtaatgctc tggaaggctc accggctgaa   480
atcaaggacc tggctgaact gtgtgcggca ctgaaaggca ctagtgacaa aaacaatggc   540
tctggtagca agagaaaaa caaagatggc aagtactcat tcaacgctaa aggtgaactg   600
agcgaaaaaa cgatcctgcg tgcgaatggc accgtctgg aatacaccga atcaaatcc   660
gatggtacgg gcaaagcaaa ggaagtcctg aaagattttg ctctggaagg taccctggcg   720
gccgacaaaa ccacgctgaa ggtgacgtgc ggcaccgtgg ttctgagcaa acatattccg   780
aactctggtg aaatcaccgt tgaactgaac gatagcaatt ctacgcaggc aaccaaaaag   840
acgggcaaat gggacagtaa tacctccacg ctgaccattt cagtcaactc gaaaaagacc   900
aaaaatattg tgttcacgaa ggaagatacg atcaccgttc aaaaatatga ctccgcgggc   960
accaacctgg aaggcaatgc cgtcgaaatc aaaaccctgg atgaactgtg taatgctctg  1020
aag                                                                 1023
```

<210> SEQ ID NO 57
<211> LENGTH: 330
<212> TYPE: PRT
<213> ORGANISM: Artificial Sequence
<220> FEATURE:
<223> OTHER INFORMATION: Lip-S3D1-S4D1_His_aa
<220> FEATURE:
<221> NAME/KEY: LIPID
<222> LOCATION: (1)..(1)
<223> OTHER INFORMATION: LIPIDATION

<400> SEQUENCE: 57

```
Cys Ser Ser Phe Asn Glu Lys Gly Lys Leu Ser Glu Lys Val Val Thr
1               5                   10                  15

Arg Ala Asn Gly Thr Arg Leu Glu Tyr Thr Glu Ile Lys Asn Asp Gly
            20                  25                  30
```

Ser Gly Lys Ala Lys Glu Val Leu Lys Gly Phe Ala Leu Glu Gly Thr
            35                  40                  45

Leu Thr Asp Gly Gly Glu Thr Lys Leu Thr Val Thr Cys Gly Thr Val
        50                  55                  60

Thr Leu Ser Lys Asn Ile Ser Lys Ser Gly Glu Ile Thr Val Ala Leu
65                  70                  75                  80

Asn Asp Thr Glu Thr Thr Pro Ala Asp Lys Lys Thr Gly Glu Trp Lys
                85                  90                  95

Ser Asp Thr Ser Thr Leu Thr Ile Ser Lys Asn Ser Gln Lys Pro Lys
            100                 105                 110

Gln Leu Val Phe Thr Lys Glu Asn Thr Ile Thr Val Gln Asn Tyr Asn
        115                 120                 125

Arg Ala Gly Asn Ala Leu Glu Gly Ser Pro Ala Glu Ile Lys Asp Leu
130                 135                 140

Ala Glu Leu Cys Ala Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Ala
                165                 170                 175

Lys Gly Glu Leu Ser Lys Thr Ile Leu Arg Ala Asn Gly Thr Arg
            180                 185                 190

Leu Glu Tyr Thr Glu Ile Lys Ser Asp Gly Thr Gly Lys Ala Lys Glu
        195                 200                 205

Val Leu Lys Asp Phe Ala Leu Glu Gly Thr Leu Ala Ala Asp Lys Thr
210                 215                 220

Thr Leu Lys Val Thr Cys Gly Thr Val Val Leu Ser Lys His Ile Pro
225                 230                 235                 240

Asn Ser Gly Glu Ile Thr Val Glu Leu Asn Asp Ser Asn Ser Thr Gln
                245                 250                 255

Ala Thr Lys Lys Thr Gly Lys Trp Asp Ser Asn Thr Ser Thr Leu Thr
            260                 265                 270

Ile Ser Val Asn Ser Lys Lys Thr Lys Asn Ile Val Phe Thr Lys Glu
        275                 280                 285

Asp Thr Ile Thr Val Gln Lys Tyr Asp Ser Ala Gly Thr Asn Leu Glu
        290                 295                 300

Gly Asn Ala Val Glu Ile Lys Thr Leu Asp Glu Leu Cys Asn Ala Leu
305                 310                 315                 320

Lys Gly Leu Glu His His His His His His
                325                 330

<210> SEQ ID NO 58
<211> LENGTH: 1050
<212> TYPE: DNA
<213> ORGANISM: Artificial Sequence
<220> FEATURE:
<223> OTHER INFORMATION: Lip-S3D1-S4D1_His_nt

<400> SEQUENCE: 58
atgaaagcta ctaaactggt actgggcgcg gtaatcctgg ttctactct gctggcaggt      60 tgctcaagct tcaacgaaaa gggcaaactg tcggaaaaag tggtcacccg cgcaaatggc    120
acccgcctgg aatacacgga atcaaaaac gatggtagcg gcaaagcgaa ggaagttctg    180
aaaggctttg ccctggaagg tacgctgacg gatggcggtg aaaccaaact gaccgtgacg    240
tgcggcaccg ttacgctgtc taaaaacatt agcaagtctg gtgaaatcac ggtcgcactg    300
aatgataccg aaaccacgcc ggctgacaaa aagaccggcg aatggaaaag tgacacctcc    360

-continued

```
acgctgacca tttcaaagaa ctcgcagaaa ccgaagcaac tggtcttcac caaagaaaac    420
acgatcaccg tgcagaacta taatcgtgcc ggtaatgctc tggaaggctc accggctgaa    480
atcaaggacc tggctgaact gtgtgcggca ctgaaaggca ctagtgacaa aaacaatggc    540
tctggtagca aagagaaaaa caaagatggc aagtactcat tcaacgctaa aggtgaactg    600
agcgaaaaaa cgatcctgcg tgcgaatggc acccgtctgg aatacaccga atcaaatcc    660 gatggtacgg gcaaagcaaa ggaagtcctg aaagattttg ctctggaagg taccctggcg    720
gccgacaaaa ccacgctgaa ggtgacgtgc ggcaccgtgg ttctgagcaa acatattccg    780
aactctggtg aaatcaccgt tgaactgaac gatagcaatt ctacgcaggc aaccaaaaag    840
acgggcaaat gggacagtaa tacctccacg ctgaccattt cagtcaactc gaaaaagacc    900
aaaaatattg tgttcacgaa ggaagatacg atcaccgttc aaaaatatga ctccgcgggc    960
accaacctgg aaggcaatgc cgtcgaaatc aaaaccctgg atgaactgtg taatgctctg   1020
aagggtctcg agcaccacca ccaccaccac                                    1050
```

<210> SEQ ID NO 59
<211> LENGTH: 318
<212> TYPE: PRT
<213> ORGANISM: Artificial Sequence
<220> FEATURE:
<223> OTHER INFORMATION: S5D4-S6D4_aa

<400> SEQUENCE: 59

```
Phe Asn Glu Lys Gly Glu Ile Ser Glu Lys Thr Ile Val Arg Ala Cys
1               5                   10                  15

Gly Thr Arg Leu Glu Tyr Thr Asp Ile Lys Ser Asp Lys Thr Gly Lys
                20                  25                  30

Ala Lys Glu Val Leu Lys Asp Phe Thr Leu Glu Gly Thr Leu Ala Ala
            35                  40                  45

Asp Gly Lys Thr Thr Leu Lys Val Thr Glu Gly Thr Val Thr Leu Ser
        50                  55                  60

Lys Asn Ile Ser Lys Ser Gly Glu Ile Thr Val Ala Leu Asp Asp Thr
65                  70                  75                  80

Asp Ser Ser Gly Asn Lys Lys Ser Gly Thr Trp Asp Ser Gly Thr Ser
                85                  90                  95

Thr Leu Thr Ile Ser Lys Asn Arg Thr Lys Thr Lys Gln Leu Val Phe
                100                 105                 110

Thr Lys Glu Cys Thr Ile Thr Val Gln Asn Tyr Asp Ser Ala Gly Thr
            115                 120                 125

Asn Leu Glu Gly Lys Ala Val Glu Ile Thr Thr Leu Lys Glu Leu Lys
        130                 135                 140

Asn Ala Leu Lys Gly Thr Ser Asp Lys Asn Gly Ser Gly Ser Lys
145                 150                 155                 160

Glu Lys Asn Lys Asp Gly Lys Tyr Ser Phe Asn Gly Lys Gly Glu Thr
                165                 170                 175

Ser Glu Lys Thr Ile Val Arg Ala Cys Gly Thr Arg Leu Glu Tyr Thr
            180                 185                 190

Asp Ile Lys Ser Asp Gly Ser Gly Lys Ala Lys Glu Val Leu Lys Asp
        195                 200                 205

Phe Thr Leu Glu Gly Thr Leu Ala Ala Asp Gly Lys Thr Thr Leu Lys
    210                 215                 220

Val Thr Glu Gly Thr Val Val Leu Ser Lys Asn Ile Leu Lys Ser Gly
225                 230                 235                 240
```

```
Glu Ile Thr Ala Ala Leu Asp Asp Ser Asp Thr Arg Ala Thr Lys
            245                 250                 255

Lys Thr Gly Lys Trp Asp Ser Lys Thr Ser Thr Leu Thr Ile Ser Val
        260                 265                 270

Asn Ser Gln Lys Thr Lys Asn Leu Val Phe Thr Lys Glu Cys Thr Ile
        275                 280                 285

Thr Val Gln Arg Tyr Asp Ser Ala Gly Thr Asn Leu Glu Gly Lys Ala
        290                 295                 300

Val Glu Ile Thr Thr Leu Lys Glu Leu Lys Asn Ala Leu Lys
305                 310                 315
```

<210> SEQ ID NO 60
<211> LENGTH: 1023
<212> TYPE: DNA
<213> ORGANISM: Artificial Sequence
<220> FEATURE:
<223> OTHER INFORMATION: Lip-S5D4-S6D4_nt

<400> SEQUENCE: 60

```
atgaaagcta ctaaactggt actgggcgcg gtaatcctgg gttctactct gctggcaggt      60
tgctcaagct tcaacgaaaa gggcgaaatc agtgaaaaaa ccattgtgcg tgcgtgtggc     120
acccgtctgg aatataccga catcaagagc gataaaacgg gtaaagcgaa ggaagttctg     180
aaagatttta cgctggaagg taccctggca gcagacggta aaaccacgct gaaggtgacc     240
gaaggtaccg ttacgctgtc caaaaacatt agtaagtccg gcgaaatcac ggtcgccctg     300
gatgacaccg atagctctgg caacaaaaag agcggtacct gggactcagg cacctcgacg     360
ctgaccattt ctaaaaatcg tacgaaaacc aagcagctgg tcttcacgaa gaatgcacg     420
atcaccgtgc aaaactatga tagcgcaggt accaatctgg aaggcaaagc tgtggaaatt     480
accacgctga agaactgaa gaatgctctg aaaggtacta gtgacaaaaa caatggctct     540
ggtagcaaag agaaaaacaa agatggcaag tactcattca cggcaaagg tgaaacgagt     600
gaaaaaacga ttgttcgcgc ctgtggcacc cgcctggaat acacggatat caagtcggat     660
ggttcgggca agcaaagga gtcctgaaa gattttacgc tggaaggtac cctggcagca     720
gacggtaaaa ccacgctgaa ggtgacggaa ggcaccgtgg ttctgtcaaa aacattctg     780
aagtcgggtg aaatcaccgc agctctggat gacagcgata ccacgcgtgc tacgaaaaag     840
accggtaaat gggacagcaa gacctctacg ctgaccatta gtgtcaactc ccagaaaacg     900
aagaatctgg tgttcaccaa gaatgcacg atcaccgttc aacgctatga tagtgcgggc     960
accaacctgg aaggcaaagc cgttgaaatt accacgctga agaactgaa gaatgctctg    1020
aaa                                                                1023
```

<210> SEQ ID NO 61
<211> LENGTH: 330
<212> TYPE: PRT
<213> ORGANISM: Artificial Sequence
<220> FEATURE:
<223> OTHER INFORMATION: Lip-S5D4-S6D4_His_aa
<220> FEATURE:
<221> NAME/KEY: LIPID
<222> LOCATION: (1)..(1)
<223> OTHER INFORMATION: LIPIDATION

<400> SEQUENCE: 61

```
Cys Ser Ser Phe Asn Glu Lys Gly Glu Ile Ser Glu Lys Thr Ile Val
1               5                   10                  15
```

```
Arg Ala Cys Gly Thr Arg Leu Glu Tyr Thr Asp Ile Lys Ser Asp Lys
             20                  25                  30

Thr Gly Lys Ala Lys Glu Val Leu Lys Asp Phe Thr Leu Glu Gly Thr
         35                  40                  45

Leu Ala Ala Asp Gly Lys Thr Thr Leu Lys Val Thr Glu Gly Thr Val
 50                  55                  60

Thr Leu Ser Lys Asn Ile Ser Lys Ser Gly Glu Ile Thr Val Ala Leu
 65                  70                  75                  80

Asp Asp Thr Asp Ser Ser Gly Asn Lys Lys Ser Gly Thr Trp Asp Ser
                 85                  90                  95

Gly Thr Ser Thr Leu Thr Ile Ser Lys Asn Arg Thr Lys Thr Lys Gln
                100                 105                 110

Leu Val Phe Thr Lys Glu Cys Thr Ile Thr Val Gln Asn Tyr Asp Ser
            115                 120                 125

Ala Gly Thr Asn Leu Glu Gly Lys Ala Val Glu Ile Thr Thr Leu Lys
        130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Cys Gly Thr Arg Leu
                180                 185                 190

Glu Tyr Thr Asp Ile Lys Ser Asp Gly Ser Gly Lys Ala Lys Glu Val
            195                 200                 205

Leu Lys Asp Phe Thr Leu Glu Gly Thr Leu Ala Ala Asp Gly Lys Thr
        210                 215                 220

Thr Leu Lys Val Thr Glu Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Cys Thr Ile Thr Val Gln Arg Tyr Asp Ser Ala Gly Thr Asn Leu Glu
290                 295                 300

Gly Lys Ala Val Glu Ile Thr Thr Leu Lys Glu Leu Lys Asn Ala Leu
305                 310                 315                 320

Lys Gly Leu Glu His His His His His His
                325                 330
```

<210> SEQ ID NO 62
<211> LENGTH: 1050
<212> TYPE: DNA
<213> ORGANISM: Artificial Sequence
<220> FEATURE:
<223> OTHER INFORMATION: Lip-S5D4-S6D4_His_nt

<400> SEQUENCE: 62

```
atgaaagcta ctaaactggt actgggcgcg gtaatcctgg ttctactctc gctggcaggt      60
tgctcaagct tcaacgaaaa gggcgaaatc agtgaaaaaa ccattgtgcg tgcgtgtggc     120
acccgtctgg aatataccga catcaagagc gataaaacgg gtaaagcgaa ggaagttctg     180
aaagatttta cgctggaagg tacccctggca gcagacggta aaaccacgct gaaggtgacc     240
gaaggtaccg ttacgctgtc caaaaacatt agtaagtccg gcgaaatcac ggtcgccctg     300
```

-continued

```
gatgacaccg atagctctgg caacaaaaag agcggtacct gggactcagg cacctcgacg    360
ctgaccattt ctaaaaatcg tacgaaaacc aagcagctgg tcttcacgaa agaatgcacg    420
atcaccgtgc aaaactatga tagcgcaggt accaatctgg aaggcaaagc tgtggaaatt    480
accacgctga agaactgaa gaatgctctg aaaggtacta gtgacaaaaa caatggctct     540
ggtagcaaag agaaaaacaa agatggcaag tactcattca acggcaaagg tgaaacgagt    600
gaaaaacga ttgttcgcgc ctgtggcacc cgcctggaat acacggatat caagtcggat     660
ggttcgggca agcaaagga agtcctgaaa gattttacgc tggaaggtac cctggcagca     720
gacggtaaaa ccacgctgaa ggtgacggaa ggcaccgtgg ttctgtcaaa aaacattctg    780
aagtcgggtg aaatcaccgc agctctggat gacagcgata ccacgcgtgc tacgaaaaag    840
accggtaaat gggacagcaa gacctctacg ctgaccatta gtgtcaactc ccagaaaacg    900
aagaatctgg tgttcaccaa agaatgcacg atcaccgttc aacgctatga tagtgcgggc    960
accaacctgg aaggcaaagc cgttgaaatt accacgctga agaactgaa gaatgctctg    1020
aaaggtctcg agcaccacca ccaccaccac                                     1050
```

<210> SEQ ID NO 63
<211> LENGTH: 318
<212> TYPE: PRT
<213> ORGANISM: Artificial Sequence
<220> FEATURE:
<223> OTHER INFORMATION: S5D1-S6D1_aa

<400> SEQUENCE: 63

```
Phe Asn Glu Lys Gly Glu Ile Ser Glu Lys Thr Ile Val Arg Ala Asn
1               5                   10                  15
Gly Thr Arg Leu Glu Tyr Thr Asp Ile Lys Ser Asp Lys Thr Gly Lys
            20                  25                  30
Ala Lys Glu Val Leu Lys Asp Phe Thr Leu Glu Gly Thr Leu Ala Ala
        35                  40                  45
Asp Gly Lys Thr Thr Leu Lys Val Thr Cys Gly Thr Val Thr Leu Ser
    50                  55                  60
Lys Asn Ile Ser Lys Ser Gly Glu Ile Thr Val Ala Leu Asp Asp Thr
65                  70                  75                  80
Asp Ser Ser Gly Asn Lys Lys Ser Gly Thr Trp Asp Ser Gly Thr Ser
                85                  90                  95
Thr Leu Thr Ile Ser Lys Asn Arg Thr Lys Thr Lys Gln Leu Val Phe
            100                 105                 110
Thr Lys Glu Asp Thr Ile Thr Val Gln Asn Tyr Asp Ser Ala Gly Thr
        115                 120                 125
Asn Leu Glu Gly Lys Ala Val Glu Ile Thr Thr Leu Lys Glu Leu Cys
    130                 135                 140
Asn Ala Leu Lys Gly Thr Ser Asp Lys Asn Asn Gly Ser Gly Ser Lys
145                 150                 155                 160
Glu Lys Asn Lys Asp Gly Lys Tyr Ser Phe Asn Gly Lys Gly Glu Thr
                165                 170                 175
Ser Glu Lys Thr Ile Val Arg Ala Asn Gly Thr Arg Leu Glu Tyr Thr
            180                 185                 190
Asp Ile Lys Ser Asp Gly Ser Gly Lys Ala Lys Glu Val Leu Lys Asp
        195                 200                 205
Phe Thr Leu Glu Gly Thr Leu Ala Ala Asp Gly Lys Thr Thr Leu Lys
    210                 215                 220
```

Val Thr Cys Gly Thr Val Val Leu Ser Lys Asn Ile Leu Lys Ser Gly
225                 230                 235                 240

Glu Ile Thr Ala Ala Leu Asp Asp Ser Asp Thr Thr Arg Ala Thr Lys
            245                 250                 255

Lys Thr Gly Lys Trp Asp Ser Lys Thr Ser Thr Leu Thr Ile Ser Val
        260                 265                 270

Asn Ser Gln Lys Thr Lys Asn Leu Val Phe Thr Lys Glu Asp Thr Ile
        275                 280                 285

Thr Val Gln Arg Tyr Asp Ser Ala Gly Thr Asn Leu Glu Gly Lys Ala
        290                 295                 300

Val Glu Ile Thr Thr Leu Lys Glu Leu Cys Asn Ala Leu Lys
305                 310                 315

<210> SEQ ID NO 64
<211> LENGTH: 1023
<212> TYPE: DNA
<213> ORGANISM: Artificial Sequence
<220> FEATURE:
<223> OTHER INFORMATION: Lip-S5D1-S6D1_nt

<400> SEQUENCE: 64

```
atgaaagcta ctaaactggt actgggcgcg gtaatcctgg gttctactct gctggcaggt      60
tgctcaagct tcaacgaaaa gggcgaaatc tcagaaaaaa ccatcgtccg cgctaacggc     120
acccgcctgg aatacaccga catcaaatca gacaagaccg gtaaagcgaa ggaagttctg     180
aaagatttta cgctggaagg tacccctggca gcagacggta aaaccacgct gaaggtgacc     240
tgcggtaccg ttacgctgtc caaaaacatt agtaagtccg gcgaaatcac ggtcgccctg     300
gatgacaccg atagctctgg caacaaaaag agcggtacct gggattcagg cacctcgacg     360
ctgaccattt ctaaaaatcg tacgaaaacc aagcagctgg tcttcacgaa agaagatacg     420
atcaccgtgc aaaactatga cagcgcaggt accaatctgg aaggcaaagc tgtggaaatt     480
accacgctga agaactgtg taatgctctg aaaggtacta gtgacaaaaa caatggctct     540
ggtagcaaag agaaaaacaa agatggcaag tactcattca acggcaaagg tgaaacgagc     600
gaaaagacca tcgtgcgtgc gaacggtacc cgcctggaat atacggacat aaaatcggac     660
ggcagcggca aagcaaagga agtcctgaaa gattttacgc tggaaggtac cctggcagca     720
gacggtaaaa ccacgctgaa ggtgacgtgc ggcaccgtgg ttctgtcaaa aacattctg     780
aagtcgggtg aaatcaccgc agctctggat gacagcgata ccacgcgtgc tacgaaaaag     840
accggtaaat gggatagcaa gacctctacg ctgaccatta gtgtcaactc ccagaaaacg     900
aagaatctgg tgttcaccaa agaagatacg atcaccgttc aacgctatga cagtgcgggc     960
accaacctgg aaggcaaagc cgttgaaatt accacgctga agaactgtg taatgctctg    1020
aaa                                                                   1023
```

<210> SEQ ID NO 65
<211> LENGTH: 330
<212> TYPE: PRT
<213> ORGANISM: Artificial Sequence
<220> FEATURE:
<223> OTHER INFORMATION: Lip-S5D1-S6D1_His_aa
<220> FEATURE:
<221> NAME/KEY: LIPID
<222> LOCATION: (1)..(1)
<223> OTHER INFORMATION: LIPIDATION

<400> SEQUENCE: 65

Cys Ser Ser Phe Asn Glu Lys Gly Glu Ile Ser Glu Lys Thr Ile Val

```
1               5                    10                   15
Arg Ala Asn Gly Thr Arg Leu Glu Tyr Thr Asp Ile Lys Ser Asp Lys
                20                   25                  30

Thr Gly Lys Ala Lys Glu Val Leu Lys Asp Phe Thr Leu Glu Gly Thr
            35                  40                  45

Leu Ala Ala Asp Gly Lys Thr Thr Leu Lys Val Thr Cys Gly Thr Val
        50                  55                  60

Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
            100                 105                 110

Leu Val Phe Thr Lys Glu Asp Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Asn Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Cys Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Asp Thr Ile Thr Val Gln Arg Tyr Asp Ser Ala Gly Thr Asn Leu Glu
    290                 295                 300

Gly Lys Ala Val Glu Ile Thr Thr Leu Lys Glu Leu Cys Asn Ala Leu
305                 310                 315                 320

Lys Gly Leu Glu His His His His His His
                325                 330

<210> SEQ ID NO 66
<211> LENGTH: 1050
<212> TYPE: DNA
<213> ORGANISM: Artificial Sequence
<220> FEATURE:
<223> OTHER INFORMATION: Lip-S5D1-S6D1_His_nt

<400> SEQUENCE: 66
atgaaagcta ctaaactggt actgggcgcg gtaatcctgg ttctactct gctggcaggt        60 tgctcaagct tcaacgaaaa gggcgaaatc tcagaaaaaa ccatcgtccg cgctaacggc      120
acccgcctgg aatacaccga catcaaatca gacaagaccg taaagcgaa ggaagttctg       180 aaagatttta cgctggaagg taccctggca gcagacggta aaaccacgct gaaggtgacc      240
```

```
tgcggtaccg ttacgctgtc caaaaacatt agtaagtccg gcgaaatcac ggtcgccctg      300
gatgacaccg atagctctgg caacaaaaag agcggtacct gggattcagg cacctcgacg      360
ctgaccattt ctaaaaatcg tacgaaaacc aagcagctgg tcttcacgaa agaagatacg      420
atcaccgtgc aaaactatga cagcgcaggt accaatctgg aaggcaaagc tgtggaaatt      480
accacgctga agaactgtg taatgctctg aaaggtacta gtgacaaaaa caatggctct       540
ggtagcaaag agaaaaacaa agatggcaag tactcattca acggcaaagg tgaaacgagc      600
gaaaagacca tcgtgcgtgc gaacggtacc cgcctggaat atacggacat taaatcggac      660
ggcagcggca agcaaagga gtcctgaaa gattttacgc tggaaggtac cctggcagca       720
gacggtaaaa ccacgctgaa ggtgacgtgc ggcaccgtgg ttctgtcaaa aaacattctg      780
aagtcgggtg aaatcaccgc agctctggat gacagcgata ccacgcgtgc tacgaaaaag      840
accggtaaat gggatagcaa gacctctacg ctgaccatta gtgtcaactc ccagaaaacg      900
aagaatctgg tgttcaccaa agaagatacg atcaccgttc aacgctatga cagtgcgggc      960
accaacctgg aaggcaaagc cgttgaaatt accacgctga agaactgtg taatgctctg      1020 aaaggtctcg agcaccacca ccaccaccac                                       1050
```

<210> SEQ ID NO 67
<211> LENGTH: 317
<212> TYPE: PRT
<213> ORGANISM: Artificial Sequence
<220> FEATURE:
<223> OTHER INFORMATION: S2D4-S1D4_aa

<400> SEQUENCE: 67

```
Phe Asn Glu Lys Gly Glu Leu Ser Ala Lys Thr Met Thr Arg Glu Cys
1               5                   10                  15

Gly Thr Lys Leu Glu Tyr Thr Glu Met Lys Ser Asp Gly Thr Gly Lys
                20                  25                  30

Ala Lys Glu Val Leu Lys Asn Phe Thr Leu Glu Gly Lys Val Ala Asn
            35                  40                  45

Asp Lys Val Thr Leu Glu Val Lys Glu Gly Thr Val Thr Leu Ser Lys
        50                  55                  60

Glu Ile Ala Lys Ser Gly Glu Val Thr Val Ala Leu Asn Asp Thr Asn
65                  70                  75                  80

Thr Thr Gln Ala Thr Lys Lys Thr Gly Ala Trp Asp Ser Lys Thr Ser
                85                  90                  95

Thr Leu Thr Ile Ser Val Asn Ser Lys Lys Thr Thr Gln Leu Val Phe
            100                 105                 110

Thr Lys Gln Cys Thr Ile Thr Val Gln Lys Tyr Asp Ser Ala Gly Thr
        115                 120                 125

Asn Leu Glu Gly Thr Ala Val Glu Ile Lys Thr Leu Asp Glu Leu Lys
    130                 135                 140

Asn Ala Leu Lys Gly Thr Ser Asp Lys Asn Gly Ser Gly Ser Lys
145                 150                 155                 160

Glu Lys Asn Lys Asp Gly Lys Tyr Ser Phe Asn Glu Lys Gly Glu Val
                165                 170                 175

Ser Glu Lys Ile Ile Thr Arg Ala Cys Gly Thr Arg Leu Glu Tyr Thr
            180                 185                 190

Gly Ile Lys Ser Asp Gly Ser Gly Lys Ala Lys Glu Val Leu Lys Asn
        195                 200                 205

Phe Thr Leu Glu Gly Lys Val Ala Asn Asp Lys Thr Thr Leu Val Val
```

-continued

```
                    210                 215                 220
Lys Glu Gly Thr Val Thr Leu Ser Lys Asn Ile Ser Lys Ser Gly Glu
225                 230                 235                 240

Val Ser Val Glu Leu Asn Asp Thr Asp Ser Ser Ala Ala Thr Lys Lys
                245                 250                 255

Thr Ala Ala Trp Asn Ser Gly Thr Ser Thr Leu Thr Ile Thr Val Asn
                260                 265                 270

Ser Lys Lys Thr Lys Asp Leu Val Phe Thr Lys Glu Cys Thr Ile Thr
                275                 280                 285

Val Gln Gln Tyr Asp Ser Asn Gly Thr Lys Leu Glu Gly Ser Ala Val
                290                 295                 300

Glu Ile Thr Lys Leu Asp Glu Ile Lys Asn Ala Leu Lys
305                 310                 315
```

<210> SEQ ID NO 68
<211> LENGTH: 1020
<212> TYPE: DNA
<213> ORGANISM: Artificial Sequence
<220> FEATURE:
<223> OTHER INFORMATION: Lip-S2D4-S1D4_nt

<400> SEQUENCE: 68

```
atgaaagcta ctaaactggt actgggcgcg gtaatcctgg gttctactct gctggcaggt      60
tgctcaagct tcaacgaaaa aggcgaactg tcggcgaaaa cgatgacgcg tgaatgcggc     120
accaaactgg aatatacgga atgaaaagc gatggcaccg gtaaagcgaa agaagttctg     180
aaaaacttta ccctggaagg caaagtcgcc aatgacaaag tcaccctgga agtgaaagaa     240
ggcaccgtta cgctgtcaaa agaaattgca aaatcgggtg aagtgaccgt tgctctgaac     300
gatacgaata ccacgcaagc gaccaagaaa accggcgcct gggacagcaa aacctctacg     360
ctgaccatta gtgttaacag caagaaaacc acgcagctgg tcttcaccaa caatgtacg     420
atcaccgtgc agaaatacga tagtgcgggt accaacctgg aaggcaccgc tgttgaaatc     480
aaaaccctgg acgaactgaa aaacgccctg aaaggcacta gtgacaaaaa caatggctct     540
ggtagcaaag agaaaaacaa agatggcaag tactcattca cgaaaaaggg cgaagtctcg     600
gaaaaaatca ttacccgtgc ttgcggcacc cgtctggaat acaccggcat taaatcggat     660
ggcagcggca aagcgaagga agttctgaaa aactttaccc tggaaggcaa agtcgcaaat     720
gataagacca ccctggtggt gaaagaaggc accgttacgc tgagcaaaaa cattagtaag     780
tccggtgaag tctctgtgga actgaatgat accgacagct ctgcggccac caaaaagacg     840
gcagcttgga actcaggcac ctcgacgctg accattacgg ttaattccaa aaagaccaaa     900
gatctggtct tcacgaaaga atgcaccatc acggtgcagc aatatgacag caacggtacc     960
aaactggaag gctctgcggt ggaaatcacg aaactggatg aaatcaaaaa tgcactgaaa    1020
```

<210> SEQ ID NO 69
<211> LENGTH: 329
<212> TYPE: PRT
<213> ORGANISM: Artificial Sequence
<220> FEATURE:
<223> OTHER INFORMATION: Lip-S2D4-S1D4_His_aa
<220> FEATURE:
<221> NAME/KEY: LIPID
<222> LOCATION: (1)..(1)
<223> OTHER INFORMATION: LIPIDATION

<400> SEQUENCE: 69

Cys Ser Ser Phe Asn Glu Lys Gly Glu Leu Ser Ala Lys Thr Met Thr

```
  1               5                  10                 15
Arg Glu Cys Gly Thr Lys Leu Glu Tyr Thr Glu Met Lys Ser Asp Gly
                20                 25                 30

Thr Gly Lys Ala Lys Glu Val Leu Lys Asn Phe Thr Leu Glu Gly Lys
             35                 40                 45

Val Ala Asn Asp Lys Val Thr Leu Glu Val Lys Glu Gly Thr Val Thr
         50                 55                 60

Leu Ser Lys Glu Ile Ala Lys Ser Gly Glu Val Thr Val Ala Leu Asn
 65                 70                 75                 80

Asp Thr Asn Thr Thr Gln Ala Thr Lys Lys Thr Gly Ala Trp Asp Ser
                 85                 90                 95

Lys Thr Ser Thr Leu Thr Ile Ser Val Asn Ser Lys Lys Thr Thr Gln
                100                105                110

Leu Val Phe Thr Lys Gln Cys Thr Ile Thr Val Gln Lys Tyr Asp Ser
                115                120                125

Ala Gly Thr Asn Leu Glu Gly Thr Ala Val Glu Ile Lys Thr Leu Asp
            130                135                140

Glu Leu Lys Asn Ala Leu Lys Gly Thr Ser Asp Lys Asn Asn Gly Ser
145                150                155                160

Gly Ser Lys Glu Lys Asn Lys Asp Gly Lys Tyr Ser Phe Asn Glu Lys
                165                170                175

Gly Glu Val Ser Glu Lys Ile Ile Thr Arg Ala Cys Gly Thr Arg Leu
                180                185                190

Glu Tyr Thr Gly Ile Lys Ser Asp Gly Ser Gly Lys Ala Lys Glu Val
            195                200                205

Leu Lys Asn Phe Thr Leu Glu Gly Lys Val Ala Asn Asp Lys Thr Thr
210                215                220

Leu Val Val Lys Glu Gly Thr Val Thr Leu Ser Lys Asn Ile Ser Lys
225                230                235                240

Ser Gly Glu Val Ser Val Glu Leu Asn Asp Thr Asp Ser Ser Ala Ala
                245                250                255

Thr Lys Lys Thr Ala Ala Trp Asn Ser Gly Thr Ser Thr Leu Thr Ile
            260                265                270

Thr Val Asn Ser Lys Lys Thr Lys Asp Leu Val Phe Thr Lys Glu Cys
            275                280                285

Thr Ile Thr Val Gln Gln Tyr Asp Ser Asn Gly Thr Lys Leu Glu Gly
            290                295                300

Ser Ala Val Glu Ile Thr Lys Leu Asp Glu Ile Lys Asn Ala Leu Lys
305                310                315                320

Gly Leu Glu His His His His His His
                325
```

<210> SEQ ID NO 70
<211> LENGTH: 1047
<212> TYPE: DNA
<213> ORGANISM: Artificial Sequence
<220> FEATURE:
<223> OTHER INFORMATION: Lip-S2D4-S1D4_His_nt

<400> SEQUENCE: 70

```
atgaaagcta ctaaactggt actgggcgcg gtaatcctgg ttctactctc gctggcaggt      60
tgctcaagct tcaacgaaaa aggcgaactg tcggcgaaaa cgatgacgcg tgaatgcggc     120
accaaactgg aatatacgga aatgaaaagc gatggcaccg gtaaagcgaa agaagttctg     180
aaaaacttta ccctggaagg caaagtcgcc aatgacaaag tcaccctgga agtgaaagaa     240
```

```
ggcaccgtta cgctgtcaaa agaaattgca aaatcgggtg aagtgaccgt tgctctgaac      300
gatacgaata ccacgcaagc gaccaagaaa accggcgcct gggacagcaa aacctctacg      360
ctgaccatta gtgttaacag caagaaaacc acgcagctgg tcttcaccaa acaatgtacg      420
atcaccgtgc agaaatacga tagtgcgggt accaacctgg aaggcaccgc tgttgaaatc      480
aaaaccctgg acgaactgaa aaacgccctg aaaggcacta gtgacaaaaa caatggctct      540
ggtagcaaag agaaaaacaa agatggcaag tactcattca cgaaaaaggg cgaagtctcg      600
gaaaaaatca ttacccgtgc ttgcggcacc cgtctggaat acaccggcat aaatcggat       660 ggcagcggca agcgaagga gttctgaaa aactttaccc tggaaggcaa agtcgcaaat        720
gataagacca ccctggtggt gaaagaaggc accgttacgc tgagcaaaaa cattagtaag      780
tccggtgaag tctctgtgga actgaatgat accgacagct ctgcggccac caaaaagacg      840
gcagcttgga actcaggcac ctcgacgctg accattacgg ttaattccaa aaagaccaaa      900
gatctggtct tcacgaaaga atgcaccatc acggtgcagc aatatgacag caacggtacc      960
aaactggaag ctctgcggt ggaaatcacg aaactggatg aaatcaaaaa tgcactgaaa       1020
ggtctcgagc accaccacca ccaccac                                          1047
```

<210> SEQ ID NO 71
<211> LENGTH: 316
<212> TYPE: PRT
<213> ORGANISM: Artificial Sequence
<220> FEATURE:
<223> OTHER INFORMATION: S2D1-S1D1_aa

<400> SEQUENCE: 71

```
Asn Glu Lys Gly Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Cys Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Thr Gly Ala Trp Asp Ser Lys Thr Ser Thr
            85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Cys Asn
    130                 135                 140

Ala Leu Lys Gly Thr Ser Asp Lys Asn Asn Gly Ser Gly Ser Lys Glu
145                 150                 155                 160

Lys Asn Lys Asp Gly Lys Tyr Ser Phe Asn Glu Lys Gly Glu Val Ser
                165                 170                 175

Glu Lys Ile Ile Thr Arg Ala Asp Gly Thr Arg Leu Glu Tyr Thr Gly
            180                 185                 190

Ile Lys Ser Asp Gly Ser Gly Lys Ala Lys Glu Val Leu Lys Asn Phe
        195                 200                 205

Thr Leu Glu Gly Lys Val Ala Asn Asp Lys Thr Thr Leu Val Val Lys
```

```
              210                 215                 220
Cys Gly Thr Val Thr Leu Ser Lys Asn Ile Ser Lys Ser Gly Glu Val
225                 230                 235                 240

Ser Val Glu Leu Asn Asp Thr Asp Ser Ser Ala Ala Thr Lys Lys Thr
                245                 250                 255

Ala Ala Trp Asn Ser Gly Thr Ser Thr Leu Thr Ile Thr Val Asn Ser
            260                 265                 270

Lys Lys Thr Lys Asp Leu Val Phe Thr Lys Glu Asn Thr Ile Thr Val
        275                 280                 285

Gln Gln Tyr Asp Ser Asn Gly Thr Lys Leu Glu Gly Ser Ala Val Glu
    290                 295                 300

Ile Thr Lys Leu Asp Glu Ile Cys Asn Ala Leu Lys
305                 310                 315
```

<210> SEQ ID NO 72
<211> LENGTH: 1020
<212> TYPE: DNA
<213> ORGANISM: Artificial Sequence
<220> FEATURE:
<223> OTHER INFORMATION: Lip-S2D1-S1D1_nt

<400> SEQUENCE: 72

```
atgaaagcta ctaaactggt actgggcgcg gtaatcctgg gttctactct gctggcaggt    60
tgctcaagct tcaacgaaaa aggcgaactg tcggcgaaaa cgatgacgcg tgaaaacggc   120
accaaactgg aatatacgga atgaaaagc gatggcaccg gtaaagcgaa agaagttctg   180
aaaaacttta ccctggaagg caaagtcgcc aatgacaaag tcaccctgga agtgaaatgc   240
ggcaccgtta cgctgtcaaa agaaattgca aaatcgggtg aagtgaccgt tgctctgaac   300
gatacgaata ccacgcaagc gaccaagaaa accggcgcct gggacagcaa aacctctacg   360
ctgaccatta gtgttaatag caagaaaacc acgcagctgg tcttcaccaa caagatacg   420
atcaccgtgc agaaatacga cagtgcgggt accaacctgg aaggcacggc tgttgaaatc   480
aaaaccctgg acgaactgtg taacgccctg aaaggcacta gtgacaaaaa caatggctct   540
ggtagcaaag agaaaaacaa agatggcaag tactcattca cgaaaaagg cgaagtcagc   600
gaaaaaatca ttacccgcgc agacggcacc cgcctggaat acaccggcat caaatcggac   660
ggcagcggca agcgaaaga agttctgaaa aactttaccc tggaaggcaa agtcgcaaat   720
gataaaacca ccctggtggt gaaatgcggc accgttacgc tgagcaaaaa cattagtaaa   780
tccggtgaag tctctgtgga actgaatgat accgacagct gcggccacc aagaaaacc    840
gcagcttgga actcaggcac ctcgacgctg accattacgg ttaatagcaa gaaaaccaaa   900
gatctggtct tcacgaaaga aaacaccatc acggtcagc aatatgacag caatggtacc   960
aaactggaag ctccgctgt ggaaatcacg aaactggatg aaatctgtaa tgcactgaaa  1020
```

<210> SEQ ID NO 73
<211> LENGTH: 329
<212> TYPE: PRT
<213> ORGANISM: Artificial Sequence
<220> FEATURE:
<223> OTHER INFORMATION: Lip-S2D1-S1D1_His_aa
<220> FEATURE:
<221> NAME/KEY: LIPID
<222> LOCATION: (1)..(1)
<223> OTHER INFORMATION: LIPIDATION

<400> SEQUENCE: 73

Cys Ser Ser Phe Asn Glu Lys Gly Glu Leu Ser Ala Lys Thr Met Thr

```
 1               5                  10                 15
Arg Glu Asn Gly Thr Lys Leu Glu Tyr Thr Glu Met Lys Ser Asp Gly
                20                 25                 30

Thr Gly Lys Ala Lys Glu Val Leu Lys Asn Phe Thr Leu Glu Gly Lys
            35                 40                 45

Val Ala Asn Asp Lys Val Thr Leu Glu Val Lys Cys Gly Thr Val Thr
        50                 55                 60

Leu Ser Lys Glu Ile Ala Lys Ser Gly Glu Val Thr Val Ala Leu Asn
65                  70                 75                 80

Asp Thr Asn Thr Thr Gln Ala Thr Lys Lys Thr Gly Ala Trp Asp Ser
                85                 90                 95

Lys Thr Ser Thr Leu Thr Ile Ser Val Asn Ser Lys Lys Thr Thr Gln
            100                105                110

Leu Val Phe Thr Lys Gln Asp Thr Ile Thr Val Gln Lys Tyr Asp Ser
        115                120                125

Ala Gly Thr Asn Leu Glu Gly Thr Ala Val Glu Ile Lys Thr Leu Asp
130                 135                140

Glu Leu Cys Asn Ala Leu Lys Gly Thr Ser Asp Lys Asn Asn Gly Ser
145                 150                155                160

Gly Ser Lys Glu Lys Asn Lys Asp Gly Lys Tyr Ser Phe Asn Glu Lys
            165                170                175

Gly Glu Val Ser Glu Lys Ile Ile Thr Arg Ala Asp Gly Thr Arg Leu
        180                185                190

Glu Tyr Thr Gly Ile Lys Ser Asp Gly Ser Gly Lys Ala Lys Glu Val
            195                200                205

Leu Lys Asn Phe Thr Leu Glu Gly Lys Val Ala Asn Asp Lys Thr Thr
210                 215                220

Leu Val Val Lys Cys Gly Thr Val Thr Leu Ser Lys Asn Ile Ser Lys
225                 230                235                240

Ser Gly Glu Val Ser Val Glu Leu Asn Asp Thr Asp Ser Ser Ala Ala
            245                250                255

Thr Lys Lys Thr Ala Ala Trp Asn Ser Gly Thr Ser Thr Leu Thr Ile
            260                265                270

Thr Val Asn Ser Lys Lys Thr Lys Asp Leu Val Phe Thr Lys Glu Asn
        275                280                285

Thr Ile Thr Val Gln Gln Tyr Asp Ser Asn Gly Thr Lys Leu Glu Gly
        290                295                300

Ser Ala Val Glu Ile Thr Lys Leu Asp Glu Ile Cys Asn Ala Leu Lys
305                 310                315                320

Gly Leu Glu His His His His His His
                325
```

<210> SEQ ID NO 74
<211> LENGTH: 1047
<212> TYPE: DNA
<213> ORGANISM: Artificial Sequence
<220> FEATURE:
<223> OTHER INFORMATION: Lip-S2D1-S1D1_His_nt

<400> SEQUENCE: 74

```
atgaaagcta ctaaactggt actgggcgcg gtaatcctgg ttctactctc gctggcaggt      60
tgctcaagct tcaacgaaaa aggcgaactg tcggcgaaaa cgatgacgcg tgaaaacggc     120
accaaactgg aatatacgga aatgaaaagc gatggcaccg gtaaagcgaa agaagttctg     180
aaaaacttta ccctggaagg caaagtcgcc aatgacaaag tcaccctgga agtgaaatgc     240
```

```
ggcaccgtta cgctgtcaaa agaaattgca aaatcgggtg aagtgaccgt tgctctgaac      300
gatacgaata ccacgcaagc gaccaagaaa accggcgcct gggacagcaa aacctctacg      360
ctgaccatta gtgttaatag caagaaaacc acgcagctgg tcttcaccaa acaagatacg      420
atcaccgtgc agaaatacga cagtgcgggt accaacctgg aaggcacggc tgttgaaatc      480
aaaaccctgg acgaactgtg taacgccctg aaaggcacta gtgacaaaaa caatggctct      540
ggtagcaaag agaaaacaa agatggcaag tactcattca cgaaaaagg cgaagtcagc       600 gaaaaaatca ttacccgcgc agacggcacc cgcctggaat acaccggcat caaatcggac      660
ggcagcggca agcgaaaga gttctgaaa aactttaccc tggaaggcaa agtcgcaaat       720
gataaaacca ccctggtggt gaaatgcggc accgttacgc tgagcaaaaa cattagtaaa      780
tccggtgaag tctctgtgga actgaatgat accgacagct ctgcggccac caagaaaacc      840
gcagcttgga actcaggcac ctcgacgctg accattacgg ttaatagcaa gaaaaccaaa      900
gatctggtct tcacgaaaga aaacaccatc acggtgcagc aatatgacag caatggtacc      960
aaactggaag gctccgctgt ggaaatcacg aaactggatg aaatctgtaa tgcactgaaa     1020
ggtctcgagc accaccacca ccaccac                                           1047
```

<210> SEQ ID NO 75
<211> LENGTH: 318
<212> TYPE: PRT
<213> ORGANISM: Artificial Sequence
<220> FEATURE:
<223> OTHER INFORMATION: S4D4-S3D4_aa

<400> SEQUENCE: 75

```
Phe Asn Ala Lys Gly Glu Leu Ser Glu Lys Thr Ile Leu Arg Ala Cys
1               5                   10                  15

Gly Thr Arg Leu Glu Tyr Thr Glu Ile Lys Ser Asp Gly Thr Gly Lys
            20                  25                  30

Ala Lys Glu Val Leu Lys Asp Phe Ala Leu Glu Gly Thr Leu Ala Ala
        35                  40                  45

Asp Lys Thr Thr Leu Lys Val Thr Glu Gly Thr Val Val Leu Ser Lys
    50                  55                  60

His Ile Pro Asn Ser Gly Glu Ile Thr Val Glu Leu Asn Asp Ser Asn
65                  70                  75                  80

Ser Thr Gln Ala Thr Lys Lys Thr Gly Lys Trp Asp Ser Asn Thr Ser
                85                  90                  95

Thr Leu Thr Ile Ser Val Asn Ser Lys Lys Thr Lys Asn Ile Val Phe
            100                 105                 110

Thr Lys Glu Cys Thr Ile Thr Val Gln Lys Tyr Asp Ser Ala Gly Thr
        115                 120                 125

Asn Leu Glu Gly Asn Ala Val Glu Ile Lys Thr Leu Asp Glu Leu Lys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Asp Lys Gly Lys Leu
                165                 170                 175

Ser Glu Lys Val Val Thr Arg Ala Cys Gly Thr Arg Leu Glu Tyr Thr
            180                 185                 190

Glu Ile Lys Asn Asp Gly Ser Gly Lys Ala Lys Glu Val Leu Lys Gly
        195                 200                 205

Phe Ala Leu Glu Gly Thr Leu Thr Asp Gly Gly Glu Thr Lys Leu Thr
```

Val Thr Glu Gly Thr Val Thr Leu Ser Lys Asn Ile Ser Lys Ser Gly
225                 230                 235                 240

Glu Ile Thr Val Ala Leu Asn Asp Thr Glu Thr Thr Pro Ala Asp Lys
            245                 250                 255

Lys Thr Gly Glu Trp Lys Ser Asp Thr Ser Thr Leu Thr Ile Ser Lys
            260                 265                 270

Asn Ser Gln Lys Pro Lys Gln Leu Val Phe Thr Lys Glu Cys Thr Ile
        275                 280                 285

Thr Val Gln Asn Tyr Asn Arg Ala Gly Asn Ala Leu Glu Gly Ser Pro
    290                 295                 300

Ala Glu Ile Lys Asp Leu Ala Glu Leu Lys Ala Ala Leu Lys
305                 310                 315

<210> SEQ ID NO 76
<211> LENGTH: 1023
<212> TYPE: DNA
<213> ORGANISM: Artificial Sequence
<220> FEATURE:
<223> OTHER INFORMATION: Lip-S4D4-S3D4_nt

<400> SEQUENCE: 76
atgaaagcta ctaaactggt actgggcgcg gtaatcctgg gttctactct gctggcaggt      60
tgctcaagct tcaacgctaa aggtgaactg tcggaaaaaa ccatcctgcg cgcctgtggc     120
acccgcctgg aatacacgga atcaagtcg gacggcacgg gcaaagcaaa ggaagtcctg      180
aaagattttg ctctggaagg taccctggcg gccgacaaaa ccacgctgaa ggtgacggaa     240
ggcaccgtgg ttctgagcaa acatattccg aactctggtg aaatcaccgt tgaactgaac     300
gatagcaatt ctacgcaggc gaccaaaaag acgggcaaat gggacagtaa tacctccacg     360
ctgaccattt cagtcaactc gaaaaagacc aaaaatattg tgttcacgaa ggaatgcacg     420
atcaccgttc aaaatatga ttccgcaggt accaacctgg aaggcaacgc tgtgaaaatc      480
aaaaccctgg acgaactgaa aaacgccctg aagggtacta gtgacaaaaa caatggctct     540
ggtagcaaag agaaaaacaa agatggcaag tactcattta cgataaggg caaactgtca      600
gaaaaagtgg tcacccgcgc ttgtggcacc cgcctggaat acaccgaaat caaaaacgac     660
ggctcgggca agcgaagga agttctgaaa ggctttgccc tggaaggtac cctgacggat      720
ggcggtgaaa ccaaactgac cgtgacggaa ggcaccgtta cgctgtctaa aacattagc      780
aagtctggtg aaatcacggt cgcactgaat gataccgaaa ccacgccggc tgacaaaaag     840
accggcgaat ggaaaagtga cacctccacg ctgaccattt caaagaactc gcagaaaccg     900
aagcaactgg tcttcaccaa gaatgcacg atcaccgtgc agaactataa tcgtgccggt      960
aatgctctgg aaggctcccc ggctgaaatc aaggacctgg cggaactgaa ggcggcactg    1020
aaa                                                                  1023

<210> SEQ ID NO 77
<211> LENGTH: 330
<212> TYPE: PRT
<213> ORGANISM: Artificial Sequence
<220> FEATURE:
<223> OTHER INFORMATION: Lip-S4D4-S3D4_His_aa
<220> FEATURE:
<221> NAME/KEY: LIPID
<222> LOCATION: (1)..(1)
<223> OTHER INFORMATION: LIPIDATION

<400> SEQUENCE: 77

Cys Ser Ser Phe Asn Ala Lys Gly Glu Leu Ser Glu Lys Thr Ile Leu
1               5                   10                  15

Arg Ala Cys Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
                35                  40                  45

Leu Ala Ala Asp Lys Thr Thr Leu Lys Val Thr Glu Gly Thr Val Val
50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
                100                 105                 110

Ile Val Phe Thr Lys Glu Cys Thr Ile Thr Val Gln Lys Tyr Asp Ser
            115                 120                 125

Ala Gly Thr Asn Leu Glu Gly Asn Ala Val Glu Ile Lys Thr Leu Asp
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Cys Gly Thr Arg Leu
                180                 185                 190

Glu Tyr Thr Glu Ile Lys Asn Asp Gly Ser Gly Lys Ala Lys Glu Val
            195                 200                 205

Leu Lys Gly Phe Ala Leu Glu Gly Thr Leu Thr Asp Gly Gly Glu Thr
    210                 215                 220

Lys Leu Thr Val Thr Glu Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
    275                 280                 285

Cys Thr Ile Thr Val Gln Asn Tyr Asn Arg Ala Gly Asn Ala Leu Glu
    290                 295                 300

Gly Ser Pro Ala Glu Ile Lys Asp Leu Ala Glu Leu Lys Ala Ala Leu
305                 310                 315                 320

Lys Gly Leu Glu His His His His His His
                325                 330

<210> SEQ ID NO 78
<211> LENGTH: 1050
<212> TYPE: DNA
<213> ORGANISM: Artificial Sequence
<220> FEATURE:
<223> OTHER INFORMATION: Lip-S4D4-S3D4_His_nt

<400> SEQUENCE: 78
atgaaagcta ctaaactggt actgggcgcg gtaatcctgg gttctactct gctggcaggt      60
tgctcaagct tcaacgctaa aggtgaactg tcggaaaaaa ccatcctgcg cgcctgtggc     120
acccgcctgg aatacacgga aatcaagtcg acggcacgg gcaaagcaaa ggaagtcctg     180

```
aaagattttg ctctggaagg taccctggcg gccgacaaaa ccacgctgaa ggtgacggaa      240
ggcaccgtgg ttctgagcaa acatattccg aactctggtg aaatcaccgt tgaactgaac      300
gatagcaatt ctacgcaggc gaccaaaaag acgggcaaat gggacagtaa tacctccacg      360
ctgaccattt cagtcaactc gaaaaagacc aaaaatattg tgttcacgaa ggaatgcacg      420
atcaccgttc aaaaatatga ttccgcaggt accaacctgg aaggcaacgc tgtggaaatc      480
aaaaccctgg acgaactgaa aaacgccctg aagggtacta gtgacaaaaa caatggctct      540
ggtagcaaag agaaaaacaa agatggcaag tactcattta acgataaggg caaactgtca      600
gaaaaagtgg tcacccgcgc ttgtggcacc cgcctggaat acaccgaaat caaaaacgac      660
ggctcgggca agcgaagga agttctgaaa ggctttgccc tggaaggtac cctgacggat      720
ggcggtgaaa ccaaactgac cgtgacggaa ggcaccgtta cgctgtctaa aaacattagc      780
aagtctggtg aaatcacggt cgcactgaat gataccgaaa ccacgccggc tgacaaaaag      840
accggcgaat ggaaaagtga cacctccacg ctgaccattt caaagaactc gcagaaaccg      900
aagcaactgg tcttcaccaa agaatgcacg atcaccgtgc agaactataa tcgtgccggt      960
aatgctctgg aaggctcccc ggctgaaatc aaggacctgg cggaactgaa ggcggcactg     1020
aaaggtctcg agcaccacca ccaccaccac                                      1050
```

<210> SEQ ID NO 79
<211> LENGTH: 318
<212> TYPE: PRT
<213> ORGANISM: Artificial Sequence
<220> FEATURE:
<223> OTHER INFORMATION: S4D1-S3D1_aa

<400> SEQUENCE: 79

```
Phe Asn Ala Lys Gly Glu Leu Ser Glu Lys Thr Ile Leu Arg Ala Asn
1               5                   10                  15

Gly Thr Arg Leu Glu Tyr Thr Glu Ile Lys Ser Asp Gly Thr Gly Lys
            20                  25                  30

Ala Lys Glu Val Leu Lys Asp Phe Ala Leu Glu Gly Thr Leu Ala Ala
        35                  40                  45

Asp Lys Thr Thr Leu Lys Val Thr Cys Gly Thr Val Val Leu Ser Lys
    50                  55                  60

His Ile Pro Asn Ser Gly Glu Ile Thr Val Glu Leu Asn Asp Ser Asn
65                  70                  75                  80

Ser Thr Gln Ala Thr Lys Lys Thr Gly Lys Trp Asp Ser Asn Thr Ser
                85                  90                  95

Thr Leu Thr Ile Ser Val Asn Ser Lys Lys Thr Lys Asn Ile Val Phe
            100                 105                 110

Thr Lys Glu Asp Thr Ile Thr Val Gln Lys Tyr Asp Ser Ala Gly Thr
        115                 120                 125

Asn Leu Glu Gly Asn Ala Val Glu Ile Lys Thr Leu Asp Glu Leu Cys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Asp Lys Gly Lys Leu
                165                 170                 175

Ser Glu Lys Val Val Thr Arg Ala Asn Gly Thr Arg Leu Glu Tyr Thr
            180                 185                 190

Glu Ile Lys Asn Asp Gly Ser Gly Lys Ala Lys Glu Val Leu Lys Gly
        195                 200                 205
```

```
Phe Ala Leu Glu Gly Thr Leu Thr Asp Gly Gly Glu Thr Lys Leu Thr
    210                 215                 220

Val Thr Cys Gly Thr Val Thr Leu Ser Lys Asn Ile Ser Lys Ser Gly
225                 230                 235                 240

Glu Ile Thr Val Ala Leu Asn Asp Thr Glu Thr Thr Pro Ala Asp Lys
                245                 250                 255

Lys Thr Gly Glu Trp Lys Ser Asp Thr Ser Thr Leu Thr Ile Ser Lys
            260                 265                 270

Asn Ser Gln Lys Pro Lys Gln Leu Val Phe Thr Lys Glu Asn Thr Ile
        275                 280                 285

Thr Val Gln Asn Tyr Asn Arg Ala Gly Asn Ala Leu Glu Gly Ser Pro
    290                 295                 300

Ala Glu Ile Lys Asp Leu Ala Glu Leu Cys Ala Ala Leu Lys
305                 310                 315
```

<210> SEQ ID NO 80
<211> LENGTH: 1023
<212> TYPE: DNA
<213> ORGANISM: Artificial Sequence
<220> FEATURE:
<223> OTHER INFORMATION: Lip-S4D1-S3D1_nt

<400> SEQUENCE: 80

```
atgaaagcta ctaaactggt actgggcgcg gtaatcctgg gttctactct gctggcaggt      60
tgctcaagct tcaatgctaa gggcgaactg agcgaaaaaa cgatcctgcg tgcgaatggc     120
acccgtctgg aatacaccga atcaaatccc gatggtacgg gcaaagcaaa ggaagtcctg     180
aaagattttg ctctggaagg taccctggcg ccgacaaaaa ccacgctgaa ggtgacgtgc     240
ggcaccgtgt tctgagcaa acatattccg aactctggtg aaatcaccgt tgaactgaac     300
gatagcaatt ctacgcaggc aaccaaaaag acgggcaaat gggacagtaa tacctccacg     360
ctgaccattt cagtcaactc gaaaaagacc aaaaatattg tgttcacgaa ggaagatacg     420
atcaccgttc aaaaatatga ctccgcgggc accaacctgg aaggcaatgc cgtcgaaatc     480 aaaacccctgg atgaactgtg taacgccctg aagggtacta gtgacaaaaa caatggctct     540
ggtagcaaag agaaaaacaa agatggcaag tactcattta cgataaaggg caaactgtcg     600
gaaaaagtgg tcacccgcgc aaatggcacc cgcctggaat acacggaaat caaaaacgat     660
ggtagcggca agcgaagga agttctgaaa ggctttgccc tggaaggtac cctgacggat     720
ggcggtgaaa ccaaactgac cgtgacgtgc ggcaccgtta cgctgtctaa aacattagc     780 aagtctggtg aaatcacggt cgcactgaat gataccgaaa ccacgccggc tgacaaaaag     840
accggcgaat ggaaaagtga cacctccacg ctgaccattt caaagaactc gcagaaaccg     900
aagcaactgg tcttcaccaa agaaaacacg atcaccgtgc agaactataa tcgtgccggt     960
aatgctctgg aaggctcacc ggctgaaatc aaggacctgg ctgaactgtg tgcggcactg    1020
aaa                                                                  1023
```

<210> SEQ ID NO 81
<211> LENGTH: 330
<212> TYPE: PRT
<213> ORGANISM: Artificial Sequence
<220> FEATURE:
<223> OTHER INFORMATION: Lip-S4D1-S3D1_His_aa
<220> FEATURE:
<221> NAME/KEY: LIPID
<222> LOCATION: (1)..(1)
<223> OTHER INFORMATION: LIPIDATION

<400> SEQUENCE: 81

| | | | | | | | | | | | | | | |
|---|---|---|---|---|---|---|---|---|---|---|---|---|---|---|
|Cys|Ser|Ser|Phe|Asn|Ala|Lys|Gly|Glu|Leu|Ser|Glu|Lys|Thr|Ile|Leu|
|1| | | |5| | | | |10| | | | |15| |

Arg Ala Asn Gly Thr Arg Leu Glu Tyr Thr Glu Ile Lys Ser Asp Gly
              20                  25                  30

Thr Gly Lys Ala Lys Glu Val Leu Lys Asp Phe Ala Leu Glu Gly Thr
         35                  40                  45

Leu Ala Ala Asp Lys Thr Leu Lys Val Thr Cys Gly Thr Val Val
 50                  55                  60

Leu Ser Lys His Ile Pro Asn Ser Gly Glu Ile Thr Val Glu Leu Asn
 65                  70                  75                  80

Asp Ser Asn Ser Thr Gln Ala Thr Lys Lys Thr Gly Lys Trp Asp Ser
              85                  90                  95

Asn Thr Ser Thr Leu Thr Ile Ser Val Asn Ser Lys Lys Thr Lys Asn
              100                 105                 110

Ile Val Phe Thr Lys Glu Asp Thr Ile Thr Val Gln Lys Tyr Asp Ser
              115                 120                 125

Ala Gly Thr Asn Leu Glu Gly Asn Ala Val Glu Ile Lys Thr Leu Asp
 130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
              165                 170                 175

Gly Lys Leu Ser Glu Lys Val Val Thr Arg Ala Asn Gly Thr Arg Leu
              180                 185                 190

Glu Tyr Thr Glu Ile Lys Asn Asp Gly Ser Gly Lys Ala Lys Glu Val
              195                 200                 205

Leu Lys Gly Phe Ala Leu Glu Gly Thr Leu Thr Asp Gly Gly Glu Thr
 210                 215                 220

Lys Leu Thr Val Thr Cys Gly Thr Val Thr Leu Ser Lys Asn Ile Ser
225                 230                 235                 240

Lys Ser Gly Glu Ile Thr Val Ala Leu Asn Asp Thr Glu Thr Thr Pro
              245                 250                 255

Ala Asp Lys Lys Thr Gly Glu Trp Lys Ser Asp Thr Ser Thr Leu Thr
              260                 265                 270

Ile Ser Lys Asn Ser Gln Lys Pro Lys Gln Leu Val Phe Thr Lys Glu
              275                 280                 285

Asn Thr Ile Thr Val Gln Asn Tyr Asn Arg Ala Gly Asn Ala Leu Glu
              290                 295                 300

Gly Ser Pro Ala Glu Ile Lys Asp Leu Ala Glu Leu Cys Ala Ala Leu
305                 310                 315                 320

Lys Gly Leu Glu His His His His His His
              325                 330

<210> SEQ ID NO 82
<211> LENGTH: 1050
<212> TYPE: DNA
<213> ORGANISM: Artificial Sequence
<220> FEATURE:
<223> OTHER INFORMATION: Lip-S4D1-S3D1_His_nt

<400> SEQUENCE: 82
atgaaagcta ctaaactggt actgggcgcg gtaatcctgg ttctactct gctggcaggt      60 tgctcaagct tcaatgctaa gggcgaactg agcgaaaaaa cgatcctgcg tgcgaatggc    120

```
acccgtctgg aatacaccga atcaaatcc gatggtacgg gcaaagcaaa ggaagtcctg      180
aaagattttg ctctggaagg taccctggcg gccgacaaaa ccacgctgaa ggtgacgtgc      240
ggcaccgtgg ttctgagcaa acatattccg aactctggtg aaatcaccgt tgaactgaac      300
gatagcaatt ctacgcaggc aaccaaaaag acgggcaaat gggacagtaa tacctccacg      360
ctgaccattt cagtcaactc gaaaagacc aaaaatattg tgttcacgaa ggaagatacg      420
atcaccgttc aaaatatga ctccgcgggc accaacctgg aaggcaatgc cgtcgaaatc      480
aaaaccctgg atgaactgtg taacgccctg aagggtacta gtgacaaaaa caatggctct      540
ggtagcaaag agaaaaacaa agatggcaag tactcattta cgataaggg caaactgtcg      600
gaaaagtgg tcacccgcgc aaatggcacc cgcctggaat acacggaaat caaaaacgat      660
ggtagcggca agcgaagga agttctgaaa ggctttgccc tggaaggtac cctgacggat      720
ggcggtgaaa ccaaactgac cgtgacgtgc ggcaccgtta cgctgtctaa aaacattagc      780
aagtctggtg aaatcacggt cgcactgaat gataccgaaa ccacgccggc tgacaaaaag      840
accggcgaat ggaaaagtga cacctccacg ctgaccattt caaagaactc gcagaaaccg      900
aagcaactgg tcttcaccaa agaaaacacg atcaccgtgc agaactataa tcgtgccggt      960
aatgctctgg aaggctcacc ggctgaaatc aaggacctgg ctgaactgtg tgcggcactg     1020
aaaggtctcg agcaccacca ccaccaccac                                     1050

<210> SEQ ID NO 83
<211> LENGTH: 318
<212> TYPE: PRT
<213> ORGANISM: Artificial Sequence
<220> FEATURE:
<223> OTHER INFORMATION: S6D4-S5D4_aa

<400> SEQUENCE: 83

Phe Asn Gly Lys Gly Glu Thr Ser Glu Lys Thr Ile Val Arg Ala Cys
1               5                   10                  15

Gly Thr Arg Leu Glu Tyr Thr Asp Ile Lys Ser Asp Gly Ser Gly Lys
                20                  25                  30

Ala Lys Glu Val Leu Lys Asp Phe Thr Leu Glu Gly Thr Leu Ala Ala
            35                  40                  45

Asp Gly Lys Thr Thr Leu Lys Val Thr Glu Gly Thr Val Val Leu Ser
        50                  55                  60

Lys Asn Ile Leu Lys Ser Gly Glu Ile Thr Ala Ala Leu Asp Asp Ser
65                  70                  75                  80

Asp Thr Thr Arg Ala Thr Lys Lys Thr Gly Lys Trp Asp Ser Lys Thr
                85                  90                  95

Ser Thr Leu Thr Ile Ser Val Asn Ser Gln Lys Thr Lys Asn Leu Val
            100                 105                 110

Phe Thr Lys Glu Cys Thr Ile Thr Val Gln Arg Tyr Asp Ser Ala Gly
        115                 120                 125

Thr Asn Leu Glu Gly Lys Ala Val Glu Ile Thr Thr Leu Lys Glu Leu
    130                 135                 140

Lys Asn Ala Leu Lys Gly Thr Ser Asp Lys Asn Asn Gly Ser Gly Ser
145                 150                 155                 160

Lys Glu Lys Asn Lys Asp Gly Lys Tyr Ser Phe Asn Glu Lys Gly Glu
                165                 170                 175

Ile Ser Glu Lys Thr Ile Val Arg Ala Cys Gly Thr Arg Leu Glu Tyr
            180                 185                 190
```

```
Thr Asp Ile Lys Ser Asp Lys Thr Gly Lys Ala Lys Glu Val Leu Lys
        195                 200                 205

Asp Phe Thr Leu Glu Gly Thr Leu Ala Ala Asp Gly Lys Thr Thr Leu
210                 215                 220

Lys Val Thr Glu Gly Thr Val Thr Leu Ser Lys Asn Ile Ser Lys Ser
225                 230                 235                 240

Gly Glu Ile Thr Val Ala Leu Asp Asp Thr Asp Ser Ser Gly Asn Lys
                245                 250                 255

Lys Ser Gly Thr Trp Asp Ser Gly Thr Ser Thr Leu Thr Ile Ser Lys
            260                 265                 270

Asn Arg Thr Lys Thr Lys Gln Leu Val Phe Thr Lys Glu Cys Thr Ile
        275                 280                 285

Thr Val Gln Asn Tyr Asp Ser Ala Gly Thr Asn Leu Glu Gly Lys Ala
    290                 295                 300

Val Glu Ile Thr Thr Leu Lys Glu Leu Lys Asn Ala Leu Lys
305                 310                 315

<210> SEQ ID NO 84
<211> LENGTH: 1023
<212> TYPE: DNA
<213> ORGANISM: Artificial Sequence
<220> FEATURE:
<223> OTHER INFORMATION: Lip-S6D4-S5D4_nt

<400> SEQUENCE: 84
atgaaagcta ctaaactggt actgggcgcg gtaatcctgg gttctactct gctggcaggt       60
tgctcaagct tcaacggcaa aggtgaaacg agtgaaaaaa cgattgttcg cgcctgtggc      120
acccgcctgg aatacacgga tatcaagtcg gatggttcgg gcaaagcaaa ggaagtcctg      180
aaagatttta cgctggaagg taccctggca gcagacggta aaaccacgct gaaggtgacg      240
gaaggcaccg tggttctgtc aaaaaacatt ctgaagtcgg gtgaaatcac cgcagctctg      300
gatgacagcg ataccacgcg tgctacgaaa aagaccggta atgggacag caagaccctct      360 acgctgacca ttagtgtcaa ctcccagaaa acgaagaatc tggtgttcac caaagaatgc      420
acgatcaccg ttcaacgcta tgatagtgcg ggcaccaacc tggaaggcaa agccgttgaa      480
attaccacgc tgaaagaact gaagaatgct ctgaaaggta ctagtgacaa aacaatggc      540 tctggtagca agagaaaaa caaagatggc aagtactcat tcaacgaaaa aggcgaaatc      600
agtgaaaaaa ccattgtgcg tgcgtgtggc acccgtctgg aatataccga catcaagagc      660
gataaaacgg gtaaagcgaa ggaagttctg aaagatttta cgctggaagg taccctggca      720
gcagacggta aaaccacgct gaaggtgacc gaaggtaccg ttacgctgtc aaaaaacatt      780
agtaagtccg gcgaaatcac ggtcgccctg gatgacaccg atagctctgg caacaaaaag      840
agcggtacct gggactcagg cacctcgacg ctgaccattt ctaaaaatcg tacgaaaacc      900
aagcagctgg tcttcacgaa agaatgcacg atcaccgtgc aaaactatga tagcgcaggt      960
accaatctgg aaggcaaagc tgtggaaatt accacgctga agaactgaa gaatgctctg      1020 aaa                                                                    1023

<210> SEQ ID NO 85
<211> LENGTH: 330
<212> TYPE: PRT
<213> ORGANISM: Artificial Sequence
<220> FEATURE:
<223> OTHER INFORMATION: Lip-S6D4-S5D4_His_aa
<220> FEATURE:
<221> NAME/KEY: LIPID
```

<222> LOCATION: (1)..(1)
<223> OTHER INFORMATION: LIPIDATION

<400> SEQUENCE: 85

```
Cys Ser Ser Phe Asn Gly Lys Gly Glu Thr Ser Glu Lys Thr Ile Val
1               5                   10                  15

Arg Ala Cys Gly Thr Arg Leu Glu Tyr Thr Asp Ile Lys Ser Asp Gly
            20                  25                  30

Ser Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Glu Gly Thr Val
    50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Thr Gly Lys Trp Asp
                85                  90                  95

Ser Lys Thr Ser Thr Leu Thr Ile Ser Val Asn Ser Gln Lys Thr Lys
                100                 105                 110

Asn Leu Val Phe Thr Lys Glu Cys Thr Ile Thr Val Gln Arg Tyr Asp
            115                 120                 125

Ser Ala Gly Thr Asn Leu Glu Gly Lys Ala Val Glu Ile Thr Thr Leu
        130                 135                 140

Lys Glu Leu Lys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Cys Gly Thr Arg
            180                 185                 190

Leu Glu Tyr Thr Asp Ile Lys Ser Asp Lys Thr Gly Lys Ala Lys Glu
        195                 200                 205

Val Leu Lys Asp Phe Thr Leu Glu Gly Thr Leu Ala Ala Asp Gly Lys
    210                 215                 220

Thr Thr Leu Lys Val Thr Glu Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
            260                 265                 270

Ile Ser Lys Asn Arg Thr Lys Thr Lys Gln Leu Val Phe Thr Lys Glu
        275                 280                 285

Cys Thr Ile Thr Val Gln Asn Tyr Asp Ser Ala Gly Thr Asn Leu Glu
    290                 295                 300

Gly Lys Ala Val Glu Ile Thr Thr Leu Lys Glu Leu Lys Asn Ala Leu
305                 310                 315                 320

Lys Gly Leu Glu His His His His His His
                325                 330
```

<210> SEQ ID NO 86
<211> LENGTH: 1050
<212> TYPE: DNA
<213> ORGANISM: Artificial Sequence
<220> FEATURE:
<223> OTHER INFORMATION: Lip-S6D4-S5D4_His_nt

<400> SEQUENCE: 86

```
atgaaagcta ctaaactggt actgggcgcg gtaatcctgg ttctactctc gctggcaggt    60
```

```
tgctcaagct tcaacggcaa aggtgaaacg agtgaaaaaa cgattgttcg cgcctgtggc    120
acccgcctgg aatacacgga tatcaagtcg gatggttcgg gcaaagcaaa ggaagtcctg    180
aaagatttta cgctggaagg taccctggca gcagacggta aaaccacgct gaaggtgacg    240
gaaggcaccg tggttctgtc aaaaaacatt ctgaagtcgg gtgaaatcac cgcagctctg    300
gatgacagcg ataccacgcg tgctacgaaa aagaccggta aatgggacag caagacctct    360
acgctgacca ttagtgtcaa ctcccagaaa acgaagaatc tggtgttcac caagaatgc    420
acgatcaccg ttcaacgcta tgatagtgcg ggcaccaacc tggaaggcaa agccgttgaa    480
attaccacgc tgaaagaact gaagaatgct ctgaaaggta ctagtgacaa aacaatggc    540
tctggtagca aagagaaaaa caaagatggc aagtactcat tcaacgaaaa aggcgaaatc    600
agtgaaaaaa ccattgtgcg tgcgtgtggc acccgtctgg aatataccga catcaagagc    660
gataaaacgg gtaaagcgaa ggaagttctg aaagatttta cgctggaagg taccctggca    720
gcagacggta aaaccacgct gaaggtgacc gaaggtaccg ttacgctgtc caaaaacatt    780
agtaagtccg gcgaaatcac ggtcgccctg gatgacaccg atagctctgg caacaaaaag    840
agcggtacct gggactcagg cacctcgacg ctgaccattt ctaaaaatcg tacgaaaacc    900
aagcagctgg tcttcacgaa agaatgcacg atcaccgtgc aaaactatga tagcgcaggt    960
accaatctgg aaggcaaagc tgtggaaatt accacgctga agaactgaa gaatgctctg   1020
aaaggtctcg agcaccacca ccaccaccac                                    1050
```

<210> SEQ ID NO 87
<211> LENGTH: 318
<212> TYPE: PRT
<213> ORGANISM: Artificial Sequence
<220> FEATURE:
<223> OTHER INFORMATION: S6D1-S5D1_aa

<400> SEQUENCE: 87

Phe Asn Gly Lys Gly Glu Thr Ser Glu Lys Thr Ile Val Arg Ala Asn
1               5                   10                  15

Gly Thr Arg Leu Glu Tyr Thr Asp Ile Lys Ser Asp Gly Ser Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Cys Gly Thr Val Val Leu Ser
    50                  55                  60

Lys Asn Ile Leu Lys Ser Gly Glu Ile Thr Ala Ala Leu Asp Asp Ser
65                  70                  75                  80

Asp Thr Thr Arg Ala Thr Lys Lys Thr Gly Lys Trp Asp Ser Lys Thr
                85                  90                  95

Ser Thr Leu Thr Ile Ser Val Asn Ser Gln Lys Thr Lys Asn Leu Val
            100                 105                 110

Phe Thr Lys Glu Asp Thr Ile Thr Val Gln Arg Tyr Asp Ser Ala Gly
        115                 120                 125

Thr Asn Leu Glu Gly Lys Ala Val Glu Ile Thr Thr Leu Lys Glu Leu
    130                 135                 140

Cys Asn Ala Leu Lys Gly Thr Ser Asp Lys Asn Gly Ser Gly Ser
145                 150                 155                 160

Lys Glu Lys Asn Lys Asp Gly Lys Tyr Ser Phe Asn Glu Lys Gly Glu
                165                 170                 175

Ile Ser Glu Lys Thr Ile Val Arg Ala Asn Gly Thr Arg Leu Glu Tyr

```
            180                 185                 190
Thr Asp Ile Lys Ser Asp Lys Thr Gly Lys Ala Lys Glu Val Leu Lys
                195                 200                 205

Asp Phe Thr Leu Glu Gly Thr Leu Ala Ala Asp Gly Lys Thr Thr Leu
    210                 215                 220

Lys Val Thr Cys Gly Thr Val Thr Leu Ser Lys Asn Ile Ser Lys Ser
225                 230                 235                 240

Gly Glu Ile Thr Val Ala Leu Asp Asp Thr Asp Ser Ser Gly Asn Lys
                245                 250                 255

Lys Ser Gly Thr Trp Asp Ser Gly Thr Ser Thr Leu Thr Ile Ser Lys
                260                 265                 270

Asn Arg Thr Lys Thr Lys Gln Leu Val Phe Thr Lys Glu Asp Thr Ile
                275                 280                 285

Thr Val Gln Asn Tyr Asp Ser Ala Gly Thr Asn Leu Glu Gly Lys Ala
                290                 295                 300

Val Glu Ile Thr Thr Leu Lys Glu Leu Cys Asn Ala Leu Lys
305                 310                 315
```

<210> SEQ ID NO 88
<211> LENGTH: 1023
<212> TYPE: DNA
<213> ORGANISM: Artificial Sequence
<220> FEATURE:
<223> OTHER INFORMATION: Lip-S6D1-S5D1_nt

<400> SEQUENCE: 88

```
atgaaagcta ctaaactggt actgggcgcg gtaatcctgg ttctactct gctggcaggt      60
tgctcaagct tcaacggcaa aggtgaaacg agcgaaaaga ccatcgtgcg tgcgaacggt    120
acccgcctgg aatatacgga cattaaatcg acggcagcg gcaaagcaaa ggaagtcctg    180
aaagatttta cgctggaagg taccctggca gcagacggta aaaccacgct gaaggtgacg    240
tgcggcaccg tggttctgtc aaaaaacatt ctgaagtcgg gtgaaatcac cgcagctctg    300
gatgacagcg ataccacgcg tgctacgaaa agaccggta atgggatag caagacctct    360
acgctgacca ttagtgtcaa ctcccagaaa acgaagaatc tggtgttcac caagaagat    420
acgatcaccg ttcaacgcta tgacagtgcg ggcaccaacc tggaaggcaa agccgttgaa    480
attaccacgc tgaaagaact gtgtaatgct ctgaaaggta ctagtgacaa aacaatggc    540
tctggtagca agagaaaaa caagatggc aagtactcat tcaacgaaaa aggcgaaatc    600
tcagaaaaaa ccatcgtccg cgctaacggc acccgcctgg aatacaccga catcaaatca    660
gacaagaccg gtaaagcgaa ggaagttctg aaagatttta cgctggaagg taccctggca    720
gcagacggta aaaccacgct gaaggtgacc tgcggtaccg ttacgctgtc caaaaacatt    780
agtaagtccg gcgaaatcac ggtcgccctg gatgacaccg atagctctgg caacaaaaag    840
agcggtacct gggattcagg cacctcgacg ctgaccattt ctaaaaatcg tacgaaaacc    900
aagcagctgg tcttcacgaa agaagatacg atcaccgtgc aaaactatga cagcgcaggt    960
accaatctgg aaggcaaagc tgtggaaatt accacgctga agaactgtg taatgctctg   1020
aaa                                                                 1023
```

<210> SEQ ID NO 89
<211> LENGTH: 330
<212> TYPE: PRT
<213> ORGANISM: Artificial Sequence
<220> FEATURE:
<223> OTHER INFORMATION: Lip-S6D1-S5D1_His_aa
<220> FEATURE:
<221> NAME/KEY: LIPID
<222> LOCATION: (1)..(1)
<223> OTHER INFORMATION: LIPIDATION

<400> SEQUENCE: 89

Cys Ser Ser Phe Asn Gly Lys Gly Glu Thr Ser Glu Lys Thr Ile Val
1               5                   10                  15

Arg Ala Asn Gly Thr Arg Leu Glu Tyr Thr Asp Ile Lys Ser Asp Gly
            20                  25                  30

Ser Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
    50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
            100                 105                 110

Asn Leu Val Phe Thr Lys Glu Asp Thr Ile Thr Val Gln Arg Tyr Asp
        115                 120                 125

Ser Ala Gly Thr Asn Leu Glu Gly Lys Ala Val Glu Ile Thr Thr Leu
    130                 135                 140

Lys Glu Leu Cys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Asn Gly Thr Arg
            180                 185                 190

Leu Glu Tyr Thr Asp Ile Lys Ser Asp Lys Thr Gly Lys Ala Lys Glu
        195                 200                 205

Val Leu Lys Asp Phe Thr Leu Glu Gly Thr Leu Ala Ala Asp Gly Lys
    210                 215                 220

Thr Thr Leu Lys Val Thr Cys Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
            260                 265                 270

Ile Ser Lys Asn Arg Thr Lys Thr Lys Gln Leu Val Phe Thr Lys Glu
        275                 280                 285

Asp Thr Ile Thr Val Gln Asn Tyr Asp Ser Ala Gly Thr Asn Leu Glu
    290                 295                 300

Gly Lys Ala Val Glu Ile Thr Thr Leu Lys Glu Leu Cys Asn Ala Leu
305                 310                 315                 320

Lys Gly Leu Glu His His His His His His
                325                 330

<210> SEQ ID NO 90
<211> LENGTH: 1050
<212> TYPE: DNA
<213> ORGANISM: Artificial Sequence
<220> FEATURE:
<223> OTHER INFORMATION: Lip-S6D1-S5D1_His_nt

<400> SEQUENCE: 90

```
atgaaagcta ctaaactggt actgggcgcg gtaatcctgg gttctactct gctggcaggt    60
tgctcaagct tcaacggcaa aggtgaaacg agcgaaaaga ccatcgtgcg tgcgaacggt   120
acccgcctgg aatatacgga cattaaatcg gacggcagcg gcaaagcaaa ggaagtcctg   180
aaagatttta cgctggaagg taccctggca gcagacggta aaaccacgct gaaggtgacg   240
tgcggcaccg tggttctgtc aaaaaacatt ctgaagtcgg gtgaaatcac cgcagctctg   300
gatgacagcg ataccacgcg tgctacgaaa aagaccggta atgggatag  caagacctct   360
acgctgacca ttagtgtcaa ctcccagaaa acgaagaatc tggtgttcac caagaagat   420
acgatcaccg ttcaacgcta tgacagtgcg ggcaccaacc tggaaggcaa agccgttgaa   480
attaccacgc tgaaagaact gtgtaatgct ctgaaaggta ctagtgacaa aacaatggc   540
tctggtagca agagaaaaa  caagatggc  aagtactcat tcaacgaaaa aggcgaaatc   600
tcagaaaaaa ccatcgtccg cgctaacggc acccgcctgg aatacaccga catcaaatca   660
gacaagaccg gtaaagcgaa ggaagttctg aaagatttta cgctggaagg taccctggca   720
gcagacggta aaaccacgct gaaggtgacc tgcggtaccg ttacgctgtc caaaaacatt   780
agtaagtccg gcgaaatcac ggtcgccctg gatgacaccg atagctctgg caacaaaaag   840
agcggtacct gggattcagg cacctcgacg ctgaccattt ctaaaaatcg tacgaaaacc   900
aagcagctgg tcttcacgaa agaagatacg atcaccgtgc aaaactatga cagcgcaggt   960
accaatctgg aaggcaaagc tgtggaaatt accacgctga agaactgtg  taatgctctg  1020
aaaggtctcg agcaccacca ccaccaccac                                    1050
```

<210> SEQ ID NO 91  
<211> LENGTH: 317  
<212> TYPE: PRT  
<213> ORGANISM: Artificial Sequence  
<220> FEATURE:  
<223> OTHER INFORMATION: S1D4-S2D1_aa

<400> SEQUENCE: 91

```
Phe Asn Glu Lys Gly Glu Val Ser Glu Lys Ile Ile Thr Arg Ala Cys
1               5                   10                  15

Gly Thr Arg Leu Glu Tyr Thr Gly Ile Lys Ser Asp Gly Ser Gly Lys
            20                  25                  30

Ala Lys Glu Val Leu Lys Asn Phe Thr Leu Glu Gly Lys Val Ala Asn
        35                  40                  45

Asp Lys Thr Thr Leu Val Val Lys Glu Gly Thr Val Thr Leu Ser Lys
    50                  55                  60

Asn Ile Ser Lys Ser Gly Glu Val Ser Val Glu Leu Asn Asp Thr Asp
65                  70                  75                  80

Ser Ser Ala Ala Thr Lys Lys Thr Ala Ala Trp Asn Ser Gly Thr Ser
                85                  90                  95

Thr Leu Thr Ile Thr Val Asn Ser Lys Lys Thr Lys Asp Leu Val Phe
            100                 105                 110

Thr Lys Glu Cys Thr Ile Thr Val Gln Gln Tyr Asp Ser Asn Gly Thr
        115                 120                 125

Lys Leu Glu Gly Ser Ala Val Glu Ile Thr Lys Leu Asp Glu Ile Lys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Glu Lys Gly Glu Leu
                165                 170                 175
```

Ser Ala Lys Thr Met Thr Arg Glu Asn Gly Thr Lys Leu Glu Tyr Thr
            180                 185                 190

Glu Met Lys Ser Asp Gly Thr Gly Lys Ala Lys Glu Val Leu Lys Asn
        195                 200                 205

Phe Thr Leu Glu Gly Lys Val Ala Asn Asp Lys Val Thr Leu Glu Val
    210                 215                 220

Lys Cys Gly Thr Val Thr Leu Ser Lys Glu Ile Ala Lys Ser Gly Glu
225                 230                 235                 240

Val Thr Val Ala Leu Asn Asp Thr Asn Thr Thr Gln Ala Thr Lys Lys
                245                 250                 255

Thr Gly Ala Trp Asp Ser Lys Ser Thr Leu Thr Ile Ser Val Asn
            260                 265                 270

Ser Lys Lys Thr Thr Gln Leu Val Phe Thr Lys Gln Asp Thr Ile Thr
        275                 280                 285

Val Gln Lys Tyr Asp Ser Ala Gly Thr Asn Leu Glu Gly Thr Ala Val
    290                 295                 300

Glu Ile Lys Thr Leu Asp Glu Leu Cys Asn Ala Leu Lys
305                 310                 315

<210> SEQ ID NO 92
<211> LENGTH: 1020
<212> TYPE: DNA
<213> ORGANISM: Artificial Sequence
<220> FEATURE:
<223> OTHER INFORMATION: Lip-S1D4-S2D1_nt

<400> SEQUENCE: 92

```
atgaaagcta ctaaactggt actgggcgcg gtaatcctgg ttctactct gctggcaggt      60
tgctcaagct tcaacgaaaa gggcgaagtc tcggaaaaaa tcattaccccg tgcttgcggc    120
acccgtctgg aatacaccgg cattaaatcg gatggcagcg gcaaagcgaa ggaagttctg    180
aaaaacttta ccctggaagg caaagtcgca atgataaga ccaccctggt ggtgaaagaa     240
ggcaccgtta cgctgagcaa aacattagt aagtccggtg aagtctctgt ggaactgaat     300
gataccgaca gctctgcggc caccaaaaag acggcagctt ggaactcagg cacctcgacg    360
ctgaccatta cggttaattc caaaaagacc aaagatctgg tcttcacgaa agaatgcacc    420
atcacggtgc agcaatatga cagcaacggt accaaactgg aaggctctgc ggtggaaatc    480
acgaaactgg atgaaatcaa aaatgctctg aaaggtacta gtgacaaaaa caatggctct    540
ggtagcaaag agaaaaacaa agatggcaag tactcattca cgaaaaaggg cgaactgtcg    600
gcgaaaacga tgacgcgtga aaacggcacc aaactggaat atacggaaat gaaaagcgat    660
ggcaccggta agcgaaaga agttctgaaa aactttaccc tggaaggcaa agtcgccaat    720
gacaaagtca ccctggaagt gaaatgcggc accgttacgc tgtcaaaaga aattgcaaaa    780
tcgggtgaag tgaccgttgc tctgaacgat acgaatacca cgcaagcgac caagaaaacc    840
ggcgcctggg acagcaaaac ctctacgctg accattagtg ttaatagcaa gaaaaccacg    900
cagctggtct tcaccaaaca agatacgatc accgtgcaga atacgacag tgcgggtacc    960
aacctggaag gcacggctgt tgaaatcaaa ccctggacg aactgtgtaa cgccctgaaa    1020
```

<210> SEQ ID NO 93
<211> LENGTH: 329
<212> TYPE: PRT
<213> ORGANISM: Artificial Sequence
<220> FEATURE:
<223> OTHER INFORMATION: Lip-S1D4-S2D1_His_aa

```
<220> FEATURE:
<221> NAME/KEY: LIPID
<222> LOCATION: (1)..(1)
<223> OTHER INFORMATION: LIPIDATION

<400> SEQUENCE: 93

Cys Ser Ser Phe Asn Glu Lys Gly Glu Val Ser Glu Lys Ile Ile Thr
1               5                   10                  15

Arg Ala Cys Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Glu Gly Thr Val Thr
50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110

Leu Val Phe Thr Lys Glu Cys Thr Ile Thr Val Gln Gln Tyr Asp Ser
        115                 120                 125

Asn Gly Thr Lys Leu Glu Gly Ser Ala Val Glu Ile Thr Lys Leu Asp
130                 135                 140

Glu Ile Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Asn Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
210                 215                 220

Leu Glu Val Lys Cys Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
                245                 250                 255

Thr Lys Lys Thr Gly Ala Trp Asp Ser Lys Thr Ser Thr Leu Thr Ile
            260                 265                 270

Ser Val Asn Ser Lys Lys Thr Thr Gln Leu Val Phe Thr Lys Gln Asp
        275                 280                 285

Thr Ile Thr Val Gln Lys Tyr Asp Ser Ala Gly Thr Asn Leu Glu Gly
290                 295                 300

Thr Ala Val Glu Ile Lys Thr Leu Asp Glu Leu Cys Asn Ala Leu Lys
305                 310                 315                 320

Gly Leu Glu His His His His His His
                325

<210> SEQ ID NO 94
<211> LENGTH: 1047
<212> TYPE: DNA
<213> ORGANISM: Artificial Sequence
<220> FEATURE:
<223> OTHER INFORMATION: Lip-S1D4-S2D1_His_nt

<400> SEQUENCE: 94
```

```
atgaaagcta ctaaactggt actgggcgcg gtaatcctgg gttctactct gctggcaggt    60
tgctcaagct tcaacgaaaa gggcgaagtc tcggaaaaaa tcattacccg tgcttgcggc   120
acccgtctgg aatacaccgg cattaaatcg gatggcagcg gcaaagcgaa ggaagttctg   180
aaaaacttta ccctggaagg caaagtcgca atgataagaa ccaccctggt ggtgaaagaa   240
ggcaccgtta cgctgagcaa aaacattagt aagtccggtg aagtctctgt ggaactgaat   300
gataccgaca gctctgcggc caccaaaaag acggcagctt ggaactcagg cacctcgacg   360
ctgaccatta cggttaattc caaaaagacc aaagatctgg tcttcacgaa agaatgcacc   420
atcacggtgc agcaatatga cagcaacggt accaaactgg aaggctctgc ggtggaaatc   480
acgaaactgg atgaaatcaa aaatgctctg aaaggtacta gtgacaaaaa caatggctct   540
ggtagcaaag agaaaaacaa agatggcaag tactcattca cgaaaaaggg cgaactgtcg   600
gcgaaaacga tgacgcgtga aaacggcacc aaactggaat atacggaaat gaaaagcgat   660
ggcaccggta agcgaaaga agttctgaaa aactttaccc tggaaggcaa agtcgccaat   720
gacaaagtca ccctggaagt gaaatgcggc accgttacgc tgtcaaaaga aattgcaaaa   780
tcgggtgaag tgaccgttgc tctgaacgat acgaatacca cgcaagcgac caagaaaacc   840
ggcgcctggg acagcaaaac ctctacgctg accattagtg ttaatagcaa gaaaaccacg   900
cagctggtct tcaccaaaca agatacgatc ccgtgcaga atacgacag tgcgggtacc   960
aacctggaag gcacggctgt tgaaatcaaa accctggacg aactgtgtaa cgccctgaaa  1020
ggcctcgagc accaccacca ccaccac                                      1047

<210> SEQ ID NO 95
<211> LENGTH: 317
<212> TYPE: PRT
<213> ORGANISM: Artificial Sequence
<220> FEATURE:
<223> OTHER INFORMATION: S1D1-S2D4_aa

<400> SEQUENCE: 95

Phe Asn Glu Lys Gly Glu Val Ser Glu Lys Ile Ile Thr Arg Ala Asp
1               5                   10                  15

Gly Thr Arg Leu Glu Tyr Thr Gly Ile Lys Ser Asp Gly Ser Gly Lys
            20                  25                  30

Ala Lys Glu Val Leu Lys Asn Phe Thr Leu Glu Gly Lys Val Ala Asn
        35                  40                  45

Asp Lys Thr Thr Leu Val Val Lys Cys Gly Thr Val Thr Leu Ser Lys
    50                  55                  60

Asn Ile Ser Lys Ser Gly Glu Val Ser Val Glu Leu Asn Asp Thr Asp
65                  70                  75                  80

Ser Ser Ala Ala Thr Lys Lys Thr Ala Ala Trp Asn Ser Gly Thr Ser
                85                  90                  95

Thr Leu Thr Ile Thr Val Asn Ser Lys Lys Thr Lys Asp Leu Val Phe
            100                 105                 110

Thr Lys Glu Asn Thr Ile Thr Val Gln Gln Tyr Asp Ser Asn Gly Thr
        115                 120                 125

Lys Leu Glu Gly Ser Ala Val Glu Ile Thr Lys Leu Asp Glu Ile Cys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Glu Lys Gly Glu Leu
                165                 170                 175
```

```
Ser Ala Lys Thr Met Thr Arg Glu Cys Gly Thr Lys Leu Glu Tyr Thr
            180                 185                 190

Glu Met Lys Ser Asp Gly Thr Gly Lys Ala Lys Glu Val Leu Lys Asn
        195                 200                 205

Phe Thr Leu Glu Gly Lys Val Ala Asn Asp Lys Val Thr Leu Glu Val
    210                 215                 220

Lys Glu Gly Thr Val Thr Leu Ser Lys Glu Ile Ala Lys Ser Gly Glu
225                 230                 235                 240

Val Thr Val Ala Leu Asn Asp Thr Asn Thr Thr Gln Ala Thr Lys Lys
                245                 250                 255

Thr Gly Ala Trp Asp Ser Lys Ser Thr Leu Thr Ile Ser Val Asn
            260                 265                 270

Ser Lys Lys Thr Thr Gln Leu Val Phe Thr Lys Gln Cys Thr Ile Thr
        275                 280                 285

Val Gln Lys Tyr Asp Ser Ala Gly Thr Asn Leu Glu Gly Thr Ala Val
    290                 295                 300

Glu Ile Lys Thr Leu Asp Glu Leu Lys Asn Ala Leu Lys
305                 310                 315
```

<210> SEQ ID NO 96
<211> LENGTH: 1020
<212> TYPE: DNA
<213> ORGANISM: Artificial Sequence
<220> FEATURE:
<223> OTHER INFORMATION: Lip-S1D1-S2D4_nt

<400> SEQUENCE: 96

```
atgaaagcta ctaaactggt actgggcgcg gtaatcctgg gttctactct gctggcaggt    60
tgctcaagct tcaacgaaaa gggcgaagtc agcgaaaaaa tcattacccg cgcagacggc   120
acccgcctgg aatacaccgg catcaaatcg gacggcagcg gcaaagcgaa agaagttctg   180
aaaaacttta ccctggaagg caaagtcgca atgataaaaa ccaccctggt ggtgaaatgc   240
ggcaccgtta cgctgagcaa aaacattagt aaatccggtg aagtctctgt ggaactgaat   300
gataccgaca gctctgcggc caccaagaaa accgcagctt ggaactcagg cacctcgacg   360
ctgaccatta cggttaatag caagaaaacc aaagatctgg tcttcacgaa agaaaacacc   420
atcacggtgc agcaatatga cagcaatggt accaaactgg aaggctccgc tgtgaaaatc   480
acgaaactgg atgaaatctg taatgctctg aaaggtacta gtgacaaaaa caatggctct   540
ggtagcaaag agaaaaacaa agatggcaag tactcattca cgaaaaaggc gaactgtcg   600
gcgaaaacga tgacgcgtga atgcggcacc aaactggaat atacggaaat gaaaagcgat   660
ggcaccggta agcgaaaga agttctgaaa aactttaccc tggaaggcaa agtcgccaat   720
gacaaagtca ccctggaagt gaagaaggc accgttacgc tgtcaaaaga aattgcaaaa   780
tcgggtgaag tgaccgttgc tctgaacgat acgaatacca cgcaagcgac caagaaaacc   840
ggcgcctggg acagcaaaac ctctacgctg accattagtg ttaacagcaa gaaaaccacg   900
cagctggtct tcaccaaaca atgtacgatc accgtgcaga aatacgatag tgcgggtacc   960
aacctggaag gcaccgctgt tgaaatcaaa ccctggacg aactgaaaaa cgccctgaaa  1020
```

<210> SEQ ID NO 97
<211> LENGTH: 329
<212> TYPE: PRT
<213> ORGANISM: Artificial Sequence
<220> FEATURE:
<223> OTHER INFORMATION: Lip-S1D1-S2D4_His_aa

```
<220> FEATURE:
<221> NAME/KEY: LIPID
<222> LOCATION: (1)..(1)
<223> OTHER INFORMATION: LIPIDATION

<400> SEQUENCE: 97
```

Cys Ser Ser Phe Asn Glu Lys Gly Glu Val Ser Glu Lys Ile Ile Thr
1               5                   10                  15

Arg Ala Asp Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Cys Gly Thr Val Thr
50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110

Leu Val Phe Thr Lys Glu Asn Thr Ile Thr Val Gln Gln Tyr Asp Ser
        115                 120                 125

Asn Gly Thr Lys Leu Glu Gly Ser Ala Val Glu Ile Thr Lys Leu Asp
130                 135                 140

Glu Ile Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Cys Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
210                 215                 220

Leu Glu Val Lys Glu Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
                245                 250                 255

Thr Lys Lys Thr Gly Ala Trp Asp Ser Lys Thr Ser Thr Leu Thr Ile
            260                 265                 270

Ser Val Asn Ser Lys Lys Thr Thr Gln Leu Val Phe Thr Lys Gln Cys
        275                 280                 285

Thr Ile Thr Val Gln Lys Tyr Asp Ser Ala Gly Thr Asn Leu Glu Gly
290                 295                 300

Thr Ala Val Glu Ile Lys Thr Leu Asp Glu Leu Lys Asn Ala Leu Lys
305                 310                 315                 320

Gly Leu Glu His His His His His His
                325

```
<210> SEQ ID NO 98
<211> LENGTH: 1047
<212> TYPE: DNA
<213> ORGANISM: Artificial Sequence
<220> FEATURE:
<223> OTHER INFORMATION: Lip-S1D1-S2D4_His_nt

<400> SEQUENCE: 98
```

-continued

```
atgaaagcta ctaaactggt actgggcgcg gtaatcctgg gttctactct gctggcaggt      60
tgctcaagct tcaacgaaaa gggcgaagtc agcgaaaaaa tcattacccg cgcagacggc     120
acccgcctgg aatacaccgg catcaaatcg acggcagcg gcaaagcgaa agaagttctg      180
aaaaacttta ccctggaagg caaagtcgca atgataaaa ccaccctggt ggtgaaatgc      240
ggcaccgtta cgctgagcaa aacattagt aaatccggtg aagtctctgt ggaactgaat      300
gataccgaca gctctgcggc caccaagaaa accgcagctt ggaactcagg cacctcgacg     360
ctgaccatta cggttaatag caagaaaacc aaagatctgg tcttcacgaa agaaaacacc     420
atcacggtgc agcaatatga cagcaatggt accaaactgg aaggctccgc tgtggaaatc     480
acgaaactgg atgaaatctg taatgctctg aaaggtacta gtgacaaaaa caatggctct     540
ggtagcaaag agaaaaacaa agatggcaag tactcattca cgaaaaagg cgaactgtcg      600
gcgaaaacga tgacgcgtga atgcggcacc aaactggaat atacggaaat gaaaagcgat     660
ggcaccggta agcgaaaga agttctgaaa aactttaccc tggaaggcaa agtcgccaat     720
gacaaagtca ccctggaagt gaaagaaggc accgttacgc tgtcaaaaga aattgcaaaa     780
tcgggtgaag tgaccgttgc tctgaacgat acgaatacca cgcaagcgac caagaaaacc     840
ggcgcctggg acagcaaaac ctctacgctg accattagtg ttaacagcaa gaaaaccacg     900
cagctggtct tcaccaaaca atgtacgatc ccgtgcaga aatacgatag tgcgggtacc      960
aacctggaag gcaccgctgt tgaaatcaaa accctggacg aactgaaaaa cgccctgaaa    1020
ggcctcgagc accaccacca ccaccac                                         1047
```

<210> SEQ ID NO 99
<211> LENGTH: 318
<212> TYPE: PRT
<213> ORGANISM: Artificial Sequence
<220> FEATURE:
<223> OTHER INFORMATION: S3D4-S4D1_aa

<400> SEQUENCE: 99

```
Phe Asn Glu Lys Gly Lys Leu Ser Glu Lys Val Val Thr Arg Ala Cys
1               5                   10                  15

Gly Thr Arg Leu Glu Tyr Thr Glu Ile Lys Asn Asp Gly Ser Gly Lys
            20                  25                  30

Ala Lys Glu Val Leu Lys Gly Phe Ala Leu Glu Gly Thr Leu Thr Asp
        35                  40                  45

Gly Gly Glu Thr Lys Leu Thr Val Thr Glu Gly Thr Val Thr Leu Ser
    50                  55                  60

Lys Asn Ile Ser Lys Ser Gly Glu Ile Thr Val Ala Leu Asn Asp Thr
65                  70                  75                  80

Glu Thr Thr Pro Ala Asp Lys Lys Thr Gly Glu Trp Lys Ser Asp Thr
                85                  90                  95

Ser Thr Leu Thr Ile Ser Lys Asn Ser Gln Lys Pro Lys Gln Leu Val
            100                 105                 110

Phe Thr Lys Glu Cys Thr Ile Thr Val Gln Asn Tyr Asn Arg Ala Gly
        115                 120                 125

Asn Ala Leu Glu Gly Ser Pro Ala Glu Ile Lys Asp Leu Ala Glu Leu
    130                 135                 140

Lys Ala Ala Leu Lys Gly Thr Ser Asp Lys Asn Asn Gly Ser Gly Ser
145                 150                 155                 160

Lys Glu Lys Asn Lys Asp Gly Lys Tyr Ser Phe Asn Ala Lys Gly Glu
                165                 170                 175
```

Leu Ser Glu Lys Thr Ile Leu Arg Ala Asn Gly Thr Arg Leu Glu Tyr
            180                 185                 190

Thr Glu Ile Lys Ser Asp Gly Thr Gly Lys Ala Lys Glu Val Leu Lys
        195                 200                 205

Asp Phe Ala Leu Glu Gly Thr Leu Ala Ala Asp Lys Thr Thr Leu Lys
210                 215                 220

Val Thr Cys Gly Thr Val Val Leu Ser Lys His Ile Pro Asn Ser Gly
225                 230                 235                 240

Glu Ile Thr Val Glu Leu Asn Asp Ser Asn Ser Thr Gln Ala Thr Lys
            245                 250                 255

Lys Thr Gly Lys Trp Asp Ser Asn Thr Ser Thr Leu Thr Ile Ser Val
            260                 265                 270

Asn Ser Lys Lys Thr Lys Asn Ile Val Phe Thr Lys Glu Asp Thr Ile
        275                 280                 285

Thr Val Gln Lys Tyr Asp Ser Ala Gly Thr Asn Leu Glu Gly Asn Ala
    290                 295                 300

Val Glu Ile Lys Thr Leu Asp Glu Leu Cys Asn Ala Leu Lys
305                 310                 315

<210> SEQ ID NO 100
<211> LENGTH: 1023
<212> TYPE: DNA
<213> ORGANISM: Artificial Sequence
<220> FEATURE:
<223> OTHER INFORMATION: Lip-S3D4-S4D1_nt

<400> SEQUENCE: 100
atgaaagcta ctaaactggt actgggcgcg gtaatcctgg gttctactct gctggcaggt      60
tgctcaagct tcaacgaaaa gggcaaactg tcagaaaaag tggtcacccg cgcttgtggc     120
acccgcctgg aatacaccga atcaaaaac  gacggctcgg gcaaagcgaa ggaagttctg     180
aaaggctttg ccctggaagg tacccctgacg gatggcggtg aaaccaaact gaccgtgacg    240
gaaggcaccg ttacgctgtc taaaaacatt agcaagtctg gtgaaatcac ggtcgcactg    300
aatgataccg aaaccacgcc ggctgacaaa agaccggcg  aatggaaaag tgacacctcc    360
acgctgacca tttcaaagaa ctcgcagaaa ccgaagcaac tggtcttcac caaagaatgc    420
acgatcaccg tgcagaacta taatcgtgcc ggtaatgctc tggaaggctc cccggctgaa    480
atcaaggacc tggcggaact gaaggcggca ctgaaaggca ctagtgacaa aaacaatggc    540
tctggtagca agagaaaaa  caaagatggc aagtactcat tcaacgctaa aggtgaactg    600
agcgaaaaaa cgatcctgcg tgcgaatggc acccgtctgg aatacaccga atcaaatcc     660
gatggtacgg gcaaagcaaa ggaagtcctg aaagattttg ctctggaagg tacccctggcg   720
gccgacaaaa ccacgctgaa ggtgacgtgc ggcaccgtgg ttctgagcaa acatattccg    780
aactctggtg aaatcaccgt tgaactgaac gatagcaatt ctacgcaggc aaccaaaaag    840
acgggcaaat gggacagtaa taccctccacg ctgaccattt cagtcaactc gaaaaagacc   900
aaaaatattg tgttcacgaa ggaagatacg atcaccgttc aaaaatatga ctccgcgggc    960
accaacctgg aaggcaatgc cgtcgaaatc aaaaccctgg atgaactgtg taatgctctg   1020
aag                                                                  1023

<210> SEQ ID NO 101
<211> LENGTH: 330
<212> TYPE: PRT
<213> ORGANISM: Artificial Sequence
<220> FEATURE:
<223> OTHER INFORMATION: Lip-S3D4-S4D1_His_aa
<220> FEATURE:
<221> NAME/KEY: LIPID
<222> LOCATION: (1)..(1)
<223> OTHER INFORMATION: LIPIDATION

<400> SEQUENCE: 101

Cys Ser Ser Phe Asn Glu Lys Gly Lys Leu Ser Glu Lys Val Val Thr
1               5                   10                  15

Arg Ala Cys Gly Thr Arg Leu Glu Tyr Thr Glu Ile Lys Asn Asp Gly
            20                  25                  30

Ser Gly Lys Ala Lys Glu Val Leu Lys Gly Phe Ala Leu Glu Gly Thr
        35                  40                  45

Leu Thr Asp Gly Gly Glu Thr Lys Leu Thr Val Thr Glu Gly Thr Val
50                  55                  60

Thr Leu Ser Lys Asn Ile Ser Lys Ser Gly Glu Ile Thr Val Ala Leu
65                  70                  75                  80

Asn Asp Thr Glu Thr Thr Pro Ala Asp Lys Lys Thr Gly Glu Trp Lys
                85                  90                  95

Ser Asp Thr Ser Thr Leu Thr Ile Ser Lys Asn Ser Gln Lys Pro Lys
            100                 105                 110

Gln Leu Val Phe Thr Lys Glu Cys Thr Ile Thr Val Gln Asn Tyr Asn
        115                 120                 125

Arg Ala Gly Asn Ala Leu Glu Gly Ser Pro Ala Glu Ile Lys Asp Leu
130                 135                 140

Ala Glu Leu Lys Ala Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Ala
                165                 170                 175

Lys Gly Glu Leu Ser Glu Lys Thr Ile Leu Arg Ala Asn Gly Thr Arg
            180                 185                 190

Leu Glu Tyr Thr Glu Ile Lys Ser Asp Gly Thr Gly Lys Ala Lys Glu
        195                 200                 205

Val Leu Lys Asp Phe Ala Leu Glu Gly Thr Leu Ala Ala Asp Lys Thr
210                 215                 220

Thr Leu Lys Val Thr Cys Gly Thr Val Val Leu Ser Lys His Ile Pro
225                 230                 235                 240

Asn Ser Gly Glu Ile Thr Val Glu Leu Asn Asp Ser Asn Ser Thr Gln
                245                 250                 255

Ala Thr Lys Lys Thr Gly Lys Trp Asp Ser Asn Thr Ser Thr Leu Thr
            260                 265                 270

Ile Ser Val Asn Ser Lys Lys Thr Lys Asn Ile Val Phe Thr Lys Glu
        275                 280                 285

Asp Thr Ile Thr Val Gln Lys Tyr Asp Ser Ala Gly Thr Asn Leu Glu
290                 295                 300

Gly Asn Ala Val Glu Ile Lys Thr Leu Asp Glu Leu Cys Asn Ala Leu
305                 310                 315                 320

Lys Gly Leu Glu His His His His His His
                325                 330

<210> SEQ ID NO 102
<211> LENGTH: 1050
<212> TYPE: DNA
<213> ORGANISM: Artificial Sequence
<220> FEATURE:
<223> OTHER INFORMATION: Lip-S3D4-S4D1_His_nt

<400> SEQUENCE: 102

```
atgaaagcta ctaaactggt actgggcgcg gtaatcctgg gttctactct gctggcaggt      60
tgctcaagct tcaacgaaaa gggcaaactg tcagaaaaag tggtcacccg cgcttgtggc     120
acccgcctgg aatacaccga aatcaaaaac gacggctcgg gcaaagcgaa ggaagttctg     180
aaaggctttg ccctggaagg taccctgacg gatggcggtg aaaccaaact gaccgtgacg     240
gaaggcaccg ttacgctgtc taaaaacatt agcaagtctg gtgaaatcac ggtcgcactg     300
aatgataccg aaaccacgcc ggctgacaaa aagaccggcg aatggaaaag tgacacctcc     360
acgctgacca tttcaaagaa ctcgcagaaa ccgaagcaac tggtcttcac caaagaatgc     420
acgatcaccg tgcagaacta taatcgtgcc ggtaatgctc tggaaggctc cccggctgaa     480
atcaaggacc tggcggaact gaaggcggca ctgaaaggca ctagtgacaa aaacaatggc     540
tctggtagca agagaaaaa caaagatggc aagtactcat tcaacgctaa aggtgaactg     600
agcgaaaaaa cgatcctgcg tgcgaatggc accgtctgg aatacaccga aatcaaatcc     660
gatggtacgg gcaaagcaaa ggaagtcctg aaagattttg ctctggaagg taccctggcg     720
gccgacaaaa ccacgctgaa ggtgacgtgc ggcaccgtgg ttctgagcaa acatattccg     780
aactctggtg aaatcaccgt tgaactgaac gatagcaatt ctacgcaggc aaccaaaaag     840
acgggcaaat gggacagtaa tacctccacg ctgaccattt cagtcaactc gaaaaagacc     900
aaaaatattg tgttcacgaa ggaagatacg atcaccgttc aaaaatatga ctccgcgggc     960
accaacctgg aaggcaatgc cgtcgaaatc aaaaccctgg atgaactgtg taatgctctg    1020
aagggtctcg agcaccacca ccaccaccac                                      1050
```

<210> SEQ ID NO 103
<211> LENGTH: 318
<212> TYPE: PRT
<213> ORGANISM: Artificial Sequence
<220> FEATURE:
<223> OTHER INFORMATION: S3D1-S4D4_aa

<400> SEQUENCE: 103

```
Phe Asn Glu Lys Gly Lys Leu Ser Glu Lys Val Val Thr Arg Ala Asn
1               5                   10                  15

Gly Thr Arg Leu Glu Tyr Thr Glu Ile Lys Asn Asp Gly Ser Gly Lys
            20                  25                  30

Ala Lys Glu Val Leu Lys Gly Phe Ala Leu Glu Gly Thr Leu Thr Asp
        35                  40                  45

Gly Gly Glu Thr Lys Leu Thr Val Thr Cys Gly Thr Val Thr Leu Ser
    50                  55                  60

Lys Asn Ile Ser Lys Ser Gly Glu Ile Thr Val Ala Leu Asn Asp Thr
65                  70                  75                  80

Glu Thr Thr Pro Ala Asp Lys Lys Thr Gly Glu Trp Lys Ser Asp Thr
                85                  90                  95

Ser Thr Leu Thr Ile Ser Lys Asn Ser Gln Lys Pro Lys Gln Leu Val
            100                 105                 110

Phe Thr Lys Glu Asn Thr Ile Thr Val Gln Asn Tyr Asn Arg Ala Gly
        115                 120                 125

Asn Ala Leu Glu Gly Ser Pro Ala Glu Ile Lys Asp Leu Ala Glu Leu
    130                 135                 140

Cys Ala Ala Leu Lys Gly Thr Ser Asp Lys Asn Asn Gly Ser Gly Ser
145                 150                 155                 160
```

```
Lys Glu Lys Asn Lys Asp Gly Lys Tyr Ser Phe Asn Ala Lys Gly Glu
                165                 170                 175
Leu Ser Glu Lys Thr Ile Leu Arg Ala Cys Gly Thr Arg Leu Glu Tyr
            180                 185                 190
Thr Glu Ile Lys Ser Asp Gly Thr Gly Lys Ala Lys Glu Val Leu Lys
        195                 200                 205
Asp Phe Ala Leu Glu Gly Thr Leu Ala Ala Asp Lys Thr Thr Leu Lys
    210                 215                 220
Val Thr Glu Gly Thr Val Val Leu Ser Lys His Ile Pro Asn Ser Gly
225                 230                 235                 240
Glu Ile Thr Val Glu Leu Asn Asp Ser Asn Ser Thr Gln Ala Thr Lys
                245                 250                 255
Lys Thr Gly Lys Trp Asp Ser Asn Thr Ser Thr Leu Thr Ile Ser Val
            260                 265                 270
Asn Ser Lys Lys Thr Lys Asn Ile Val Phe Thr Lys Glu Cys Thr Ile
        275                 280                 285
Thr Val Gln Lys Tyr Asp Ser Ala Gly Thr Asn Leu Glu Gly Asn Ala
    290                 295                 300
Val Glu Ile Lys Thr Leu Asp Glu Leu Lys Asn Ala Leu Lys
305                 310                 315
```

<210> SEQ ID NO 104
<211> LENGTH: 1023
<212> TYPE: DNA
<213> ORGANISM: Artificial Sequence
<220> FEATURE:
<223> OTHER INFORMATION: Lip-S3D1-S4D4_nt

<400> SEQUENCE: 104

```
atgaaagcta ctaaactggt actgggcgcg gtaatcctgg gttctactct gctggcaggt      60
tgctcaagct tcaacgaaaa gggcaaactg tcggaaaaag tggtcacccg cgcaaatggc     120
acccgcctgg aatacacgga aatcaaaaac gatggtagcg gcaaagcgaa ggaagttctg     180
aaaggctttg ccctggaagg taccctgacg gatgcggtg aaaccaaact gaccgtgacg     240
tgcggcaccg ttacgctgtc taaaaacatt agcaagtctg gtgaaatcac ggtcgcactg     300
aatgataccg aaaccacgcc ggctgacaaa aagaccggcg aatggaaaag tgacacctcc     360
acgctgacca tttcaaagaa ctcgcagaaa ccgaagcaac tggtcttcac caaagaaaac     420
acgatcaccg tgcagaacta taatcgtgcc ggtaatgctc tggaaggctc accggctgaa     480
atcaaggacc tggctgaact gtgtgcggca ctgaaaggca ctagtgacaa aacaatggc     540
tctggtagca agagaaaaa caagatggc aagtactcat tcaacgctaa aggtgaactg     600
tcggaaaaaa ccatcctgcg cgcctgtggc acccgcctgg aatacacgga aatcaagtcg     660
gacggcacgg gcaaagcaaa ggaagtcctg aaagattttg ctctggaagg taccctggcg     720
gccgacaaaa ccacgctgaa ggtgacggaa ggcaccgtgg ttctgagcaa acatattccg     780
aactctggtg aaatcaccgt tgaactgaac gatagcaatt ctacgcaggc gaccaaaaag     840
acgggcaaat gggacagtaa taccctccacg ctgaccattt cagtcaactc gaaaaagacc     900
aaaaatattg tgttcacgaa ggaatgcacg atcaccgttc aaaaatatga ttccgcaggt     960
accaacctgg aaggcaacgc tgtggaaatc aaaaccctgg acgaactgaa aaatgctctg    1020
aag                                                                  1023
```

<210> SEQ ID NO 105
<211> LENGTH: 330

```
<212> TYPE: PRT
<213> ORGANISM: Artificial Sequence
<220> FEATURE:
<223> OTHER INFORMATION: Lip-S3D1-S4D4_His_aa
<220> FEATURE:
<221> NAME/KEY: LIPID
<222> LOCATION: (1)..(1)
<223> OTHER INFORMATION: LIPIDATION

<400> SEQUENCE: 105
```

| | | | | | | | | | | | | | | |
|---|---|---|---|---|---|---|---|---|---|---|---|---|---|---|
| Cys | Ser | Ser | Phe | Asn | Glu | Lys | Gly | Lys | Leu | Ser | Glu | Lys | Val | Val | Thr |
| 1 | | | | 5 | | | | | 10 | | | | | 15 | |
| Arg | Ala | Asn | Gly | Thr | Arg | Leu | Glu | Tyr | Thr | Glu | Ile | Lys | Asn | Asp | Gly |
| | | | 20 | | | | | 25 | | | | | 30 | | |
| Ser | Gly | Lys | Ala | Lys | Glu | Val | Leu | Lys | Gly | Phe | Ala | Leu | Glu | Gly | Thr |
| | | 35 | | | | | 40 | | | | | 45 | | | |
| Leu | Thr | Asp | Gly | Gly | Glu | Thr | Lys | Leu | Thr | Val | Thr | Cys | Gly | Thr | Val |
| | 50 | | | | | 55 | | | | | 60 | | | | |
| Thr | Leu | Ser | Lys | Asn | Ile | Ser | Lys | Ser | Gly | Glu | Ile | Thr | Val | Ala | Leu |
| 65 | | | | | 70 | | | | | 75 | | | | | 80 |
| Asn | Asp | Thr | Glu | Thr | Thr | Pro | Ala | Asp | Lys | Lys | Thr | Gly | Glu | Trp | Lys |
| | | | | 85 | | | | | 90 | | | | | 95 | |
| Ser | Asp | Thr | Ser | Thr | Leu | Thr | Ile | Ser | Lys | Asn | Ser | Gln | Lys | Pro | Lys |
| | | | 100 | | | | | 105 | | | | | 110 | | |
| Gln | Leu | Val | Phe | Thr | Lys | Glu | Asn | Thr | Ile | Thr | Val | Gln | Asn | Tyr | Asn |
| | | | 115 | | | | | 120 | | | | | 125 | | |
| Arg | Ala | Gly | Asn | Ala | Leu | Glu | Gly | Ser | Pro | Ala | Glu | Ile | Lys | Asp | Leu |
| | 130 | | | | | 135 | | | | | 140 | | | | |
| Ala | Glu | Leu | Cys | Ala | Ala | Leu | Lys | Gly | Thr | Ser | Asp | Lys | Asn | Asn | Gly |
| 145 | | | | | 150 | | | | | 155 | | | | | 160 |
| Ser | Gly | Ser | Lys | Glu | Lys | Asn | Lys | Asp | Gly | Lys | Tyr | Ser | Phe | Asn | Ala |
| | | | | 165 | | | | | 170 | | | | | 175 | |
| Lys | Gly | Glu | Leu | Ser | Glu | Lys | Thr | Ile | Leu | Arg | Ala | Cys | Gly | Thr | Arg |
| | | | 180 | | | | | 185 | | | | | 190 | | |
| Leu | Glu | Tyr | Thr | Glu | Ile | Lys | Ser | Asp | Gly | Thr | Gly | Lys | Ala | Lys | Glu |
| | | | 195 | | | | | 200 | | | | | 205 | | |
| Val | Leu | Lys | Asp | Phe | Ala | Leu | Glu | Gly | Thr | Leu | Ala | Ala | Asp | Lys | Thr |
| | 210 | | | | | 215 | | | | | 220 | | | | |
| Thr | Leu | Lys | Val | Thr | Glu | Gly | Thr | Val | Val | Leu | Ser | Lys | His | Ile | Pro |
| 225 | | | | | 230 | | | | | 235 | | | | | 240 |
| Asn | Ser | Gly | Glu | Ile | Thr | Val | Glu | Leu | Asn | Asp | Ser | Asn | Ser | Thr | Gln |
| | | | | 245 | | | | | 250 | | | | | 255 | |
| Ala | Thr | Lys | Lys | Thr | Gly | Lys | Trp | Asp | Ser | Asn | Thr | Ser | Thr | Leu | Thr |
| | | | 260 | | | | | 265 | | | | | 270 | | |
| Ile | Ser | Val | Asn | Ser | Lys | Lys | Thr | Lys | Asn | Ile | Val | Phe | Thr | Lys | Glu |
| | | | 275 | | | | | 280 | | | | | 285 | | |
| Cys | Thr | Ile | Thr | Val | Gln | Lys | Tyr | Asp | Ser | Ala | Gly | Thr | Asn | Leu | Glu |
| | 290 | | | | | 295 | | | | | 300 | | | | |
| Gly | Asn | Ala | Val | Glu | Ile | Lys | Thr | Leu | Asp | Glu | Leu | Lys | Asn | Ala | Leu |
| 305 | | | | | 310 | | | | | 315 | | | | | 320 |
| Lys | Gly | Leu | Glu | His | His | His | His | His | His |
| | | | | 325 | | | | | 330 |

```
<210> SEQ ID NO 106
<211> LENGTH: 1050
<212> TYPE: DNA
<213> ORGANISM: Artificial Sequence
```

```
<220> FEATURE:
<223> OTHER INFORMATION: Lip-S3D1-S4D4_His_nt

<400> SEQUENCE: 106
atgaaagcta ctaaactggt actgggcgcg gtaatcctgg gttctactct gctggcaggt      60
tgctcaagct tcaacgaaaa gggcaaactg tcggaaaaag tggtcacccg cgcaaatggc     120
acccgcctgg aatacacgga atcaaaaac gatggtagcg gcaaagcgaa ggaagttctg      180
aaaggctttg ccctggaagg taccctgacg gatggcggtg aaaccaaact gaccgtgacg     240
tgcggcaccg ttacgctgtc taaaaacatt agcaagtctg gtgaaatcac ggtcgcactg     300
aatgataccg aaaccacgcc ggctgacaaa agaccggcg aatggaaaag tgacacctcc      360
acgctgacca tttcaaagaa ctcgcagaaa ccgaagcaac tggtcttcac caaagaaaac     420
acgatcaccg tgcagaacta taatcgtgcc ggtaatgctc tggaaggctc accggctgaa     480
atcaaggacc tggctgaact gtgtgcggca ctgaaaggca ctagtgacaa aacaatggc     540
tctggtagca agagaaaaa caagatggc aagtactcat tcaacgctaa aggtgaactg      600
tcggaaaaaa ccatcctgcg cgcctgtggc acccgcctgg aatacacgga atcaagtcg     660
gacggcacgg gcaaagcaaa ggaagtcctg aaagattttg ctctggaagg tacccctggcg    720
gccgacaaaa ccacgctgaa ggtgacggaa ggcaccgtgg ttctgagcaa acatattccg     780
aactctggtg aaatcaccgt tgaactgaac gatagcaatt ctacgcaggc gaccaaaaag    840
acgggcaaat gggacagtaa tacctccacg ctgaccattt cagtcaactc gaaaaagacc    900
aaaaatattg tgttcacgaa ggaatgcacg atcaccgttc aaaaatatga ttccgcaggt    960
accaacctgg aaggcaacgc tgtggaaatc aaaaccctgg acgaactgaa aaatgctctg   1020
aagggtctcg agcaccacca ccaccaccac                                     1050

<210> SEQ ID NO 107
<211> LENGTH: 318
<212> TYPE: PRT
<213> ORGANISM: Artificial Sequence
<220> FEATURE:
<223> OTHER INFORMATION: S5D4-S6D1_aa

<400> SEQUENCE: 107

Phe Asn Glu Lys Gly Glu Ile Ser Glu Lys Thr Ile Val Arg Ala Cys
1               5                   10                  15

Gly Thr Arg Leu Glu Tyr Thr Asp Ile Lys Ser Asp Lys Thr Gly Lys
                20                  25                  30

Ala Lys Glu Val Leu Lys Asp Phe Thr Leu Glu Gly Thr Leu Ala Ala
            35                  40                  45

Asp Gly Lys Thr Thr Leu Lys Val Thr Glu Gly Thr Val Thr Leu Ser
        50                  55                  60

Lys Asn Ile Ser Lys Ser Gly Glu Ile Thr Val Ala Leu Asp Asp Thr
65                  70                  75                  80

Asp Ser Ser Gly Asn Lys Lys Ser Gly Thr Trp Asp Ser Gly Thr Ser
                85                  90                  95

Thr Leu Thr Ile Ser Lys Asn Arg Thr Lys Thr Lys Gln Leu Val Phe
                100                 105                 110

Thr Lys Glu Cys Thr Ile Thr Val Gln Asn Tyr Asp Ser Ala Gly Thr
            115                 120                 125

Asn Leu Glu Gly Lys Ala Val Glu Ile Thr Thr Leu Lys Glu Leu Lys
        130                 135                 140

Asn Ala Leu Lys Gly Thr Ser Asp Lys Asn Asn Gly Ser Gly Ser Lys
```

```
                145                 150                 155                 160
Glu Lys Asn Lys Asp Gly Lys Tyr Ser Phe Asn Gly Lys Gly Glu Thr
                    165                 170                 175

Ser Glu Lys Thr Ile Val Arg Ala Asn Gly Thr Arg Leu Glu Tyr Thr
                180                 185                 190

Asp Ile Lys Ser Asp Gly Ser Gly Lys Ala Lys Glu Val Leu Lys Asp
                    195                 200                 205

Phe Thr Leu Glu Gly Thr Leu Ala Ala Asp Gly Lys Thr Thr Leu Lys
                210                 215                 220

Val Thr Cys Gly Thr Val Val Leu Ser Lys Asn Ile Leu Lys Ser Gly
225                 230                 235                 240

Glu Ile Thr Ala Ala Leu Asp Asp Ser Asp Thr Thr Arg Ala Thr Lys
                    245                 250                 255

Lys Thr Gly Lys Trp Asp Ser Lys Thr Ser Thr Leu Thr Ile Ser Val
                260                 265                 270

Asn Ser Gln Lys Thr Lys Asn Leu Val Phe Lys Glu Asp Thr Ile
                    275                 280                 285

Thr Val Gln Arg Tyr Asp Ser Ala Gly Thr Asn Leu Glu Gly Lys Ala
                290                 295                 300

Val Glu Ile Thr Thr Leu Lys Glu Leu Cys Asn Ala Leu Lys
305                 310                 315
```

<210> SEQ ID NO 108
<211> LENGTH: 1023
<212> TYPE: DNA
<213> ORGANISM: Artificial Sequence
<220> FEATURE:
<223> OTHER INFORMATION: Lip-S5D4-S6D1_nt

<400> SEQUENCE: 108

| | | |
|---|---|---|
| atgaaagcta ctaaactggt actgggcgcg gtaatcctgg ttctactct gctggcaggt | 60 |
| tgctcaagct tcaacgaaaa gggcgaaatc agtgaaaaaa ccattgtgcg tgcgtgtggc | 120 |
| acccgtctgg aatataccga catcaagagc gataaaacgg taaagcgaa ggaagttctg | 180 |
| aaagattta cgctggaagg taccctggca gcagacggta aaaccacgct gaaggtgacc | 240 |
| gaaggtaccg ttacgctgtc caaaaacatt agtaagtccg gcgaaatcac ggtcgccctg | 300 |
| gatgacaccg atagctctgg caacaaaaag agcggtacct gggactcagg cacctcgacg | 360 |
| ctgaccattt ctaaaaatcg tacgaaaacc aagcagctgg tcttcacgaa agaatgcacg | 420 |
| atcaccgtgc aaaactatga tagcgcaggt accaatctgg aaggcaaagc tgtggaaatt | 480 |
| accacgctga agaactgaa gaatgctctg aaaggtacta gtgacaaaaa caatggctct | 540 |
| ggtagcaaag agaaaaacaa agatggcaag tactcattca cggcaaagg tgaaacgagc | 600 |
| gaaaagacca tcgtgcgtgc gaacggtacc cgcctggaat atacggacat taaatcggac | 660 |
| ggcagcggca agcaaagga agtcctgaaa gattttacgc tggaaggtac cctggcagca | 720 |
| gacggtaaaa ccacgctgaa ggtgacgtgc ggcaccgtgg ttctgtcaaa aacattctg | 780 |
| aagtcgggtg aaatcaccgc agctctggat gacagcgata ccacgcgtgc tacgaaaaag | 840 |
| accggtaaat gggatagcaa gacctctacg ctgaccatta gtgtcaactc ccagaaaacg | 900 |
| aagaatctgg tgttcaccaa agaagatacg atcaccgttc aacgctatga cagtgcgggc | 960 |
| accaacctgg aaggcaaagc cgttgaaatt accacgctga agaactgtg taatgctctg | 1020 |
| aaa | 1023 |

```
<210> SEQ ID NO 109
<211> LENGTH: 330
<212> TYPE: PRT
<213> ORGANISM: Artificial Sequence
<220> FEATURE:
<223> OTHER INFORMATION: Lip-S5D4-S6D1_His_aa
<220> FEATURE:
<221> NAME/KEY: LIPID
<222> LOCATION: (1)..(1)
<223> OTHER INFORMATION: LIPIDATION

<400> SEQUENCE: 109

Cys Ser Ser Phe Asn Glu Lys Gly Glu Ile Ser Glu Lys Thr Ile Val
1               5                   10                  15

Arg Ala Cys Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Glu Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Trp Asp Ser
                85                  90                  95

Gly Thr Ser Thr Leu Thr Ile Ser Lys Asn Arg Thr Lys Thr Lys Gln
            100                 105                 110

Leu Val Phe Thr Lys Glu Cys Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Asn Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Cys Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Asp Thr Ile Thr Val Gln Arg Tyr Asp Ser Ala Gly Thr Asn Leu Glu
    290                 295                 300

Gly Lys Ala Val Glu Ile Thr Thr Leu Lys Glu Leu Cys Asn Ala Leu
305                 310                 315                 320

Lys Gly Leu Glu His His His His His His
                325                 330

<210> SEQ ID NO 110
<211> LENGTH: 1050
```

<212> TYPE: DNA
<213> ORGANISM: Artificial Sequence
<220> FEATURE:
<223> OTHER INFORMATION: Lip-S5D4-S6D1_His_nt

<400> SEQUENCE: 110

```
atgaaagcta ctaaactggt actgggcgcg gtaatcctgg gttctactct gctggcaggt      60
tgctcaagct tcaacgaaaa gggcgaaatc agtgaaaaaa ccattgtgcg tgcgtgtggc     120
acccgtctgg aatataccga catcaagagc gataaaacgg gtaaagcgaa ggaagttctg     180
aaagatttta cgctggaagg taccctggca gcagacggta aaaccacgct gaaggtgacc     240
gaaggtaccg ttacgctgtc caaaaacatt agtaagtccg gcgaaatcac ggtcgccctg     300
gatgacaccg atagctctgg caacaaaaag agcggtacct gggactcagg cacctcgacg     360
ctgaccattt ctaaaaatcg tacgaaaacc aagcagctgg tcttcacgaa gaatgcacg     420
atcaccgtgc aaaactatga tagcgcaggt accaatctgg aaggcaaagc tgtggaaatt     480
accacgctga agaactgaa gaatgctctg aaaggtacta gtgacaaaaa caatggctct     540
ggtagcaaag agaaaaacaa agatggcaag tactcattca acggcaaagg tgaaacgagc     600
gaaaagacca tcgtgcgtgc gaacggtacc cgcctggaat atacggacat aaatcggac     660
ggcagcggca aagcaaagga agtcctgaaa gattttacgc tggaaggtac cctggcagca     720
gacggtaaaa ccacgctgaa ggtgacgtgc ggcaccgtgg ttctgtcaaa aacattctg     780
aagtcgggtg aaatcaccgc agctctggat gacagcgata ccacgcgtgc tacgaaaaag     840
accggtaaat gggatagcaa gacctctacg ctgaccatta gtgtcaactc ccagaaaacg     900
aagaatctgg tgttcaccaa agaagatacg atcaccgttc aacgctatga cagtgcgggc     960
accaacctgg aaggcaaagc cgttgaaatt accacgctga agaactgtg taatgctctg    1020
aaaggtctcg agcaccacca ccaccaccac                                     1050
```

<210> SEQ ID NO 111
<211> LENGTH: 318
<212> TYPE: PRT
<213> ORGANISM: Artificial Sequence
<220> FEATURE:
<223> OTHER INFORMATION: S5D1-S6D4_aa

<400> SEQUENCE: 111

```
Phe Asn Glu Lys Gly Glu Ile Ser Glu Lys Thr Ile Val Arg Ala Asn
1               5                   10                  15

Gly Thr Arg Leu Glu Tyr Thr Asp Ile Lys Ser Asp Lys Thr Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Cys Gly Thr Val Thr Leu Ser
    50                  55                  60

Lys Asn Ile Ser Lys Ser Gly Glu Ile Thr Val Ala Leu Asp Asp Thr
65                  70                  75                  80

Asp Ser Ser Gly Asn Lys Lys Ser Gly Thr Trp Asp Ser Gly Thr Ser
                85                  90                  95

Thr Leu Thr Ile Ser Lys Asn Arg Thr Lys Thr Lys Gln Leu Val Phe
            100                 105                 110

Thr Lys Glu Asp Thr Ile Thr Val Gln Asn Tyr Asp Ser Ala Gly Thr
        115                 120                 125

Asn Leu Glu Gly Lys Ala Val Glu Ile Thr Thr Leu Lys Glu Leu Cys
    130                 135                 140
```

```
Asn Ala Leu Lys Gly Thr Ser Asp Lys Asn Gly Ser Gly Ser Lys
145                 150                 155                 160

Glu Lys Asn Lys Asp Gly Lys Tyr Ser Phe Asn Gly Lys Gly Glu Thr
                165                 170                 175

Ser Glu Lys Thr Ile Val Arg Ala Cys Gly Thr Arg Leu Glu Tyr Thr
            180                 185                 190

Asp Ile Lys Ser Asp Gly Ser Gly Lys Ala Lys Glu Val Leu Lys Asp
                195                 200                 205

Phe Thr Leu Glu Gly Thr Leu Ala Ala Asp Gly Lys Thr Thr Leu Lys
            210                 215                 220

Val Thr Glu Gly Thr Val Val Leu Ser Lys Asn Ile Leu Lys Ser Gly
225                 230                 235                 240

Glu Ile Thr Ala Ala Leu Asp Asp Ser Asp Thr Thr Arg Ala Thr Lys
                245                 250                 255

Lys Thr Gly Lys Trp Asp Ser Lys Thr Ser Thr Leu Thr Ile Ser Val
                260                 265                 270

Asn Ser Gln Lys Thr Lys Asn Leu Val Phe Thr Lys Glu Cys Thr Ile
                275                 280                 285

Thr Val Gln Arg Tyr Asp Ser Ala Gly Thr Asn Leu Glu Gly Lys Ala
                290                 295                 300

Val Glu Ile Thr Thr Leu Lys Glu Leu Lys Asn Ala Leu Lys
305                 310                 315
```

<210> SEQ ID NO 112
<211> LENGTH: 1023
<212> TYPE: DNA
<213> ORGANISM: Artificial Sequence
<220> FEATURE:
<223> OTHER INFORMATION: Lip-S5D1-S6D4_nt

<400> SEQUENCE: 112

```
atgaaagcta ctaaactggt actgggcgcg gtaatcctgg gttctactct gctggcaggt      60
tgctcaagct tcaacgaaaa gggcgaaatc tcagaaaaaa ccatcgtccg cgctaacggc     120
acccgcctgg aatacaccga catcaaatca gacaagaccg gtaaagcgaa ggaagttctg     180
aaagatttta cgctggaagg taccctggca gcagacggta aaaccacgct gaaggtgacc     240
tgcggtaccg ttacgctgtc caaaaacatt agtaagtccg gcgaaatcac ggtcgccctg     300
gatgacaccg atagctctgg caacaaaaag agcggtacct gggattcagg cacctcgacg     360
ctgaccattt ctaaaaatcg tacgaaaacc aagcagctgg tcttcacgaa agaagatacg     420
atcaccgtgc aaaactatga cagcgcaggt accaatctgg aaggcaaagc tgtggaaatt     480
accacgctga agaactgtgt aatgctctg aaaggtacta gtgacaaaaa caatggctct     540
ggtagcaaag agaaaaacaa agatggcaag tactcattca acggcaaagg tgaaacgagt     600
gaaaaaacga ttgttcgcgc ctgtggcacc cgcctggaat acacggatat caagtcggat     660
ggttcgggca agcaaaggaa gtcctgaaaa gattttacgc tggaaggtac cctggcagca     720
gacggtaaaa ccacgctgaa ggtgacggaa ggcaccgtgg ttctgtcaaa aacattctg      780
aagtcgggtg aaatcaccgc agctctggat gacagcgata ccacgcgtgc tacgaaaaag     840
accggtaaat gggacagcaa gacctctacg ctgaccatta gtgtcaactc ccagaaaacg     900
aagaatctgg tgttcaccaa gaatgcacg atcaccgttc aacgctatga tagtgcgggc     960
accaacctgg aaggcaaagc cgttgaaatt accacgctga agaactgaa gaatgctctg    1020
aaa                                                                  1023
```

```
<210> SEQ ID NO 113
<211> LENGTH: 330
<212> TYPE: PRT
<213> ORGANISM: Artificial Sequence
<220> FEATURE:
<223> OTHER INFORMATION: Lip-S5D1-S6D4_His_aa
<220> FEATURE:
<221> NAME/KEY: LIPID
<222> LOCATION: (1)..(1)
<223> OTHER INFORMATION: LIPIDATION

<400> SEQUENCE: 113

Cys Ser Ser Phe Asn Glu Lys Gly Glu Ile Ser Glu Lys Thr Ile Val
1               5                   10                  15

Arg Ala Asn Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
            100                 105                 110

Leu Val Phe Thr Lys Glu Asp Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Cys Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Glu Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Cys Thr Ile Thr Val Gln Arg Tyr Asp Ser Ala Gly Thr Asn Leu Glu
    290                 295                 300

Gly Lys Ala Val Glu Ile Thr Thr Leu Lys Glu Leu Lys Asn Ala Leu
305                 310                 315                 320

Lys Gly Leu Glu His His His His His His
                325                 330
```

<210> SEQ ID NO 114
<211> LENGTH: 1050
<212> TYPE: DNA
<213> ORGANISM: Artificial Sequence
<220> FEATURE:
<223> OTHER INFORMATION: Lip-S5D1-S6D4_His_nt

<400> SEQUENCE: 114

```
atgaaagcta ctaaactggt actgggcgcg gtaatcctgg gttctactct gctggcaggt      60
tgctcaagct tcaacgaaaa gggcgaaatc tcagaaaaaa ccatcgtccg cgctaacggc     120
acccgcctgg aatacaccga catcaaatca gacaagaccg gtaaagcgaa ggaagttctg     180
aaagatttta cgctggaagg taccctggca gcagacggta aaaccacgct gaaggtgacc     240
tgcggtaccg ttacgctgtc caaaaacatt agtaagtccg gcgaaatcac ggtcgccctg     300
gatgacaccg atagctctgg caacaaaaag agcggtacct gggattcagg cacctcgacg     360
ctgaccattt ctaaaaatcg tacgaaaacc aagcagctgg tcttcacgaa agaagatacg     420
atcaccgtgc aaaactatga cagcgcaggt accaatctgg aaggcaaagc tgtggaaatt     480
accacgctga agaactgtg taatgctctg aaaggtacta gtgacaaaaa caatggctct     540
ggtagcaaag agaaaaacaa agatggcaag tactcattca cggcaaagg tgaaacgagt     600
gaaaaaacga ttgttcgcgc ctgtggcacc cgcctggaat acacggatat caagtcggat     660
ggttcgggca agcaaagga agtcctgaaa gattttacgc tggaaggtac cctggcagca     720
gacggtaaaa ccacgctgaa ggtgacggaa ggcaccgtgg ttctgtcaaa aacattctg     780
aagtcgggtg aaatcaccgc agctctggat gacagcgata ccacgcgtgc tacgaaaaag     840
accggtaaat gggacagcaa gacctctacg ctgaccatta gtgtcaactc ccagaaaacg     900
aagaatctgg tgttcaccaa gaatgcacg atcaccgttc aacgctatga tagtgcgggc     960
accaacctgg aaggcaaagc cgttgaaatt accacgctga agaactgaa gaatgctctg    1020
aaaggtctcg agcaccacca ccaccaccac                                    1050
```

<210> SEQ ID NO 115
<211> LENGTH: 317
<212> TYPE: PRT
<213> ORGANISM: Artificial Sequence
<220> FEATURE:
<223> OTHER INFORMATION: S2D4-S1D1_aa

<400> SEQUENCE: 115

```
Phe Asn Glu Lys Gly Glu Leu Ser Ala Lys Thr Met Thr Arg Glu Cys
1               5                  10                  15

Gly Thr Lys Leu Glu Tyr Thr Glu Met Lys Ser Asp Gly Thr Gly Lys
            20                  25                  30

Ala Lys Glu Val Leu Lys Asn Phe Thr Leu Glu Gly Lys Val Ala Asn
        35                  40                  45

Asp Lys Val Thr Leu Glu Val Lys Glu Gly Thr Val Thr Leu Ser Lys
    50                  55                  60

Glu Ile Ala Lys Ser Gly Glu Val Thr Val Ala Leu Asn Asp Thr Asn
65                  70                  75                  80

Thr Thr Gln Ala Thr Lys Lys Thr Gly Ala Trp Asp Ser Lys Thr Ser
                85                  90                  95

Thr Leu Thr Ile Ser Val Asn Ser Lys Lys Thr Thr Gln Leu Val Phe
            100                 105                 110

Thr Lys Gln Cys Thr Ile Thr Val Gln Lys Tyr Asp Ser Ala Gly Thr
        115                 120                 125
```

Asn Leu Glu Gly Thr Ala Val Glu Ile Lys Thr Leu Asp Glu Leu Lys
130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Glu Lys Gly Glu Val
                165                 170                 175

Ser Glu Lys Ile Ile Thr Arg Ala Asp Gly Thr Arg Leu Glu Tyr Thr
                180                 185                 190

Gly Ile Lys Ser Asp Gly Ser Gly Lys Ala Lys Glu Val Leu Lys Asn
                195                 200                 205

Phe Thr Leu Glu Gly Lys Val Ala Asn Asp Lys Thr Thr Leu Val Val
210                 215                 220

Lys Cys Gly Thr Val Thr Leu Ser Lys Asn Ile Ser Lys Ser Gly Glu
225                 230                 235                 240

Val Ser Val Glu Leu Asn Asp Thr Asp Ser Ser Ala Ala Thr Lys Lys
                245                 250                 255

Thr Ala Ala Trp Asn Ser Gly Thr Ser Thr Leu Thr Ile Thr Val Asn
                260                 265                 270

Ser Lys Lys Thr Lys Asp Leu Val Phe Thr Lys Glu Asn Thr Ile Thr
                275                 280                 285

Val Gln Gln Tyr Asp Ser Asn Gly Thr Lys Leu Glu Gly Ser Ala Val
                290                 295                 300

Glu Ile Thr Lys Leu Asp Glu Ile Cys Asn Ala Leu Lys
305                 310                 315

<210> SEQ ID NO 116
<211> LENGTH: 1020
<212> TYPE: DNA
<213> ORGANISM: Artificial Sequence
<220> FEATURE:
<223> OTHER INFORMATION: Lip-S2D4-S1D1_nt

<400> SEQUENCE: 116
atgaaagcta ctaaactggt actgggcgcg gtaatcctgg ttctactct gctggcaggt    60 tgctcaagct tcaacgaaaa aggcgaactg tcggcgaaaa cgatgacgcg tgaatgcggc    120
accaaactgg aatatacgga atgaaaagc gatggcaccg gtaaagcgaa agaagttctg    180
aaaaacttta ccctggaagg caaagtcgcc aatgacaaag tcaccctgga agtgaaagaa    240
ggcaccgtta cgctgtcaaa agaaattgca aaatcgggtg aagtgaccgt tgctctgaac    300
gatacgaata ccacgcaagc gaccaagaaa accggcgcct gggacagcaa aacctctacg    360
ctgaccatta gtgttaacag caagaaaacc acgcagctgg tcttcaccaa caatgtacg    420 atcaccgtgc agaaatacga tagtgcgggt accaacctgg aaggcaccgc tgttgaaatc    480
aaaaccctgg acgaactgaa aacgccctg aaaggcacta gtgacaaaaa caatggctct    540
ggtagcaaag agaaaacaa agatggcaag tactcattca cgaaaaagg cgaagtcagc    600 gaaaaaatca ttacccgcgc agacggcacc cgcctggaat acaccggcat caatcggac    660 ggcagcggca aagcgaaaga agttctgaaa aactttaccc tggaaggcaa agtcgcaaat    720
gataaaacca ccctggtggt gaaatgcggc accgttacgc tgagcaaaaa cattagtaaa    780
tccggtgaag tctctgtgga actgaatgat accgacagct ctgcggccac caagaaaacc    840
gcagcttgga actcaggcac ctcgacgctg accattacgg ttaatagcaa gaaaaccaaa    900
gatctggtct tcacgaaaga aaacaccatc acggtgcagc aatatgacag caatggtacc    960
aaactggaag ctccgctgt ggaaatcacg aaactggatg aaatctgtaa tgcactgaaa    1020

```
<210> SEQ ID NO 117
<211> LENGTH: 329
<212> TYPE: PRT
<213> ORGANISM: Artificial Sequence
<220> FEATURE:
<223> OTHER INFORMATION: Lip-S2D4-S1D1_His_aa
<220> FEATURE:
<221> NAME/KEY: LIPID
<222> LOCATION: (1)..(1)
<223> OTHER INFORMATION: LIPIDATION

<400> SEQUENCE: 117

Cys Ser Ser Phe Asn Glu Lys Gly Glu Leu Ser Ala Lys Thr Met Thr
1               5                   10                  15

Arg Glu Cys Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45

Val Ala Asn Asp Lys Val Thr Leu Glu Val Lys Glu Gly Thr Val Thr
50                  55                  60

Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
            100                 105                 110

Leu Val Phe Thr Lys Gln Cys Thr Ile Thr Val Gln Lys Tyr Asp Ser
        115                 120                 125

Ala Gly Thr Asn Leu Glu Gly Thr Ala Val Glu Ile Lys Thr Leu Asp
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Asp Gly Thr Arg Leu
            180                 185                 190

Glu Tyr Thr Gly Ile Lys Ser Asp Gly Ser Gly Lys Ala Lys Glu Val
        195                 200                 205

Leu Lys Asn Phe Thr Leu Glu Gly Lys Val Ala Asn Asp Lys Thr Thr
    210                 215                 220

Leu Val Val Lys Cys Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
            260                 265                 270

Thr Val Asn Ser Lys Lys Thr Lys Asp Leu Val Phe Thr Lys Glu Asn
        275                 280                 285

Thr Ile Thr Val Gln Gln Tyr Asp Ser Asn Gly Thr Lys Leu Glu Gly
    290                 295                 300

Ser Ala Val Glu Ile Thr Lys Leu Asp Glu Ile Cys Asn Ala Leu Lys
305                 310                 315                 320

Gly Leu Glu His His His His His
            325
```

<210> SEQ ID NO 118
<211> LENGTH: 1047
<212> TYPE: DNA
<213> ORGANISM: Artificial Sequence
<220> FEATURE:
<223> OTHER INFORMATION: Lip-S2D4-S1D1_His_nt

<400> SEQUENCE: 118

```
atgaaagcta ctaaactggt actgggcgcg gtaatcctgg gttctactct gctggcaggt      60
tgctcaagct tcaacgaaaa aggcgaactg tcggcgaaaa cgatgacgcg tgaatgcggc     120
accaaactgg aatatacgga atgaaaagc gatggcaccg gtaaagcgaa agaagttctg      180
aaaaacttta ccctggaagg caaagtcgcc aatgacaaag tcaccctgga agtgaaagaa     240
ggcaccgtta cgctgtcaaa agaaattgca aaatcgggtg aagtgaccgt tgctctgaac     300
gatacgaata ccacgcaagc gaccaagaaa accggcgcct gggacagcaa aacctctacg     360
ctgaccatta gtgttaacag caagaaaacc acgcagctgg tcttcaccaa caatgtacg      420
atcaccgtgc agaaatacga tagtgcgggt accaacctgg aaggcaccgc tgttgaaatc     480
aaaaccctgg acgaactgaa aaacgccctg aaaggcacta gtgacaaaaa caatggctct     540
ggtagcaaag agaaaaacaa agatggcaag tactcattca cgaaaaagg cgaagtcagc      600
gaaaaaatca ttacccgcgc agacggcacc cgcctggaat acaccggcat caaatcggac     660
ggcagcggca agcgaaaga agttctgaaa aactttaccc tggaaggcaa agtcgcaaat      720
gataaaacca ccctggtggt gaaatgcggc accgttacgc tgagcaaaaa cattagtaaa     780
tccggtgaag tctctgtgga actgaatgat accgacagct ctgcggccac caagaaaacc     840
gcagcttgga actcaggcac ctcgacgctg accattacgg ttaatagcaa gaaaaccaaa     900
gatctggtct tcacgaaaga aaacaccatc acggtgcagc aatatgacag caatggtacc     960
aaactggaag ctccgctgt ggaaatcacg aaactggatg aaatctgtaa tgcactgaaa     1020
ggtctcgagc accaccacca ccaccac                                        1047
```

<210> SEQ ID NO 119
<211> LENGTH: 317
<212> TYPE: PRT
<213> ORGANISM: Artificial Sequence
<220> FEATURE:
<223> OTHER INFORMATION: S2D1-S1D4_aa

<400> SEQUENCE: 119

```
Phe Asn Glu Lys Gly Glu Leu Ser Ala Lys Thr Met Thr Arg Glu Asn
  1               5                  10                  15

Gly Thr Lys Leu Glu Tyr Thr Glu Met Lys Ser Asp Gly Thr Gly Lys
             20                  25                  30

Ala Lys Glu Val Leu Lys Asn Phe Thr Leu Glu Gly Lys Val Ala Asn
         35                  40                  45

Asp Lys Val Thr Leu Glu Val Lys Cys Gly Thr Val Thr Leu Ser Lys
     50                  55                  60

Glu Ile Ala Lys Ser Gly Glu Val Thr Val Ala Leu Asn Asp Thr Asn
 65                  70                  75                  80

Thr Thr Gln Ala Thr Lys Lys Thr Gly Ala Trp Asp Ser Lys Thr Ser
                 85                  90                  95

Thr Leu Thr Ile Ser Val Asn Ser Lys Lys Thr Thr Gln Leu Val Phe
            100                 105                 110

Thr Lys Gln Asp Thr Ile Thr Val Gln Lys Tyr Asp Ser Ala Gly Thr
        115                 120                 125
```

```
Asn Leu Glu Gly Thr Ala Val Glu Ile Lys Thr Leu Asp Glu Leu Cys
    130                 135                 140
Asn Ala Leu Lys Gly Thr Ser Asp Lys Asn Asn Gly Ser Gly Ser Lys
145                 150                 155                 160
Glu Lys Asn Lys Asp Gly Lys Tyr Ser Phe Asn Glu Lys Gly Glu Val
                165                 170                 175
Ser Glu Lys Ile Ile Thr Arg Ala Cys Gly Thr Arg Leu Glu Tyr Thr
            180                 185                 190
Gly Ile Lys Ser Asp Gly Ser Gly Lys Ala Lys Glu Val Leu Lys Asn
        195                 200                 205
Phe Thr Leu Glu Gly Lys Val Ala Asn Asp Lys Thr Thr Leu Val Val
    210                 215                 220
Lys Glu Gly Thr Val Thr Leu Ser Lys Asn Ile Ser Lys Ser Gly Glu
225                 230                 235                 240
Val Ser Val Glu Leu Asn Asp Thr Asp Ser Ser Ala Ala Thr Lys Lys
                245                 250                 255
Thr Ala Ala Trp Asn Ser Gly Thr Ser Thr Leu Thr Ile Thr Val Asn
            260                 265                 270
Ser Lys Lys Thr Lys Asp Leu Val Phe Thr Lys Glu Cys Thr Ile Thr
        275                 280                 285
Val Gln Gln Tyr Asp Ser Asn Gly Thr Lys Leu Glu Gly Ser Ala Val
    290                 295                 300
Glu Ile Thr Lys Leu Asp Glu Ile Lys Asn Ala Leu Lys
305                 310                 315
```

<210> SEQ ID NO 120
<211> LENGTH: 1020
<212> TYPE: DNA
<213> ORGANISM: Artificial Sequence
<220> FEATURE:
<223> OTHER INFORMATION: Lip-S2D1-S1D4_nt

<400> SEQUENCE: 120

```
atgaaagcta ctaaactggt actgggcgcg gtaatcctgg ttctactct gctggcaggt      60
tgctcaagct tcaacgaaaa aggcgaactg tcggcgaaaa cgatgacgcg tgaaaacggc    120
accaaactgg aatatacgga atgaaaagc gatggcaccg gtaaagcgaa agaagttctg    180
aaaaacttta ccctggaagg caaagtcgcc aatgacaaag tcaccctgga agtgaaatgc    240
ggcaccgtta cgctgtcaaa agaaattgca aaatcgggtg aagtgaccgt tgctctgaac    300
gatacgaata ccacgcaagc gaccaagaaa accggcgcct gggacagcaa aacctctacg    360
ctgaccatta gtgttaatag caagaaaacc acgcagctgg tcttcaccaa acaagatacg    420
atcaccgtgc agaaatacga cagtgcgggt accaacctgg aaggcacggc tgttgaaatc    480
aaaaccctgg acgaactgtg taacgccctg aaaggcacta gtgacaaaaa caatggctct    540
ggtagcaaag agaaaacaa agatggcaag tactcattca cgaaaaaggg cgaagtctcg    600
gaaaaaatca ttacccgtgc ttgcggcacc cgtctggaat acaccggcat aaatcggat    660
ggcagcggca aagcgaagga agttctgaaa aactttaccc tggaaggcaa agtcgcaaat    720
gataagacca ccctggtggt gaagaaggc accgttacgc tgagcaaaaa cattagtaag    780
tccggtgaag tctctgtgga actgaatgat accgacagct ctgcggccac caaaaagacg    840
gcagcttgga actcaggcac ctcgacgctg accattacgg ttaattccaa aaagaccaaa    900
gatctggtct tcacgaaaga atgcaccatc acggtgcagc aatatgacag caacggtacc    960
aaactggaag gctctgcggt ggaaatcacg aaactggatg aaatcaaaaa tgcactgaaa  1020
```

<210> SEQ ID NO 121
<211> LENGTH: 329
<212> TYPE: PRT
<213> ORGANISM: Artificial Sequence
<220> FEATURE:
<223> OTHER INFORMATION: Lip-S2D1-S1D4_His_aa
<220> FEATURE:
<221> NAME/KEY: LIPID
<222> LOCATION: (1)..(1)
<223> OTHER INFORMATION: LIPIDATION

<400> SEQUENCE: 121

Cys Ser Ser Phe Asn Glu Lys Gly Glu Leu Ala Lys Thr Met Thr
1               5                   10                  15

Arg Glu Asn Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45

Val Ala Asn Asp Lys Val Thr Leu Glu Val Lys Cys Gly Thr Val Thr
50                  55                  60

Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
            100                 105                 110

Leu Val Phe Thr Lys Gln Asp Thr Ile Thr Val Gln Lys Tyr Asp Ser
        115                 120                 125

Ala Gly Thr Asn Leu Glu Gly Thr Ala Val Glu Ile Lys Thr Leu Asp
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Cys Gly Thr Arg Leu
            180                 185                 190

Glu Tyr Thr Gly Ile Lys Ser Asp Gly Ser Gly Lys Ala Lys Glu Val
        195                 200                 205

Leu Lys Asn Phe Thr Leu Glu Gly Lys Val Ala Asn Asp Lys Thr Thr
    210                 215                 220

Leu Val Val Lys Glu Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
            260                 265                 270

Thr Val Asn Ser Lys Lys Thr Lys Asp Leu Val Phe Thr Lys Glu Cys
        275                 280                 285

Thr Ile Thr Val Gln Gln Tyr Asp Ser Asn Gly Thr Lys Leu Glu Gly
    290                 295                 300

Ser Ala Val Glu Ile Thr Lys Leu Asp Glu Ile Lys Asn Ala Leu Lys
305                 310                 315                 320

Gly Leu Glu His His His His His
            325

<210> SEQ ID NO 122
<211> LENGTH: 1047
<212> TYPE: DNA
<213> ORGANISM: Artificial Sequence
<220> FEATURE:
<223> OTHER INFORMATION: Lip-S2D1-S1D4_His_nt

<400> SEQUENCE: 122

```
atgaaagcta ctaaactggt actgggcgcg gtaatcctgg gttctactct gctggcaggt      60
tgctcaagct tcaacgaaaa aggcgaactg tcggcgaaaa cgatgacgcg tgaaaacggc     120
accaaactgg aatatacgga atgaaaagc gatggcaccg gtaaagcgaa agaagttctg     180
aaaaacttta ccctggaagg caaagtcgcc aatgacaaag tcaccctgga agtgaaatgc     240
ggcaccgtta cgctgtcaaa agaaattgca aaatcgggtg aagtgaccgt tgctctgaac     300
gatacgaata ccacgcaagc gaccaagaaa accggcgcct gggacagcaa aacctctacg     360
ctgaccatta gtgttaatag caagaaaacc acgcagctgg tcttcaccaa caagatacg     420
atcaccgtgc agaaatacga cagtgcgggt accaacctgg aaggcacggc tgttgaaatc     480
aaaacccctgg acgaactgtg taacgccctg aaaggcacta gtgacaaaaa caatggctct     540
ggtagcaaag agaaaaacaa agatggcaag tactcattca cgaaaaagg cgaagtctcg     600
gaaaaaatca ttacccgtgc ttgcggcacc cgtctggaat acaccggcat taaatcggat     660
ggcagcggca aagcgaagga agttctgaaa aactttaccc tggaaggcaa agtcgcaaat     720
gataagacca ccctggtggt gaaagaaggc accgttacgc tgagcaaaaa cattagtaag     780
tccggtgaag tctctgtgga actgaatgat accgacagct ctgcggccac caaaaagacg     840
gcagcttgga actcaggcac ctcgacgctg accattacgg ttaattccaa aaagaccaaa     900
gatctggtct tcacgaaaga atgcaccatc acggtgcagc aatatgacag caacggtacc     960
aaactggaag ctctgcggt ggaaatcacg aaactggatg aaatcaaaaa tgcactgaaa    1020
ggtctcgagc accaccacca ccaccac                                         1047
```

<210> SEQ ID NO 123
<211> LENGTH: 318
<212> TYPE: PRT
<213> ORGANISM: Artificial Sequence
<220> FEATURE:
<223> OTHER INFORMATION: S4D4-S3D1_aa

<400> SEQUENCE: 123

```
Phe Asn Ala Lys Gly Glu Leu Ser Glu Lys Thr Ile Leu Arg Ala Cys
1               5                   10                  15

Gly Thr Arg Leu Glu Tyr Thr Glu Ile Lys Ser Asp Gly Thr Gly Lys
            20                  25                  30

Ala Lys Glu Val Leu Lys Asp Phe Ala Leu Glu Gly Thr Leu Ala Ala
        35                  40                  45

Asp Lys Thr Thr Leu Lys Val Thr Glu Gly Thr Val Val Leu Ser Lys
    50                  55                  60

His Ile Pro Asn Ser Gly Glu Ile Thr Val Glu Leu Asn Asp Ser Asn
65                  70                  75                  80

Ser Thr Gln Ala Thr Lys Lys Thr Gly Lys Trp Asp Ser Asn Thr Ser
                85                  90                  95

Thr Leu Thr Ile Ser Val Asn Ser Lys Lys Thr Lys Asn Ile Val Phe
            100                 105                 110

Thr Lys Glu Cys Thr Ile Thr Val Gln Lys Tyr Asp Ser Ala Gly Thr
        115                 120                 125
```

Asn Leu Glu Gly Asn Ala Val Glu Ile Lys Thr Leu Asp Glu Leu Lys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Asp Lys Gly Lys Leu
                165                 170                 175

Ser Glu Lys Val Val Thr Arg Ala Asn Gly Thr Arg Leu Glu Tyr Thr
            180                 185                 190

Glu Ile Lys Asn Asp Gly Ser Gly Lys Ala Lys Glu Val Leu Lys Gly
        195                 200                 205

Phe Ala Leu Glu Gly Thr Leu Thr Asp Gly Gly Glu Thr Lys Leu Thr
210                 215                 220

Val Thr Cys Gly Thr Val Thr Leu Ser Lys Asn Ile Ser Lys Ser Gly
225                 230                 235                 240

Glu Ile Thr Val Ala Leu Asn Asp Thr Glu Thr Pro Ala Asp Lys
                245                 250                 255

Lys Thr Gly Glu Trp Lys Ser Asp Thr Ser Thr Leu Thr Ile Ser Lys
                260                 265                 270

Asn Ser Gln Lys Pro Lys Gln Leu Val Phe Thr Lys Glu Asn Thr Ile
            275                 280                 285

Thr Val Gln Asn Tyr Asn Arg Ala Gly Asn Ala Leu Glu Gly Ser Pro
        290                 295                 300

Ala Glu Ile Lys Asp Leu Ala Glu Leu Cys Ala Ala Leu Lys
305                 310                 315

<210> SEQ ID NO 124
<211> LENGTH: 1023
<212> TYPE: DNA
<213> ORGANISM: Artificial Sequence
<220> FEATURE:
<223> OTHER INFORMATION: Lip-S4D4-S3D1_nt

<400> SEQUENCE: 124

```
atgaaagcta ctaaactggt actgggcgcg gtaatcctgg ttctactct gctggcaggt      60
tgctcaagct tcaacgctaa aggtgaactg tcggaaaaaa ccatcctgcg cgcctgtggc    120
acccgcctgg aatacacgga atcaagtcg gacggcacgg gcaaagcaaa ggaagtcctg    180
aaagattttg ctctggaagg taccctggcg gccgacaaaa ccacgctgaa ggtgacggaa    240
ggcaccgtgg ttctgagcaa acatattccg aactctggtg aaatcaccgt tgaactgaac    300
gatagcaatt ctacgcaggc gaccaaaaag acgggcaaat gggacagtaa tacctccacg    360
ctgaccattt cagtcaactc gaaaaagacc aaaaatattg tgttcacgaa ggaatgcacg    420
atcaccgttc aaaaatatga ttccgcaggt accaacctgg aaggcaacgc tgtggaaatc    480
aaaaccctgg acgaactgaa aaacgccctg aagggtacta gtgacaaaaa caatggctct    540
ggtagcaaag agaaaaacaa agatggcaag tactcattta cgataaggg caaactgtcg    600
gaaaaagtgg tcacccgcgc aaatggcacc cgcctggaat acacggaaat caaaaacgat    660
ggtagcggca agcgaagga agttctgaaa ggctttgccc tggaaggtac cctgacggat    720
ggcggtgaaa ccaaactgac cgtgacgtgc ggcaccgtta cgctgtctaa aacattagc    780
aagtctggtg aaatcacggt cgcactgaat gataccgaaa ccacgccggc tgacaaaaag    840
accggcgaat ggaaaagtga cacctccacg ctgaccattt caaagaactc gcagaaaccg    900
aagcaactgg tcttcaccaa agaaaacacg atcaccgtgc agaactataa tcgtgccggt    960
aatgctctgg aaggctcacc ggctgaaatc aaggacctgg ctgaactgtg tgcggcactg   1020
``` aaa                                                                    1023

<210> SEQ ID NO 125
<211> LENGTH: 330
<212> TYPE: PRT
<213> ORGANISM: Artificial Sequence
<220> FEATURE:
<223> OTHER INFORMATION: Lip-S4D4-S3D1_His_aa
<220> FEATURE:
<221> NAME/KEY: LIPID
<222> LOCATION: (1)..(1)
<223> OTHER INFORMATION: LIPIDATION

<400> SEQUENCE: 125

Cys Ser Ser Phe Asn Ala Lys Gly Glu Leu Ser Glu Lys Thr Ile Leu
1               5                   10                  15

Arg Ala Cys Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Leu Ala Ala Asp Lys Thr Thr Leu Lys Val Thr Glu Gly Thr Val Val
50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
            100                 105                 110

Ile Val Phe Thr Lys Glu Cys Thr Ile Thr Val Gln Lys Tyr Asp Ser
        115                 120                 125

Ala Gly Thr Asn Leu Glu Gly Asn Ala Val Glu Ile Lys Thr Leu Asp
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Asn Gly Thr Arg Leu
            180                 185                 190

Glu Tyr Thr Glu Ile Lys Asn Asp Gly Ser Gly Lys Ala Lys Glu Val
        195                 200                 205

Leu Lys Gly Phe Ala Leu Glu Gly Thr Leu Thr Asp Gly Gly Glu Thr
    210                 215                 220

Lys Leu Thr Val Thr Cys Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
        275                 280                 285

Asn Thr Ile Thr Val Gln Asn Tyr Asn Arg Ala Gly Asn Ala Leu Glu
    290                 295                 300

Gly Ser Pro Ala Glu Ile Lys Asp Leu Ala Glu Leu Cys Ala Ala Leu
305                 310                 315                 320

Lys Gly Leu Glu His His His His His His
                325                 330

<210> SEQ ID NO 126
<211> LENGTH: 1050
<212> TYPE: DNA
<213> ORGANISM: Artificial Sequence
<220> FEATURE:
<223> OTHER INFORMATION: Lip-S4D4-S3D1_His_nt

<400> SEQUENCE: 126

```
atgaaagcta ctaaactggt actgggcgcg gtaatcctgg gttctactct gctggcaggt        60
tgctcaagct tcaacgctaa aggtgaactg tcggaaaaaa ccatcctgcg cgcctgtggc       120
acccgcctgg aatacacgga aatcaagtcg acggcacgg gcaaagcaaa ggaagtcctg       180
aaagattttg ctctggaagg taccctggcg ccgacaaaaa ccacgctgaa ggtgacggaa       240
ggcaccgtgg ttctgagcaa acatattccg aactctggtg aaatcaccgt tgaactgaac       300
gatagcaatt ctacgcaggc gaccaaaaag acgggcaaat gggacagtaa tacctccacg       360
ctgaccattt cagtcaactc gaaaaagacc aaaaatattg tgttcacgaa ggaatgcacg       420
atcaccgttc aaaaatatga ttccgcaggt accaacctgg aaggcaacgc tgtggaaatc       480
aaaaccctgg acgaactgaa aaacgccctg aagggtacta gtgacaaaaa caatggctct       540
ggtagcaaag agaaaaacaa agatggcaag tactcattta cgataagggg caaactgtcg       600
gaaaaagtgg tcacccgcgc aaatggcacc cgcctggaat acacggaaat caaaaacgat       660
ggtagcggca agcgaagga gttctgaaa ggctttgccc tggaaggtac cctgacggat       720
ggcggtgaaa ccaaactgac cgtgacgtgc ggcaccgtta cgctgtctaa aacattagc       780
aagtctggtg aaatcacggt cgcactgaat gataccgaaa ccacgccggc tgacaaaaag       840
accggcgaat ggaaaagtga cacctccacg ctgaccattt caaagaactc gcagaaaccg       900
aagcaactgg tcttcaccaa agaaaacacg atcaccgtgc agaactataa tcgtgccggt       960
aatgctctgg aaggctcacc ggctgaaatc aaggacctgg ctgaactgtg tgcggcactg      1020
aaaggtctcg agcaccacca ccaccaccac                                       1050
```

<210> SEQ ID NO 127
<211> LENGTH: 318
<212> TYPE: PRT
<213> ORGANISM: Artificial Sequence
<220> FEATURE:
<223> OTHER INFORMATION: S4D1-S3D4_aa

<400> SEQUENCE: 127

```
Phe Asn Ala Lys Gly Glu Leu Ser Glu Lys Thr Ile Leu Arg Ala Asn
1               5                   10                  15

Gly Thr Arg Leu Glu Tyr Thr Glu Ile Lys Ser Asp Gly Thr Gly Lys
            20                  25                  30

Ala Lys Glu Val Leu Lys Asp Phe Ala Leu Glu Gly Thr Leu Ala Ala
        35                  40                  45

Asp Lys Thr Thr Leu Lys Val Thr Cys Gly Thr Val Val Leu Ser Lys
    50                  55                  60

His Ile Pro Asn Ser Gly Glu Ile Thr Val Glu Leu Asn Asp Ser Asn
65                  70                  75                  80

Ser Thr Gln Ala Thr Lys Lys Thr Gly Lys Trp Asp Ser Asn Thr Ser
                85                  90                  95

Thr Leu Thr Ile Ser Val Asn Ser Lys Lys Thr Lys Asn Ile Val Phe
            100                 105                 110

Thr Lys Glu Asp Thr Ile Thr Val Gln Lys Tyr Asp Ser Ala Gly Thr
```

|  |  |  | 115 |  |  |  | 120 |  |  |  | 125 |  |  |
|---|---|---|---|---|---|---|---|---|---|---|---|---|---|

Asn Leu Glu Gly Asn Ala Val Glu Ile Lys Thr Leu Asp Glu Leu Cys
130                 135                 140

Asn Ala Leu Lys Gly Thr Ser Asp Lys Asn Gly Ser Gly Ser Lys
145                 150                 155                 160

Glu Lys Asn Lys Asp Gly Lys Tyr Ser Phe Asn Asp Lys Gly Lys Leu
                165                 170                 175

Ser Glu Lys Val Val Thr Arg Ala Cys Gly Thr Arg Leu Glu Tyr Thr
            180                 185                 190

Glu Ile Lys Asn Asp Gly Ser Gly Lys Ala Lys Glu Val Leu Lys Gly
                195                 200                 205

Phe Ala Leu Glu Gly Thr Leu Thr Asp Gly Gly Glu Thr Lys Leu Thr
210                 215                 220

Val Thr Glu Gly Thr Val Thr Leu Ser Lys Asn Ile Ser Lys Ser Gly
225                 230                 235                 240

Glu Ile Thr Val Ala Leu Asn Asp Thr Glu Thr Thr Pro Ala Asp Lys
                245                 250                 255

Lys Thr Gly Glu Trp Lys Ser Asp Thr Ser Thr Leu Thr Ile Ser Lys
            260                 265                 270

Asn Ser Gln Lys Pro Lys Gln Leu Val Phe Thr Lys Glu Cys Thr Ile
        275                 280                 285

Thr Val Gln Asn Tyr Asn Arg Ala Gly Asn Ala Leu Glu Gly Ser Pro
290                 295                 300

Ala Glu Ile Lys Asp Leu Ala Glu Leu Lys Ala Ala Leu Lys
305                 310                 315

<210> SEQ ID NO 128
<211> LENGTH: 1023
<212> TYPE: DNA
<213> ORGANISM: Artificial Sequence
<220> FEATURE:
<223> OTHER INFORMATION: Lip-S4D1-S3D4_nt

<400> SEQUENCE: 128

| atgaaagcta ctaaactggt actgggcgcg gtaatcctgg ttctactct gctggcaggt | 60 |
|---|---|
| tgctcaagct tcaatgctaa gggcgaactg agcgaaaaaa cgatcctgcg tgcgaatggc | 120 |
| acccgtctgg aataccgga atcaaatcc gatggtacgg gcaaagcaaa ggaagtcctg | 180 |
| aaagattttg ctctggaagg taccctggcg ccgacaaaa ccacgctgaa ggtgacgtgc | 240 |
| ggcaccgtgg ttctgagcaa acatattccg aactctggtg aaatcaccgt tgaactgaac | 300 |
| gatagcaatt ctacgcaggc aaccaaaaag acgggcaaat gggacagtaa tacctccacg | 360 |
| ctgaccattt cagtcaactc gaaaaagacc aaaaatattg tgttcacgaa ggaagatacg | 420 |
| atcaccgttc aaaaatatga ctccgcgggc accaacctgg aaggcaatgc cgtcgaaatc | 480 |
| aaaaccctgg atgaactgtg taacgccctg aagggtacta gtgacaaaaa caatggctct | 540 |
| ggtagcaaag agaaaacaa agatggcaag tactcattta cgataaggg caaactgtca | 600 |
| gaaaaagtgg tcacccgcgc ttgtggcacc cgcctggaat acaccgaaat caaaaacgac | 660 |
| ggctcgggca agcgaagga agttctgaaa ggctttgccc tggaaggtac cctgacggat | 720 |
| ggcggtgaaa ccaaactgac cgtgacggaa ggcaccgtta cgctgtctaa aacattagc | 780 |
| aagtctggtg aaatcaccgg tcgcactgaa tgataccgaaa ccacgccggc tgacaaaaag | 840 |
| accggcgaat ggaaagtga cacctccacg ctgaccattt caagaactc gcagaaaccg | 900 |
| aagcaactgg tcttcaccaa agaatgcacg atcaccgtgc agaactataa tcgtgccggt | 960 |

```
aatgctctgg aaggctcccc ggctgaaatc aaggacctgg cggaactgaa ggcggcactg    1020
aaa                                                                  1023
```

<210> SEQ ID NO 129
<211> LENGTH: 330
<212> TYPE: PRT
<213> ORGANISM: Artificial Sequence
<220> FEATURE:
<223> OTHER INFORMATION: Lip-S4D1-S3D4_His_aa
<220> FEATURE:
<221> NAME/KEY: LIPID
<222> LOCATION: (1)..(1)
<223> OTHER INFORMATION: LIPIDATION

<400> SEQUENCE: 129

```
Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Leu Ala Ala Asp Lys Thr Thr Leu Lys Val Thr Cys Gly Thr Val Val
    50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Thr Gly Lys Trp Asp Ser
                85                  90                  95

Asn Thr Ser Thr Leu Thr Ile Ser Val Asn Ser Lys Lys Thr Lys Asn
                100                 105                 110

Ile Val Phe Thr Lys Glu Asp Thr Ile Thr Val Gln Lys Tyr Asp Ser
            115                 120                 125

Ala Gly Thr Asn Leu Glu Gly Asn Ala Val Glu Ile Lys Thr Leu Asp
        130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Cys Gly Thr Arg Leu
            180                 185                 190

Glu Tyr Thr Glu Ile Lys Asn Asp Gly Ser Gly Lys Ala Lys Glu Val
        195                 200                 205

Leu Lys Gly Phe Ala Leu Glu Gly Thr Leu Thr Asp Gly Gly Glu Thr
    210                 215                 220

Lys Leu Thr Val Thr Glu Gly Thr Val Thr Leu Ser Lys Asn Ile Ser
225                 230                 235                 240

Lys Ser Gly Glu Ile Thr Val Ala Leu Asn Asp Thr Glu Thr Pro
                245                 250                 255

Ala Asp Lys Lys Thr Gly Glu Trp Lys Ser Asp Thr Ser Leu Thr
                260                 265                 270

Ile Ser Lys Asn Ser Gln Lys Pro Lys Gln Leu Val Phe Thr Lys Glu
            275                 280                 285

Cys Thr Ile Thr Val Gln Asn Tyr Asn Arg Ala Gly Asn Ala Leu Glu
        290                 295                 300

Gly Ser Pro Ala Glu Ile Lys Asp Leu Ala Glu Leu Lys Ala Ala Leu
305                 310                 315                 320
```

```
Lys Gly Leu Glu His His His His His His
            325                 330
```

<210> SEQ ID NO 130
<211> LENGTH: 1050
<212> TYPE: DNA
<213> ORGANISM: Artificial Sequence
<220> FEATURE:
<223> OTHER INFORMATION: Lip-S4D1-S3D4_His_nt

<400> SEQUENCE: 130

```
atgaaagcta ctaaactggt actgggcgcg gtaatcctgg ttctactct gctggcaggt      60
tgctcaagct tcaatgctaa gggcgaactg agcgaaaaaa cgatcctgcg tgcgaatggc    120
accgtctgg aatacaccga atcaaatcc gatggtacgg gcaaagcaaa ggaagtcctg     180
aaagattttg ctctggaagg taccctggcg gccgacaaaa ccacgctgaa ggtgacgtgc    240
ggcaccgtgg ttctgagcaa acatattccg aactctggtg aaatcaccgt tgaactgaac    300
gatagcaatt ctacgcaggc aaccaaaaag acgggcaaat gggacagtaa tacctccacg    360
ctgaccattt cagtcaactc gaaaaagacc aaaaatattg tgttcacgaa ggaagatacg    420
atcaccgttc aaaatatga ctccgcgggc accaacctgg aaggcaatgc cgtcgaaatc    480
aaaacccctgg atgaactgtg taacgccctg aagggtacta gtgacaaaaa caatggctct    540
ggtagcaaag agaaaaacaa agatggcaag tactcattta cgataaggg caaactgtca    600
gaaaaagtgg tcacccgcgc ttgtggcacc cgcctggaat acaccgaaat caaaaacgac    660
ggctcgggca agcgaagga agttctgaaa ggctttgccc tggaaggtac cctgacggat    720
ggcggtgaaa ccaaactgac cgtgacggaa ggcaccgtta cgctgtctaa aacattagc     780
aagtctggtg aaatcaccggt cgcactgaat gataccgaaa ccacgccggc tgacaaaaag    840
accggcgaat ggaaaagtga cacctccacg ctgaccattt caagaactc gcagaaaccg    900
aagcaactgg tcttcaccaa gaatgcacg atcaccgtgc agaactataa tcgtgccggt    960
aatgctctgg aaggctcccc ggctgaaatc aaggacctgg cggaactgaa ggcggcactg   1020
aaaggtctcg agcaccacca ccaccaccac                                      1050
```

<210> SEQ ID NO 131
<211> LENGTH: 318
<212> TYPE: PRT
<213> ORGANISM: Artificial Sequence
<220> FEATURE:
<223> OTHER INFORMATION: S6D4-S5D1_aa

<400> SEQUENCE: 131

```
Phe Asn Gly Lys Gly Glu Thr Ser Glu Lys Thr Ile Val Arg Ala Cys
1               5                   10                  15
Gly Thr Arg Leu Glu Tyr Thr Asp Ile Lys Ser Asp Gly Ser Gly Lys
            20                  25                  30
Ala Lys Glu Val Leu Lys Asp Phe Thr Leu Glu Gly Thr Leu Ala Ala
        35                  40                  45
Asp Gly Lys Thr Thr Leu Lys Val Thr Glu Gly Thr Val Val Leu Ser
    50                  55                  60
Lys Asn Ile Leu Lys Ser Gly Glu Ile Thr Ala Leu Asp Asp Ser
65                  70                  75                  80
Asp Thr Thr Arg Ala Thr Lys Lys Thr Gly Lys Trp Asp Ser Lys Thr
                85                  90                  95
Ser Thr Leu Thr Ile Ser Val Asn Ser Gln Lys Thr Lys Asn Leu Val
            100                 105                 110
```

```
Phe Thr Lys Glu Cys Thr Ile Thr Val Gln Arg Tyr Asp Ser Ala Gly
            115                 120                 125

Thr Asn Leu Glu Gly Lys Ala Val Glu Ile Thr Thr Leu Lys Glu Leu
        130                 135                 140

Lys Asn Ala Leu Lys Gly Thr Ser Asp Lys Asn Asn Gly Ser Gly Ser
145                 150                 155                 160

Lys Glu Lys Asn Lys Asp Gly Lys Tyr Ser Phe Asn Glu Lys Gly Glu
                165                 170                 175

Ile Ser Glu Lys Thr Ile Val Arg Ala Asn Gly Thr Arg Leu Glu Tyr
            180                 185                 190

Thr Asp Ile Lys Ser Asp Lys Thr Gly Lys Ala Lys Glu Val Leu Lys
        195                 200                 205

Asp Phe Thr Leu Glu Gly Thr Leu Ala Ala Asp Gly Lys Thr Thr Leu
    210                 215                 220

Lys Val Thr Cys Gly Thr Val Thr Leu Ser Lys Asn Ile Ser Lys Ser
225                 230                 235                 240

Gly Glu Ile Thr Val Ala Leu Asp Asp Thr Asp Ser Ser Gly Asn Lys
                245                 250                 255

Lys Ser Gly Thr Trp Asp Ser Gly Thr Ser Thr Leu Thr Ile Ser Lys
            260                 265                 270

Asn Arg Thr Lys Thr Lys Gln Leu Val Phe Thr Lys Glu Asp Thr Ile
        275                 280                 285

Thr Val Gln Asn Tyr Asp Ser Ala Gly Thr Asn Leu Glu Gly Lys Ala
    290                 295                 300

Val Glu Ile Thr Thr Leu Lys Glu Leu Cys Asn Ala Leu Lys
305                 310                 315

<210> SEQ ID NO 132
<211> LENGTH: 1023
<212> TYPE: DNA
<213> ORGANISM: Artificial Sequence
<220> FEATURE:
<223> OTHER INFORMATION: Lip-S6D4-S5D1_nt

<400> SEQUENCE: 132
atgaaagcta ctaaactggt actgggcgcg gtaatcctgg ttctactct gctggcaggt      60 tgctcaagct tcaacggcaa aggtgaaacg agtgaaaaaa cgattgttcg cgcctgtggc     120
acccgcctgg aatacacgga tatcaagtcg gatggttcgg gcaaagcaaa ggaagtcctg     180
aaagatttta cgctggaagg taccctggca gcagacggta aaaccacgct gaaggtgacg     240
gaaggcaccg tggttctgtc aaaaaacatt ctgaagtcgg gtgaaatcac cgcagctctg     300
gatgacagcg ataccacgcg tgctacgaaa aagaccggta atgggacag caagaccctct     360 acgctgacca ttagtgtcaa ctcccagaaa acgaagaatc tggtgttcac caaagaatgc     420
acgatcaccg ttcaacgcta tgatagtgcg ggcaccaacc tggaaggcaa agccgttgaa     480
attaccacgc tgaaagaact gaagaatgct ctgaaaggta ctagtgacaa aaacaatggc     540
tctggtagca agagaaaaa caaagatggc aagtactcat tcaacgaaaa aggcgaaatc     600
tcagaaaaaa ccatcgtccg cgctaacggc acccgcctgg aatacaccga catcaaatca     660
gacaagaccg gtaaagcgaa ggaagttctg aaagatttta cgctggaagg taccctggca     720
gcagacggta aaaccacgct gaaggtgacc tgcggtaccg ttacgctgtc caaaaacatt     780
agtaagtccg gcgaaatcac ggtcgccctg gatgacaccg atagctctgg caacaaaaag     840 agcggtaccct gggattcagg cacctcgacg ctgaccattt ctaaaaatcg tacgaaaacc     900
```

```
aagcagctgg tcttcacgaa agaagatacg atcaccgtgc aaaactatga cagcgcaggt    960
accaatctgg aaggcaaagc tgtggaaatt accacgctga agaactgtg taatgctctg    1020 aaa                                                                  1023
```

<210> SEQ ID NO 133
<211> LENGTH: 330
<212> TYPE: PRT
<213> ORGANISM: Artificial Sequence
<220> FEATURE:
<223> OTHER INFORMATION: Lip-S6D4-S5D1_His_aa
<220> FEATURE:
<221> NAME/KEY: LIPID
<222> LOCATION: (1)..(1)
<223> OTHER INFORMATION: LIPIDATION

<400> SEQUENCE: 133

```
Cys Ser Ser Phe Asn Gly Lys Gly Glu Thr Ser Glu Lys Thr Ile Val
1               5                   10                  15

Arg Ala Cys Gly Thr Arg Leu Glu Tyr Thr Asp Ile Lys Ser Asp Gly
            20                  25                  30

Ser Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Glu Gly Thr Val
    50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
            100                 105                 110

Asn Leu Val Phe Thr Lys Glu Cys Thr Ile Thr Val Gln Arg Tyr Asp
        115                 120                 125

Ser Ala Gly Thr Asn Leu Glu Gly Lys Ala Val Glu Ile Thr Thr Leu
    130                 135                 140

Lys Glu Leu Lys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Asn Gly Thr Arg
            180                 185                 190

Leu Glu Tyr Thr Asp Ile Lys Ser Asp Lys Thr Gly Lys Ala Lys Glu
        195                 200                 205

Val Leu Lys Asp Phe Thr Leu Glu Gly Thr Leu Ala Ala Asp Gly Lys
    210                 215                 220

Thr Thr Leu Lys Val Thr Cys Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
            260                 265                 270

Ile Ser Lys Asn Arg Thr Lys Thr Lys Gln Leu Val Phe Thr Lys Glu
        275                 280                 285

Asp Thr Ile Thr Val Gln Asn Tyr Asp Ser Ala Gly Thr Asn Leu Glu
    290                 295                 300

Gly Lys Ala Val Glu Ile Thr Thr Leu Lys Glu Leu Cys Asn Ala Leu
```

```
305                 310                 315                 320
Lys Gly Leu Glu His His His His His His
                    325                 330
```

<210> SEQ ID NO 134
<211> LENGTH: 1050
<212> TYPE: DNA
<213> ORGANISM: Artificial Sequence
<220> FEATURE:
<223> OTHER INFORMATION: Lip-S6D4-S5D1_His_nt

<400> SEQUENCE: 134

```
atgaaagcta ctaaactggt actgggcgcg gtaatcctgg gttctactct gctggcaggt    60
tgctcaagct tcaacggcaa aggtgaaacg agtgaaaaaa cgattgttcg cgcctgtggc   120
acccgcctgg aatacacgga tatcaagtcg gatggttcgg gcaaagcaaa ggaagtcctg   180
aaagatttta cgctggaagg taccctggca gcagacggta aaaccacgct gaaggtgacg   240
gaaggcaccg tggttctgtc aaaaaacatt ctgaagtcgg gtgaaatcac cgcagctctg   300
gatgacagcg ataccacgcg tgctacgaaa aagaccggta atgggacag caagacctct   360
acgctgacca ttagtgtcaa ctcccagaaa acgaagaatc tggtgttcac caagaatgc   420
acgatcaccg ttcaacgcta tgatagtgcg ggcaccaacc tggaaggcaa agccgttgaa   480
attaccacgc tgaaagaact gaagaatgct ctgaaaggta ctagtgacaa aacaatggc   540
tctggtagca agagaaaaa caagatggc aagtactcat tcaacgaaaa aggcgaaatc   600
tcagaaaaaa ccatcgtccg cgctaacggc acccgcctgg aatacaccga catcaaatca   660
gacaagaccg gtaaagcgaa ggaagttctg aaagatttta cgctggaagg taccctggca   720
gcagacggta aaaccacgct gaaggtgacc tgcggtaccg ttacgctgtc aaaaaacatt   780
agtaagtccg gcgaaatcac ggtcgccctg gatgacaccg atagctctgg caacaaaaag   840
agcggtacct gggattcagg cacctcgacg ctgaccattt ctaaaaatcg tacgaaaacc   900
aagcagctgg tcttcacgaa agaagatacg atcaccgtgc aaaactatga cagcgcaggt   960
accaatctgg aaggcaaagc tgtggaaatt accacgctga agaactgtg taatgctctg  1020
aaaggtctcg agcaccacca ccaccaccac                                  1050
```

<210> SEQ ID NO 135
<211> LENGTH: 318
<212> TYPE: PRT
<213> ORGANISM: Artificial Sequence
<220> FEATURE:
<223> OTHER INFORMATION: S6D1-S5D4_aa

<400> SEQUENCE: 135

```
Phe Asn Gly Lys Gly Glu Thr Ser Glu Lys Thr Ile Val Arg Ala Asn
1               5                   10                  15

Gly Thr Arg Leu Glu Tyr Thr Asp Ile Lys Ser Asp Gly Ser Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Cys Gly Thr Val Val Leu Ser
    50                  55                  60

Lys Asn Ile Leu Lys Ser Gly Glu Ile Thr Ala Ala Leu Asp Asp Ser
65                  70                  75                  80

Asp Thr Thr Arg Ala Thr Lys Lys Thr Gly Lys Trp Asp Ser Lys Thr
                85                  90                  95
```

```
Ser Thr Leu Thr Ile Ser Val Asn Ser Gln Lys Thr Lys Asn Leu Val
            100                 105                 110

Phe Thr Lys Glu Asp Thr Ile Thr Val Gln Arg Tyr Asp Ser Ala Gly
        115                 120                 125

Thr Asn Leu Glu Gly Lys Ala Val Glu Ile Thr Thr Leu Lys Glu Leu
    130                 135                 140

Cys Asn Ala Leu Lys Gly Thr Ser Asp Lys Asn Asn Gly Ser Gly Ser
145                 150                 155                 160

Lys Glu Lys Asn Lys Asp Gly Lys Tyr Ser Phe Asn Glu Lys Gly Glu
                165                 170                 175

Ile Ser Glu Lys Thr Ile Val Arg Ala Cys Gly Thr Arg Leu Glu Tyr
            180                 185                 190

Thr Asp Ile Lys Ser Asp Lys Thr Gly Lys Ala Lys Glu Val Leu Lys
        195                 200                 205

Asp Phe Thr Leu Glu Gly Thr Leu Ala Ala Asp Gly Lys Thr Thr Leu
    210                 215                 220

Lys Val Thr Glu Gly Thr Val Thr Leu Ser Lys Asn Ile Ser Lys Ser
225                 230                 235                 240

Gly Glu Ile Thr Val Ala Leu Asp Asp Thr Asp Ser Ser Gly Asn Lys
                245                 250                 255

Lys Ser Gly Thr Trp Asp Ser Gly Thr Ser Thr Leu Thr Ile Ser Lys
            260                 265                 270

Asn Arg Thr Lys Thr Lys Gln Leu Val Phe Thr Lys Glu Cys Thr Ile
        275                 280                 285

Thr Val Gln Asn Tyr Asp Ser Ala Gly Thr Asn Leu Glu Gly Lys Ala
    290                 295                 300

Val Glu Ile Thr Thr Leu Lys Glu Leu Lys Asn Ala Leu Lys
305                 310                 315

<210> SEQ ID NO 136
<211> LENGTH: 1023
<212> TYPE: DNA
<213> ORGANISM: Artificial Sequence
<220> FEATURE:
<223> OTHER INFORMATION: Lip-S6D1-S5D4_nt

<400> SEQUENCE: 136
atgaaagcta ctaaactggt actgggcgcg gtaatcctgg ttctactct  gctggcaggt      60 tgctcaagct tcaacggcaa aggtgaaacg agcgaaaaga ccatcgtgcg tgcgaacggt     120
acccgcctgg aatatacgga cattaaatcg gacggcagcg gcaaagcaaa ggaagtcctg     180
aaagatttta cgctggaagg taccctggca gcagacggta aaaccacgct gaaggtgacg     240
tgcggcaccg tggttctgtc aaaaaacatt ctgaagtcgg gtgaaatcac cgcagctctg     300
gatgacagcg ataccacgcg tgctacgaaa aagaccggta atgggatag  caagacctct     360 acgctgacca ttagtgtcaa ctcccagaaa acgaagaatc tggtgttcac caaagaagat     420
acgatcaccg ttcaacgcta tgacagtgcg ggcaccaacc tggaaggcaa agccgttgaa     480
attaccacgc tgaaagaact gtgtaatgct ctgaaaggta ctagtgacaa aacaatggc      540 tctggtagca agagaaaaa  caagatggca agtactcat  tcaacgaaaa aggcgaaatc     600
agtgaaaaaa ccattgtgcg tgcgtgtggc acccgtctgg aatataccga catcaagagc     660
gataaaacgg gtaaagcgaa ggaagttctg aaagattta  cgctggaagg taccctggca     720
gcagacggta aaaccacgct gaaggtgacc gaaggtaccg ttacgctgtc caaaaacatt     780
agtaagtccg gcgaaatcac ggtcgccctg gatgacaccg atagctctgg caacaaaaag     840
```

```
agcggtacct gggactcagg cacctcgacg ctgaccattt ctaaaaatcg tacgaaaacc    900
aagcagctgg tcttcacgaa agaatgcacg atcaccgtgc aaaactatga tagcgcaggt    960
accaatctgg aaggcaaagc tgtggaaatt accacgctga agaactgaa gaatgctctg    1020 aaa                                                                  1023
```

<210> SEQ ID NO 137
<211> LENGTH: 330
<212> TYPE: PRT
<213> ORGANISM: Artificial Sequence
<220> FEATURE:
<223> OTHER INFORMATION: Lip-S6D1-S5D4_His_aa
<220> FEATURE:
<221> NAME/KEY: LIPID
<222> LOCATION: (1)..(1)
<223> OTHER INFORMATION: LIPIDATION

<400> SEQUENCE: 137

```
Cys Ser Ser Phe Asn Gly Lys Gly Glu Thr Ser Glu Lys Thr Ile Val
1               5                   10                  15

Arg Ala Asn Gly Thr Arg Leu Glu Tyr Thr Asp Ile Lys Ser Asp Gly
            20                  25                  30

Ser Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
            100                 105                 110

Asn Leu Val Phe Thr Lys Glu Asp Thr Ile Thr Val Gln Arg Tyr Asp
        115                 120                 125

Ser Ala Gly Thr Asn Leu Glu Gly Lys Ala Val Glu Ile Thr Thr Leu
130                 135                 140

Lys Glu Leu Cys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Cys Gly Thr Arg
            180                 185                 190

Leu Glu Tyr Thr Asp Ile Lys Ser Asp Lys Thr Gly Lys Ala Lys Glu
        195                 200                 205

Val Leu Lys Asp Phe Thr Leu Glu Gly Thr Leu Ala Ala Asp Gly Lys
    210                 215                 220

Thr Thr Leu Lys Val Thr Glu Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
            260                 265                 270

Ile Ser Lys Asn Arg Thr Lys Thr Lys Gln Leu Val Phe Thr Lys Glu
        275                 280                 285

Cys Thr Ile Thr Val Gln Asn Tyr Asp Ser Ala Gly Thr Asn Leu Glu
    290                 295                 300
```

```
Gly Lys Ala Val Glu Ile Thr Thr Leu Lys Glu Leu Lys Asn Ala Leu
305                 310                 315                 320

Lys Gly Leu Glu His His His His His His
                325                 330
```

<210> SEQ ID NO 138
<211> LENGTH: 1050
<212> TYPE: DNA
<213> ORGANISM: Artificial Sequence
<220> FEATURE:
<223> OTHER INFORMATION: Lip-S6D1-S5D4_His_nt

<400> SEQUENCE: 138

```
atgaaagcta ctaaactggt actgggcgcg gtaatcctgg gttctactct gctggcaggt      60
tgctcaagct tcaacggcaa aggtgaaacg agcgaaaaga ccatcgtgcg tgcgaacggt     120
acccgcctgg aatatacgga cattaaatcg gacggcagcg gcaaagcaaa ggaagtcctg     180
aaagattta cgctggaagg taccctggca gcagacggta aaaccacgct gaaggtgacg     240
tgcggcaccg tggttctgtc aaaaaacatt ctgaagtcgg gtgaaatcac cgcagctctg     300
gatgacagcg ataccacgcg tgctacgaaa aagaccggta atgggatag caagacctct     360
acgctgacca ttagtgtcaa ctcccagaaa acgaagaatc tggtgttcac caagaagat     420
acgatcaccg ttcaacgcta tgacagtgcg ggcaccaacc tggaaggcaa agccgttgaa     480
attaccacgc tgaaagaact gtgtaatgct ctgaaaggta ctagtgacaa aacaatggc     540
tctggtagca agagaaaaa caagatggc aagtactcat tcaacgaaaa aggcgaaatc     600
agtgaaaaaa ccattgtgcg tgcgtgtggc acccgtctgg aatataccga catcaagagc     660
gataaaacgg gtaaagcgaa ggaagttctg aaagattta cgctggaagg taccctggca     720
gcagacggta aaaccacgct gaaggtgacc gaaggtaccg ttacgctgtc caaaaacatt     780
agtaagtccg gcgaaatcac ggtcgccctg gatgacaccg atagtctgg caacaaaag     840
agcggtacct gggactcagg cacctcgacg ctgaccattt ctaaaaatcg tacgaaaacc     900
aagcagctgg tcttcacgaa agaatgcacg atcaccgtgc aaaactatga tagcgcaggt     960
accaatctgg aaggcaaagc tgtggaaatt accacgctga agaactgaa gaatgctctg    1020
aaaggtctcg agcaccacca ccaccaccac                                    1050
```

<210> SEQ ID NO 139

<400> SEQUENCE: 139

000

<210> SEQ ID NO 140
<211> LENGTH: 156
<212> TYPE: PRT
<213> ORGANISM: Artificial Sequence
<220> FEATURE:
<223> OTHER INFORMATION: Lip-S2D0-His
<220> FEATURE:
<221> NAME/KEY: LIPID
<222> LOCATION: (1)..(1)
<223> OTHER INFORMATION: LIPIDATION

<400> SEQUENCE: 140

```
Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30
```

Lys Glu Val Leu Lys Asn Phe Thr Leu Glu Gly Lys Val Ala Asn Asp
            35                  40                  45

Lys Val Thr Leu Glu Val Lys Glu Gly Thr Val Thr Leu Ser Lys Glu
 50                  55                  60

Ile Ala Lys Ser Gly Glu Val Thr Val Ala Leu Asn Asp Thr Asn Thr
 65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Thr Thr Gln Leu Val Phe Thr
                   100                 105                 110

Lys Gln Asp Thr Ile Thr Val Gln Lys Tyr Asp Ser Ala Gly Thr Asn
               115                 120                 125

Leu Glu Gly Thr Ala Val Glu Ile Lys Thr Leu Asp Glu Leu Lys Asn
           130                 135                 140

Ala Leu Lys Gly Leu Glu His His His His His
145                 150                 155

<210> SEQ ID NO 141
<211> LENGTH: 156
<212> TYPE: PRT
<213> ORGANISM: Artificial Sequence
<220> FEATURE:
<223> OTHER INFORMATION: Lip-S2D1-His
<220> FEATURE:
<221> NAME/KEY: LIPID
<222> LOCATION: (1)..(1)
<223> OTHER INFORMATION: LIPIDATION

<400> SEQUENCE: 141

Cys Lys Gln Asn Glu Leu Ser Ala Lys Thr Met Thr Arg Glu Asn Gly
 1               5                  10                  15

Thr Lys Leu Glu Tyr Thr Glu Met Lys Ser Asp Gly Thr Gly Lys Ala
                20                  25                  30

Lys Glu Val Leu Lys Asn Phe Thr Leu Glu Gly Lys Val Ala Asn Asp
            35                  40                  45

Lys Val Thr Leu Glu Val Lys Cys Gly Thr Val Thr Leu Ser Lys Glu
 50                  55                  60

Ile Ala Lys Ser Gly Glu Val Thr Val Ala Leu Asn Asp Thr Asn Thr
 65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Thr Thr Gln Leu Val Phe Thr
                   100                 105                 110

Lys Gln Asp Thr Ile Thr Val Gln Lys Tyr Asp Ser Ala Gly Thr Asn
               115                 120                 125

Leu Glu Gly Thr Ala Val Glu Ile Lys Thr Leu Asp Glu Leu Cys Asn
           130                 135                 140

Ala Leu Lys Gly Leu Glu His His His His His
145                 150                 155

<210> SEQ ID NO 142
<211> LENGTH: 156
<212> TYPE: PRT
<213> ORGANISM: Artificial Sequence
<220> FEATURE:
<223> OTHER INFORMATION: Lip-S2D2-His
<220> FEATURE:
<221> NAME/KEY: LIPID
<222> LOCATION: (1)..(1)

<223> OTHER INFORMATION: LIPIDATION

<400> SEQUENCE: 142

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Cys Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
            85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Cys Lys Gly Leu Glu His His His His His
145                 150                 155

<210> SEQ ID NO 143
<211> LENGTH: 156
<212> TYPE: PRT
<213> ORGANISM: Artificial Sequence
<220> FEATURE:
<223> OTHER INFORMATION: Lip-S2D3-His
<220> FEATURE:
<221> NAME/KEY: LIPID
<222> LOCATION: (1)..(1)
<223> OTHER INFORMATION: LIPIDATION

<400> SEQUENCE: 143

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
            85                  90                  95

Leu Thr Ile Ser Val Asn Ser Lys Lys Thr Thr Gln Leu Val Phe Thr
            100                 105                 110

Lys Gln Asp Thr Ile Cys Val Gln Lys Tyr Asp Ser Ala Gly Thr Asn
        115                 120                 125

Leu Glu Gly Thr Cys Val Glu Ile Lys Thr Leu Asp Glu Leu Lys Asn
    130                 135                 140

Ala Leu Lys Gly Leu Glu His His His His His
145                 150                 155

```
<210> SEQ ID NO 144
<211> LENGTH: 156
<212> TYPE: PRT
<213> ORGANISM: Artificial Sequence
<220> FEATURE:
<223> OTHER INFORMATION: Lip-S2D4-His
<220> FEATURE:
<221> NAME/KEY: LIPID
<222> LOCATION: (1)..(1)
<223> OTHER INFORMATION: LIPIDATION

<400> SEQUENCE: 144

Cys Lys Gln Asn Glu Leu Ser Ala Lys Thr Met Thr Arg Glu Cys Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Cys Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Leu Lys Gly Leu Glu His His His His His His
145                 150                 155

<210> SEQ ID NO 145
<211> LENGTH: 156
<212> TYPE: PRT
<213> ORGANISM: Artificial Sequence
<220> FEATURE:
<223> OTHER INFORMATION: Lip-S2D5-His
<220> FEATURE:
<221> NAME/KEY: LIPID
<222> LOCATION: (1)..(1)
<223> OTHER INFORMATION: LIPIDATION

<400> SEQUENCE: 145

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Cys Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
```

```
                115                 120                 125
Leu Glu Gly Thr Ala Val Glu Ile Lys Thr Cys Asp Glu Leu Lys Asn
    130                 135                 140

Ala Leu Lys Gly Leu Glu His His His His His His
145                 150                 155

<210> SEQ ID NO 146
<211> LENGTH: 156
<212> TYPE: PRT
<213> ORGANISM: Artificial Sequence
<220> FEATURE:
<223> OTHER INFORMATION: Lip-S2D6-His
<220> FEATURE:
<221> NAME/KEY: LIPID
<222> LOCATION: (1)..(1)
<223> OTHER INFORMATION: LIPIDATION

<400> SEQUENCE: 146

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Cys Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Cys Lys Gly Leu Glu His His His His His His
145                 150                 155

<210> SEQ ID NO 147
<211> LENGTH: 156
<212> TYPE: PRT
<213> ORGANISM: Artificial Sequence
<220> FEATURE:
<223> OTHER INFORMATION: Lip-S2D7-His
<220> FEATURE:
<221> NAME/KEY: LIPID
<222> LOCATION: (1)..(1)
<223> OTHER INFORMATION: LIPIDATION

<400> SEQUENCE: 147

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Cys Ala Leu Asn Asp Thr Asn Thr
```

```
                65                  70                  75                  80
Thr Gln Ala Thr Lys Lys Thr Gly Ala Trp Asp Ser Lys Thr Ser Thr
                    85                  90                  95

Cys Thr Ile Ser Val Asn Ser Lys Lys Thr Thr Gln Leu Val Phe Thr
                100                 105                 110

Lys Gln Asp Thr Ile Thr Val Gln Lys Tyr Asp Ser Ala Gly Thr Asn
                115                 120                 125

Leu Glu Gly Thr Ala Val Glu Ile Lys Thr Leu Asp Glu Leu Lys Asn
            130                 135                 140

Ala Leu Lys Gly Leu Glu His His His His His His
145                 150                 155

<210> SEQ ID NO 148
<211> LENGTH: 156
<212> TYPE: PRT
<213> ORGANISM: Artificial Sequence
<220> FEATURE:
<223> OTHER INFORMATION: Lip-S2D8-His
<220> FEATURE:
<221> NAME/KEY: LIPID
<222> LOCATION: (1)..(1)
<223> OTHER INFORMATION: LIPIDATION

<400> SEQUENCE: 148

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
                20                  25                  30

Lys Glu Val Leu Lys Asn Phe Thr Leu Glu Gly Lys Val Ala Asn Asp
            35                  40                  45

Lys Val Thr Leu Glu Val Lys Glu Gly Thr Val Thr Leu Ser Lys Glu
        50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                    85                  90                  95

Leu Thr Ile Ser Val Asn Ser Lys Lys Thr Thr Gln Leu Val Phe Thr
                100                 105                 110

Lys Gln Asp Thr Cys Thr Val Gln Lys Tyr Asp Ser Ala Gly Thr Asn
                115                 120                 125

Leu Glu Gly Thr Ala Val Glu Cys Lys Thr Leu Asp Glu Leu Lys Asn
            130                 135                 140

Ala Leu Lys Gly Leu Glu His His His His His His
145                 150                 155

<210> SEQ ID NO 149
<211> LENGTH: 156
<212> TYPE: PRT
<213> ORGANISM: Artificial Sequence
<220> FEATURE:
<223> OTHER INFORMATION: Lip-S2D9-His
<220> FEATURE:
<221> NAME/KEY: LIPID
<222> LOCATION: (1)..(1)
<223> OTHER INFORMATION: LIPIDATION

<400> SEQUENCE: 149

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
```

```
                        20                  25                  30
Lys Glu Val Leu Lys Asn Phe Thr Leu Glu Gly Lys Val Ala Asn Asp
             35                  40                  45
Lys Val Thr Leu Glu Val Lys Glu Gly Cys Val Thr Leu Ser Lys Glu
         50                  55                  60
Ile Ala Lys Ser Gly Glu Val Thr Val Ala Leu Asn Asp Cys Asn Thr
 65                  70                  75                  80
Thr Gln Ala Thr Lys Lys Thr Gly Ala Trp Asp Ser Lys Thr Ser Thr
                 85                  90                  95
Leu Thr Ile Ser Val Asn Ser Lys Lys Thr Thr Gln Leu Val Phe Thr
                100                 105                 110
Lys Gln Asp Thr Ile Thr Val Gln Lys Tyr Asp Ser Ala Gly Thr Asn
                115                 120                 125
Leu Glu Gly Thr Ala Val Glu Ile Lys Thr Leu Asp Glu Leu Lys Asn
            130                 135                 140
Ala Leu Lys Gly Leu Glu His His His His His
145                 150                 155

<210> SEQ ID NO 150
<211> LENGTH: 156
<212> TYPE: PRT
<213> ORGANISM: Artificial Sequence
<220> FEATURE:
<223> OTHER INFORMATION: Lip-S2D10-His
<220> FEATURE:
<221> NAME/KEY: LIPID
<222> LOCATION: (1)..(1)
<223> OTHER INFORMATION: LIPIDATION

<400> SEQUENCE: 150

Cys Lys Gln Asn Glu Leu Ser Ala Lys Thr Met Thr Arg Glu Asn Gly
 1               5                  10                  15
Thr Lys Leu Glu Tyr Thr Glu Met Lys Ser Asp Gly Thr Gly Lys Ala
                20                  25                  30
Lys Glu Val Leu Lys Asn Phe Thr Leu Glu Gly Lys Val Ala Asn Asp
             35                  40                  45
Lys Val Thr Leu Glu Val Lys Glu Gly Thr Val Thr Leu Ser Lys Glu
         50                  55                  60
Ile Ala Lys Ser Gly Glu Val Thr Val Ala Cys Asn Asp Thr Asn Thr
 65                  70                  75                  80
Thr Gln Ala Thr Lys Lys Thr Cys Ala Trp Asp Ser Lys Thr Ser Thr
                 85                  90                  95
Leu Thr Ile Ser Val Asn Ser Lys Lys Thr Thr Gln Leu Val Phe Thr
                100                 105                 110
Lys Gln Asp Thr Ile Thr Val Gln Lys Tyr Asp Ser Ala Gly Thr Asn
                115                 120                 125
Leu Glu Gly Thr Ala Val Glu Ile Lys Thr Leu Asp Glu Leu Lys Asn
            130                 135                 140
Ala Leu Lys Gly Leu Glu His His His His His
145                 150                 155

<210> SEQ ID NO 151
<211> LENGTH: 156
<212> TYPE: PRT
<213> ORGANISM: Artificial Sequence
<220> FEATURE:
<223> OTHER INFORMATION: Lip-S2D11-His
<220> FEATURE:
<221> NAME/KEY: LIPID
```

```
<222> LOCATION: (1)..(1)
<223> OTHER INFORMATION: LIPIDATION

<400> SEQUENCE: 151

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
            85                  90                  95

Leu Thr Ile Ser Val Asn Ser Lys Thr Thr Gln Leu Val Phe Thr
            100                 105                 110

Lys Gln Asp Thr Ile Thr Val Cys Lys Tyr Asp Ser Ala Gly Thr Asn
            115                 120                 125

Leu Glu Gly Thr Cys Val Glu Ile Lys Thr Leu Asp Glu Leu Lys Asn
    130                 135                 140

Ala Leu Lys Gly Leu Glu His His His His His His
145                 150                 155

<210> SEQ ID NO 152
<211> LENGTH: 156
<212> TYPE: PRT
<213> ORGANISM: Artificial Sequence
<220> FEATURE:
<223> OTHER INFORMATION: Lip-S2D12-His
<220> FEATURE:
<221> NAME/KEY: LIPID
<222> LOCATION: (1)..(1)
<223> OTHER INFORMATION: LIPIDATION

<400> SEQUENCE: 152

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Cys Glu Gly Lys Val Ala Asn Asp
        35                  40                  45

Lys Val Thr Cys Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
            85                  90                  95

Leu Thr Ile Ser Val Asn Ser Lys Thr Thr Gln Leu Val Phe Thr
            100                 105                 110

Lys Gln Asp Thr Ile Thr Val Gln Lys Tyr Asp Ser Ala Gly Thr Asn
            115                 120                 125

Leu Glu Gly Thr Ala Val Glu Ile Lys Thr Leu Asp Glu Leu Lys Asn
    130                 135                 140

Ala Leu Lys Gly Leu Glu His His His His His
145                 150                 155
```

<210> SEQ ID NO 153
<211> LENGTH: 147
<212> TYPE: PRT
<213> ORGANISM: Artificial Sequence
<220> FEATURE:
<223> OTHER INFORMATION: Lip-S2D0
<220> FEATURE:
<221> NAME/KEY: LIPID
<222> LOCATION: (1)..(1)
<223> OTHER INFORMATION: LIPIDATION

<400> SEQUENCE: 153

```
Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Leu Lys
145
```

<210> SEQ ID NO 154
<211> LENGTH: 147
<212> TYPE: PRT
<213> ORGANISM: Artificial Sequence
<220> FEATURE:
<223> OTHER INFORMATION: Lip-S2D1
<220> FEATURE:
<221> NAME/KEY: LIPID
<222> LOCATION: (1)..(1)
<223> OTHER INFORMATION: LIPIDATION

<400> SEQUENCE: 154

```
Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Cys Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110
```

```
Lys Gln Asp Thr Ile Thr Val Gln Lys Tyr Asp Ser Ala Gly Thr Asn
            115                 120                 125

Leu Glu Gly Thr Ala Val Glu Ile Lys Thr Leu Asp Glu Leu Cys Asn
    130                 135                 140

Ala Leu Lys
145

<210> SEQ ID NO 155
<211> LENGTH: 147
<212> TYPE: PRT
<213> ORGANISM: Artificial Sequence
<220> FEATURE:
<223> OTHER INFORMATION: Lip-S2D2
<220> FEATURE:
<221> NAME/KEY: LIPID
<222> LOCATION: (1)..(1)
<223> OTHER INFORMATION: LIPIDATION

<400> SEQUENCE: 155

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Cys Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Thr Thr Gln Leu Val Phe Thr
            100                 105                 110

Lys Gln Asp Thr Ile Thr Val Gln Lys Tyr Asp Ser Ala Gly Thr Asn
            115                 120                 125

Leu Glu Gly Thr Ala Val Glu Ile Lys Thr Leu Asp Glu Leu Lys Asn
    130                 135                 140

Ala Cys Lys
145

<210> SEQ ID NO 156
<211> LENGTH: 147
<212> TYPE: PRT
<213> ORGANISM: Artificial Sequence
<220> FEATURE:
<223> OTHER INFORMATION: Lip-S2D3
<220> FEATURE:
<221> NAME/KEY: LIPID
<222> LOCATION: (1)..(1)
<223> OTHER INFORMATION: LIPIDATION

<400> SEQUENCE: 156

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60
```

```
Ile Ala Lys Ser Gly Glu Val Thr Val Ala Leu Asn Asp Thr Asn Thr
 65                  70                  75                  80

Thr Gln Ala Thr Lys Lys Thr Gly Ala Trp Asp Ser Lys Thr Ser Thr
                 85                  90                  95

Leu Thr Ile Ser Val Asn Ser Lys Lys Thr Thr Gln Leu Val Phe Thr
            100                 105                 110

Lys Gln Asp Thr Ile Cys Val Gln Lys Tyr Asp Ser Ala Gly Thr Asn
        115                 120                 125

Leu Glu Gly Thr Cys Val Glu Ile Lys Thr Leu Asp Glu Leu Lys Asn
    130                 135                 140

Ala Leu Lys
145

<210> SEQ ID NO 157
<211> LENGTH: 147
<212> TYPE: PRT
<213> ORGANISM: Artificial Sequence
<220> FEATURE:
<223> OTHER INFORMATION: Lip-S2D4
<220> FEATURE:
<221> NAME/KEY: LIPID
<222> LOCATION: (1)..(1)
<223> OTHER INFORMATION: LIPIDATION

<400> SEQUENCE: 157

Cys Lys Gln Asn Glu Leu Ser Ala Lys Thr Met Thr Arg Glu Cys Gly
  1               5                  10                  15

Thr Lys Leu Glu Tyr Thr Glu Met Lys Ser Asp Gly Thr Gly Lys Ala
                 20                  25                  30

Lys Glu Val Leu Lys Asn Phe Thr Leu Glu Gly Lys Val Ala Asn Asp
            35                  40                  45

Lys Val Thr Leu Glu Val Lys Glu Gly Thr Val Thr Leu Ser Lys Glu
        50                  55                  60

Ile Ala Lys Ser Gly Glu Val Thr Val Ala Leu Asn Asp Thr Asn Thr
 65                  70                  75                  80

Thr Gln Ala Thr Lys Lys Thr Gly Ala Trp Asp Ser Lys Thr Ser Thr
                 85                  90                  95

Leu Thr Ile Ser Val Asn Ser Lys Lys Thr Thr Gln Leu Val Phe Thr
            100                 105                 110

Lys Gln Cys Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Leu Lys
145

<210> SEQ ID NO 158
<211> LENGTH: 147
<212> TYPE: PRT
<213> ORGANISM: Artificial Sequence
<220> FEATURE:
<223> OTHER INFORMATION: Lip-S2D5
<220> FEATURE:
<221> NAME/KEY: LIPID
<222> LOCATION: (1)..(1)
<223> OTHER INFORMATION: LIPIDATION

<400> SEQUENCE: 158

Cys Lys Gln Asn Glu Leu Ser Ala Lys Thr Met Thr Arg Glu Asn Gly
  1               5                  10                  15
```

```
Thr Lys Leu Glu Tyr Thr Glu Met Lys Ser Asp Gly Thr Gly Lys Ala
             20                  25                  30

Lys Glu Val Leu Lys Asn Cys Thr Leu Glu Gly Lys Val Ala Asn Asp
         35                  40                  45

Lys Val Thr Leu Glu Val Lys Glu Gly Thr Val Thr Leu Ser Lys Glu
     50                  55                  60

Ile Ala Lys Ser Gly Glu Val Thr Val Ala Leu Asn Asp Thr Asn Thr
 65                  70                  75                  80

Thr Gln Ala Thr Lys Thr Gly Ala Trp Asp Ser Lys Thr Ser Thr
             85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
            115                 120                 125

Leu Glu Gly Thr Ala Val Glu Ile Lys Thr Cys Asp Glu Leu Lys Asn
        130                 135                 140

Ala Leu Lys
145

<210> SEQ ID NO 159
<211> LENGTH: 147
<212> TYPE: PRT
<213> ORGANISM: Artificial Sequence
<220> FEATURE:
<223> OTHER INFORMATION: Lip-S2D6
<220> FEATURE:
<221> NAME/KEY: LIPID
<222> LOCATION: (1)..(1)
<223> OTHER INFORMATION: LIPIDATION

<400> SEQUENCE: 159

Cys Lys Gln Asn Glu Leu Ser Ala Lys Thr Met Thr Arg Glu Asn Gly
 1               5                  10                  15

Thr Lys Leu Glu Tyr Thr Glu Met Lys Ser Asp Gly Thr Gly Lys Ala
             20                  25                  30

Lys Glu Val Leu Lys Asn Phe Thr Leu Glu Gly Lys Val Ala Asn Asp
         35                  40                  45

Lys Val Thr Leu Glu Val Lys Glu Gly Thr Cys Thr Leu Ser Lys Glu
     50                  55                  60

Ile Ala Lys Ser Gly Glu Val Thr Val Ala Leu Asn Asp Thr Asn Thr
 65                  70                  75                  80

Thr Gln Ala Thr Lys Thr Gly Ala Trp Asp Ser Lys Thr Ser Thr
             85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
            115                 120                 125

Leu Glu Gly Thr Ala Val Glu Ile Lys Thr Leu Asp Glu Leu Lys Asn
        130                 135                 140

Ala Cys Lys
145

<210> SEQ ID NO 160
<211> LENGTH: 147
<212> TYPE: PRT
<213> ORGANISM: Artificial Sequence
<220> FEATURE:
<223> OTHER INFORMATION: Lip-S2D7
<220> FEATURE:
```

```
<221> NAME/KEY: LIPID
<222> LOCATION: (1)..(1)
<223> OTHER INFORMATION: LIPIDATION

<400> SEQUENCE: 160

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
                20                  25                  30

Lys Glu Val Leu Lys Asn Phe Thr Leu Glu Gly Lys Val Ala Asn Asp
            35                  40                  45

Lys Val Thr Leu Glu Val Lys Glu Gly Thr Val Thr Leu Ser Lys Glu
50                  55                  60

Ile Ala Lys Ser Gly Glu Val Thr Cys Ala Leu Asn Asp Thr Asn Thr
65                  70                  75                  80

Thr Gln Ala Thr Lys Thr Gly Ala Trp Asp Ser Lys Thr Ser Thr
                85                  90                  95

Cys Thr Ile Ser Val Asn Ser Lys Lys Thr Thr Gln Leu Val Phe Thr
                100                 105                 110

Lys Gln Asp Thr Ile Thr Val Gln Lys Tyr Asp Ser Ala Gly Thr Asn
            115                 120                 125

Leu Glu Gly Thr Ala Val Glu Ile Lys Thr Leu Asp Glu Leu Lys Asn
    130                 135                 140

Ala Leu Lys
145

<210> SEQ ID NO 161
<211> LENGTH: 147
<212> TYPE: PRT
<213> ORGANISM: Artificial Sequence
<220> FEATURE:
<223> OTHER INFORMATION: Lip-S2D8
<220> FEATURE:
<221> NAME/KEY: LIPID
<222> LOCATION: (1)..(1)
<223> OTHER INFORMATION: LIPIDATION

<400> SEQUENCE: 161

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
                20                  25                  30

Lys Glu Val Leu Lys Asn Phe Thr Leu Glu Gly Lys Val Ala Asn Asp
            35                  40                  45

Lys Val Thr Leu Glu Val Lys Glu Gly Thr Val Thr Leu Ser Lys Glu
50                  55                  60

Ile Ala Lys Ser Gly Glu Val Thr Val Ala Leu Asn Asp Thr Asn Thr
65                  70                  75                  80

Thr Gln Ala Thr Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
                100                 105                 110

Lys Gln Asp Thr Cys Thr Val Gln Lys Tyr Asp Ser Ala Gly Thr Asn
            115                 120                 125

Leu Glu Gly Thr Ala Val Glu Cys Lys Thr Leu Asp Glu Leu Lys Asn
    130                 135                 140

Ala Leu Lys
145
```

<210> SEQ ID NO 162
<211> LENGTH: 147
<212> TYPE: PRT
<213> ORGANISM: Artificial Sequence
<220> FEATURE:
<223> OTHER INFORMATION: Lip-S2D9
<220> FEATURE:
<221> NAME/KEY: LIPID
<222> LOCATION: (1)..(1)
<223> OTHER INFORMATION: LIPIDATION

<400> SEQUENCE: 162

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Cys Val Thr Leu Ser Lys Glu
    50                  55                  60

Ile Ala Lys Ser Gly Glu Val Thr Val Ala Leu Asn Asp Cys Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Ser Ala Gly Thr Asn
        115                 120                 125

Leu Glu Gly Thr Ala Val Glu Ile Lys Thr Leu Asp Glu Leu Lys Asn
    130                 135                 140

Ala Leu Lys
145

<210> SEQ ID NO 163
<211> LENGTH: 147
<212> TYPE: PRT
<213> ORGANISM: Artificial Sequence
<220> FEATURE:
<223> OTHER INFORMATION: Lip-S2D10
<220> FEATURE:
<221> NAME/KEY: LIPID
<222> LOCATION: (1)..(1)
<223> OTHER INFORMATION: LIPIDATION

<400> SEQUENCE: 163

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Cys Asn Asp Thr Asn Thr
65                  70                  75                  80

Thr Gln Ala Thr Lys Lys Thr Cys Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
            115                 120                 125

Leu Glu Gly Thr Ala Val Glu Ile Lys Thr Leu Asp Glu Leu Lys Asn
        130                 135                 140

Ala Leu Lys
145

<210> SEQ ID NO 164
<211> LENGTH: 147
<212> TYPE: PRT
<213> ORGANISM: Artificial Sequence
<220> FEATURE:
<223> OTHER INFORMATION: Lip-S2D11
<220> FEATURE:
<221> NAME/KEY: LIPID
<222> LOCATION: (1)..(1)
<223> OTHER INFORMATION: LIPIDATION

<400> SEQUENCE: 164

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Thr Thr Gln Leu Val Phe Thr
            100                 105                 110

Lys Gln Asp Thr Ile Thr Val Cys Lys Tyr Asp Ser Ala Gly Thr Asn
            115                 120                 125

Leu Glu Gly Thr Cys Val Glu Ile Lys Thr Leu Asp Glu Leu Lys Asn
        130                 135                 140

Ala Leu Lys
145

<210> SEQ ID NO 165
<211> LENGTH: 147
<212> TYPE: PRT
<213> ORGANISM: Artificial Sequence
<220> FEATURE:
<223> OTHER INFORMATION: Lip-S2D12
<220> FEATURE:
<221> NAME/KEY: LIPID
<222> LOCATION: (1)..(1)
<223> OTHER INFORMATION: LIPIDATION

<400> SEQUENCE: 165

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Cys Glu Gly Lys Val Ala Asn Asp
        35                  40                  45

Lys Val Thr Cys Glu Val Lys Glu Gly Thr Val Thr Leu Ser Lys Glu
    50                  55                  60

```
Ile Ala Lys Ser Gly Glu Val Thr Val Ala Leu Asn Asp Thr Asn Thr
 65                  70                  75                  80

Thr Gln Ala Thr Lys Thr Gly Ala Trp Asp Ser Lys Thr Ser Thr
                 85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
                115                 120                 125

Leu Glu Gly Thr Ala Val Glu Ile Lys Thr Leu Asp Glu Leu Lys Asn
    130                 135                 140

Ala Leu Lys
145

<210> SEQ ID NO 166
<211> LENGTH: 143
<212> TYPE: PRT
<213> ORGANISM: Borrelia afzelii

<400> SEQUENCE: 166

Glu Leu Ser Ala Lys Thr Met Thr Arg Glu Asn Gly Thr Lys Leu Glu
 1

```
Lys Lys Thr Gly Ala Trp Asp Ser Lys Thr Ser Thr Leu Thr Ile Ser
                85                  90                  95
Val Asn Ser Lys Lys Thr Thr Gln Leu Val Phe Thr Lys Gln Asp Thr
            100                 105                 110
Ile Thr Val Gln Lys Tyr Asp Ser Ala Gly Thr Asn Leu Glu Gly Thr
        115                 120                 125
Ala Val Glu Ile Lys Thr Leu Asp Glu Leu Cys Asn Ala Leu Lys
    130                 135                 140
```

```
<210> SEQ ID NO 168
<211> LENGTH: 143
<212> TYPE: PRT
<213> ORGANISM: Artificial Sequence
<220> FEATURE:
<223> OTHER INFORMATION: S2D2

<400> SEQUENCE: 168

Glu Leu Ser Ala Lys Thr Met Thr Arg Glu Asn Gly Thr Lys Leu Glu
1               5                   10                  15
Tyr Thr Glu Met Lys Ser Asp Gly Thr Gly Lys Ala Lys Glu Val Leu
            20                  25                  30
Lys Asn Phe Thr Leu Glu Gly Lys Val Ala Asn Asp Lys Val Thr Leu
        35                  40                  45
Glu Val Lys Cys Gly Thr Val Thr Leu Ser Lys Glu Ile Ala Lys Ser
    50                  55                  60
Gly Glu Val Thr Val Ala Leu Asn Asp Thr Asn Thr Gln Ala Thr
65                  70                  75                  80
Lys Lys Thr Gly Ala Trp Asp Ser Lys Thr Ser Thr Leu Thr Ile Ser
                85                  90                  95
Val Asn Ser Lys Lys Thr Thr Gln Leu Val Phe Thr Lys Gln Asp Thr
            100                 105                 110
Ile Thr Val Gln Lys Tyr Asp Ser Ala Gly Thr Asn Leu Glu Gly Thr
        115                 120                 125
Ala Val Glu Ile Lys Thr Leu Asp Glu Leu Lys Asn Ala Cys Lys
    130                 135                 140
```

```
<210> SEQ ID NO 169
<211> LENGTH: 143
<212> TYPE: PRT
<213> ORGANISM: Artificial Sequence
<220> FEATURE:
<223> OTHER INFORMATION: S2D3

<400> SEQUENCE: 169

Glu Leu Ser Ala Lys Thr Met Thr Arg Glu Asn Gly Thr Lys Leu Glu
1               5                   10                  15
Tyr Thr Glu Met Lys Ser Asp Gly Thr Gly Lys Ala Lys Glu Val Leu
            20                  25                  30
Lys Asn Phe Thr Leu Glu Gly Lys Val Ala Asn Asp Lys Val Thr Leu
        35                  40                  45
Glu Val Lys Glu Gly Thr Val Thr Leu Ser Lys Glu Ile Ala Lys Ser
    50                  55                  60
Gly Glu Val Thr Val Ala Leu Asn Asp Thr Asn Thr Gln Ala Thr
65                  70                  75                  80
Lys Lys Thr Gly Ala Trp Asp Ser Lys Thr Ser Thr Leu Thr Ile Ser
                85                  90                  95
Val Asn Ser Lys Lys Thr Thr Gln Leu Val Phe Thr Lys Gln Asp Thr
            100                 105                 110
```

```
Ile Cys Val Gln Lys Tyr Asp Ser Ala Gly Thr Asn Leu Glu Gly Thr
        115                 120                 125

Cys Val Glu Ile Lys Thr Leu Asp Glu Leu Lys Asn Ala Leu Lys
    130                 135                 140
```

<210> SEQ ID NO 170
<211> LENGTH: 143
<212> TYPE: PRT
<213> ORGANISM: Artificial Sequence
<220> FEATURE:
<223> OTHER INFORMATION: S2D4

<400> SEQUENCE: 170

```
Glu Leu Ser Ala Lys Thr Met Thr Arg Glu Cys Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Cys Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys
    130                 135                 140
```

<210> SEQ ID NO 171
<211> LENGTH: 143
<212> TYPE: PRT
<213> ORGANISM: Artificial Sequence
<220> FEATURE:
<223> OTHER INFORMATION: S2D5

<400> SEQUENCE: 171

```
Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Cys Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Cys Asp Glu Leu Lys Asn Ala Leu Lys
    130                 135                 140
```

<210> SEQ ID NO 172
<211> LENGTH: 143
<212> TYPE: PRT
<213> ORGANISM: Artificial Sequence
<220> FEATURE:
<223> OTHER INFORMATION: S2D6

<400> SEQUENCE: 172

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Cys Thr Leu Ser Lys Glu Ile Ala Lys Ser
50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Cys Lys
    130                 135                 140

<210> SEQ ID NO 173
<211> LENGTH: 143
<212> TYPE: PRT
<213> ORGANISM: Artificial Sequence
<220> FEATURE:
<223> OTHER INFORMATION: S2D7

<400> SEQUENCE: 173

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
50                  55                  60

Gly Glu Val Thr Cys Ala Leu Asn Asp Thr Asn Thr Thr Gln Ala Thr
65                  70                  75                  80

Lys Lys Thr Gly Ala Trp Asp Ser Lys Thr Ser Thr Cys Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys
    130                 135                 140

<210> SEQ ID NO 174
<211> LENGTH: 143

```
<212> TYPE: PRT
<213> ORGANISM: Artificial Sequence
<220> FEATURE:
<223> OTHER INFORMATION: S2D8

<400> SEQUENCE: 174
```

| | | | | | | | | | | | | | | |
|---|---|---|---|---|---|---|---|---|---|---|---|---|---|---|
| Glu | Leu | Ser | Ala | Lys | Thr | Met | Thr | Arg | Glu | Asn | Gly | Thr | Lys | Leu | Glu |
| 1 | | | | 5 | | | | | 10 | | | | | 15 | |

| Tyr | Thr | Glu | Met | Lys | Ser | Asp | Gly | Thr | Gly | Lys | Ala | Lys | Glu | Val | Leu |
|---|---|---|---|---|---|---|---|---|---|---|---|---|---|---|---|
| | | | 20 | | | | | 25 | | | | | 30 | | |

| Lys | Asn | Phe | Thr | Leu | Glu | Gly | Lys | Val | Ala | Asn | Asp | Lys | Val | Thr | Leu |
|---|---|---|---|---|---|---|---|---|---|---|---|---|---|---|---|
| | | 35 | | | | | 40 | | | | | 45 | | | |

| Glu | Val | Lys | Glu | Gly | Thr | Val | Thr | Leu | Ser | Lys | Glu | Ile | Ala | Lys | Ser |
|---|---|---|---|---|---|---|---|---|---|---|---|---|---|---|---|
| 50 | | | | | 55 | | | | | 60 | | | | | |

| Gly | Glu | Val | Thr | Val | Ala | Leu | Asn | Asp | Thr | Asn | Thr | Thr | Gln | Ala | Thr |
|---|---|---|---|---|---|---|---|---|---|---|---|---|---|---|---|
| 65 | | | | 70 | | | | | 75 | | | | | 80 | |

| Lys | Lys | Thr | Gly | Ala | Trp | Asp | Ser | Lys | Thr | Ser | Thr | Leu | Thr | Ile | Ser |
|---|---|---|---|---|---|---|---|---|---|---|---|---|---|---|---|
| | | | | 85 | | | | | 90 | | | | | 95 | |

| Val | Asn | Ser | Lys | Lys | Thr | Thr | Gln | Leu | Val | Phe | Thr | Lys | Gln | Asp | Thr |
|---|---|---|---|---|---|---|---|---|---|---|---|---|---|---|---|
| | | | 100 | | | | | 105 | | | | | 110 | | |

| Cys | Thr | Val | Gln | Lys | Tyr | Asp | Ser | Ala | Gly | Thr | Asn | Leu | Glu | Gly | Thr |
|---|---|---|---|---|---|---|---|---|---|---|---|---|---|---|---|
| | | | 115 | | | | | 120 | | | | | 125 | | |

| Ala | Val | Glu | Cys | Lys | Thr | Leu | Asp | Glu | Leu | Lys | Asn | Ala | Leu | Lys |
|---|---|---|---|---|---|---|---|---|---|---|---|---|---|---|
| | 130 | | | | | 135 | | | | | 140 | | | |

```
<210> SEQ ID NO 175
<211> LENGTH: 143
<212> TYPE: PRT
<213> ORGANISM: Artificial Sequence
<220> FEATURE:
<223> OTHER INFORMATION: S2D9

<400> SEQUENCE: 175
```

| Glu | Leu | Ser | Ala | Lys | Thr | Met | Thr | Arg | Glu | Asn | Gly | Thr | Lys | Leu | Glu |
|---|---|---|---|---|---|---|---|---|---|---|---|---|---|---|---|
| 1 | | | | 5 | | | | | 10 | | | | | 15 | |

| Tyr | Thr | Glu | Met | Lys | Ser | Asp | Gly | Thr | Gly | Lys | Ala | Lys | Glu | Val | Leu |
|---|---|---|---|---|---|---|---|---|---|---|---|---|---|---|---|
| | | | 20 | | | | | 25 | | | | | 30 | | |

| Lys | Asn | Phe | Thr | Leu | Glu | Gly | Lys | Val | Ala | Asn | Asp | Lys | Val | Thr | Leu |
|---|---|---|---|---|---|---|---|---|---|---|---|---|---|---|---|
| | | 35 | | | | | 40 | | | | | 45 | | | |

| Glu | Val | Lys | Glu | Gly | Cys | Val | Thr | Leu | Ser | Lys | Glu | Ile | Ala | Lys | Ser |
|---|---|---|---|---|---|---|---|---|---|---|---|---|---|---|---|
| | 50 | | | | | 55 | | | | | 60 | | | | |

| Gly | Glu | Val | Thr | Val | Ala | Leu | Asn | Asp | Cys | Asn | Thr | Thr | Gln | Ala | Thr |
|---|---|---|---|---|---|---|---|---|---|---|---|---|---|---|---|
| 65 | | | | | 70 | | | | | 75 | | | | | 80 |

| Lys | Lys | Thr | Gly | Ala | Trp | Asp | Ser | Lys | Thr | Ser | Thr | Leu | Thr | Ile | Ser |
|---|---|---|---|---|---|---|---|---|---|---|---|---|---|---|---|
| | | | | 85 | | | | | 90 | | | | | 95 | |

| Val | Asn | Ser | Lys | Lys | Thr | Thr | Gln | Leu | Val | Phe | Thr | Lys | Gln | Asp | Thr |
|---|---|---|---|---|---|---|---|---|---|---|---|---|---|---|---|
| | | | 100 | | | | | 105 | | | | | 110 | | |

| Ile | Thr | Val | Gln | Lys | Tyr | Asp | Ser | Ala | Gly | Thr | Asn | Leu | Glu | Gly | Thr |
|---|---|---|---|---|---|---|---|---|---|---|---|---|---|---|---|
| | | | 115 | | | | | 120 | | | | | 125 | | |

| Ala | Val | Glu | Ile | Lys | Thr | Leu | Asp | Glu | Leu | Lys | Asn | Ala | Leu | Lys |
|---|---|---|---|---|---|---|---|---|---|---|---|---|---|---|
| | 130 | | | | | 135 | | | | | 140 | | | |

```
<210> SEQ ID NO 176
<211> LENGTH: 143
<212> TYPE: PRT
<213> ORGANISM: Artificial Sequence
<220> FEATURE:
<223> OTHER INFORMATION: S2D10
```

<400> SEQUENCE: 176

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
50                  55                  60

Gly Glu Val Thr Val Ala Cys Asn Asp Thr Asn Thr Thr Gln Ala Thr
65                  70                  75                  80

Lys Lys Thr Cys Ala Trp Asp Ser Lys Thr Ser Thr Leu Thr Ile Ser
                85                  90                  95

Val Asn Ser Lys Lys Thr Gln Leu Val Phe Thr Lys Gln Asp Thr
                100                 105                 110

Ile Thr Val Gln Lys Tyr Asp Ser Ala Gly Thr Asn Leu Gly Gly Thr
            115                 120                 125

Ala Val Glu Ile Lys Thr Leu Asp Glu Leu Lys Asn Ala Leu Lys
130                 135                 140

<210> SEQ ID NO 177
<211> LENGTH: 143
<212> TYPE: PRT
<213> ORGANISM: Artificial Sequence
<220> FEATURE:
<223> OTHER INFORMATION: S2D11

<400> SEQUENCE: 177

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Gln Leu Val Phe Thr Lys Gln Asp Thr
                100                 105                 110

Ile Thr Val Cys Lys Tyr Asp Ser Ala Gly Thr Asn Leu Gly Gly Thr
            115                 120                 125

Cys Val Glu Ile Lys Thr Leu Asp Glu Leu Lys Asn Ala Leu Lys
130                 135                 140

<210> SEQ ID NO 178
<211> LENGTH: 143
<212> TYPE: PRT
<213> ORGANISM: Artificial Sequence
<220> FEATURE:
<223> OTHER INFORMATION: S2D12

<400> SEQUENCE: 178

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
                20                  25                  30

Lys Asn Phe Thr Cys Glu Gly Lys Val Ala Asn Asp Lys Val Thr Cys
            35                  40                  45

Glu Val Lys Glu Gly Thr Val Thr Leu Ser Lys Glu Ile Ala Lys Ser
        50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys
    130                 135                 140

<210> SEQ ID NO 179
<211> LENGTH: 148
<212> TYPE: PRT
<213> ORGANISM: Artificial Sequence
<220> FEATURE:
<223> OTHER INFORMATION: B. burgdorferi s.s. (strain B31, serotype 1),
      OspA_aa 126-273 with replaced hLFA-like sequence from serotype 1
      OspA

<400> SEQUENCE: 179

Phe Asn Glu Lys Gly Glu Val Ser Glu Lys Ile Ile Thr Arg Ala Asp
1               5                   10                  15

Gly Thr Arg Leu Glu Tyr Thr Gly Ile Lys Ser Asp Gly Ser Gly Lys
                20                  25                  30

Ala Lys Glu Val Leu Lys Asn Phe Thr Leu Glu Gly Lys Val Ala Asn
            35                  40                  45

Asp Lys Thr Thr Leu Val Val Lys Glu Gly Thr Val Thr Leu Ser Lys
        50                  55                  60

Asn Ile Ser Lys Ser Gly Glu Val Ser Val Glu Leu Asn Asp Thr Asp
65                  70                  75                  80

Ser Ser Ala Ala Thr Lys Lys Thr Ala Ala Trp Asn Ser Gly Thr Ser
                85                  90                  95

Thr Leu Thr Ile Thr Val Asn Ser Lys Lys Thr Lys Asp Leu Val Phe
            100                 105                 110

Thr Lys Glu Asn Thr Ile Thr Val Gln Gln Tyr Asp Ser Asn Gly Thr
        115                 120                 125

Lys Leu Glu Gly Ser Ala Val Glu Ile Thr Lys Leu Asp Glu Ile Lys
    130                 135                 140

Asn Ala Leu Lys
145

<210> SEQ ID NO 180
<211> LENGTH: 149
<212> TYPE: PRT
<213> ORGANISM: Borrelia garinii

<400> SEQUENCE: 180

Phe Asn Asp Lys Gly Lys Leu Ser Glu Lys Val Val Thr Arg Ala Asn
1               5                   10                  15

Gly Thr Arg Leu Glu Tyr Thr Glu Ile Lys Asn Asp Gly Ser Gly Lys
                20                  25                  30

Ala Lys Glu Val Leu Lys Gly Phe Ala Leu Glu Gly Thr Leu Thr Asp
            35                  40                  45

Gly Gly Glu Thr Lys Leu Thr Val Thr Gly Thr Val Thr Leu Ser
 50                  55                  60

Lys Asn Ile Ser Lys Ser Gly Glu Ile Thr Val Ala Leu Asn Asp Thr
 65                  70                  75                  80

Glu Thr Thr Pro Ala Asp Lys Lys Thr Gly Glu Trp Lys Ser Asp Thr
                 85                  90                  95

Ser Thr Leu Thr Ile Ser Lys Asn Ser Gln Lys Pro Lys Gln Leu Val
                100                 105                 110

Phe Thr Lys Glu Asn Thr Ile Thr Val Gln Asn Tyr Asn Arg Ala Gly
                115                 120                 125

Asn Ala Leu Glu Gly Ser Pro Ala Glu Ile Lys Asp Leu Ala Glu Leu
            130                 135                 140

Lys Ala Ala Leu Lys
145

<210> SEQ ID NO 181
<211> LENGTH: 148
<212> TYPE: PRT
<213> ORGANISM: Borrelia bavariensis

<400> SEQUENCE: 181

Phe Asn Ala Lys Gly Glu Leu Ser Glu Lys Thr Ile Leu Arg Ala Asn
 1               5                  10                  15

Gly Thr Arg Leu Glu Tyr Thr Glu Ile Lys Ser Asp Gly Thr Gly Lys
             20                  25                  30

Ala Lys Glu Val Leu Lys Asp Phe Ala Leu Glu Gly Thr Leu Ala Ala
            35                  40                  45

Asp Lys Thr Thr Leu Lys Val Thr Glu Gly Thr Val Val Leu Ser Lys
 50                  55                  60

His Ile Pro Asn Ser Gly Glu Ile Thr Val Glu Leu Asn Asp Ser Asn
 65                  70                  75                  80

Ser Thr Gln Ala Thr Lys Lys Thr Gly Lys Trp Asp Ser Asn Thr Ser
                 85                  90                  95

Thr Leu Thr Ile Ser Val Asn Ser Lys Lys Thr Lys Asn Ile Val Phe
                100                 105                 110

Thr Lys Glu Asp Thr Ile Thr Val Gln Lys Tyr Asp Ser Ala Gly Thr
                115                 120                 125

Asn Leu Glu Gly Asn Ala Val Glu Ile Lys Thr Leu Asp Glu Leu Lys
            130                 135                 140

Asn Ala Leu Lys
145

<210> SEQ ID NO 182
<211> LENGTH: 148
<212> TYPE: PRT
<213> ORGANISM: Borrelia garinii

<400> SEQUENCE: 182

Phe Asn Glu Lys Gly Glu Ile Ser Glu Lys Thr Ile Val Arg Ala Asn
 1               5                  10                  15

Gly Thr Arg Leu

```
Asp Gly Lys Thr Thr Leu Lys Val Thr Glu Gly Thr Val Thr Leu Ser
    50                  55                  60
Lys Asn Ile Ser Lys Ser Gly Glu Ile Thr Val Ala Leu Asp Asp Thr
65                  70                  75                  80
Asp Ser Ser Gly Asn Lys Lys Ser Gly Thr Trp Asp Ser Gly Thr Ser
                85                  90                  95
Thr Leu Thr Ile Ser Lys Asn Arg Thr Lys Thr Lys Gln Leu Val Phe
                100                 105                 110
Thr Lys Glu Asp Thr Ile Thr Val Gln Asn Tyr Asp Ser Ala Gly Thr
                115                 120                 125
Asn Leu Glu Gly Lys Ala Val Glu Ile Thr Thr Leu Lys Glu Leu Lys
        130                 135                 140
Asn Ala Leu Lys
145

<210> SEQ ID NO 183
<211> LENGTH: 149
<212> TYPE: PRT
<213> ORGANISM: Borrelia garinii

<400> SEQUENCE: 183

Phe Asn Gly Lys Gly Glu Thr Ser Glu Lys Thr Ile Val Arg Ala Asn
1                   5                   10                  15
Gly Thr Arg Leu Glu Tyr Thr Asp Ile Lys Ser Asp Gly Ser Gly Lys
                20                  25                  30
Ala Lys Glu Val Leu Lys Asp Phe Thr Leu Glu Gly Thr Leu Ala Ala
            35                  40                  45
Asp Gly Lys Thr Thr Leu Lys Val Thr Glu Gly Thr Val Val Leu Ser
    50                  55                  60
Lys Asn Ile Leu Lys Ser Gly Glu Ile Thr Ala Ala Leu Asp Asp Ser
65                  70                  75                  80
Asp Thr Thr Arg Ala Thr Lys Lys Thr Gly Lys Trp Asp Ser Lys Thr
                85                  90                  95
Ser Thr Leu Thr Ile Ser Val Asn Ser Gln Lys Thr Lys Asn Leu Val
                100                 105                 110
Phe Thr Lys Glu Asp Thr Ile Thr Val Gln Arg Tyr Asp Ser Ala Gly
                115                 120                 125
Thr Asn Leu Glu Gly Lys Ala Val Glu Ile Thr Thr Leu Lys Glu Leu
        130                 135                 140
Lys Asn Ala Leu Lys
145

<210> SEQ ID NO 184
<211> LENGTH: 21
<212> TYPE: PRT
<213> ORGANISM: Artificial Sequence
<220> FEATURE:
<223> OTHER INFORMATION: LN1 peptide linker constructed from two
      separate loop regions of the N-terminal half of OspA from B.
      burgdorferi s.s. strain B31 (aa 65-74 and aa 42-53, amino acid
      exchange at position 53: D53S)

<400> SEQUENCE: 184

Gly Thr Ser Asp Lys Asn Asn Gly Ser Gly Ser Lys Glu Lys Asn Lys
1                   5                   10                  15
Asp Gly Lys Tyr Ser
                20
```

```
<210> SEQ ID NO 185
<211> LENGTH: 320
<212> TYPE: PRT
<213> ORGANISM: Artificial Sequence
<220> FEATURE:
<223> OTHER INFORMATION: Lip-S1D4-S2D4_aa
<220> FEATURE:
<221> NAME/KEY: LIPID
<222> LOCATION: (1)..(1)
<223> OTHER INFORMATION: LIPIDATION

<400> SEQUENCE: 185

Cys Ser Ser Phe Asn Glu Lys Gly Glu Val Ser Glu Lys Ile Ile Thr
1               5                   10                  15

Arg Ala Cys Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Glu Gly Thr Val Thr
    50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110

Leu Val Phe Thr Lys Glu Cys Thr Ile Thr Val Gln Gln Tyr Asp Ser
        115                 120                 125

Asn Gly Thr Lys Leu Glu Gly Ser Ala Val Glu Ile Thr Lys Leu Asp
    130                 135                 140

Glu Ile Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
            165                 170                 175

Gly Glu Leu Ser Ala Lys Thr Met Thr Arg Glu Cys Gly Thr Lys Leu
        180                 185                 190

Glu Tyr Thr Glu Met Lys Ser Asp Gly Thr Gly Lys Ala Lys Glu Val
    195                 200                 205

Leu Lys Asn Phe Thr Leu Glu Gly Lys Val Ala Asn Asp Lys Val Thr
    210                 215                 220

Leu Glu Val Lys Glu Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
            245                 250                 255

Thr Lys Lys Thr Gly Ala Trp Asp Ser Lys Thr Ser Thr Leu Thr Ile
        260                 265                 270

Ser Val Asn Ser Lys Lys Thr Thr Gln Leu Val Phe Thr Lys Gln Cys
    275                 280                 285

Thr Ile Thr Val Gln Lys Tyr Asp Ser Ala Gly Thr Asn Leu Glu Gly
    290                 295                 300

Thr Ala Val Glu Ile Lys Thr Leu Asp Glu Leu Lys Asn Ala Leu Lys
305                 310                 315                 320

<210> SEQ ID NO 186
<211> LENGTH: 320
<212> TYPE: PRT
<213> ORGANISM: Artificial Sequence
```

<220> FEATURE:
<223> OTHER INFORMATION: Lip-S1D1-S2D1_aa
<220> FEATURE:
<221> NAME/KEY: LIPID
<222> LOCATION: (1)..(1)
<223> OTHER INFORMATION: LIPIDATION

<400> SEQUENCE: 186

Cys Ser Ser Phe Asn Glu Lys Gly Glu Val Ser Glu Lys Ile Ile Thr
1               5                   10                  15

Arg Ala Asp Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Cys Gly Thr Val Thr
    50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110

Leu Val Phe Thr Lys Glu Asn Thr Ile Thr Val Gln Gln Tyr Asp Ser
        115                 120                 125

Asn Gly Thr Lys Leu Glu Gly Ser Ala Val Glu Ile Thr Lys Leu Asp
    130                 135                 140

Glu Ile Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Asn Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
    210                 215                 220

Leu Glu Val Lys Cys Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
                245                 250                 255

Thr Lys Lys Thr Gly Ala Trp Asp Ser Lys Thr Ser Thr Leu Thr Ile
            260                 265                 270

Ser Val Asn Ser Lys Lys Thr Thr Gln Leu Val Phe Thr Lys Gln Asp
        275                 280                 285

Thr Ile Thr Val Gln Lys Tyr Asp Ser Ala Gly Thr Asn Leu Glu Gly
    290                 295                 300

Thr Ala Val Glu Ile Lys Thr Leu Asp Glu Leu Cys Asn Ala Leu Lys
305                 310                 315                 320

<210> SEQ ID NO 187
<211> LENGTH: 321
<212> TYPE: PRT
<213> ORGANISM: Artificial Sequence
<220> FEATURE:
<223> OTHER INFORMATION: Lip-S3D4-S4D4_aa
<220> FEATURE:
<221> NAME/KEY: LIPID
<222> LOCATION: (1)..(1)

<223> OTHER INFORMATION: LIPIDATION

<400> SEQUENCE: 187

```
Cys Ser Ser Phe Asn Glu Lys Gly Lys Leu Ser Glu Lys Val Val Thr
1               5                   10                  15
Arg Ala Cys Gly Thr Arg Leu Glu Tyr Thr Glu Ile Lys Asn Asp Gly
            20                  25                  30
Ser Gly Lys Ala Lys Glu Val Leu Lys Gly Phe Ala Leu Glu Gly Thr
        35                  40                  45
Leu Thr Asp Gly Gly Glu Thr Lys Leu Thr Val Thr Glu Gly Thr Val
    50                  55                  60
Thr Leu Ser Lys Asn Ile Ser Lys Ser Gly Glu Ile Thr Val Ala Leu
65                  70                  75                  80
Asn Asp Thr Glu Thr Thr Pro Ala Asp Lys Lys Thr Gly Glu Trp Lys
                85                  90                  95
Ser Asp Thr Ser Thr Leu Thr Ile Ser Lys Asn Ser Gln Lys Pro Lys
            100                 105                 110
Gln Leu Val Phe Thr Lys Glu Cys Thr Ile Thr Val Gln Asn Tyr Asn
        115                 120                 125
Arg Ala Gly Asn Ala Leu Glu Gly Ser Pro Ala Glu Ile Lys Asp Leu
    130                 135                 140
Ala Glu Leu Lys Ala Ala Leu Lys Gly Thr Ser Asp Lys Asn Asn Gly
145                 150                 155                 160
Ser Gly Ser Lys Glu Lys Asn Lys Asp Gly Lys Tyr Ser Phe Asn Ala
                165                 170                 175
Lys Gly Glu Leu Ser Glu Lys Thr Ile Leu Arg Ala Cys Gly Thr Arg
            180                 185                 190
Leu Glu Tyr Thr Glu Ile Lys Ser Asp Gly Thr Gly Lys Ala Lys Glu
        195                 200                 205
Val Leu Lys Asp Phe Ala Leu Glu Gly Thr Leu Ala Ala Asp Lys Thr
    210                 215                 220
Thr Leu Lys Val Thr Glu Gly Thr Val Val Leu Ser Lys His Ile Pro
225                 230                 235                 240
Asn Ser Gly Glu Ile Thr Val Glu Leu Asn Asp Ser Asn Ser Thr Gln
                245                 250                 255
Ala Thr Lys Lys Thr Gly Lys Trp Asp Ser Asn Thr Ser Thr Leu Thr
            260                 265                 270
Ile Ser Val Asn Ser Lys Lys Thr Lys Asn Ile Val Phe Thr Lys Glu
        275                 280                 285
Cys Thr Ile Thr Val Gln Lys Tyr Asp Ser Ala Gly Thr Asn Leu Glu
    290                 295                 300
Gly Asn Ala Val Glu Ile Lys Thr Leu Asp Glu Leu Lys Asn Ala Leu
305                 310                 315                 320
Lys
```

<210> SEQ ID NO 188
<211> LENGTH: 321
<212> TYPE: PRT
<213> ORGANISM: Artificial Sequence
<220> FEATURE:
<223> OTHER INFORMATION: Lip-S3D1-S4D1_aa
<220> FEATURE:
<221> NAME/KEY: LIPID
<222> LOCATION: (1)..(1)
<223> OTHER INFORMATION: LIPIDATION

<400> SEQUENCE: 188

Cys Ser Ser Phe Asn Glu Lys Gly Lys Leu Ser Glu Lys Val Val Thr
1               5                   10                  15

Arg Ala Asn Gly Thr Arg Leu Glu Tyr Thr Glu Ile Lys Asn Asp Gly
            20                  25                  30

Ser Gly Lys Ala Lys Glu Val Leu Lys Gly Phe Ala Leu Glu Gly Thr
                35                  40                  45

Leu Thr Asp Gly Gly Glu Thr Lys Leu Thr Val Thr Cys Gly Thr Val
    50                  55                  60

Thr Leu Ser Lys Asn Ile Ser Lys Ser Gly Glu Ile Thr Val Ala Leu
65                  70                  75                  80

Asn Asp Thr Glu Thr Thr Pro Ala Asp Lys Thr Gly Glu Trp Lys
                85                  90                  95

Ser Asp Thr Ser Thr Leu Thr Ile Ser Lys Asn Ser Gln Lys Pro Lys
                100                 105                 110

Gln Leu Val Phe Thr Lys Glu Asn Thr Ile Thr Val Gln Asn Tyr Asn
            115                 120                 125

Arg Ala Gly Asn Ala Leu Glu Gly Ser Pro Ala Glu Ile Lys Asp Leu
    130                 135                 140

Ala Glu Leu Cys Ala Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Ala
                165                 170                 175

Lys Gly Glu Leu Ser Glu Lys Thr Ile Leu Arg Ala Asn Gly Thr Arg
                180                 185                 190

Leu Glu Tyr Thr Glu Ile Lys Ser Asp Gly Thr Gly Lys Ala Lys Glu
            195                 200                 205

Val Leu Lys Asp Phe Ala Leu Glu Gly Thr Leu Ala Ala Asp Lys Thr
    210                 215                 220

Thr Leu Lys Val Thr Cys Gly Thr Val Val Leu Ser Lys His Ile Pro
225                 230                 235                 240

Asn Ser Gly Glu Ile Thr Val Glu Leu Asn Asp Ser Asn Ser Thr Gln
                245                 250                 255

Ala Thr Lys Lys Thr Gly Lys Trp Asp Ser Asn Thr Ser Thr Leu Thr
                260                 265                 270

Ile Ser Val Asn Ser Lys Lys Thr Lys Asn Ile Val Phe Thr Lys Glu
            275                 280                 285

Asp Thr Ile Thr Val Gln Lys Tyr Asp Ser Ala Gly Thr Asn Leu Glu
    290                 295                 300

Gly Asn Ala Val Glu Ile Lys Thr Leu Asp Glu Leu Cys Asn Ala Leu
305                 310                 315                 320

Lys

<210> SEQ ID NO 189
<211> LENGTH: 321
<212> TYPE: PRT
<213> ORGANISM: Artificial Sequence
<220> FEATURE:
<223> OTHER INFORMATION: Lip-S5D4-S6D4_aa
<220> FEATURE:
<221> NAME/KEY: LIPID
<222> LOCATION: (1)..(1)
<223> OTHER INFORMATION: LIPIDATION

<400> SEQUENCE: 189

Cys Ser Ser Phe Asn Glu Lys Gly Glu Ile Ser Glu Lys Thr Ile Val
1               5                   10                  15

Arg Ala Cys Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Glu Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
            100                 105                 110

Leu Val Phe Thr Lys Glu Cys Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Cys Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Glu Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Cys Thr Ile Thr Val Gln Arg Tyr Asp Ser Ala Gly Thr Asn Leu Glu
    290                 295                 300

Gly Lys Ala Val Glu Ile Thr Thr Leu Lys Glu Leu Lys Asn Ala Leu
305                 310                 315                 320

Lys

<210> SEQ ID NO 190
<211> LENGTH: 321
<212> TYPE: PRT
<213> ORGANISM: Artificial Sequence
<220> FEATURE:
<223> OTHER INFORMATION: Lip-S5D1-S6D1_aa
<220> FEATURE:
<221> NAME/KEY: LIPID
<222> LOCATION: (1)..(1)
<223> OTHER INFORMATION: LIPIDATION

<400> SEQUENCE: 190

Cys Ser Ser Phe Asn Glu Lys Gly Glu Ile Ser Glu Lys Thr Ile Val
1               5                   10                  15

Arg Ala Asn Gly Thr Arg Leu Glu Tyr Thr Asp Ile Lys Ser Asp Lys
            20                  25                  30

```
Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
 50                  55                  60

Thr Leu Ser Lys Asn Ile Ser Lys Ser Gly Glu Ile Thr Val Ala Leu
 65                  70                  75                  80

Asp Asp Thr Asp Ser Ser Gly Asn Lys Lys Ser Gly Thr Trp Asp Ser
                 85                  90                  95

Gly Thr Ser Thr Leu Thr Ile Ser Lys Asn Arg Thr Lys Thr Lys Gln
                100                 105                 110

Leu Val Phe Thr Lys Glu Asp Thr Ile Thr Val Gln Asn Tyr Asp Ser
            115                 120                 125

Ala Gly Thr Asn Leu Glu Gly Lys Ala Val Glu Ile Thr Thr Leu Lys
        130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Asn Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
210                 215                 220

Thr Leu Lys Val Thr Cys Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Asp Thr Ile Thr Val Gln Arg Tyr Asp Ser Ala Gly Thr Asn Leu Glu
        290                 295                 300

Gly Lys Ala Val Glu Ile Thr Thr Leu Lys Glu Leu Cys Asn Ala Leu
305                 310                 315                 320

Lys

<210> SEQ ID NO 191
<211> LENGTH: 320
<212> TYPE: PRT
<213> ORGANISM: Artificial Sequence
<220> FEATURE:
<223> OTHER INFORMATION: Lip-S2D4-S1D4_aa
<220> FEATURE:
<221> NAME/KEY: LIPID
<222> LOCATION: (1)..(1)
<223> OTHER INFORMATION: LIPIDATION

<400> SEQUENCE: 191

Cys Ser Ser Phe Asn Glu Lys Gly Glu Leu Ser Ala Lys Thr Met Thr
 1               5                  10                  15

Arg Glu Cys Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45
```

Val Ala Asn Asp Lys Val Thr Leu Glu Val Lys Glu Gly Thr Val Thr
50                  55                  60

Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
                100                 105                 110

Leu Val Phe Thr Lys Gln Cys Thr Ile Thr Val Gln Lys Tyr Asp Ser
            115                 120                 125

Ala Gly Thr Asn Leu Glu Gly Thr Ala Val Glu Ile Lys Thr Leu Asp
        130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Cys Gly Thr Arg Leu
                180                 185                 190

Glu Tyr Thr Gly Ile Lys Ser Asp Gly Ser Gly Lys Ala Lys Glu Val
                195                 200                 205

Leu Lys Asn Phe Thr Leu Glu Gly Lys Val Ala Asn Asp Lys Thr Thr
210                 215                 220

Leu Val Val Lys Glu Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
                260                 265                 270

Thr Val Asn Ser Lys Lys Thr Lys Asp Leu Val Phe Thr Lys Glu Cys
                275                 280                 285

Thr Ile Thr Val Gln Gln Tyr Asp Ser Asn Gly Thr Lys Leu Glu Gly
            290                 295                 300

Ser Ala Val Glu Ile Thr Lys Leu Asp Glu Ile Lys Asn Ala Leu Lys
305                 310                 315                 320

<210> SEQ ID NO 192
<211> LENGTH: 320
<212> TYPE: PRT
<213> ORGANISM: Artificial Sequence
<220> FEATURE:
<223> OTHER INFORMATION: Lip-S2D1-S1D1_aa
<220> FEATURE:
<221> NAME/KEY: LIPID
<222> LOCATION: (1)..(1)
<223> OTHER INFORMATION: LIPIDATION

<400> SEQUENCE: 192

Cys Ser Ser Phe Asn Glu Lys Gly Glu Leu Ser Ala Lys Thr Met Thr
1               5                   10                  15

Arg Glu Asn Gly Thr Lys Leu Glu Tyr Thr Glu Met Lys Ser Asp Gly
                20                  25                  30

Thr Gly Lys Ala Lys Glu Val Leu Lys Asn Phe Thr Leu Glu Gly Lys
            35                  40                  45

Val Ala Asn Asp Lys Val Thr Leu Glu Val Lys Cys Gly Thr Val Thr
        50                  55                  60

Leu Ser Lys Glu Ile Ala Lys Ser Gly Glu Val Thr Val Ala Leu Asn 65                  70                  75                  80
Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
            100                 105                 110

Leu Val Phe Thr Lys Gln Asp Thr Ile Thr Val Gln Lys Tyr Asp Ser
            115                 120                 125

Ala Gly Thr Asn Leu Glu Gly Thr Ala Val Glu Ile Lys Thr Leu Asp
        130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Asp Gly Thr Arg Leu
            180                 185                 190

Glu Tyr Thr Gly Ile Lys Ser Asp Gly Ser Gly Lys Ala Lys Glu Val
            195                 200                 205

Leu Lys Asn Phe Thr Leu Glu Gly Lys Val Ala Asn Asp Lys Thr Thr
        210                 215                 220

Leu Val Val Lys Cys Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
            260                 265                 270

Thr Val Asn Ser Lys Lys Thr Lys Asp Leu Val Phe Thr Lys Glu Asn
        275                 280                 285

Thr Ile Thr Val Gln Gln Tyr Asp Ser Asn Gly Thr Lys Leu Glu Gly
            290                 295                 300

Ser Ala Val Glu Ile Thr Lys Leu Asp Glu Ile Cys Asn Ala Leu Lys
305                 310                 315                 320

<210> SEQ ID NO 193
<211> LENGTH: 321
<212> TYPE: PRT
<213> ORGANISM: Artificial Sequence
<220> FEATURE:
<223> OTHER INFORMATION: Lip-S4D4-S3D4_aa
<220> FEATURE:
<221> NAME/KEY: LIPID
<222> LOCATION: (1)..(1)
<223> OTHER INFORMATION: LIPIDATION

<400> SEQUENCE: 193

Cys Ser Ser Phe Asn Ala Lys Gly Glu Leu Ser Glu Lys Thr Ile Leu
1               5                   10                  15

Arg Ala Cys Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Leu Ala Ala Asp Lys Thr Thr Leu Lys Val Thr Glu Gly Thr Val Val
    50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

```
Asn Thr Ser Thr Leu Thr Ile Ser Val Asn Ser Lys Lys Thr Lys Asn
            100                 105                 110

Ile Val Phe Thr Lys Glu Cys Thr Ile Thr Val Gln Lys Tyr Asp Ser
        115                 120                 125

Ala Gly Thr Asn Leu Glu Gly Asn Ala Val Glu Ile Lys Thr Leu Asp
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Cys Gly Thr Arg Leu
            180                 185                 190

Glu Tyr Thr Glu Ile Lys Asn Asp Gly Ser Gly Lys Ala Lys Glu Val
        195                 200                 205

Leu Lys Gly Phe Ala Leu Glu Gly Thr Leu Thr Asp Gly Gly Glu Thr
    210                 215                 220

Lys Leu Thr Val Thr Glu Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
        275                 280                 285

Cys Thr Ile Thr Val Gln Asn Tyr Asn Arg Ala Gly Asn Ala Leu Glu
    290                 295                 300

Gly Ser Pro Ala Glu Ile Lys Asp Leu Ala Glu Leu Lys Ala Ala Leu
305                 310                 315                 320

Lys

<210> SEQ ID NO 194
<211> LENGTH: 321
<212> TYPE: PRT
<213> ORGANISM: Artificial Sequence
<220> FEATURE:
<223> OTHER INFORMATION: Lip-S4D1-S3D1_aa
<220> FEATURE:
<221> NAME/KEY: LIPID
<222> LOCATION: (1)..(1)
<223> OTHER INFORMATION: LIPIDATION

<400> SEQUENCE: 194

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Leu Ala Ala Asp Lys Thr Thr Leu Lys Val Thr Cys Gly Thr Val Val
    50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
            100                 105                 110
```

```
Ile Val Phe Thr Lys Glu Asp Thr Ile Thr Val Gln Lys Tyr Asp Ser
            115                 120                 125

Ala Gly Thr Asn Leu Glu Gly Asn Ala Val Glu Ile Lys Thr Leu Asp
130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Asn Gly Thr Arg Leu
            180                 185                 190

Glu Tyr Thr Glu Ile Lys Asn Asp Gly Ser Gly Lys Ala Lys Glu Val
        195                 200                 205

Leu Lys Gly Phe Ala Leu Glu Gly Thr Leu Thr Asp Gly Gly Glu Thr
210                 215                 220

Lys Leu Thr Val Thr Cys Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
        275                 280                 285

Asn Thr Ile Thr Val Gln Asn Tyr Asn Arg Ala Gly Asn Ala Leu Glu
290                 295                 300

Gly Ser Pro Ala Glu Ile Lys Asp Leu Ala Glu Leu Cys Ala Ala Leu
305                 310                 315                 320

Lys

<210> SEQ ID NO 195
<211> LENGTH: 321
<212> TYPE: PRT
<213> ORGANISM: Artificial Sequence
<220> FEATURE:
<223> OTHER INFORMATION: Lip-S6D4-S5D4_aa
<220> FEATURE:
<221> NAME/KEY: LIPID
<222> LOCATION: (1)..(1)
<223> OTHER INFORMATION: LIPIDATION

<400> SEQUENCE: 195

Cys Ser Ser Phe Asn Gly Lys Gly Glu Thr Ser Glu Lys Thr Ile Val
1               5                   10                  15

Arg Ala Cys Gly Thr Arg Leu Glu Tyr Thr Asp Ile Lys Ser Asp Gly
            20                  25                  30

Ser Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Glu Gly Thr Val
50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
            100                 105                 110

Asn Leu Val Phe Thr Lys Glu Cys Thr Ile Thr Val Gln Arg Tyr Asp
        115                 120                 125
```

```
Ser Ala Gly Thr Asn Leu Glu Gly Lys Ala Val Glu Ile Thr Thr Leu
    130                 135                 140

Lys Glu Leu Lys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Cys Gly Thr Arg
                180                 185                 190

Leu Glu Tyr Thr Asp Ile Lys Ser Asp Lys Thr Gly Lys Ala Lys Glu
            195                 200                 205

Val Leu Lys Asp Phe Thr Leu Glu Gly Thr Leu Ala Ala Asp Gly Lys
210                 215                 220

Thr Thr Leu Lys Val Thr Glu Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
            260                 265                 270

Ile Ser Lys Asn Arg Thr Lys Thr Lys Gln Leu Val Phe Thr Lys Glu
        275                 280                 285

Cys Thr Ile Thr Val Gln Asn Tyr Asp Ser Ala Gly Thr Asn Leu Glu
    290                 295                 300

Gly Lys Ala Val Glu Ile Thr Thr Leu Lys Glu Leu Lys Asn Ala Leu
305                 310                 315                 320

Lys

<210> SEQ ID NO 196
<211> LENGTH: 321
<212> TYPE: PRT
<213> ORGANISM: Artificial Sequence
<220> FEATURE:
<223> OTHER INFORMATION: Lip-S6D1-S5D1_aa
<220> FEATURE:
<221> NAME/KEY: LIPID
<222> LOCATION: (1)..(1)
<223> OTHER INFORMATION: LIPIDATION

<400> SEQUENCE: 196

Cys Ser Ser Phe Asn Gly Lys Gly Glu Thr Ser Glu Lys Thr Ile Val
1               5                   10                  15

Arg Ala Asn Gly Thr Arg Leu Glu Tyr Thr Asp Ile Lys Ser Asp Gly
                20                  25                  30

Ser Gly Lys Ala Lys Glu Val Leu Lys Asp Phe Thr Leu Glu Gly Thr
            35                  40                  45

Leu Ala Ala Asp Gly Lys Thr Thr Leu Lys Val Thr Cys Gly Thr Val
    50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
                100                 105                 110

Asn Leu Val Phe Thr Lys Glu Asp Thr Ile Thr Val Gln Arg Tyr Asp
            115                 120                 125

Ser Ala Gly Thr Asn Leu Glu Gly Lys Ala Val Glu Ile Thr Thr Leu
    130                 135                 140
```

```
Lys Glu Leu Cys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Asn Gly Thr Arg
            180                 185                 190

Leu Glu Tyr Thr Asp Ile Lys Ser Asp Lys Thr Gly Lys Ala Lys Glu
                195                 200                 205

Val Leu Lys Asp Phe Thr Leu Glu Gly Thr Leu Ala Ala Asp Gly Lys
            210                 215                 220

Thr Thr Leu Lys Val Thr Cys Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
                260                 265                 270

Ile Ser Lys Asn Arg Thr Lys Thr Lys Gln Leu Val Phe Thr Lys Glu
                275                 280                 285

Asp Thr Ile Thr Val Gln Asn Tyr Asp Ser Ala Gly Thr Asn Leu Glu
                290                 295                 300

Gly Lys Ala Val Glu Ile Thr Thr Leu Lys Glu Leu Cys Asn Ala Leu
305                 310                 315                 320

Lys

<210> SEQ ID NO 197
<211> LENGTH: 320
<212> TYPE: PRT
<213> ORGANISM: Artificial Sequence
<220> FEATURE:
<223> OTHER INFORMATION: Lip-S1D4-S2D1_aa
<220> FEATURE:
<221> NAME/KEY: LIPID
<222> LOCATION: (1)..(1)
<223> OTHER INFORMATION: LIPIDATION

<400> SEQUENCE: 197

Cys Ser Ser Phe Asn Glu Lys Gly Glu Val Ser Glu Lys Ile Ile Thr
1               5                   10                  15

Arg Ala Cys Gly Thr Arg Leu Glu Tyr Thr Gly Ile Lys Ser Asp Gly
                20                  25                  30

Ser Gly Lys Ala Lys Glu Val Leu Lys Asn Phe Thr Leu Glu Gly Lys
            35                  40                  45

Val Ala Asn Asp Lys Thr Thr Leu Val Val Lys Glu Gly Thr Val Thr
50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
                100                 105                 110

Leu Val Phe Thr Lys Glu Cys Thr Ile Thr Val Gln Gln Tyr Asp Ser
            115                 120                 125

Asn Gly Thr Lys Leu Glu Gly Ser Ala Val Glu Ile Thr Lys Leu Asp
                130                 135                 140

Glu Ile Lys Asn Ala Leu Lys Gly Thr Ser Asp Lys Asn Asn Gly Ser
145                 150                 155                 160
```

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Asn Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
210                 215                 220

Leu Glu Val Lys Cys Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
            245                 250                 255

Thr Lys Lys Thr Gly Ala Trp Asp Ser Lys Thr Ser Thr Leu Thr Ile
            260                 265                 270

Ser Val Asn Ser Lys Lys Thr Thr Gln Leu Val Phe Thr Lys Gln Asp
        275                 280                 285

Thr Ile Thr Val Gln Lys Tyr Asp Ser Ala Gly Thr Asn Leu Glu Gly
        290                 295                 300

Thr Ala Val Glu Ile Lys Thr Leu Asp Glu Leu Cys Asn Ala Leu Lys
305                 310                 315                 320

<210> SEQ ID NO 198
<211> LENGTH: 320
<212> TYPE: PRT
<213> ORGANISM: Artificial Sequence
<220> FEATURE:
<223> OTHER INFORMATION: Lip-S1D1-S2D4_aa
<220> FEATURE:
<221> NAME/KEY: LIPID
<222> LOCATION: (1)..(1)
<223> OTHER INFORMATION: LIPIDATION

<400> SEQUENCE: 198

Cys Ser Ser Phe Asn Glu Lys Gly Glu Val Ser Glu Lys Ile Ile Thr
1               5                   10                  15

Arg Ala Asp Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Cys Gly Thr Val Thr
50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
            85                  90                  95

Gly Thr Ser Thr Leu Thr Ile Thr Val Asn Ser Lys Lys Thr Lys Asp
            100                 105                 110

Leu Val Phe Thr Lys Glu Asn Thr Ile Thr Val Gln Gln Tyr Asp Ser
        115                 120                 125

Asn Gly Thr Lys Leu Glu Gly Ser Ala Val Glu Ile Thr Lys Leu Asp
130                 135                 140

Glu Ile Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
            165                 170                 175

Gly Glu Leu Ser Ala Lys Thr Met Thr Arg Glu Cys Gly Thr Lys Leu
            180                 185                 190

```
Glu Tyr Thr Glu Met Lys Ser Asp Gly Thr Gly Lys Ala Lys Glu Val
            195                 200                 205

Leu Lys Asn Phe Thr Leu Glu Gly Lys Val Ala Asn Asp Lys Val Thr
210                 215                 220

Leu Glu Val Lys Glu Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
                245                 250                 255

Thr Lys Lys Thr Gly Ala Trp Asp Ser Lys Thr Ser Thr Leu Thr Ile
                260                 265                 270

Ser Val Asn Ser Lys Lys Thr Thr Gln Leu Val Phe Thr Lys Gln Cys
            275                 280                 285

Thr Ile Thr Val Gln Lys Tyr Asp Ser Ala Gly Thr Asn Leu Glu Gly
        290                 295                 300

Thr Ala Val Glu Ile Lys Thr Leu Asp Glu Leu Lys Asn Ala Leu Lys
305                 310                 315                 320

Lys

<210> SEQ ID NO 199
<211> LENGTH: 321
<212> TYPE: PRT
<213> ORGANISM: Artificial Sequence
<220> FEATURE:
<223> OTHER INFORMATION: Lip-S3D4-S4D1_aa
<220> FEATURE:
<221> NAME/KEY: LIPID
<222> LOCATION: (1)..(1)
<223> OTHER INFORMATION: LIPIDATION

<400> SEQUENCE: 199

Cys Ser Ser Phe Asn Glu Lys Gly Lys Leu Ser Glu Lys Val Val Thr
1               5                   10                  15

Arg Ala Cys Gly Thr Arg Leu Glu Tyr Thr Glu Ile Lys Asn Asp Gly
            20                  25                  30

Ser Gly Lys Ala Lys Glu Val Leu Lys Gly Phe Ala Leu Glu Gly Thr
        35                  40                  45

Leu Thr Asp Gly Gly Glu Thr Lys Leu Thr Val Thr Glu Gly Thr Val
50                  55                  60

Thr Leu Ser Lys Asn Ile Ser Lys Ser Gly Glu Ile Thr Val Ala Leu
65                  70                  75                  80

Asn Asp Thr Glu Thr Thr Pro Ala Asp Lys Lys Thr Gly Glu Trp Lys
                85                  90                  95

Ser Asp Thr Ser Thr Leu Thr Ile Ser Lys Asn Ser Gln Lys Pro Lys
            100                 105                 110

Gln Leu Val Phe Thr Lys Glu Cys Thr Ile Thr Val Gln Asn Tyr Asn
        115                 120                 125

Arg Ala Gly Asn Ala Leu Glu Gly Ser Pro Ala Glu Ile Lys Asp Leu
    130                 135                 140

Ala Glu Leu Lys Ala Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Ala
                165                 170                 175

Lys Gly Glu Leu Ser Glu Lys Thr Ile Leu Arg Ala Asn Gly Thr Arg
            180                 185                 190

Leu Glu Tyr Thr Glu Ile Lys Ser Asp Gly Thr Gly Lys Ala Lys Glu
        195                 200                 205

Val Leu Lys Asp Phe Ala Leu Glu Gly Thr Leu Ala Ala Asp Lys Thr
```

```
                210                 215                 220

Thr Leu Lys Val Thr Cys Gly Thr Val Val Leu Ser Lys His Ile Pro
225                 230                 235                 240

Asn Ser Gly Glu Ile Thr Val Glu Leu Asn Asp Ser Asn Ser Thr Gln
                245                 250                 255

Ala Thr Lys Lys Thr Gly Lys Trp Asp Ser Asn Thr Ser Thr Leu Thr
                260                 265                 270

Ile Ser Val Asn Ser Lys Lys Thr Lys Asn Ile Val Phe Thr Lys Glu
                275                 280                 285

Asp Thr Ile Thr Val Gln Lys Tyr Asp Ser Ala Gly Thr Asn Leu Glu
                290                 295                 300

Gly Asn Ala Val Glu Ile Lys Thr Leu Asp Glu Leu Cys Asn Ala Leu
305                 310                 315                 320

Lys

<210> SEQ ID NO 200
<211> LENGTH: 321
<212> TYPE: PRT
<213> ORGANISM: Artificial Sequence
<220> FEATURE:
<223> OTHER INFORMATION: Lip-S3D1-S4D4_aa
<220> FEATURE:
<221> NAME/KEY: LIPID
<222> LOCATION: (1)..(1)
<223> OTHER INFORMATION: LIPIDATION

<400> SEQUENCE: 200

Cys Ser Ser Phe Asn Glu Lys Gly Lys Leu Ser Glu Lys Val Val Thr
1               5                   10                  15

Arg Ala Asn Gly Thr Arg Leu Glu Tyr Thr Glu Ile Lys Asn Asp Gly
                20                  25                  30

Ser Gly Lys Ala Lys Glu Val Leu Lys Gly Phe Ala Leu Glu Gly Thr
                35                  40                  45

Leu Thr Asp Gly Gly Glu Thr Lys Leu Thr Val Thr Cys Gly Thr Val
                50                  55                  60

Thr Leu Ser Lys Asn Ile Ser Lys Ser Gly Glu Ile Thr Val Ala Leu
65                  70                  75                  80

Asn Asp Thr Glu Thr Thr Pro Ala Asp Lys Lys Thr Gly Glu Trp Lys
                85                  90                  95

Ser Asp Thr Ser Thr Leu Thr Ile Ser Lys Asn Ser Gln Lys Pro Lys
                100                 105                 110

Gln Leu Val Phe Thr Lys Glu Asn Thr Ile Thr Val Gln Asn Tyr Asn
                115                 120                 125

Arg Ala Gly Asn Ala Leu Glu Gly Ser Pro Ala Glu Ile Lys Asp Leu
                130                 135                 140

Ala Glu Leu Cys Ala Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Ala
                165                 170                 175

Lys Gly Glu Leu Ser Glu Lys Thr Ile Leu Arg Ala Cys Gly Thr Arg
                180                 185                 190

Leu Glu Tyr Thr Glu Ile Lys Ser Asp Gly Thr Gly Lys Ala Lys Glu
                195                 200                 205

Val Leu Lys Asp Phe Ala Leu Glu Gly Thr Leu Ala Ala Asp Lys Thr
                210                 215                 220

Thr Leu Lys Val Thr Glu Gly Thr Val Val Leu Ser Lys His Ile Pro
```

```
                225                 230                 235                 240
Asn Ser Gly Glu Ile Thr Val Glu Leu Asn Asp Ser Asn Ser Thr Gln
                    245                 250                 255

Ala Thr Lys Lys Thr Gly Lys Trp Asp Ser Asn Thr Ser Thr Leu Thr
                260                 265                 270

Ile Ser Val Asn Ser Lys Lys Thr Lys Asn Ile Val Phe Thr Lys Glu
                275                 280                 285

Cys Thr Ile Thr Val Gln Lys Tyr Asp Ser Ala Gly Thr Asn Leu Glu
        290                 295                 300

Gly Asn Ala Val Glu Ile Lys Thr Leu Asp Glu Leu Lys Asn Ala Leu
305                 310                 315                 320

Lys

<210> SEQ ID NO 201
<211> LENGTH: 321
<212> TYPE: PRT
<213> ORGANISM: Artificial Sequence
<220> FEATURE:
<223> OTHER INFORMATION: Lip-S5D4-S6D1_aa
<220> FEATURE:
<221> NAME/KEY: LIPID
<222> LOCATION: (1)..(1)
<223> OTHER INFORMATION: LIPIDATION

<400> SEQUENCE: 201

Cys Ser Ser Phe Asn Glu Lys Gly Glu Ile Ser Glu Lys Thr Ile Val
1               5                   10                  15

Arg Ala Cys Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Glu Gly Thr Val
    50                  55                  60

Thr Leu Ser Lys Asn Ile Ser Lys Ser Gly Ile Thr Val Ala Leu
65                  70                  75                  80

Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
                100                 105                 110

Leu Val Phe Thr Lys Glu Cys Thr Ile Thr Val Gln Asn Tyr Asp Ser
            115                 120                 125

Ala Gly Thr Asn Leu Glu Gly Lys Ala Val Glu Ile Thr Thr Leu Lys
        130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Asn Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Cys Gly Thr Val Val Leu Ser Lys Asn Ile Leu
225                 230                 235                 240

Lys Ser Gly Glu Ile Thr Ala Ala Leu Asp Asp Ser Asp Thr Thr Arg
```

```
                     245                 250                 255
Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
            275                 280                 285

Asp Thr Ile Thr Val Gln Arg Tyr Asp Ser Ala Gly Thr Asn Leu Glu
            290                 295                 300

Gly Lys Ala Val Glu Ile Thr Thr Leu Lys Glu Leu Cys Asn Ala Leu
305                 310                 315                 320

Lys

<210> SEQ ID NO 202
<211> LENGTH: 321
<212> TYPE: PRT
<213> ORGANISM: Artificial Sequence
<220> FEATURE:
<223> OTHER INFORMATION: Lip-S5D1-S6D4_aa
<220> FEATURE:
<221> NAME/KEY: LIPID
<222> LOCATION: (1)..(1)
<223> OTHER INFORMATION: LIPIDATION

<400> SEQUENCE: 202

Cys Ser Ser Phe Asn Glu Lys Gly Glu Ile Ser Glu Lys Thr Ile Val
1               5                   10                  15

Arg Ala Asn Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
50                  55                  60

Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
            100                 105                 110

Leu Val Phe Thr Lys Glu Asp Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Cys Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Glu Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
```

```
                  260                 265                 270
Ile Ser Val Asn Ser Gln Lys Thr Lys Asn Leu Val Phe Thr Lys Glu
                275                 280                 285

Cys Thr Ile Thr Val Gln Arg Tyr Asp Ser Ala Gly Thr Asn Leu Glu
                290                 295                 300

Gly Lys Ala Val Glu Ile Thr Thr Leu Lys Glu Leu Lys Asn Ala Leu
305                 310                 315                 320

Lys

<210> SEQ ID NO 203
<211> LENGTH: 320
<212> TYPE: PRT
<213> ORGANISM: Artificial Sequence
<220> FEATURE:
<223> OTHER INFORMATION: Lip-S2D4-S1D1_aa
<220> FEATURE:
<221> NAME/KEY: LIPID
<222> LOCATION: (1)..(1)
<223> OTHER INFORMATION: LIPIDATION

<400> SEQUENCE: 203

Cys Ser Ser Phe Asn Glu Lys Gly Glu Leu Ser Ala Lys Thr Met Thr
1               5                   10                  15

Arg Glu Cys Gly Thr Lys Leu Glu Tyr Thr Glu Met Lys Ser Asp Gly
                20                  25                  30

Thr Gly Lys Ala Lys Glu Val Leu Lys Asn Phe Thr Leu Glu Gly Lys
                35                  40                  45

Val Ala Asn Asp Lys Val Thr Leu Glu Val Lys Glu Gly Thr Val Thr
50                  55                  60

Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
                100                 105                 110

Leu Val Phe Thr Lys Gln Cys Thr Ile Thr Val Gln Lys Tyr Asp Ser
                115                 120                 125

Ala Gly Thr Asn Leu Glu Gly Thr Ala Val Glu Ile Lys Thr Leu Asp
                130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Asp Gly Thr Arg Leu
                180                 185                 190

Glu Tyr Thr Gly Ile Lys Ser Asp Gly Ser Gly Lys Ala Lys Glu Val
                195                 200                 205

Leu Lys Asn Phe Thr Leu Glu Gly Lys Val Ala Asn Asp Lys Thr Thr
                210                 215                 220

Leu Val Val Lys Cys Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
                260                 265                 270

Thr Val Asn Ser Lys Lys Thr Lys Asp Leu Val Phe Thr Lys Glu Asn
```

```
                     275                 280                 285
Thr Ile Thr Val Gln Gln Tyr Asp Ser Asn Gly Thr Lys Leu Glu Gly
    290                 295                 300

Ser Ala Val Glu Ile Thr Lys Leu Asp Glu Ile Cys Asn Ala Leu Lys
305                 310                 315                 320

<210> SEQ ID NO 204
<211> LENGTH: 320
<212> TYPE: PRT
<213> ORGANISM: Artificial Sequence
<220> FEATURE:
<223> OTHER INFORMATION: Lip-S2D1-S1D4_aa
<220> FEATURE:
<221> NAME/KEY: LIPID
<222> LOCATION: (1)..(1)
<223> OTHER INFORMATION: LIPIDATION

<400> SEQUENCE: 204

Cys Ser Ser Phe Asn Glu Lys Gly Glu Leu Ser Ala Lys Thr Met Thr
1               5                   10                  15

Arg Glu Asn Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45

Val Ala Asn Asp Lys Val Thr Leu Glu Val Lys Cys Gly Thr Val Thr
50                  55                  60

Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
            100                 105                 110

Leu Val Phe Thr Lys Gln Asp Thr Ile Thr Val Gln Lys Tyr Asp Ser
        115                 120                 125

Ala Gly Thr Asn Leu Glu Gly Thr Ala Val Glu Ile Lys Thr Leu Asp
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Cys Gly Thr Arg Leu
            180                 185                 190

Glu Tyr Thr Gly Ile Lys Ser Asp Gly Ser Gly Lys Ala Lys Glu Val
        195                 200                 205

Leu Lys Asn Phe Thr Leu Glu Gly Lys Val Ala Asn Asp Lys Thr Thr
    210                 215                 220

Leu Val Val Lys Glu Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
            260                 265                 270

Thr Val Asn Ser Lys Lys Thr Lys Asp Leu Val Phe Thr Lys Glu Cys
        275                 280                 285

Thr Ile Thr Val Gln Gln Tyr Asp Ser Asn Gly Thr Lys Leu Glu Gly
    290                 295                 300
```

Ser Ala Val Glu Ile Thr Lys Leu Asp Glu Ile Lys Asn Ala Leu Lys
305                 310                 315                 320

<210> SEQ ID NO 205
<211> LENGTH: 321
<212> TYPE: PRT
<213> ORGANISM: Artificial Sequence
<220> FEATURE:
<223> OTHER INFORMATION: Lip-S4D4-S3D1_aa
<220> FEATURE:
<221> NAME/KEY: LIPID
<222> LOCATION: (1)..(1)
<223> OTHER INFORMATION: LIPIDATION

<400> SEQUENCE: 205

Cys Ser Ser Phe Asn Ala Lys Gly Glu Leu Ser Glu Lys Thr Ile Leu
1               5                   10                  15

Arg Ala Cys Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Leu Ala Ala Asp Lys Thr Thr Leu Lys Val Thr Glu Gly Thr Val Val
    50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
            100                 105                 110

Ile Val Phe Thr Lys Glu Cys Thr Ile Thr Val Gln Lys Tyr Asp Ser
        115                 120                 125

Ala Gly Thr Asn Leu Glu Gly Asn Ala Val Glu Ile Lys Thr Leu Asp
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Asn Gly Thr Arg Leu
            180                 185                 190

Glu Tyr Thr Glu Ile Lys Asn Asp Gly Ser Gly Lys Ala Lys Glu Val
        195                 200                 205

Leu Lys Gly Phe Ala Leu Glu Gly Thr Leu Thr Asp Gly Gly Glu Thr
    210                 215                 220

Lys Leu Thr Val Thr Cys Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
        275                 280                 285

Asn Thr Ile Thr Val Gln Asn Tyr Asn Arg Ala Gly Asn Ala Leu Glu
    290                 295                 300

Gly Ser Pro Ala Glu Ile Lys Asp Leu Ala Glu Leu Cys Ala Ala Leu
305                 310                 315                 320

Lys

<210> SEQ ID NO 206
<211> LENGTH: 321
<212> TYPE: PRT
<213> ORGANISM: Artificial Sequence
<220> FEATURE:
<223> OTHER INFORMATION: Lip-S4D1-S3D4_aa
<220> FEATURE:
<221> NAME/KEY: LIPID
<222> LOCATION: (1)..(1)
<223> OTHER INFORMATION: LIPIDATION

<400> SEQUENCE: 206

```
Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Leu Ala Ala Asp Lys Thr Thr Leu Lys Val Thr Cys Gly Thr Val Val
50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
            100                 105                 110

Ile Val Phe Thr Lys Glu Asp Thr Ile Thr Val Gln Lys Tyr Asp Ser
        115                 120                 125

Ala Gly Thr Asn Leu Glu Gly Asn Ala Val Glu Ile Lys Thr Leu Asp
130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Cys Gly Thr Arg Leu
            180                 185                 190

Glu Tyr Thr Glu Ile Lys Asn Asp Gly Ser Gly Lys Ala Lys Glu Val
        195                 200                 205

Leu Lys Gly Phe Ala Leu Glu Gly Thr Leu Thr Asp Gly Gly Glu Thr
210                 215                 220

Lys Leu Thr Val Thr Glu Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
        275                 280                 285

Cys Thr Ile Thr Val Gln Asn Tyr Asn Arg Ala Gly Asn Ala Leu Glu
290                 295                 300

Gly Ser Pro Ala Glu Ile Lys Asp Leu Ala Glu Leu Lys Ala Ala Leu
305                 310                 315                 320

Lys
```

<210> SEQ ID NO 207
<211> LENGTH: 321

```
<212> TYPE: PRT
<213> ORGANISM: Artificial Sequence
<220> FEATURE:
<223> OTHER INFORMATION: Lip-S6D4-S5D1_aa
<220> FEATURE:
<221> NAME/KEY: LIPID
<222> LOCATION: (1)..(1)
<223> OTHER INFORMATION: LIPIDATION

<400> SEQUENCE: 207
```

| | | | | | | | | | | | | | | |
|---|---|---|---|---|---|---|---|---|---|---|---|---|---|---|
| Cys | Ser | Ser | Phe | Asn | Gly | Lys | Gly | Glu | Thr | Ser | Glu | Lys | Thr | Ile | Val |
| 1 | | | | 5 | | | | | 10 | | | | | 15 | |

Cys Ser Ser Phe Asn Gly Lys Gly Glu Thr Ser Glu Lys Thr Ile Val
1               5                   10                  15

Arg Ala Cys Gly Thr Arg Leu Glu Tyr Thr Asp Ile Lys Ser Asp Gly
            20                  25                  30

Ser Gly Lys Ala Lys Glu Val Leu Lys Asp Phe Thr Leu Glu Gly Thr
            35                  40                  45

Leu Ala Ala Asp Gly Lys Thr Thr Leu Lys Val Thr Glu Gly Thr Val
50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
                100                 105                 110

Asn Leu Val Phe Thr Lys Glu Cys Thr Ile Thr Val Gln Arg Tyr Asp
                115                 120                 125

Ser Ala Gly Thr Asn Leu Glu Gly Lys Ala Val Glu Ile Thr Thr Leu
            130                 135                 140

Lys Glu Leu Lys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Asn Gly Thr Arg
                180                 185                 190

Leu Glu Tyr Thr Asp Ile Lys Ser Asp Lys Thr Gly Lys Ala Lys Glu
            195                 200                 205

Val Leu Lys Asp Phe Thr Leu Glu Gly Thr Leu Ala Ala Asp Gly Lys
            210                 215                 220

Thr Thr Leu Lys Val Thr Cys Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
                260                 265                 270

Ile Ser Lys Asn Arg Thr Lys Thr Lys Gln Leu Val Phe Thr Lys Glu
                275                 280                 285

Asp Thr Ile Thr Val Gln Asn Tyr Asp Ser Ala Gly Thr Asn Leu Glu
                290                 295                 300

Gly Lys Ala Val Glu Ile Thr Thr Leu Lys Glu Leu Cys Asn Ala Leu
305                 310                 315                 320

Lys

```
<210> SEQ ID NO 208
<211> LENGTH: 321
<212> TYPE: PRT
<213> ORGANISM: Artificial Sequence
<220> FEATURE:
```

<223> OTHER INFORMATION: Lip-S6D1-S5D4_aa
<220> FEATURE:
<221> NAME/KEY: LIPID
<222> LOCATION: (1)..(1)
<223> OTHER INFORMATION: LIPIDATION

<400> SEQUENCE: 208

Cys Ser Ser Phe Asn Gly Lys Gly Glu Thr Ser Glu Lys Thr Ile Val
1               5                   10                  15

Arg Ala Asn Gly Thr Arg Leu Glu Tyr Thr Asp Ile Lys Ser Asp Gly
            20                  25                  30

Ser Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
50                  55                  60

Val Leu Ser Lys Asn Ile Leu Lys Ser Gly Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
            100                 105                 110

Asn Leu Val Phe Thr Lys Glu Asp Thr Ile Thr Val Gln Arg Tyr Asp
        115                 120                 125

Ser Ala Gly Thr Asn Leu Glu Gly Lys Ala Val Glu Ile Thr Thr Leu
130                 135                 140

Lys Glu Leu Cys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Cys Gly Thr Arg
            180                 185                 190

Leu Glu Tyr Thr Asp Ile Lys Ser Asp Lys Thr Gly Lys Ala Lys Glu
        195                 200                 205

Val Leu Lys Asp Phe Thr Leu Glu Gly Thr Leu Ala Ala Asp Gly Lys
210                 215                 220

Thr Thr Leu Lys Val Thr Glu Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
            260                 265                 270

Ile Ser Lys Asn Arg Thr Lys Thr Lys Gln Leu Val Phe Thr Lys Glu
        275                 280                 285

Cys Thr Ile Thr Val Gln Asn Tyr Asp Ser Ala Gly Thr Asn Leu Glu
        290                 295                 300

Gly Lys Ala Val Glu Ile Thr Thr Leu Lys Glu Leu Lys Asn Ala Leu
305                 310                 315                 320

Lys

<210> SEQ ID NO 209
<211> LENGTH: 266
<212> TYPE: PRT
<213> ORGANISM: Artificial Sequence
<220> FEATURE:
<223> OTHER INFORMATION: B. afzelii (strain K78; OspA serotype 2) aa
      17-273, lipidation signal sequence removed, C-terminal His tag

<400> SEQUENCE: 209

```
Cys Lys Gln Asn Val Ser Ser Leu Asp Glu Lys Asn Ser Ala Ser Val
1               5                   10                  15

Asp Leu Pro Gly Glu Met Lys Val Leu Val Ser Lys Glu Lys Asp Lys
            20                  25                  30

Asp Gly Lys Tyr Ser Leu Lys Ala Thr Val Asp Lys Ile Glu Leu Lys
        35                  40                  45

Gly Thr Ser Asp Lys Asp Asn Gly Ser Gly Val Leu Glu Gly Thr Lys
    50                  55                  60

Asp Asp Lys Ser Lys Ala Lys Leu Thr Ile Ala Asp Asp Leu Ser Lys
65                  70                  75                  80

Thr Thr Phe Glu Leu Phe Lys Glu Asp Gly Lys Thr Leu Val Ser Arg
                85                  90                  95

Lys Val Ser Ser Lys Asp Lys Thr Ser Thr Asp Glu Met Phe Asn Glu
            100                 105                 110

Lys Gly Glu Leu Ser Ala Lys Thr Met Thr Arg Glu Asn Gly Thr Lys
        115                 120                 125

Leu Glu Tyr Thr Glu Met Lys Ser Asp Gly Thr Gly Lys Ala Lys Glu
    130                 135                 140

Val Leu Lys Asn Phe Thr Leu Glu Gly Lys Val Ala Asn Asp Lys Val
145                 150                 155                 160

Thr Leu Glu Val Lys Glu Gly Thr Val Thr Leu Ser Lys Glu Ile Ala
                165                 170                 175

Lys Ser Gly Glu Val Thr Val Ala Leu Asn Asp Thr Asn Thr Thr Gln
            180                 185                 190

Ala Thr Lys Lys Thr Gly Ala Trp Asp Ser Lys Thr Ser Thr Leu Thr
        195                 200                 205

Ile Ser Val Asn Ser Lys Lys Thr Thr Gln Leu Val Phe Thr Lys Gln
    210                 215                 220

Asp Thr Ile Thr Val Gln Lys Tyr Asp Ser Ala Gly Thr Asn Leu Glu
225                 230                 235                 240

Gly Thr Ala Val Glu Ile Lys Thr Leu Asp Glu Leu Lys Asn Ala Leu
                245                 250                 255

Lys Gly Leu Glu His His His His His His
            260                 265
```

<210> SEQ ID NO 210
<211> LENGTH: 268
<212> TYPE: PRT
<213> ORGANISM: Borrelia burgdorferi
<220> FEATURE:
<221> NAME/KEY: LIPID
<222> LOCATION: (1)..(1)
<223> OTHER INFORMATION: LIPIDATION

<400> SEQUENCE: 210

```
Cys Ser Ser Phe Lys Gln Asn Val Ser Ser Leu Asp Glu Lys Asn Ser
1               5                   10                  15

Val Ser Val Asp Leu Pro Gly Glu Met Lys Val Leu Val Ser Lys Glu
            20                  25                  30

Lys Asn Lys Asp Gly Lys Tyr Asp Leu Ile Ala Thr Val Asp Lys Leu
        35                  40                  45

Glu Leu Lys Gly Thr Ser Asp Lys Asn Asn Gly Ser Gly Val Leu Glu
    50                  55                  60

Gly Val Lys Ala Asp Lys Ser Lys Val Lys Leu Thr Ile Ser Asp Asp
65                  70                  75                  80
```

```
Leu Gly Gln Thr Thr Leu Glu Val Phe Lys Glu Asp Gly Lys Thr Leu
                85                  90                  95

Val Ser Lys Lys Val Thr Ser Lys Asp Lys Ser Ser Thr Glu Glu Lys
            100                 105                 110

Phe Asn Glu Lys Gly Glu Val Ser Glu Lys Ile Ile Thr Arg Ala Asp
        115                 120                 125

Gly Thr Arg Leu Glu Tyr Thr Gly Ile Lys Ser Asp Gly Ser Gly Lys
    130                 135                 140

Ala Lys Glu Val Leu Lys Gly Tyr Val Leu Glu Gly Thr Leu Thr Ala
145                 150                 155                 160

Glu Lys Thr Thr Leu Val Val Lys Glu Gly Thr Val Thr Leu Ser Lys
                165                 170                 175

Asn Ile Ser Lys Ser Gly Glu Val Ser Val Glu Leu Asn Asp Thr Asp
            180                 185                 190

Ser Ser Ala Ala Thr Lys Lys Thr Ala Ala Trp Asn Ser Gly Thr Ser
        195                 200                 205

Thr Leu Thr Ile Thr Val Asn Ser Lys Lys Thr Lys Asp Leu Val Phe
    210                 215                 220

Thr Lys Glu Asn Thr Ile Thr Val Gln Gln Tyr Asp Ser Asn Gly Thr
225                 230                 235                 240

Lys Leu Glu Gly Ser Ala Val Glu Ile Thr Lys Leu Asp Glu Ile Lys
                245                 250                 255

Asn Ala Leu Lys Leu Glu His His His His His His
            260                 265

<210> SEQ ID NO 211
<211> LENGTH: 4
<212> TYPE: PRT
<213> ORGANISM: Borrelia afzelii

<400> SEQUENCE: 211

Cys Lys Gln Asn
1

<210> SEQ ID NO 212
<211> LENGTH: 257
<212> TYPE: PRT
<213> ORGANISM: Artificial Sequence
<220> FEATURE:
<223> OTHER INFORMATION: Chimeric OspA Serotype1/Serotype2
<220> FEATURE:
<221> NAME/KEY: LIPID
<222> LOCATION: (1)..(1)
<223> OTHER INFORMATION: LIPIDATION

<400> SEQUENCE: 212

Cys Ala Gln Lys Gly Ala Glu Ser Ile Gly Ser Val Ser Val Asp Leu
1               5                   10                  15

Pro Gly Glu Met Lys Val Leu Val Ser Lys Glu Lys Asp Lys Asn Gly
            20                  25                  30

Lys Tyr Asp Leu Ile Ala Thr Val Asp Lys Leu Glu Leu Lys Gly Thr
        35                  40                  45

Ser Asp Lys Asn Asn Gly Ser Gly Val Leu Glu Gly Val Lys Thr Asn
    50                  55                  60

Lys Ser Lys Val Lys Leu Thr Ile Ser Asp Asp Leu Gly Gln Thr Thr
65                  70                  75                  80

Leu Glu Val Phe Lys Glu Asp Gly Lys Thr Leu Val Ser Lys Lys Val
                85                  90                  95
```

```
Thr Ser Lys Asp Lys Ser Ser Thr Glu Glu Lys Phe Asn Glu Lys Gly
            100                 105                 110

Glu Val Ser Glu Lys Ile Ile Thr Met Ala Asp Gly Thr Arg Leu Glu
            115                 120                 125

Tyr Thr Gly Ile Lys Ser Asp Gly Thr Gly Lys Ala Lys Tyr Val Leu
        130                 135                 140

Lys Asn Phe Thr Leu Glu Gly Lys Val Ala Asn Asp Lys Thr Leu
145                 150                 155                 160

Glu Val Lys Glu Gly Thr Val Thr Leu Ser Met Asn Ile Ser Lys Ser
                    165                 170                 175

Gly Glu Val Ser Val Glu Leu Asn Asp Thr Asp Ser Ser Ala Ala Thr
                180                 185                 190

Lys Lys Thr Ala Ala Trp Asn Ser Lys Thr Ser Thr Leu Thr Ile Ser
            195                 200                 205

Val Asn Ser Lys Lys Thr Thr Gln Leu Val Phe Thr Lys Gln Asp Thr
        210                 215                 220

Ile Thr Val Gln Lys Tyr Asp Ser Ala Gly Thr Asn Leu Glu Gly Thr
225                 230                 235                 240

Ala Val Glu Ile Lys Thr Leu Asp Glu Leu Lys Asn Ala Leu Lys Leu
                    245                 250                 255

Glu

<210> SEQ ID NO 213
<211> LENGTH: 149
<212> TYPE: PRT
<213> ORGANISM: Borrelia garinii

<400> SEQUENCE: 213

Phe Asn Asp Lys Gly Lys Leu Ser Glu Lys Val Val Thr Arg Ala Asn
1               5                   10                  15

Gly Thr Arg Leu Glu Tyr Thr Glu Ile Gln Asn Asp Gly Ser Gly Lys
            20                  25                  30

Ala Lys Glu Val Leu Lys Ser Leu Thr Leu Glu Gly Thr Leu Thr Ala
        35                  40                  45

Asp Gly Glu Thr Lys Leu Thr Val Glu Ala Gly Thr Val Thr Leu Ser
    50                  55                  60

Lys Asn Ile Ser Glu Ser Gly Glu Ile Thr Val Glu Leu Lys Asp Thr
65                  70                  75                  80

Glu Thr Thr Pro Ala Asp Lys Lys Ser Gly Thr Trp Asp Ser Lys Thr
                85                  90                  95

Ser Thr Leu Thr Ile Ser Lys Asn Ser Gln Lys Thr Lys Gln Leu Val
            100                 105                 110

Phe Thr Lys Glu Asn Thr Ile Thr Val Gln Lys Tyr Asn Thr Ala Gly
        115                 120                 125

Thr Lys Leu Glu Gly Ser Pro Ala Glu Ile Lys Asp Leu Glu Ala Leu
    130                 135                 140

Lys Ala Ala Leu Lys
145

<210> SEQ ID NO 214
<211> LENGTH: 20
<212> TYPE: DNA
<213> ORGANISM: Artificial Sequence
<220> FEATURE:
<223> OTHER INFORMATION: pcr primer
```

<400> SEQUENCE: 214
catgctcttg atcctgttta                                                  20

<210> SEQ ID NO 215
<211> LENGTH: 9
<212> TYPE: PRT
<213> ORGANISM: Artificial Sequence
<220> FEATURE:
<223> OTHER INFORMATION: C-terminal His tag

<400> SEQUENCE: 215

Gly Leu Glu His His His His His His
1               5

<210> SEQ ID NO 216
<211> LENGTH: 20
<212> TYPE: DNA
<213> ORGANISM: Artificial Sequence
<220> FEATURE:
<223> OTHER INFORMATION: pcr primer

<400> SEQUENCE: 216
cccatttctc catctatctc                                                  20

<210> SEQ ID NO 217
<211> LENGTH: 148
<212> TYPE: PRT
<213> ORGANISM: Artificial Sequence
<220> FEATURE:
<223> OTHER INFORMATION: S1D1

<400> SEQUENCE: 217

Phe Asn Glu Lys Gly Glu Val Ser Glu Lys Ile Ile Thr Arg Ala Asp
1               5                   10                  15

Gly Thr Arg Leu Glu Tyr Thr Gly Ile Lys Ser Asp Gly Ser Gly Lys
            20                  25                  30

Ala Lys Glu Val Leu Lys Asn Phe Thr Leu Glu Gly Lys Val Ala Asn
        35                  40                  45

Asp Lys Thr Thr Leu Val Val Lys Cys Gly Thr Val Thr Leu Ser Lys
    50                  55                  60

Asn Ile Ser Lys Ser Gly Glu Val Ser Val Glu Leu Asn Asp Thr Asp
65                  70                  75                  80

Ser Ser Ala Ala Thr Lys Lys Thr Ala Ala Trp Asn Ser Gly Thr Ser
                85                  90                  95

Thr Leu Thr Ile Thr Val Asn Ser Lys Lys Thr Lys Asp Leu Val Phe
            100                 105                 110

Thr Lys Glu Asn Thr Ile Thr Val Gln Gln Tyr Asp Ser Asn Gly Thr
        115                 120                 125

Lys Leu Glu Gly Ser Ala Val Glu Ile Thr Lys Leu Asp Glu Ile Cys
    130                 135                 140

Asn Ala Leu Lys
145

<210> SEQ ID NO 218
<211> LENGTH: 148
<212> TYPE: PRT
<213> ORGANISM: Artificial Sequence
<220> FEATURE:
<223> OTHER INFORMATION: S5D1

<400> SEQUENCE: 218

-continued

```
Phe Asn Glu Lys Gly Glu Ile Ser Glu Lys Thr Ile Val Arg Ala Asn
 1               5                  10                  15

Gly Thr Arg Leu Glu Tyr Thr Asp Ile Lys Ser Asp Lys Thr Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Cys Gly Thr Val Thr Leu Ser
    50                  55                  60

Lys Asn Ile Ser Lys Ser Gly Glu Ile Thr Val Ala Leu Asp Asp Thr
 65                  70                  75                  80

Asp Ser Ser Gly Asn Lys Lys Ser Gly Thr Trp Asp Ser Gly Thr Ser
                85                  90                  95

Thr Leu Thr Ile Ser Lys Asn Arg Thr Lys Thr Lys Gln Leu Val Phe
            100                 105                 110

Thr Lys Glu Asp Thr Ile Thr Val Gln Asn Tyr Asp Ser Ala Gly Thr
        115                 120                 125

Asn Leu Glu Gly Lys Ala Val Glu Ile Thr Thr Leu Lys Glu Leu Cys
    130                 135                 140

Asn Ala Leu Lys
145
```

MUTANT FRAGMENTS OF OSPA AND METHODS AND USES RELATING THERETO

RELATED APPLICATIONS

This application is a continuation of U.S. application Ser. No. 14/412,722, filed Jan. 5, 2015, which is a national stage filing under 35 U.S.C. § 371 of international application PCT/EP2013/064403, filed Jul. 8, 2013, which was published under PCT Article 21(2) in English, claims the benefit under 35 U.S.C. § 120 of U.S. application Ser. No. 13/802,991, filed Mar. 14, 2013, and claims the benefit under 35 U.S.C. § 119(e) of U.S. provisional application Ser. No. 61/668,627, filed Jul. 6, 2012, the disclosures of which are incorporated by reference herein in their entireties.

FIELD OF THE INVENTION

The present invention relates to compositions and methods for the prevention and treatment of *Borrelia* infection. Particularly, the present invention relates to a polypeptide comprising a mutant fragment of an outer surface protein A (OspA), a nucleic acid coding the same, a pharmaceutical composition (particularly for use as a medicament of in a method of treating or preventing a *Borrelia* infection) comprising the polypeptide and/or the nucleic acid, a method of treating or preventing a *Borrelia* infection and a method of immunizing a subject.

BACKGROUND OF THE INVENTION

Lyme borreliosis, or Lyme disease, is the most commonly reported tick-borne disease in Europe and North America. The disease is caused by the arthropod-borne gram-negative-like spirochete, *Borrelia burgdorferi* sensu lato (*B. burgdorferi* s.l.), and is an infection that can involve multiple organs or tissues, resulting in skin, cardiac, musculoskeletal and neurological disorders. In most countries, Lyme borreliosis is not a notifiable disease and no exact data regarding annual incident rates are available. In the United States, the causative agent is *B. burgdorferi* sensu stricto (*B. burgdorferi* s.s.) and Lyme borreliosis is localized to north-eastern, mid-Atlantic and upper north-central states. In 2010, a total of about 30,000 cases of Lyme borreliosis were reported for the US to the Centers for Disease Control and Prevention (CDC). In Europe, *B. afzelii* and *B. garinii* are the main causative agents of Lyme borreliosis, as well as *B. burgdorferi* s.s. and *B. bavariensis*, which contribute to a lesser extent depending on the geographic location. The prevalence of Lyme borreliosis varies considerably in different European countries with an overall increased prevalence from west to cast. In much of Europe, the number of reported cases of Lyme borreliosis has increased since the early 1990s (e.g., the Czech Republic, Estonia, Lithuania; see Lyme borreliosis in Europe, WHO report of 2006), and the geographic distribution of cases has also expanded.

*Borrelia* belongs to the family Spirochaetaceae, which is subdivided into the medically important genera *Treponema, Leptospira* and *Borrelia*. *B. burgdorferi* s.l. is a spiral-shaped, vigorously motile gram-negative bacterium, about 10-20 μm long and 0.2-0.5 μm wide, that grows under microaerophilic conditions. The spirochetal cell wall consists of a cytoplasmic membrane surrounded by peptidoglycan and several flagella and then by a loosely-associated outer membrane.

Lyme borreliosis generally occurs in stages characterized by different clinical manifestations, with remissions and exacerbations. Stage 1, early infection, consists of a localized infection of the skin, followed within days or weeks by stage 2, disseminated infection, and months to years later by stage 3, persistent infection. However, the infection is variable; some patients have only localized infections of the skin, while others display only later manifestations of the illness, such as arthritis. Different clinical syndromes of Lyme borreliosis are also caused by infection with diverse *B. burgdorferi* s.l. species. *B. burgdorferi* s.s. more often causes joint manifestations (arthritis) and heart problems, *B. afzelii* causes mainly dermal symptoms (erythema migrans; EM and acrodermatitis chronica atrophicans; ACA), whereas *B. garinii* is implicated in most cases of neuroborreliosis.

Localized infection—The most common symptom of stage 1 of an infection is erythema migrans, which occurs in 70-80% of infected people. This skin lesion is often followed by flu-like symptoms, such as myalgia, arthralgia, headache and fever. These non-specific symptoms occur in 50% of patients with erythema migrans.

Disseminated infection—During stage 2, the bacteria move into the blood stream from the site of infection to distal tissues and organs. Neurological, cardiovascular and arthritic symptoms that occur in this stage include meningitis, cranial neuropathy and intermittent inflammatory arthritis.

Persistent infection—Stage 3 of the infection is chronic and occurs from months to years after the tick bite. The most common symptom in North America is rheumatoid arthritis, caused by an infection with *B. burgdorferi* s.s. Persistent infection of the central nervous system with *B. garinii* causes more severe neurological symptoms during stage 3, and a persistent infection of the skin with *B. afzelii* results in acrodermatitis chronica atrophicans.

In some risk groups, such as farmers, forestry workers, hikers, runners or vacationers, seroprevalence and disease incidence rates have increased, as in children under 15 years of age and adults between 39 and 59, without gender preference. This increased incidence of Lyme borreliosis is linked to changes in forest habitats as well as social factors. Environmental changes, such as forest fragmentation, have led to a sharp reduction of rodent predators such as foxes and birds of prey, which in turn has led to an increase in the mouse population, with a subsequent increase in the tick population. More recently, patchy reforestation has increased the number of deer and thus the number of ticks. Suburban sprawl and the increasing use of woodland areas for recreation such as camping and hiking has brought humans into greater contact with the larger number of tick *Borrelia* vectors. All of these factors together have contributed to a wider distribution of *Borrelia* and a higher incidence of Lyme borreliosis.

Antimicrobial agents are the principle method of treatment of *Borrelia* infection. The antibiotic used depends on the stage of the disease, symptoms, and the patient's allergies to medication. The length of the antibiotic course also depends on the stage of the disease and the severity of symptoms. Early Lyme borreliosis is typically treated with oral tetracyclines, such as doxycycline, and semi-synthetic penicillins, such as amoxicillin or penicillin V. Arthritic and neurological disorders are treated with high-dose intravenous penicillin G or ceftriaxone. Up to 30% of Lyme borreliosis patients do not display the early characteristic symptoms of infection with *Borrelia*, making diagnosis and treatment problematic. The antibiotic course can be long (up to several months) and sometimes ineffective and is thus debated in the *Borrelia* field, especially during later-stage disease. Even in the case of effective treatment of *Borrelia*, patients can be left with debilitating fatigue, pain, or neurological symptoms for years afterwards referred to as post-treatment Lyme disease syndrome. In general, the use of antibiotics can have undesirable consequences, such as the development of resistance by the target micro-organisms. Finally, antibiotic therapy may effectively cure Lyme borreliosis, but provides no protection against subsequent infections.

A monovalent serotype 1-OspA-based vaccine (LYMErix™) was approved and marketed in the USA for the prevention of Lyme disease caused by *Borrelia burgdorferi* s.s. However, heterogeneity in OspA sequences across different serotypes in Europe and elsewhere precludes efficient protection with a vaccine based on OspA from only a single serotype.

Chimeric OspA molecules comprising the proximal portion from one OspA serotype, together with the distal portion form another OspA serotype, while retaining antigenic properties of both of the parent polypeptides, may be used in the prevention and treatment of Lyme disease or borreliosis (WO2011/143617, WO2011/143623).

Currently, there is no preventative medicament for Lyme borreliosis on the market and thus there is a need in the art for the development of such a medicament that can provide effective protection against *Borrelia* that are present in the USA, Europe and elsewhere, especially for the development of a medicament that can provide effective protection against several *Borrelia* serotypes simultaneously.

SUMMARY OF THE INVENTION

The present invention relates to a polypeptide comprising a mutant fragment of *Borrelia* outer surface protein A (OspA), a nucleic acid encoding the same, a vector which comprises such nucleic acid molecule, and a host cell comprising such vector. Furthermore, the invention provides a process for producing such polypeptide and a process for producing a cell which expresses such polypeptide. Moreover, the present invention provides antibodies specifically binding to such polypeptide, a hybridoma cell producing such antibodies, methods for producing such antibodies, a pharmaceutical composition comprising such polypeptide, nucleic acid molecule, vector or antibody, the use of such polypeptide, nucleic acid molecule, vector or antibody for the preparation of a medicament or a pharmaceutical composition (particularly for use as a vaccine or in a method of treating or preventing a *Borrelia* infection), methods for diagnosing an infection and methods for treating or preventing a *Borrelia* infection and methods of immunizing a subject.

Efforts to develop a subunit vaccine for prevention of Lyme borreliosis have been focused in large part on the use of borrelial outer surface protein A (OspA) as an antigen. The OspA protein is expressed by *Borrelia* only when it is in the gut of the tick vector. Thus, OspA antibodies produced by vaccination do not fight infection in the body, but rather enter the gut of the tick when it takes a blood meal. There, the antibodies neutralise the spirochetes and block the migration of bacteria from the midgut to the salivary glands of the tick, the route through which *Borrelia* enters the vertebrate host. Thus, OspA-specific antibodies prevent the transmission of *Borrelia* from the tick vector to the human host.

The lipidated form of OspA from *B. burgdorferi* s.s., strain ZS7, together with aluminium hydroxide was commercially developed as a vaccine against *Borrelia* (LYMErix™) by SmithKline Beecham, now GlaxoSmithKline (GSK) for the US market. Three doses of LYIVIErix™ over a period of one year were needed for optimal protection. After the first two doses, vaccine efficacy against Lyme borreliosis was 49%, and after the third dose 76%. However, shortly after LYMErix™ was commercially available, it was withdrawn from the market in 2002. Reasons cited were matters of practical application of the vaccine, for example the need for booster injections every year or every other year, as well as the relatively high cost of this preventive approach compared with antibiotic treatment of early infection. In addition, there was a concern that LYMErix™ could trigger autoimmune reactions in a subgroup of the population due to sequence homology with a human protein, though this was never proven. In addition, cross-protection against other clinically important *Borrelia* species was not provided by this vaccine.

Accordingly, in one embodiment, it was an object of the present invention to provide an improved vaccine for the prevention of Lyme borreliosis. Preferably, the vaccine is easily produced while being protective, safe and more effective than existing therapies and/or provides protection against more than one *Borrelia* species.

The problem underlying the present invention is solved by a polypeptide comprising a mutant fragment of an outer surface protein A (OspA), wherein the mutant fragment consists of a C-terminal domain of an OspA protein of *Borrelia* and differs from the corresponding wild-type fragment at least by the introduction of at least one disulfide bond.

Surprisingly, it was found that the introduction of at least one disulfide bond in a mutant fragment increases the protective capacity of the polypeptide comprising the mutant OspA fragment relative to a polypeptide comprising the wild-type OspA fragment, as shown in an in vivo model of infection. As shown in the Examples, the introduction of at least one disulfide bond into the *B. afzelii* OspA C-terminal fragment increased its protective capacity relative to the wild-type OspA fragment without a disulfide bond. Tables 2 and 3 provide data demonstrating the protective capacity of mutant fragments with an introduced disulfide bond ("S2D1-5") as compared to the wild-type OspA fragment ("S2D0"), as fewer animals were infected after immunization with mutant OspA fragments in comparison to wild-type OspA fragments. Some of the mutant OspA fragments tested provided protection comparable to that conveyed by the positive control antigen, the non-lipidated full-length OspA protein.

DETAILED DESCRIPTION OF THE INVENTION

Accordingly, in a first aspect, the present invention relates to a polypeptide comprising a mutant fragment of an outer surface protein A (OspA), wherein the mutant fragment consists of a C-terminal domain of an OspA of *Borrelia* and differs from the corresponding wild-type fragment at least by the introduction of at least one disulfide bond.

The term *B. burgdorferi* s.l. encompasses at least 13 *Borrelia* species (Table A-1). These species occur in different geographic regions, and live in nature in enzootic cycles involving ticks of the *Ixodes ricinus* complex (also called *Ixodes persulcatus* complex) and a wide range of animal hosts. Four *Borrelia* species are responsible for the majority of infections in humans: *B. burgdorferi* s.s., *B. afzelii, B. bavariensis* and *B. garinii*. Three other species, *B. lusitaniae, B. bissettii* and *B. spielmanii*, have occasionally been detected in humans, but their role in Lyme borreliosis is uncertain at present. New species of *Borrelia* are still being reported.

TABLE A-1

| | Principal tick vector | Location |
|---|---|---|
| Pathogenic species (4) | | |
| *Borrelia burgdorferi* (*Borrelia burgdorferi* s.s.) | *Ixodes scapularis* | Northeastern/north-central US |
| | *Ixodes pacificus* | Western US |
| | *Ixodes ricinus* | Europe |
| | *Ixodes persulcatus* | Asia |
| *Borrelia garinii* | *Ixodes ricinus* | Europe |
| | *Ixodes persulcatus* | Asia |
| *Borrelia afzelii* | *Ixodes ricinus* | Europe |
| | *Ixodes persulcatus* | Asia |
| *Borrelia bavariensis* | *Ixodes ricinus* | Europe |
| | *Ixodes persulcatus* | Asia |
| Minimally pathogenic or non-pathogenic species (9) | | |
| *Borrelia andersonii* | *Ixodes dentatus* | Eastern US |
| *Borrelia bissettii* | *Ixodes spinipalpis* | Western US |
| | *Ixodes pacificus* | Europe |
| | *Ixodes ricinus* | |
| *Borrelia valaisiana* | *Ixodes ricinus* | Europe and Asia |
| | *Ixodes columnae* | |
| *Borrelia lusitaniae* | *Ixodes ricinus* | Europe |
| *Borrelia spielmanii* | *Ixodes ricinus* | Europe |
| *Borrelia japonica* | *Ixodes ovatus* | Japan |
| *Borrelia tanukii* | *Ixodes tanuki* | Japan |
| *Borrelia turdi* | *Ixodes turdus* | Japan |
| *Borrelia sinica* | *Ixodes persulcatus* | China |

As detailed above, *Borrelia* outer surface protein A (OspA) is an abundant immunogenic lipoprotein of *Borrelia* of particular interest because of its potential as a vaccine candidate. OspA of *B. burgdorferi* s.l. is a basic lipoprotein that has a molecular mass of approximately 30 kDa and is encoded on a linear plasmid. An important aspect of the OspA protein is its N-terminal lipidation; that is, the N-terminal cysteine residue is substituted with fatty acids with a chain length of between C14 and C19 with or without double-bonds, a feature that enhances the immunogenicity of the OspA protein. It has been shown that poorly-immunogenic synthetic peptides induce stronger antibody responses when lipidated; for example, when covalently coupled to $Pam_3Cys$ (Bessler and Jung, Research Immunology (1992) 143:548-552), a fatty acid substitution found at the amino terminus of many bacterial lipoproteins that are synthesized with a signal sequence specifying lipid attachment. Additionally, the $Pam_3Cys$ moiety was shown to enhance immune responses to OspA in mice, partially through its interaction with TLR-2 (Yoder, et al. (2003) Infection and Immunity 71:3894-3900). Therefore, lipidation of a C-terminal fragment of OspA would be expected to enhance the immunogenicity and protective capacity of the fragment.

Analysis of isolates of *B. burgdorferi* s.l. obtained in North America and Europe has revealed that OspA has antigenic variability and that several distinct groups can be defined based on serology. Anti-OspA mAbs which bind to specific N- and C-terminal antigenic determinants have been reported. X-ray crystallography and NMR analysis have been used to identify immunologically important hypervariable domains in OspA and have mapped the LA-2 epitope to C-terminal amino acids 203-257 (Ding et al., Mol. Biol. 302: 1153-64, 2000). Previous studies have shown that the production of antibodies against the C-terminal epitope LA-2 correlates with protective immunity after vaccination with OspA (Van Hoecke et al. Vaccine (1996) 14(17-18):1620-6 and Steere et al., N Engl J Med (1998) 339:209-215). Antibodies to LA-2 were shown to block the transmission of *Borrelia* from tick to host (Golde et al., Infect Immun (1997) 65(3):882-889). These studies suggested that the C-terminal portion of the OspA protein may be sufficient for inducing protective immunity. It should be noted that the sequence of the C-terminal portion of OspA is less highly-conserved between *Borrelia* serotypes than is the N-terminal portion (see FIG. 1).

Based on information from the studies outlined above, along with others, truncated forms of OspA comprising the C-terminal portion (also referred to herein as "OspA fragment" or "monomer") were used in the current invention. These truncated forms of OspA proved to be less protective than the full-length OspA protein. Surprisingly, however, it was found in the course of the current invention that the introduction of a disulfide bond in the truncated form (also referred to herein as "mutant OspA fragment" or "mutant fragment") overcomes this disadvantage. While not being limited to a specific mechanism, it is thought that improved protection is due to increased stability of the OspA fragment, as shown in assays measuring thermal stability.

In accordance with the present invention, the mutant OspA fragment may be derived from any *Borrelia* species; however, due to their relevance in the medical field, particularly for humans, *B. burgdorferi* s.s., *B. afzelii, B. bavariensis* and *B. garinii* are preferred. In this regard, these four *Borrelia* species can be further classified according to their OspA serotypes, which have been determined by analysis with monoclonal antibodies specific to the respective OspA protein. Serotypes 1-7, which account for the majority of human *Borrelia* infections, along with their rates of prevalence, are shown in Table A-2 below.

TABLE A-2

Serotype designation and prevalence of *B. burdorferi* s.s., *B. afzelii*, *B. bavariensis* and *B. garinii*. *Borrelia* isolated from human cerebrospinal fluid or skin or from tick vectors were serotyped by probing whole-cell lysates with mouse monoclonal antibodies, each specific to a particular epitope of OspA (as described by Wilske et al, J. of Clin Microbiol (1993) 31(2): 340-350 and presented by Baxter Bioscience at "Climate change effect on ticks and tick-borne diseases", Brussels, 6 Feb. 2009).

| *Borrelia* sp. | OspA serotype defined by mAb testing | Prevalence in human disease | Strain source for sequence | Seq ID No: |
|---|---|---|---|---|
| *B. burgdorferi* s.s. | 1 | 11% | B31 | 20 |
| *B. afzelii* | 2 | 63% | K78 | 19 |
| *B. garinii* | 3 | 1.5% | PBr | 21 |
| *B. bavariensis* | 4 | 4% | PBi | 22 |
| *B. garinii* | 5 | 6% | PHEi | 23 |
| *B. garinii* | 6 | 13% | DK29 | 24 |
| *B. garinii* | 7 | 0.5% | T25 | 25 |

The structure of the OspA protein from *B. burgdorferi* s.s. strain B31 was determined by Li et al. (Proc Natl Acad Sci (1997) 94:3584-3589). It is composed of N-terminal (β-strands 1 to 4) and central β-sheets (β-strands 5 to 14n [N-terminal part]), barrel sheet 1 (β-strands 14c [C-terminal part] to 16), barrel sheet 2 (β-strands 17 to 21) and a C-terminal α-helix. The term "OspA C-terminal domain" or "C-terminal domain" or "wild-type fragment" or "C-terminal portion" with respect to OspA as used throughout the present specification shall mean the C-terminal amino acid sequence of OspA, i.e. OspA lacking at least the N-terminal β-sheet (including β-strands 1 to 4). In OspA from *B. burgdorferi* s.s. strain B31, the N-terminal sheet consists of amino acids 17 to 70 (following post-translational cleavage of the 16 aa long lipidation signal peptide).

The C-terminal OspA fragment of the current invention may also include a lipidation signal sequence at the N-terminus, e.g., the lipidation signal sequence of amino acids 1 to 16 of OspA (SEQ ID NO: 14) or OspB (SEQ ID NO: 15) from *B. burgdorferi* s.s. strain B31, a lipidation signal sequence from *E. coli*, referred to herein as the "lpp lipidation signal" (SEQ ID NO: 16), or any other signal sequence, e.g., as defined below.

Lipidation of a protein with an N-terminal lipidation signal sequence, such as those present on a nascent OspA polypeptide, occurs in the *E. coli* expression vector by the step-wise action of the enzymes diacylglyceryl transferase, signal peptidase II and transacylase, respectively. The first step is the transfer of a diacylglyceride to the cysteine sulphydryl group of the unmodified prolipoprotein, followed by the cleavage of the signal peptide by signal peptidase II and, finally, the acylation of the α-amino group of the N-terminal cysteine of the apolipoprotein. The result is the placement of one lipid and a glycerol group substituted with two further lipids on the N-terminal cysteine residue of the polypeptide. The lipidation signal sequence, which is cleaved off during lipidation, is not present in the final polypeptide sequence.

According to the current invention, the mutant OspA fragment may be a lipidated protein, also lipoprotein, wherein the lipid moieties, along with the glycerol group, is also referred to as "Lip". According to the invention, Lip comprises one to three lipids such as $C_{14-20}$ alkyl and/or $C_{14-20}$ alkenyl attached to a glycerol and the N-terminal cysteine of the polypeptide of the invention, or preferably wherein Lip is a moiety of formula (I) below, Formula (I)

$$\begin{array}{c} O & & O \\ \parallel & & \parallel \\ O-C-R_1 & & HN-C-R_3, \\ | & & | \\ CH_2-CH-CH_2-S-CH_2-CH \\ | & & | \\ O-C-R_2 & & C=O \\ \parallel & & | \\ O & & X \end{array}$$

in which one of $R_1$, $R_2$ or $R_3$ is $C_{14}$-$C_{20}$ alkyl or alkenyl, and each of the others, independently is $C_{14}$-$C_{20}$ alkyl or $C_{14}$-$C_{20}$ alkenyl, and X is an amino acid sequence attached to the cysteine residue shown in Formula (I). More preferably, Lip plus the N-terminal cysteine of the polypeptide is N-palmitoyl-S-(2RS)-2,3-bis-(palmitoyloxy) propyl cysteine (referred to herein as "Pam$_3$Cys") and is connected via the carbonyl C of the cysteine to said amino acid sequence of the invention. In Formula (I) above $R_1$, $R_2$ and $R_3$ would be palmitoyl moieties and X is an amino acid sequence attached to the cysteine residue.

In accordance with the current invention, the C-terminal domain of an OspA from a strain other than *B. burgdorferi* s.s. B31 is defined by (i) lacking at least amino acids 17 to 70 and/or (ii) by lacking at least the N-terminal domain homologous to amino acids 17 to 70 of OspA from *B. burgdorferi* s.s. B31. Additionally, the OspA C-terminal domain according to the present invention may also lack further portions of the central sheet as defined by Li and co-workers (Li et al., supra), particularly further strands such as the amino acid portions from amino acid 17 to 82, 93, 105, 118 or 119, preferably 17 to 129, more preferably 1 to 125, 1 to 129 or 1 to 130 of any *Borrelia*, particularly *B. burgdorferi* s.s. B31, or homologous portions of an OspA protein from a *Borrelia* sp. other than *B. burgdorferi* s.s. B31.

In the context of the present invention, the OspA C-terminal domain is also referred to as "OspA fragment" or "fragment of OspA".

The "mutant fragment" in the context of the polypeptide of the present invention and as used throughout the present specification shall mean the OspA C-terminal fragment, as defined above, which differs from the wild-type fragment at least by at least two introduced cysteines that can form a disulfide bond. Without being bound to that theory, it is assumed that the disulfide bond stabilizes the fragment in a conformation conducive to the induction of antibody binding. The fold of the wild-type C-terminal fragment of OspA shows reduced temperature stability in comparison to the full-length protein (Koide et al., Structure-based Design of a Second-generation Lyme Disease Vaccine Based on a C-terminal Fragment of *Borrelia burgdorferi* OspA, J. Mol. Biol. (2005) 350:290-299). For the present invention, the sequence of the C-terminal domain of the *B. burgdorferi* s.s. B31 OspA has been in silico analyzed to determine positions for introduced disulfide bridges that may enhance the stability of the fold of this C-terminal domain. The results of the analysis have been transferred to homologous OspA fragments of other *Borrelia* species with the assumption that the fold is conserved across species.

Typically, the disulfide bond may be introduced by the introduction of one or more cysteine residues, wherein a disulfide bond (S—S bridge) is formed between the thiol groups of two cysteine residues. Only one cysteine residue need be introduced if a disulfide bond is formed with a cysteine residue present in the wild-type fragment. The one, or preferably two, cysteine(s) may be introduced by amino acid addition or, preferably, substitution.

The OspA mutant fragment may also comprise further mutations relative to the wild-type. As detailed above, the structure and surface domain of OspA are known in the art. Accordingly, the mutant fragment may comprise further mutations, particularly at sites not on the surface of the protein and/or not involved in the immune response and, therefore not impacting antigenic capacity. These can include one or more amino acid deletion(s), particularly small (e.g., up to 10 amino acids) deletions, one or more amino acid addition(s) (particularly C- or N-terminally), one or more amino acid substitution(s), particularly one or more conservative amino acid substitutions. Examples of conservative amino acid substitutions include, but are not limited to, those listed below:

| | |
|---|---|
| Ala | Ser |
| Arg | Lys |
| Asn | Gln; His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Asn |
| Met | Leu; Ile |
| Phe | Met; Leu; Tyr |
| Ser | Thr |
| Thr | Ser |

-continued

| | |
|---|---|
| Trp | Tyr |
| Tyr | Trp; Phe |
| Val | Ile; Leu |

Preferred mutations include changes in selected portions of the fragment, for example, wherein the sequence with sequence similarity to human leukocyte function-associated antigen (hLFA-1), which exists in *B. burgdorferi* s.s., is modified, for example, replaced by a homologous sequence from an OspA protein from another *Borrelia* sp. The rationale for this modification is to reduce the risk for inducing immunological cross-reaction with human proteins. Also possible is the addition of a signal sequence for lipidation in the final, or an intermediate, fragment, or the addition of a marker protein (e.g., for identification or purification).

In some embodiments, the mutant OspA fragment has an amino acid sequence that has 60%, preferably at least 70%, more preferably at least 80%, more preferably 85%, more preferably 90%, even more preferably 95% sequence identity to the wild-type fragment. In another embodiment, the sequence differs by at most 10%, at most 9%, at most 8%, at most 7%, at most 6%, 5%, 4%, 3%, 2%, most preferably at most 1%, due to a sequence addition, deletion or substitution.

Identity, as known in the art and as used herein, is the relationship between two or more polypeptide sequences, as determined by comparing the sequences. In the art, identity also means the degree of sequence relatedness between polypeptide or polynucleotide sequences, as the case may be, as determined by the match between strings of such sequences. Identity can be readily calculated. While a number of methods exist to measure identity between two polynucleotides or two polypeptide sequences, the term is well known to skilled artisans (e.g. *Sequence Analysis in Molecular Biology*, von Heinje, G., Academic Press, 1987). Preferred methods to determine identity are designed to give the largest match between the sequences tested. Methods to determine identity are codified in computer programs. Preferred computer program methods to determine identity between two sequences include, but are not limited to, the GCG program package (Devereux, J. et al., 1984), BLASTP, BLASTN, and FASTA (Altschul, S. et al., 1990).

In contrast to the mutant OspA fragment, the "wild-type fragment" in the context of the present invention relates to a fragment of a naturally-occurring OspA of *Borrelia*. The wild-type fragment is obtained by N-terminal deletions, but it does not comprise internal deletions (except from signal sequences as detailed herein) or mutations. In relation to the mutant OspA fragment, the wild-type fragment consists of an identical part of the OspA (identical length and same strain of OspA, etc.) and differs only in the mutation(s) detailed above, particularly in the introduction of at least one disulfide bond or the replacement of a sequence with human homology, for example hLFA-1 (see above).

According to a preferred embodiment of the present invention, the polypeptide of the present invention does not comprise or consist of the full-length OspA polypeptide having at least one disulfide bond introduced.

In one embodiment of the present invention, the mutant OspA fragment may differ from the respective wild-type fragment only by the introduction of at least one, preferably exactly one, disulfide bond.

A polypeptide is a single linear polymer of amino acids linked by peptide bonds, in some cases also by disulfide bonds. In accordance with the present invention, the polypeptide may also compromise one or more posttranslational modifications; i.e., an attached biochemical functional group, such as an attached acetate, phosphate, lipid or carbohydrate, preferably a lipid or lipids attached to the N-terminal cysteine along with a glycerol, more preferably 1 to 3 $C_{14}$-$C_{20}$ alkyl or alkenyl moieties, even more preferably 1 to 3 palmitoyl groups, most preferably three palmitoyl groups ($Pam_3$).

In accordance with the present invention, the polypeptide of the present invention comprises the above-described mutant OspA fragment. According to the present invention, it does not comprise (i) the N-terminal sheet as defined above and (ii) optionally one or more further strands of the central sheet as defined above. However, the polypeptide may comprise one or more functional sequences such as a signal sequence, e.g., a lipidation signal sequence or a posttranslational modification, such as lipidation.

In a further embodiment of the present invention, the polypeptide of the present invention consists of (i) one or more mutant OspA fragments, optionally joined by linkers, e.g., as defined below and (ii) optionally one or more amino acids heterologous to OspA, particularly a signal sequence and (iii) optionally a posttranslational modification, such as lipidation.

The polypeptide of the present invention has protective capacity. As detailed above, the introduction of a disulfide bond into the mutant OspA fragment increases the protective capacity of the polypeptide relative to a polypeptide comprising the respective fragment without the disulfide bond(s). In some embodiments, the protective capacity is increased by at least 10%, more preferably by at least 20%, more preferably by at least 30%, more preferably by at least 40%, more preferably by at least 50%, more preferably by at least 60%, more preferably by at least 70%, more preferably by at least 80%, even more preferably by at least 90% relative to a polypeptide comprising the respective fragment without the disulfide bond(s).

The term protective capacity describes the ability to protect a subject against a *Borrelia* infection. With respect to the polypeptide of the invention, protective capacity relates to the ability of the polypeptide to induce an immune response that protects a subject against a *Borrelia* infection. Protective capacity can be tested by administering to a subject the polypeptide in a manner to induce an immune reaction against the polypeptide. Thereafter, the subject may be challenged with *Borrelia*. The subject's reaction to the infection is monitored. Particularly, the presence of *Borrelia* in the subject may be determined. For example, the polypeptide is protective if *Borrelia* cannot be detected in the subject. The presence of *Borrelia* can be determined by detecting *Borrelia*-specific nucleic acids (e.g., by PCR) or *Borrelia*-specific antibodies (e.g., by ELISA or Western blot) or by detecting *Borrelia* itself (e.g., culturing organs or tissues in growth medium and verifying the presence of *Borrelia* by microscopy). In particular, the protective capacity ("pc"), reported as a percentage, for a particular dose is defined as follows:

$$pc(\%) = [(\text{number of total tested subjects} - \text{number of } Borrelia\text{-infected subjects})/\text{number of total tested subjects}] \times 100$$

Differences in protective capacity (Δpc) may be determined by, e.g. comparing the protective capacity (pc) of a mutant OspA fragment with a disulfide bond(s) (pc [with bond]) to the protective capacity of an OspA fragment without a disulfide bond(s) (pc [w/o bond]). In accordance with the present invention, the polypeptides to be compared differ only in the introduction of at least one disulfide bond. The change in protective capacity (Δpc) by the introduction of the disulfide bond(s) is determined as follows:

$$\Delta pc = (pc[\text{sample}] - pc[\text{control}])$$

e.g. $\Delta pc = (pc[\text{with bond}] - pc[\text{w/o bond}])$

If Δpc is greater than zero (>0), assuming all other parameters (e.g., dose and assay) are the same, then the protective capacity of the sample (e.g. the mutant OspA fragment with a disulfide bond(s)) is better than the protective capacity of the control (e.g. the OspA fragment without a disulfide bond(s)). Conversely, if Δpc is less than zero (<0) and assuming all other parameters (e.g., dose and assay) are the same, then the protective capacity of the sample (e.g. the mutant OspA fragment with a disulfide bond(s)) is less than the protective capacity of the comparison (e.g., the OspA fragment without a disulfide bond(s)).

Preferably, the polypeptide of the present invention is assessed for its protective capacity by an in vivo challenge assay wherein mice immunized with the polypeptide of the invention or with a placebo control are challenged with *Borrelia* introduced into the immunized subjects with a hypodermic needle (Needle Challenge Method) or by introduction by a tick vector (Tick Challenge Method).

The Needle Challenge Method is carried out for the desired *Borrelia* strain (e.g., *B. burgdorferi*, strain N40) by subcutaneously introducing *Borrelia* at a dose between 20 and 50 times the Infectious Dose ($ID_{50}$) to mice that are immunized with said first polypeptide of the first aspect or with an appropriate placebo (negative) control, such as buffer or adjuvant alone and comparing the rates of infection in the challenged mice. The $ID_{50}$ is defined as the dose at which 50% of the challenged mice are infected. The dose of *Borrelia* is measured in numbers of bacteria. The challenge dose can vary widely and is strain-dependent; therefore, the virulence of the strain must first be assessed by challenge experiments for determination of $ID_{50}$. Four weeks after needle challenge, blood and tissues are collected for readout methods to determine the infection status. These readout methods can be e.g. VlsE ELISA on sera or qPCR on collected tissues for identification of *Borrelia*, as described herein, or other methods.

The Tick Challenge Method is carried out by applying at least one tick nymph (e.g., *I. ricinus*) infected with *Borrelia* (e.g., *B. afzelii*, strain IS1), to a mouse that is immunized with said first polypeptide of the first aspect; and b) applying at least one infected tick nymph to a second mouse that is immunized with said second polypeptide of the first aspect; and c) comparing the rates of infection in the two mice, generally six weeks after challenge. Preferably, the assay or test is done with a group of mice per polypeptide to be tested. A suitable test is also described and illustrated in the Examples. Assessment of infection status can be done using VlsE ELISA on sera or qPCR on collected tissues, or using other suitable methods.

In a preferred embodiment of the present invention, the products of the invention such as, e.g. the polypeptides of the invention comprising the mutant OspA fragment with a disulfide bond(s) administered 3 times to a subject at a dose of 30 μg, preferably 10 μg, preferably 5.0 μg, preferably 1.0 μg, preferably 0.3 μg or lower have a protective capacity of 50% or more, preferably 60% or more, more preferably 70% or more, more preferably 80% or more, more preferably 90% or more, even more preferably 95% or more, most preferred 99% or more. In one embodiment, the protective capacity is assessed in an in vivo challenge method, preferably a Tick Challenge Method, more preferably a Needle Challenge Method, e.g. as described in the Examples. It has been surprisingly observed that immunization with an OspA mutant fragment of one serotype can provide cross-protection against other another serotype (Example 4, Table 4). Based on this finding, it might be anticipated that the dose of polypeptide of the present invention could be even further reduced.

In a preferred embodiment, the difference in protective capacity (Δpc) between the polypeptides of the invention comprising the mutant OspA fragment with a disulfide bond(s) and the placebo (negative) control is at least 50%, especially at least 60%, preferably at least 70%, more preferably at least 80%, even more preferably 90%, even more preferably 95%, most preferably at least 95%, when administered 3 times to a subject at a dose of 30 μg, preferably 10 μg, preferably 5.0 μg, preferably 1.0 μg, preferably 0.3 μg or lower.

In a preferred embodiment of the present invention, the C-terminal domain is defined as a fragment consisting of at least the C-terminal 150 amino acids of the OspA protein. In one embodiment, the C-terminal domain is between 140 and 152 amino acids in length. In a further embodiment, the C-terminal domain consists of no more than the last 152 amino acids of the OspA protein, preferably the last 151 amino acids, more preferably the last 150 amino acids. In an alternative embodiment, the C-terminal domain consists of no less than the last 140 amino acids of the OspA protein, preferably the last 141 amino acids, preferably the last 142 amino acids, most preferably the last 143 amino acids. The last amino acids of the OspA protein are defined herein as the most C-terminal contiguous amino acid sequence of the OspA protein.

In another embodiment, the C-terminal domain of an OspA protein of *Borrelia* comprises, essentially consists of or consists of (i) the amino acids from position 126, 131 or 130 to position 273 of the OspA of *B. afzelii*, strain K78 or (ii) the homologous domain to amino acids of OspA from a *Borrelia* strain other than *B. afzelii*, strain K78.

The polypeptide of the present invention may comprise or essentially consists of or consist of (i) one or more of these mutant fragments, optionally joined by linkers, e.g., as defined below and (ii) optionally one or more amino acids heterologous to OspA, particularly a signal sequence or site for a post-translational modification such as lipidation and (iii) optionally a posttranslational modification, such as lipidation.

In accordance with the present invention, the polypeptide of the present invention may comprise or essentially consists of or consist of the elements as defined herein, particularly the one or more mutant OspA fragments and optionally one or more further elements such as homologous domain, a linker peptide, a signal sequence or a site for lipidation. "Essentially consists" in this context means that the element(s) may have some minor amino acid changes with respect to the above sequences, such as amino acid additions, substitutions or deletions, preferably relating to at most 10%, 5%, 4%, 3%, 2% or 1% of the amino acids of the elements as defined herein.

In accordance with the present invention, at least one disulfide bond is introduced into an OspA fragment. This may preferably be achieved by introducing into the fragment at least 1 or 2 cysteine(s), particularly 2 cysteines, in order to allow for the formation of the at least one disulfide bond. Only one cysteine may be introduced, if another cysteine in the fragment is available for a disulfide bond. However, preferably two cysteines are introduced. The cysteine(s)

is/are introduced by amino acid addition or substitution, preferably substitution. In case of addition, the cysteine is inserted into the amino acid sequence between two amino acids, whereas in case of substitution one amino acid is replaced with the cysteine.

In accordance with the present invention, the OspA may be from any *Borrelia* strain, particularly from those specified herein such as *B. burgdorferi* s.s., *B. garinii*, *B. afzelii*, *B. andersoni*, *B. bissettii*, *B. valaisiana*, *B. lusitaniae*, *B. spielmanii*, *B. japonica*, *B. tanukii*, *B. turdi* or *B. sinica*, *B. bavariensis*, preferably from *B. burgdorferi* s.s., *B. afzelii*, *B. bavariensis* or *B. garinii*. Preferably, the OspA is from *B. afzelii*, particularly strain K78, OspA serotype 2 (SEQ ID NO: 19); *B. burgdorferi* s.s., particularly strain B31, OspA serotype 1 (SEQ ID NO: 20); *B. garinii*, particularly strain PBr, OspA serotype 3 (SEQ ID NO: 21); *B. bavariensis*, particularly strain PBi, OspA serotype 4 (SEQ ID NO: 22); *B. garinii*, particularly strain PHei, OspA serotype 5 (SEQ ID NO: 23); *B. garinii*, particularly strain DK29, OspA serotype 6 (SEQ ID NO: 24) or *B. garinii*, particularly strain T25, OspA serotype 7 (SEQ ID NO: 25). The amino acid sequences of these OspA proteins (full-length) are given below.

TABLE A-3

Accession numbers of OspA sequences from selected strains of *Borrelia* species.

| Organism_Strain | db\|accession.version | Organism_Strain | db\|accession.version | Organism_Strain | db\|accession.version |
|---|---|---|---|---|---|
| Bbu_156a (serotype 1) | gb\|ACL33776.1 | Bbu_K48 | emb\|CAA44492.1 | Bga_Mng4702 | gb\|ABF29559.1 |
| Baf_K78 (serotype 2) | emb\|CAA49828.1 | Bbu_N40 | gb\|ACS94765.1 | Bga_N34 | emb\|CAB64763.1 |
| Bga_PBr (serotype 3) | emb\|CAA56549.1 | Bbu_P0A3N6.1 | sp\|P0A3N6.1 | Bga_Nov1006 | gb\|ACD02016.1 |
| Bga_PBi (serotype 4) | emb\|CAA56550.1 | Bbu_PBo | emb\|CAA56468.1 | Bga_Nov105 | gb\|ABF29551.1 |
| Bbu_PHei (serotype 5) | tr\|Q06228 | Bbu_PBre | emb\|CAA59742.1 | Bga_Nov14506 | gb\|ACD02013.1 |
| Bbu_DK29 (serotype 6) | emb\|CAA45010.1 | Bbu_PHei | emb\|CAA56544.1 | Bga_Nov14606 | gb\|ACD02017.1 |
| Bga_T25 (serotype 7) | emb\|CAA56547.1 | Bbu_PKa | emb\|CAA56467.1 | Bga_Nov2005 | gb\|ABF29553.1 |
| Baf_ACA-1 | gb\|ACJ73559.1 | Bbu_PKo | emb\|CAA46550.1 | Bga_Nov2006 | gb\|ACD02018.1 |
| Baf_K78 | (sequenced) | Bbu_Poti_B1 | emb\|CAB64754.1 | Bga_Nov3305 | gb\|ABF29554.1 |
| Baf_Khab_625 | gb\|AAR96311.1 | Bbu_Poti_B2 | emb\|CAB64755.1 | Bga_Nov405 | gb\|ABF29552.1 |
| Baf_Khab2-Sakh | gb\|AAP94134.1 | Bbu_Poti_B3 | emb\|CAB64756.1 | Bga_Nov7006 | gb\|ACD02014.1 |
| Baf_Khab470 | gb\|AAO91923.1 | Bbu_PTro | emb\|CAA56471.1 | Bga_Nov9906 | gb\|ACD02015.1 |
| Baf_Khab505 | gb\|AAO91925.1 | Bbu_PWudI | emb\|CAA56469.1 | Bga_PBi | gb\|AAT93773.1 |
| Baf_LU192 | (sequenced, partial) | Bbu_PWudI/6 | emb\|CAA56470.1 | Bga_PBr | emb\|CAA56549.1 |
| Baf_Mng3602 | gb\|ABF29573.1 | Bbu_PWudII | emb\|CAA56546.1 | Bga_Q1HLH6 | gb\|ABF29564.1 |
| Baf_Mng4302 | gb\|ABF29574.1 | Bbu_Q04851.1 | sp\|Q04851.1 | Bga_T25 | emb\|CAA56547.1 |
| Baf_Mng6702 | gb\|ABF29578.1 | Bbu_Q04968.1 | sp\|Q04968.1 | Bga_TIsl | emb\|CAA59727.1 |
| Baf_Mng702 | gb\|ABF29572.1 | Bbu_Q09086.1 | sp\|Q09086.1 | Bga_TN | emb\|CAA56545.1 |
| Baf_Nov1105 | gb\|ABF29569.1 | Bbu_Q09087.1 | sp\|Q09087.1 | Bga_Tom1003 | gb\|ABF29564.1 |
| Baf_Nov11506 | gb\|ACD02019.1 | Bbu_Q44738 | tr\|Q44738 | Bga_Tom1805 | gb\|ABF29567.1 |
| Baf_Nov3005 | gb\|ABF29570.1 | Bbu_Q44956 | emb\|CAA56937.1 | Bga_Tom203 | gb\|ABF29562.1 |
| Baf_P0A3N7.1 | sp\|P0A3N7.1 | Bbu_Q44962 | dbj\|BAA06133.1 | Bga_Tom2903 | gb\|ABF29565.1 |
| Baf_PHo | emb\|CAA59724.1 | Bbu_Q45039 | emb\|CAR95556.1 | Bga_Tom3005 | gb\|ABF29568.1 |
| Baf_PKo | gb\|ABH02138.1 | Bbu_Q45040 | tr\|Q45040 | Bga_Tom303 | gb\|ABF29563.1 |
| Baf_PLe | emb\|CAA59970.1 | Bbu_S-1-10 | gb\|AAB96354.1 | Bga_Tom3101 | gb\|ABF29557.1 |
| Baf_PLj7 | emb\|CAA59725.1 | Bbu_T.R.O. | emb\|CAA46549.1 | Bga_Tom3803 | gb\|ABF29566.1 |
| Baf_PLud | emb\|CAA59726.1 | Bbu_T255 | emb\|CAA59730.1 | Bga_Tom5102 | gb\|ABF29560.1 |
| Baf_Tom1103 | gb\|ABF29581.1 | Bbu_UK | emb\|CAB64758.1 | Bga_Tom5202 | gb\|ABF29561.1 |
| Baf_Tom1303 | gb\|ABF29582.1 | Bbu_VS116 | emb\|CAB64757.1 | Bga_Tom7105 | gb\|ABF29556.1 |
| Baf_Tom1503 | gb\|ABF29583.1 | Bbu_VS461 | emb\|CAA82329.1 | Bga_VS100 | emb\|CAB64765.1 |
| Baf_Tom2303 | gb\|ABF29584.1 | Bbu_WI91-23 | ref\|ZP_03091138.1 | Bga_VS307 | emb\|CAB64764.1 |
| Baf_Tom2403 | gb\|ABF29585.1 | Bbu_ZQ1 | emb\|CAA01704.1 | Bga_WABSou | emb\|CAA59728.1 |
| Baf_Tom2504 | gb\|ABF29577.1 | Bbu_ZS7 | gb\|ACK74228.1 | Bja_Cow611 | emb\|CAB64759.1 |
| Baf_Tom2803 | gb\|ABF29586.1 | Bga_BgVir-1 | gb\|ABF29555.1 | Bja_F63 | emb\|CAB64760.1 |
| Baf_Tom3401 | gb\|ABF29571.1 | Bga_Far04 | ref\|ZP_03328706.1 | Bja_HO14 | emb\|CAB64762.1 |
| Baf_Tom3703 | gb\|ABF29587.1 | Bga_FujiP2 | gb\|AAA92301.1 | Bja_IKA2 | emb\|CAB64761.1 |
| Baf_Tom4703 | gb\|ABF29588.1 | Bga_IP90 | emb\|CAJ75754.1 | Blu_A8D057 | gb\|ABR22627.1 |
| Baf_Tom5403 | gb\|ABF29575.1 | Bga_Ip90 | emb\|CAJ75754.1 | Blu_A8D060 | gb\|ABR22625.1 |
| Baf_Tom603 | gb\|ABF29579.1 | Bga_JEM1 | gb\|AAB81567.1 | Blu_A8D075 | gb\|ABR22628.1 |
| Baf_Tom6303 | gb\|ABF29576.1 | Bga_JEM2 | gb\|AAB81569.1 | Blu_A8D079 | gb\|ABR22629.1 |
| Baf_Tom703 | gb\|ABF29580.1 | Bga_JEM3 | gb\|AAB81571.1 | Blu_ABR22624.1 | gb\|ABR22624.1 |
| Baf_XJ23 | gb\|AAB95225.1 | Bga_JEM4 | dbj\|BAA19222.1 | Blu_ABR22S26.1 | gb\|ABR22626.1 |
| Bbu_118a | ref\|ZP_02720644.1 | Bga_JEM5 | gb\|AAB81573.1 | Bsp_A14S | gb\|AAD16455.1 |
| Bbu_156a | gb\|ACL33776.1 | Bga_JEM6 | gb\|AAB81575.1 | Btu_Ya501 | dbj\|BAA32513.1 |
| Bbu_19857 | emb\|CAA48196.1 | Bga_JEM7 | gb\|AAB81577.1 | Bva_AR-2 | gb\|AAF00571.1 |
| Bbu_2005348A | prf\|2005348A | Bga_JEM8 | gb\|AAB81579.1 | Bva_M19 | gb\|AAF00573.1 |
| Bbu_2005348B | prf\|2005348B | Bga_Khab3155 | gb\|AAR96310.1 | Bva_M49 | gb\|AAF00574.1 |
| Bbu_297 | emb\|CAA59729.1 | Bga_Khab550 | gb\|AAR96306.1 | Bva_M52 | gb\|AAF00575.1 |
| Bbu_29805 | ref\|ZP_03092996.1 | Bga_Khab616 | gb\|AAR96307.1 | Bva_M53 | gb\|AAF00576.1 |
| Bbu_64b | ref\|ZP_03097520.1 | Bga_Khab648 | gb\|AAR96308.1 | Bva_M7 | gb\|AAF00572.1 |
| Bbu_72a | ref\|ZP_02724465.1 | Bga_Khab722 | gb\|AAR96309.1 | Bva_Q9RM88 | emb\|CAB56150.1 |
| Bbu_80a | ref\|ZP_03088001.1 | Bga_Khab23 | gb\|AAP94125.1 | Bva_QLZSP1 | gb\|ACA13516.1 |
| Bbu_94a | ref\|ZP_02725946.1 | Bga_Khab24 | gb\|AAP94126.1 | Bva_QSDS4 | gb\|ACA13517.1 |
| Bbu_AAB23809.1 | gb\|AAB23809.1 | Bga_Khab31 | gb\|AAP94127.1 | Bva_QSYSP3 | gb\|ACA13518.1 |
| Bbu_AAB23810.1 | gb\|AAB23810.1 | Bga_Khab31a | gb\|AAP94128.1 | Bva_QSYSP4 | gb\|ACA13519.1 |
| Bbu_B29 | gb\|AAA18508.1 | Bga_Khab-466 | gb\|AAP94129.1 | Bva_QTMP2 | gb\|ACA13520.1 |
| Bbu_B31 | gb\|AAC66260.1 | Bga_Khab489 | gb\|AAP94130.1 | Bva_QX-S13 | gb\|ACA13521.1 |
| Bbu_Bol26 | ref\|ZP_02531917.1 | Bga_Khab5-Sakh | gb\|AAO91932.1 | Bva_UK | gb\|AAF00570.1 |
| Bbu_C-1-11 | gb\|AAB96351.1 | Bga_Khab506 | gb\|AAP94132.1 | Bva_VS116 | gb\|AAF00569.1 |
| Bbu_CA-11.2a_1 | ref\|ZP_03094587.1 | Bga_Khab516 | gb\|AAP94133.1 | Bsp_10MT | dbj\|BAA32516.1 |

TABLE A-3-continued

Accession numbers of OspA sequences from selected strains of *Borrelia* species.

| Organism_Strain | db\|accession.version | Organism_Strain | db\|accession.version | Organism_Strain | db\|accession.version |
|---|---|---|---|---|---|
| Bbu_CA-11.2a_2 | ref\|ZP_03094587.1 | Bga_Khab721 | gb\|AAP94131.1 | Bsp_5MT | dbj\|BAA32515.1 |
| Bbu_CA-11.2a_CA-112a | ref\|ZP_03094587.1 | Bga_Khab2119 | gb\|AAO91928.1 | Bsp_Am501 | dbj\|BAA32514.1 |
| Bbu_CAA00316.1 | emb\|CAA00316.1 | Bga_Khab2559 | gb\|AAO91929.1 | Bsp_LV5 | gb\|AAB96353.1 |
| Bbu_CAA42842.1 | emb\|CAA42842.1 | Bga_Khab2560 | gb\|AAO91930.0 | Bsp_PAnz | emb\|CAJ43585.1 |
| Bbu_CAA44258.1 | emb\|CAA44258.1 | Bga_Khab2594 | gb\|AAO91931.1 | Bsp_PHaP_PHap | emb\|CAJ43582.1 |
| Bbu_CAR95597.1 | emb\|CAR95597.1 | Bga_Khab430 | gb\|AAO91919.1 | Bsp_PJes | emb\|CAJ43586.1 |
| Bbu_DK1 | gb\|AAA22955.1 | Bga_Khab448 | gb\|AAO91920.1 | Bsp_PMai | emb\|CAJ43584.1 |
| Bbu_DK29 | emb\|CAA45010.1 | Bga_Khab457 | gb\|AAO91921.1 | Bsp_PMew | emb\|CAJ43583.1 |
| Bbu_DK6_Danish_isolate | emb\|CAA58601.1 | Bga_Khab468 | gb\|AAO91922.1 | Bsp_PSigII | emb\|CAJ43581.1 |
| Bbu_G2 | gb\|AAA88846.1 | Bga_Khab492 | gb\|AAO91924.1 | Bsp_SV1 | ref\|ZP_03095680.1 |
| Bbu_G25 | emb\|CAA82328.1 | Bga_Khab511 | gb\|AAO91926.1 | Bbi_25015 | gb\|AAB21761.1 |
| Bbu_H.E. | emb\|CAA46551.1 | Bga_Khab560 | gb\|AAO91927.1 | Bbi_DN127 | emb\|CAB64766.1 |
| Bbu_HB19 | gb\|AAC18776.1 | Bga_LV4 | gb\|AAB96352.1 | Bbi_Q09087.1 | gb\|AAB21761.1 |

Abbreviations: Baf = *Borrelia afzelii*, Bbu = *Borrelia burgdorferi* s.s., Bga = *Borrelia garinii*, Bsp = *Borrelia spielmanii*, Bbi = *Borrelia bissettii*, Bva = *Borrelia valaisiana*, Btu = *Borrelia turicatae*, Bdu = *Borrelia duttonii*, Blu = *Borrelia lusitaniae*, Bja = *Borrelia japonica*, gb = GenBank, emb = EMBL, tr = UniProt/tremble, sp = UniProt/Swissprot, prf = Protein Research Foundation, dbj = DNA Databank of Japan (DDBJ), pdb = Protein Data Bank, db = database In accordance with the present invention, the disulfide bond may be formed between cysteines that have been introduced at any position of the OspA fragment allowing or supporting appropriate folding of the fragment. The positions may be selected, as detailed above, based on the known structure of the OspA. In a preferred embodiment, the polypeptide of the current invention contains at least one disulfide bond between any of positions 182+/−3 and any of positions 269+/−3 (disulfide bond type 1); any of positions 182+/−3 and any of positions 272+/−3 (disulfide bond type 2); any of positions 244+/−3 and any of positions 259+/−3 (disulfide bond type 3); any of positions 141+/−3 and any of positions 241+/−3 (disulfide bond type 4); any of positions 165+/−3 and any of positions 265+/−3 (disulfide bond type 5); any of positions 185+/−3 and any of positions 272+/−3 (disulfide bond type 6); any of positions 199+/−3 and any of positions 223+/−3 (disulfide bond type 7); any of positions 243+/−3 and any of positions 262+/−3 (disulfide bond type 8); any of positions 184+/−3 and any of positions 204+/−3 (disulfide bond type 9); any of positions 201+/−3 and any of positions 214+/−3 (disulfide bond type 10); any of positions 246+/−3 and any of positions 259+/−3 (disulfide bond type 11); and/or any of positions 167+/−3 and any of positions 178+/−3 (disulfide bond type 12) of a *B. afzelii*, particularly *B. afzelii* K78 serotype 2 OspA, or the homologous amino acids of an OspA from a *Borrelia* sp. other than *B. afzelii*, such as *B. burgdorferi* s.s., particularly strain B31, serotype 1; *B. garinii*, particularly strain PBr, serotype 3; *B. bavariensis*, particularly strain PBi, serotype 4; *B. garinii*, particularly strain PHei, serotype 5; *B. garinii*, particularly strain DK29, serotype 6 or *B. garinii*, particularly strain T25, serotype 7.

More particularly, the polypeptide of the current invention contains the at least one disulfide bond between any of positions 182 and 269 (disulfide bond type 1); positions 182 and 272 (disulfide bond type 2); positions 244 and 259 (disulfide bond type 3); positions 141 and 241 (disulfide bond type 4); positions 165 and 265 (disulfide bond type 5); positions 185 and 272 (disulfide bond type 6); positions 199 and 223 (disulfide bond type 7); positions 243 and 262 (disulfide bond type 8); positions 184 and 204 (disulfide bond type 9); positions 201 and 214 (disulfide bond type 10); positions 246 and 259 (disulfide bond type 11); and/or positions 167 and 178 (disulfide bond type 12) of a *B. afzelii*, particularly *B. afzelii* K78 serotype 2 OspA, or the homologous amino acids of an OspA from a *Borrelia* other than *B. afzelii*, such as *B. burgdorferi* s.s., particularly strain B31, serotype 1; *B. garinii*, particularly strain PBr, serotype 3; *B. bavariensis*, particularly strain PBi, serotype 4; *B. garinii*, particularly strain PHei, serotype 5; *B. garinii*, particularly strain DK29, serotype 6 or *B. garinii*, particularly strain T25, serotype 7.

TABLE A-4

Disulfide bond types with nomenclature and the position of the cysteine substitutions in the serotype 2 OspA protein.

| Disulfide bond type | Nomenclature | Position of cysteines in *B. afzelii* K78 serotype 2 OspA |
|---|---|---|
| wild-type sequence | D0 | No cysteine substitutions |
| 1 | D1 | 182 and 269 |
| 2 | D2 | 182 and 272 |
| 3 | D3 | 244 and 259 |
| 4 | D4 | 141 and 241 |
| 5 | D5 | 165 and 265 |
| 6 | D6 | 185 and 272 |
| 7 | D7 | 199 and 223 |
| 8 | D8 | 243 and 262 |
| 9 | D9 | 184 and 204 |
| 10 | D10 | 201 and 214 |
| 11 | D11 | 246 and 259 |
| 12 | D12 | 167 and 178 |

Even more preferred are disulfide bond types 1 to 5, especially disulfide bond types 1 to 4.

It is noted that:

Position 182+/−3 is an abbreviation for position 179, 180, 181, 182, 183, 184 or 185, preferably 182.

Position 269+/−3 is an abbreviation for position 266, 267, 268, 269, 270, 271 or 272, preferably 269.

Position 272+/−3 is an abbreviation for position 269, 270, 271, 272, 273, 274 or 275, preferably 272.

Position 244+/−3 is an abbreviation for position 241, 242, 243, 244, 245, 246 or 247, preferably 244.

Position 259+/−3 is an abbreviation for position 256, 257, 258, 259, 260, 261 or 262, preferably 259.

Position 141+/−3 is an abbreviation for position 138, 139, 140, 141, 142, 143 or 144, preferably 141.

Position 241+/−3 is an abbreviation for position 238, 239, 240, 241, 242, 243 or 244, preferably 241.

Position 165+/−3 is an abbreviation for position 162, 163, 164, 165, 166, 167 or 168, preferably 165.

Position 265+/−3 is an abbreviation for position 262, 263, 264, 265, 266, 267 or 268, preferably 265.

Position 185+/−3 is an abbreviation for position 182, 183, 184, 185, 186, 187 or 188, preferably 185.

Position 199+/−3 is an abbreviation for position 196, 197, 198, 199, 200, 201 or 202, preferably 199.

Position 223+/−3 is an abbreviation for position 220, 221, 222, 223, 224, 225 or 226, preferably 223.

Position 243+/−3 is an abbreviation for position 240, 241, 242, 243, 244, 245 or 246, preferably 143.

Position 262+/−3 is an abbreviation for position 259, 260, 261, 262, 263, 264 or 265, preferably 262.

Position 184+/−3 is an abbreviation for position 181, 182, 183, 184, 185, 186 or 187, preferably 184.

Position 204+/−3 is an abbreviation for position 201, 202, 203, 204, 205, 206 or 207, preferably 204.

Position 201+/−3 is an abbreviation for position 198, 199, 200, 201, 202, 203 or 204, preferably 201.

Position 214+/−3 is an abbreviation for position 211, 212, 213, 214, 215, 216 or 217, preferably 214.

Position 246+/−3 is an abbreviation for position 243, 244, 245, 246, 247, 248 or 249, preferably 246.

Position 167+/−3 is an abbreviation for position 164, 165, 166, 167, 168, 169 or 170, preferably 167.

Position 178+/3 is an abbreviation for position 175, 176, 177, 178, 179, 180 or 181, preferably 178.

In a preferred embodiment, the mutant fragment is derived from the amino acids from position 126, 130 or 131 to position 273 of the wild-type sequence of the OspA of *B. afzelii* strain K78, serotype 2 (SEQ ID NO: 18) and differs only by the introduction of at least one disulfide bond, particularly wherein the at least one disulfide bond is between positions 182 and 269 (disulfide bond type 1); positions 182 and 272 (disulfide bond type 2); positions 244 and 259 (disulfide bond type 3); positions 141 and 241 (disulfide bond type 4); positions 165 and 265 (disulfide bond type 5); positions 185 and 272 (disulfide bond type 6); positions 199 and 223 (disulfide bond type 7); positions 243 and 262 (disulfide bond type 8); positions 184 and 204 (disulfide bond type 9); positions 201 and 214 (disulfide bond type 10); positions 246 and 259 (disulfide bond type 11); and/or positions 167 and 178 (disulfide bond type 12), or the homologous fragments and positions of an OspA from a *Borrelia* sp. other than *B. afzelii*, such as *B. burgdorferi* s.s., particularly strain B31, serotype 1; *B. garinii*, particularly strain PBr, serotype 3; *B. bavariensis*, particularly strain PBi, serotype 4; *B. garinii*, particularly strain PHci, serotype 5; *B. garinii*, particularly strain DK29, serotype 6 or *B. garinii*, particularly strain T25, serotype 7.

In a still more preferred embodiment, the mutant fragment has an amino acid sequence selected from the group consisting of SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178 and an amino acid sequence that has 80%, more preferably 85%, more preferably 90%, even more preferably 95% sequence identity to at least one of sequences with SEQ ID NOs: 2 to 13, wherein the cysteines are not replaced. Further details on mutations and sequence identity are given above.

As detailed above, the polypeptide of the present invention may comprise signal sequences. It has been shown that lipidation confers adjuvant properties on OspA. Accordingly, lipidated forms of the polypeptide of the invention or polypeptides comprising a lipidation signal are preferred. In a preferred embodiment, the polypeptide of the current invention comprises a lipidation signal, preferably a lipidation signal of a *Borrelia* outer surface protein, OspA or OspB (SEQ ID NOs: 14 and 15, respectively) or more preferably an *E. coli* lpp lipidation signal sequence (SEQ ID NO: 16). The OspA fragment of the invention comprising a lipidation signal is lipidated during processing and the lipidation signal peptide is cleaved off. Therefore the signal peptide is no longer present in the mature lipidated protein.

Lipidated proteins according to the current invention are labeled with "Lip" at the N-terminus to indicate the addition of 3 fatty acid groups and a glycerol to the polypeptide (see FIG. 4). Suitable lipidation signals as described above include MKKYLLGIGLILALIA (SEQ ID NO: 14), MRLLIGFALALALIG (SEQ ID NO: 15) and MKATKLVLGAVILGSTLLAG (SEQ ID NO: 16). Because lipid moieties and a glycerol are attached to the N-terminal cysteine residue which is present in the full-length wild-type OspA protein, OspA C-terminal fragments for lipidation may additionally comprise a peptide comprising a cysteine residue followed by additional amino acids, herein referred to as "Lipidation Peptide" or "LP" (see FIGS. 1 and 2). For example, sequences such as CSS or CKQN (SEQ ID NO: 211) immediately C-terminal to the lipidation signal sequence provide an N-terminal cysteine residue for lipidation upon cleavage of the lipidation signal peptide. The lipidated cysteine-containing peptides are present in the final lipidated polypeptide of the invention.

It has been found that the OspA protein of *B. burgdorferi* s.s. comprises a sequence with the capacity to bind to a T-cell receptor that also has the capacity to bind to human leukocyte function-associated antigen (hLFA-1) (herein referred to also as "hLFA-1-like sequence"). The similarity of this OspA region to hLFA-1 may result in an immune response with cross-reactivity upon administration of *B. burgdorferi* s.s. OspA to a human subject and may induce autoimmune diseases, particularly autoimmune arthritis, in susceptible individuals. Accordingly, in a preferred embodiment, the polypeptide of the current invention does not comprise a sequence with binding capacity to the T-cell receptor that has a binding capacity to the human leukocyte function-associated antigen (hLFA-1), and particularly does not comprise the amino acid sequence GYVLEGTLTAE (SEQ ID NO: 17). To this end, the hLFA-1-like sequence, particularly the amino acid sequence GYVLEGTLTAE (SEQ ID NO: 17), may be replaced with a homologous sequence from an OspA protein of another *Borrelia* sp., particularly with NFTLEGKVAND (SEQ ID NO: 18).

In a preferred embodiment, the polypeptide of the current invention comprising at least one disulfide bond essentially establishes the same protective capacity with said polypeptide against a *Borrelia* infection relative to at least one of the wild-type full-length OspA proteins derived from at least one *Borrelia* strain, particularly *B. afrelii* K78, OspA serotype 2 (SEQ ID NO: 19); *B. burgdorferi* s.s., particularly strain B31, serotype 1 (SEQ ID NO: 20); *B. garinii*, particularly strain PBr, serotype 3 (SEQ ID NO: 21); *B. bavariensis*, particularly strain PBi, serotype 4 (SEQ ID NO: 22); *B. garinii*, particularly strain PHei, serotype 5 (SEQ ID NO: 23); *B. garinii*, particularly strain DK29, serotype 6 (SEQ ID NO: 24) or *B. garinii*, particularly strain T25, serotype 7 (SEQ ID NO: 25).

In order to provide cross-protection against different *Borrelia* species or OspA serotypes, the development of a multivalent vaccine is desirable. Accordingly, in another preferred embodiment, the polypeptide of the first aspect comprises at least two mutant fragments from two different *Borrelia* serotypes as defined above. In a preferred embodiment, the polypeptide of the first aspect comprises at least two mutant OspA fragments which are selected from the group consisting of fragment with disulfide bond type 1 and fragment with disulfide bond type 2;

fragment with disulfide bond type 1 and fragment with disulfide bond type 3;
fragment with disulfide bond type 1 and fragment with disulfide bond type 4;
fragment with disulfide bond type 1 and fragment with disulfide bond type 5;
fragment with disulfide bond type 1 and fragment with disulfide bond type 6;
fragment with disulfide bond type 1 and fragment with disulfide bond type 7;
fragment with disulfide bond type 1 and fragment with disulfide bond type 8;
fragment with disulfide bond type 1 and fragment with disulfide bond type 9;
fragment with disulfide bond type 1 and fragment with disulfide bond type 10;
fragment with disulfide bond type 1 and fragment with disulfide bond type 11;
fragment with disulfide bond type 1 and fragment with disulfide bond type 12;
fragment with disulfide bond type 2 and fragment with disulfide bond type 3;
fragment with disulfide bond type 2 and fragment with disulfide bond type 4;
fragment with disulfide bond type 2 and fragment with disulfide bond type 5;
fragment with disulfide bond type 2 and fragment with disulfide bond type 6;
fragment with disulfide bond type 2 and fragment with disulfide bond type 7;
fragment with disulfide bond type 2 and fragment with disulfide bond type 8;
fragment with disulfide bond type 2 and fragment with disulfide bond type 9;
fragment with disulfide bond type 2 and fragment with disulfide bond type 10;
fragment with disulfide bond type 2 and fragment with disulfide bond type 11;
fragment with disulfide bond type 2 and fragment with disulfide bond type 12;
fragment with disulfide bond type 3 and fragment with disulfide bond type 4;
fragment with disulfide bond type 3 and fragment with disulfide bond type 5;
fragment with disulfide bond type 3 and fragment with disulfide bond type 6;
fragment with disulfide bond type 3 and fragment with disulfide bond type 7;
fragment with disulfide bond type 3 and fragment with disulfide bond type 8;
fragment with disulfide bond type 3 and fragment with disulfide bond type 9;
fragment with disulfide bond type 3 and fragment with disulfide bond type 10;
fragment with disulfide bond type 3 and fragment with disulfide bond type 11;
fragment with disulfide bond type 3 and fragment with disulfide bond type 12;
fragment with disulfide bond type 4 and fragment with disulfide bond type 5;
fragment with disulfide bond type 4 and fragment with disulfide bond type 6;
fragment with disulfide bond type 4 and fragment with disulfide bond type 7;
fragment with disulfide bond type 4 and fragment with disulfide bond type 8;
fragment with disulfide bond type 4 and fragment with disulfide bond type 9;
fragment with disulfide bond type 4 and fragment with disulfide bond type 10;
fragment with disulfide bond type 4 and fragment with disulfide bond type 11;
fragment with disulfide bond type 4 and fragment with disulfide bond type 12;
fragment with disulfide bond type 5 and fragment with disulfide bond type 6;
fragment with disulfide bond type 5 and fragment with disulfide bond type 7;
fragment with disulfide bond type 5 and fragment with disulfide bond type 8;
fragment with disulfide bond type 5 and fragment with disulfide bond type 9;
fragment with disulfide bond type 5 and fragment with disulfide bond type 10;
fragment with disulfide bond type 5 and fragment with disulfide bond type 11;
fragment with disulfide bond type 5 and fragment with disulfide bond type 12;
fragment with disulfide bond type 6 and fragment with disulfide bond type 7;
fragment with disulfide bond type 6 and fragment with disulfide bond type 8;
fragment with disulfide bond type 6 and fragment with disulfide bond type 9;
fragment with disulfide bond type 6 and fragment with disulfide bond type 10;
fragment with disulfide bond type 6 and fragment with disulfide bond type 11;
fragment with disulfide bond type 6 and fragment with disulfide bond type 12;
fragment with disulfide bond type 7 and fragment with disulfide bond type 8;
fragment with disulfide bond type 7 and fragment with disulfide bond type 9;
fragment with disulfide bond type 7 and fragment with disulfide bond type 10;
fragment with disulfide bond type 7 and fragment with disulfide bond type 11;
fragment with disulfide bond type 7 and fragment with disulfide bond type 12;
fragment with disulfide bond type 8 and fragment with disulfide bond type 9;
fragment with disulfide bond type 8 and fragment with disulfide bond type 10;
fragment with disulfide bond type 8 and fragment with disulfide bond type 11;
fragment with disulfide bond type 8 and fragment with disulfide bond type 12;
fragment with disulfide bond type 9 and fragment with disulfide bond type 10;
fragment with disulfide bond type 9 and fragment with disulfide bond type 11;
fragment with disulfide bond type 9 and fragment with disulfide bond type 12;
fragment with disulfide bond type 10 and fragment with disulfide bond type 11;
fragment with disulfide bond type 10 and fragment with disulfide bond type 12;
fragment with disulfide bond type 11 and fragment with disulfide bond type 12;

and particularly wherein the fragment with disulfide bond type 1 has the amino acid sequence of SEQ ID NO: 2 or an amino acid sequence that has at least 80%, more preferably 85%, more preferably 90%, even more preferably 95% sequence identity to SEQ ID NO: 2, wherein the cysteines are not replaced;

the fragment with disulfide bond type 2 has the amino acid sequence of SEQ ID NO: 3 or an amino acid sequence that has at least 80%, more preferably 85%, more preferably 90%, even more preferably 95% sequence identity to SEQ ID NO: 3, wherein the cysteines are not replaced;

the fragment with disulfide bond type 3 has the amino acid sequence of SEQ ID NO: 4 or an amino acid sequence that has at least 80%, more preferably 85%, more preferably 90%, even more preferably 95% sequence identity to SEQ ID NO: 4, wherein the cysteines are not replaced;

the fragment with disulfide bond type 4 has the amino acid sequence of SEQ ID NO: 5 or an amino acid sequence that has at least 80%, more preferably 85%, more preferably 90%, even more preferably 95% sequence identity to SEQ ID NO: 5, wherein the cysteines are not replaced;

the fragment with disulfide bond type 5 has the amino acid sequence of SEQ ID NO: 6 or an amino acid sequence that has at least 80%, more preferably 85%, more preferably 90%, even more preferably 95% sequence identity to SEQ ID NO: 6, wherein the cysteines are not replaced;

the fragment with disulfide bond type 6 has the amino acid sequence of SEQ ID NO: 7 or an amino acid sequence that has at least 80%, more preferably 85%, more preferably 90%, even more preferably 95% sequence identity to SEQ ID NO: 7, wherein the cysteines are not replaced;

the fragment with disulfide bond type 7 has the amino acid sequence of SEQ ID NO: 8 or an amino acid sequence that has at least 80%, more preferably 85%, more preferably 90%, even more preferably 95% sequence identity to SEQ ID NO: 8, wherein the cysteines are not replaced;

the fragment with disulfide bond type 8 has the amino acid sequence of SEQ ID NO: 9 or an amino acid sequence that has at least 80%, more preferably 85%, more preferably 90%, even more preferably 95% sequence identity to SEQ ID NO: 9, wherein the cysteines are not replaced;

the fragment with disulfide bond type 9 has the amino acid sequence of SEQ ID NO: 10 or an amino acid sequence that has at least 80%, more preferably 85%, more preferably 90%, even more preferably 95% sequence identity to SEQ ID NO: 10, wherein the cysteines are not replaced;

the fragment with disulfide bond type 10 has the amino acid sequence of SEQ ID NO: 11 or an amino acid sequence that has at least 80%, more preferably 85%, more preferably 90%, even more preferably 95% sequence identity to SEQ ID NO: 11, wherein the cysteines are not replaced;

the fragment with disulfide bond type 11 has the amino acid sequence of SEQ ID NO: 12 or an amino acid sequence that has at least 80%, more preferably 85%, more preferably 90%, even more preferably 95% sequence identity to SEQ ID NO: 12, wherein the cysteines are not replaced; and/or the fragment with disulfide bond type 12 has the amino acid sequence of SEQ ID NO: 13 or an amino acid sequence that has at least 80%, more preferably 85%, more preferably 90%, even more preferably 95% sequence identity to SEQ ID NO: 13, wherein the cysteines are not replaced.

Please note that further details on mutations and sequence identity arc given above.

TABLE A-5

Nomenclature and SEQ ID NOs. of mutant OspA fragment heterodimers, non-lipidated and lipidated, described in the current invention.

| Mutant OspA fragment heterodimer* | SEQ ID NO: | Lipidated mutant OspA fragment heterodimer* | SEQ ID NO: |
|---|---|---|---|
| S1D4-S2D4 | 43 | Lip-S1D4-S2D4 | 185 |
| S1D1-S2D1 | 47 | Lip-S1D1-S2D1 | 186 |
| S3D4-S4D4 | 51 | Lip-S3D4-S4D4 | 187 |
| S3D1-S4D1 | 55 | Lip-S3D1-S4D1 | 188 |
| S5D4-S6D4 | 59 | Lip-S5D4-S6D4 | 189 |
| S5D1-S6D1 | 63 | Lip-S5D1-S6D1 | 190 |
| S2D4-S1D4 | 67 | Lip-S2D4-S1D4 | 191 |
| S2D1-S1D1 | 71 | Lip-S2D1-S1D1 | 192 |
| S4D4-S3D4 | 75 | Lip-S4D4-S3D4 | 193 |
| S4D1-S3D1 | 79 | Lip-S4D1-S3D1 | 194 |
| S6D4-S5D4 | 83 | Lip-S6D4-S5D4 | 195 |
| S6D1-S5D1 | 87 | Lip-S6D1-S5D1 | 196 |
| S1D4-S2D1 | 91 | Lip-S1D4-S2D1 | 197 |
| S1D1-S2D4 | 95 | Lip-S1D1-S2D4 | 198 |
| S3D4-S4D1 | 99 | Lip-S3D4-S4D1 | 199 |
| S3D1-S4D4 | 103 | Lip-S3D1-S4D4 | 200 |
| S5D4-S6D1 | 107 | Lip-S5D4-S6D1 | 201 |
| S5D1-S6D4 | 111 | Lip-S5D1-S6D4 | 202 |
| S2D4-S1D1 | 115 | Lip-S2D4-S1D1 | 203 |
| S2D1-S1D4 | 119 | Lip-S2D1-S1D4 | 204 |
| S4D4-S3D1 | 123 | Lip-S4D4-S3D1 | 205 |
| S4D1-S3D4 | 127 | Lip-S4D1-S3D4 | 206 |
| S6D4-S5D1 | 131 | Lip-S6D4-S5D1 | 207 |
| S6D1-S5D4 | 135 | Lip-S6D1-S5D4 | 208 |

*S = Serotype (1-6) (see Table A-2); D = Disulfide Bond Type (see Table A-4); Lip = lipidation: the N-terminal addition of glycerol and fatty acid residues.

In another preferred embodiment, the polypeptide according to the first aspect comprises at least two or three mutant fragments which are connected via one or more linkers. A linker is a rather short amino acid sequence employed to connect two fragments. It should be designed in order to avoid any negative impact on the fragments, their interaction in subjects to be treated or vaccinated or upon their protective capacity. Preferred are short linkers of at most 21 amino acids, particularly at most 15 amino acids, especially at most 12 or 8 amino acids. More preferably, the one or more linkers is/are composed of small amino acids in order to reduce or minimize interactions with the fragments, such as glycine, serine and alanine. Examples or preferred linkers include linkers comprising or consisting of polyG, such as $(G)_8$ (SEQ ID NO: 36) $(G)_{12}$ (SEQ ID NO: 37), GAGA (SEQ ID NO: 38), $(GAGA)_2$ (SEQ ID NO: 39), $(GAGA)_3$ (SEQ ID NO: 40), $(GGGS)_2$ (SEQ ID NO: 41), or $(GGGS)_3$ (SEQ ID NO: 42). A more preferred linker is the "LN1" peptide linker, a fusion of two separate loop regions of the N-terminal half of OspA from *B. burgdorferi* s.s., strain B31 (aa 65-74 and aa 42-53, with an amino acid exchange at position 53 of D53S) which has the following sequence: GTSDKNNGSGSKEKNKDGKYS (SEQ ID NO: 184).

In another preferred embodiment, the polypeptide according to the first aspect comprises a polypeptide with a total size of at most 500 amino acids, comprising two or three different mutant fragments as defined in preferred embodiments of the first aspect; or a polypeptide which consists of essentially two or three different mutant fragments, one or two linkers and, optionally, an N-terminal cysteine; and/or a polypeptide which consists of essentially two or three different mutant fragments, an N-terminal extension of the fragment consisting of at most 24, 23, 22, 21, 20, 19, 18, 17, 16, 15, 14, 13, 12 or 11 amino acids, preferably at most 10, 9, 8, 7 or 6 amino acids, still more preferably at most 5, 4, 3, 2 or 1 amino acid(s), wherein the N-terminal extension is located directly N-terminally from the fragment in the respective *Borrelia* OspA and, optionally, an N-terminal cysteine. The N-terminal cysteine may optionally be followed by a short peptide linker from 1-10 amino acids long, and preferably takes the form of an N-terminal CSS peptide or CKQN peptide (SEQ ID NO: 211).

In a second aspect, the present invention relates to a nucleic acid encoding for the polypeptide according to the first aspect.

The invention further provides a nucleic acid encoding a polypeptide of the invention. For the purposes of the invention the term "nucleic acid(s)" generally refers to any polyribonucleotide or polydeoxynbonucleotide, which may be unmodified RNA or DNA or modified RNA or DNA including single and double-stranded regions/forms.

The term "nucleic acid encoding a polypeptide" as used herein encompasses polynucleotides that include a sequence encoding a peptide or polypeptide of the invention. The term also encompasses polynucleotides that include a single continuous region or discontinuous regions encoding the peptide or polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

It will be appreciated by those of ordinary skill in the art that, as a result of the degeneracy of the genetic code, there are many nucleotide sequences that encode a polypeptide as described herein. Some of these polynucleotides bear minimal similarity to the nucleotide sequence of any native (i.e., naturally occurring) gene. Nonetheless, polynucleotides that vary due to differences in codon usage are specifically contemplated by the present invention, for example polynucleotides that are optimized for human and/or primate and/or *E. coli* codon selection.

Sequences encoding a desired polypeptide may be synthesized, in whole or in part, using chemical methods well known in the art (see Caruthers, M. H. of al., Nucl. Acids Res. Symp. Ser. pp. 215-223 (1980), Horn et al., Nucl. Acids Res. Symp. Ser. pp. 225-232 (1980)). Alternatively, the protein itself may be produced using chemical methods to synthesize the amino acid sequence of a polypeptide, or a portion thereof. For example, peptide synthesis can be performed using various solid-phase techniques (Roberge et al., Science 269:202-204 (1995)) and automated synthesis may be achieved, for example, using the ASI 431 A Peptide Synthesizer (Perkin Elmer, Palo Alto, Calif.).

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In a further aspect of the invention the present invention relates vector comprising a nucleic acid of the invention linked to an inducible promoter such that when the promoter is induced a polypeptide encoded by the nucleic acid is expressed. In a preferred embodiment, the vector is pET28b (+).

A further aspect of the invention comprises said vector wherein the inducible promoter is activated by addition of a sufficient quantity of IPTG (Isopropyl β-D-1-thiogalactopyranoside) preferably to the growth medium. Optionally this is at a concentration of between 0.1 and 10 mM, 0.1 and 5 mM, 0.1 and 2.5 mM, 0.2 and 10 mM, 0.2 and 5 mM, 0.2 and 2.5 mM, 0.4 and 10 mM, 1 and 10 mM, 1 and 5 mM, 2.5 and 10 mM, 2.5 and 5 mM, 5 and 10 mM. Alternatively the promoter may be induced by a change in temperature or pH.

Nucleic acid molecule as used herein generally refers to any ribonucleic acid molecule or deoxyribonucleic acid molecule, which may be unmodified RNA or DNA or modified RNA or DNA.

Thus, for instance, nucleic acid molecule as used herein refers to at least single- and double-stranded DNA, hybrid molecules comprising DNA and RNA that may be single-stranded or, more typically, double-stranded, or a mixture of single- and double-stranded regions. As used herein, the term nucleic acid molecule includes DNA or RNA molecules as described above that contain one or more modified bases. Thus, DNA or RNA molecules with backbones modified for stability or for other reasons are "nucleic acid molecule" as that term is intended herein. Moreover, DNA or RNA species comprising unusual bases, such as inosine, or modified bases, such as tritylated bases, to name just two examples, are also nucleic acid molecules as defined herein. It will be appreciated that a great variety of modifications have been made to DNA and RNA molecules that serve many useful purposes known to those of skill in the art. The term nucleic acid molecule as used herein embraces such chemically, enzymatically or metabolically modified forms of nucleic acid molecules, as well as the chemical forms of DNA and RNA characteristic of viruses and cells, including simple and complex cells, inter alia. The term nucleic acid molecule also encompasses short nucleic acid molecules often referred to as oligonucleotide(s). The terms "polynucleotide" and "nucleic acid" or "nucleic acid molecule" are used interchangeably herein.

The nucleic acids according to the present invention may be chemically synthesized. Alternatively, the nucleic acids can be isolated from *Borrelia* and modified by methods known to one skilled in the art. The same applies to the polypeptides according to the present invention.

Furthermore, the nucleic acid of the present invention can be functionally linked, using standard techniques such as cloning, to any desired sequence(s), whether a *Borrelia* regulatory sequence or a heterologous regulatory sequence, heterologous leader sequence, heterologous marker sequence or a heterologous coding sequence to create a fusion gene.

Nucleic acid molecules of the present invention may be in the form of RNA, such as mRNA or cRNA, or in the form of DNA, including, for instance, cDNA and genomic DNA obtained by cloning or produced by chemical synthesis techniques or by a combination thereof. The DNA may be triple-stranded, double-stranded or single-stranded. Single-stranded DNA may be the coding strand, also known as the sense strand, or it may be the non-coding strand, also referred to as the anti-sense strand.

The nucleic acid of the present invention may be comprised in a vector or in a cell. The vector may comprise the above-mentioned nucleic acid in such a manner that the vector is replicable and can express the protein encoded by the nucleotide sequence in a host cell.

For recombinant production of the polypeptides of the invention, host cells can be genetically engineered to incorporate expression systems or portions thereof or nucleic acid of the invention. Introduction of a nucleic acid into the host cell can be effected by methods described in many standard laboratory manuals, such as Davis, et al., BASIC METHODS IN MOLECULAR BIOLOGY, (1986) and Sambrook, et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, conjugation, transduction, scrape loading, ballistic introduction and infection.

Representative examples of appropriate hosts include gram negative bacterial cells, such as cells of *E. coli, Acinetobacter, Actinobacillus, Bordetella, Brucella, Campylobacter, Cyanobacteria, Enterobacter, Erwinia, Franciscella, Helicobacter, hemophilus, Klebsiella, Legionella, Moraxella, Neisseria, Pasteurella, Proteus, Pseudomonas, Salmonella, Serratia, Shigella, Treponema, Vibrio, Yersinia*. In one embodiment the host cell is an *Escherichia coli* cell. In a preferred embodiment, the host cell is an *E. coli* BL21 (DE3) cell or an *E. coli* BL21 Star™ (DE3) cell.

Alternatively gram positive bacterial cells may also be used. A great variety of expression systems can be used to produce the polypeptides of the invention. In one embodiment the vector is derived from bacterial plasmids. Generally any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

In one embodiment of the current invention, the cells are grown under selective pressure, such as in the presence of antibiotics, preferably kanamycin. In another embodiment, cells are grown in the absence of antibiotics.

A great variety of expression vectors can be used to express the polypeptides according to the present invention. Generally, any vector suitable to maintain, propagate or express nucleic acids to express a polypeptide in a host may be used for expression in this regard. In accordance with this aspect of the invention the vector may be, for example, a plasmid vector, a single- or double-stranded phage vector or a single- or double-stranded RNA or DNA viral vector. Starting plasmids disclosed herein are either commercially available, publicly available, or can be constructed from available plasmids by routine application of well-known, published procedures. Preferred among vectors, in certain respects, are those for expression of nucleic acid molecules and the polypeptides according to the present invention. Nucleic acid constructs in host cells can be used in a conventional manner to produce the gene product encoded by the recombinant sequence. Alternatively, the polypeptides according to the present invention can be synthetically produced by conventional peptide synthesizers.

In addition, the present invention relates to a host cell comprising this vector. Representative examples of appropriate host cells include bacteria, such as streptococci, staphylococci, *E. coli, Streptomyces* and *Bacillus subtilis*; fungi, such as yeast and *Aspergillus*; insect cells such as *Drosophila* S2 and *Spodoptera* Sf9 cells; mammalian cells such as CHO, COS, HeLa, C127, 3T3, BHK, 293 or Bowes melanoma cells; and plant cells. Cell-free translation systems can also be employed to produce such proteins using RNA derived from the DNA construct of the present invention.

In order to express the desired amino acid sequence practically by introducing the vector according to the present invention into a host cell, the vector may contain, in addition to the nucleic acid sequence according to the present invention, other sequences for controlling the expression (e.g., promoter sequences, terminator sequences and enhancer sequences) and gene markers for selecting microorganisms, insect cells, animal culture cells, or the like (e.g., neomycin resistance genes and kanamycin resistance genes). Furthermore, the vector may contain the nucleic acid sequence according to the present invention in a repeated form (e.g., in tandem). The vector may be constructed based on procedures and manners which are conventionally used in the field of genetic engineering.

The host cells may be cultured in an appropriate medium, and the protein according to the present invention may be obtained from the culture product. The protein according to the present invention may be recovered from the culture medium and purified in the conventional manner.

The problem underlying the present invention is furthermore solved by a method for producing a polypeptide as defined above, characterized by the following steps:

a) introducing a vector encoding the polypeptide into a host cell,
b) growing the host cell under conditions allowing for expression of said polypeptide,
c) homogenizing said host cell, and
d) subjecting the host cell homogenate to purification steps.

The invention further relates to a method for producing a polypeptide as defined above, characterized by the following steps:

a) introducing a nucleic acid encoding a polypeptide into a vector,
b) introducing said vector into a host cell,
c) growing said host cell under conditions allowing for expression of polypeptide,
d) homogenizing said host cell,
e) enriching polypeptide in the lipid phase by phase separation, and
f) further purifying over a gel filtration column The invention further relates to a method for producing a polypeptide as defined above, characterized by the following steps:

a) introducing a nucleic acid encoding a polypeptide into a vector,
b) introducing said vector into a host cell,
c) growing said host cell under conditions allowing for expression of polypeptide,
d) homogenizing said host cell,
e) enriching polypeptide in the lipid phase by phase separation,
g) purifying over a gel filtration column, and
h) optionally, further processing over a buffer exchange column The problem underlying the present invention is solved in a further aspect by an antibody, or at least an effective part thereof, which specifically binds to at least a selective part of a polypeptide, as defined above.

In a preferred embodiment the antibody is a monoclonal antibody.

In another preferred embodiment said effective part comprises an Fab fragment, an F(ab) fragment, an F(ab)N fragment, an F(ab)$_2$ fragment or an F$_v$ fragment.

In still another embodiment of the invention the antibody is a chimeric antibody.

In yet another embodiment the antibody is a humanized antibody.

In a preferred aspect, antibodies of the invention bind specifically to mutant OspA fragment polypeptides of the invention, but not to corresponding wild-type OspA fragment polypeptides. In a more preferred aspect, the antibody binds specifically to the disulfide bond of the mutant OspA fragment of the invention.

The term "specificity" refers to the number of different types of antigens or antigenic determinants to which a particular antigen-binding molecule or antigen-binding protein (such as a Nanobody or a polypeptide of the invention) molecule can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$).

As will be clear to the skilled person (for example on the basis of the further disclosure herein), affinity can be determined in a manner known per se, depending on the specific antigen of interest. Avidity is the measure of the strength of binding between an antigen-binding molecule (such as an antibody or an effective part thereof of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as an antibody or an effective part thereof of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ $M^{-1}$) liters/mol is generally considered to indicate non-specific binding. Preferably, a monovalent immunoglobulin sequence of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art, as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more than $10^4$ moles/liter or $10^3$ moles/liter (e.g., of $10^{-2}$ moles/liter). Optionally, as will also be clear to the skilled person, the (actual or apparent) dissociation constant may be calculated on the basis of the (actual or apparent) association constant ($K_A$), by means of the relationship [$K_D$=1/$K_A$].

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of $(mol/liter)^{-1}$ (or $M^{-1}$). In the present specification, the stability of the interaction between two molecules (such as an amino acid sequence, Nanobody or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$ value characterizes the strength of a molecular interaction also in a thermodynamic sense as it is related to the free energy (DG) of binding by the well known relation $DG=RT\cdot\ln(K_D)$ (equivalently $DG=-RT\cdot\ln(K_A)$), where R equals the gas constant, T equals the absolute temperature and ln denotes the natural logarithm.

The $K_D$ for biological interactions which are considered meaningful (e.g. specific) are typically in the range of $10^{-10}$ M (0.1 nM) to $10^{-5}$M (10000 nM). The stronger an interaction, the lower its $K_D$.

In a preferred embodiment, the $K_D$ of the antibody of the invention is between $10^{-12}$ M and $10^{-5}$ M, preferably less than $10^{-6}$, preferably less than $10^{-7}$, preferably less than $10^{-8}$ M, preferably less than $10^{-9}$ M, more preferably less than $10^{-10}$ M, even more preferably less than $10^{-11}$ M, most preferably less than $10^{-12}$M.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units $s^{-1}$ (where s is the SI unit notation for second). The on-rate $k_{on}$ has units $M^{-1}$ $s^{-1}$. The on-rate may vary between $10^2$ $M^{-1}$ $s^{-1}$ to about $10^7$ $M^{-1}$ $s^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$ $s^{-1}$ (near irreversible complex with a $t_i p$ of multiple days) to 1 $s^{-1}$ ($t_{1/2}$=0.69 s).

The affinity of a molecular interaction between two molecules can be measured via different techniques known per se, such as the well known surface plasmon resonance (SPR) biosensor technique (see for example Ober et al., Intern Immunology, 13, 1551-1559, 2001) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE instruments.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol Methods, 77, 305-19, 1985). This method establishes a solution phase binding equilibrium measurement and avoids possible artefacts relating to adsorption of one of the molecules on a support such as plastic.

However, the accurate measurement of $K_D$ may be quite labor-intensive; therefore, apparent $K_D$ values are often determined in order to assess the binding strength of two molecules. It should be noted that as long all measurements are made in a consistent way (e.g. keeping the assay conditions unchanged), apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or flow cytometry or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an Inhibitory Concentration $(IC)_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC_{50}/(1+C_{ref}/K_{Dref})$. Note that if $c_{ref} \ll K_{Dref}$, $K_D \approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

Another aspect of the invention relates to a hybridoma cell line, which produces an antibody as defined above.

The problem underlying the present invention is furthermore solved by a method for producing an antibody as defined above, characterized by the following steps:

a) initiating an immune response in a non-human animal by administering a polypeptide as defined above to said animal, b) removing an antibody containing body fluid from said animal, and c) producing the antibody by subjecting said antibody containing body fluid to further purification steps.

The invention further relates to a method for producing an antibody as defined above, characterized by the following steps:

a) initiating an immune response in a non-human animal by administering a polypeptide as defined above to said animal, b) removing the spleen or spleen cells from said animal, c) producing hybridoma cells of said spleen or spleen cells, d) selecting and cloning hybridoma cells specific for said polypeptide, e) producing the antibody by cultivation of said cloned hybridoma cells, and f) optionally conducting further purification steps.

Another aspect of the present invention is related to a pharmaceutical composition comprising an antibody as specified above.

Still another aspect relates to an antibody as defined above or a pharmaceutical composition comprising an antibody as defined above for the treatment or prevention of an infection with *Borrelia* species, more preferably pathogenic *Borrelia* species as disclosed herein more preferably comprising *B. burgdorferi* s.s., *B. afzelii*, *B. bavariensis* and *B. garinii*.

The problem underlying the present invention is solved in another aspect by the use of an antibody as defined above for the preparation of a pharmaceutical composition for treating or preventing infections with *Borrelia* species, more preferably pathogenic *Borrelia* species as disclosed herein more preferably comprising *B. burgdorferi* s.s., *B. afzelii*, *B. bavariensis* and *B. garinii*.

In a third aspect the present invention relates to a pharmaceutical composition comprising the polypeptide according to the first aspect and/or the nucleic acid according to the second aspect. The pharmaceutical composition may optionally contain any pharmaceutically acceptable carrier or excipient, such as buffer substances, stabilisers or further active ingredients, especially ingredients known in connection with pharmaceutical compositions and/or vaccine production. Preferably, the pharmaceutical composition is used as a medicament, particularly as a vaccine or for preventing or treating an infection caused by *Borrelia* species, more preferably pathogenic *Borrelia* species as disclosed herein more preferably comprising *B. burgdorferi* s.s., *B. afzelii*, *B. bavariensis* and *B. garinii*, and/or other pathogens against which the antigens have been included in the vaccine.

In one embodiment the pharmaceutical composition further comprises an adjuvant. The choice of a suitable adjuvant to be mixed with bacterial toxins or conjugates made using the processes of the invention is within the knowledge of the person skilled in the art. Suitable adjuvants include an aluminium salt such as aluminium hydroxide or aluminum phosphate, but may also be other metal salts such as those of calcium, magnesium, iron or zinc, or may be an insoluble suspension of acylated tyrosine, or acylated sugars, cationically or anionically derivatized saccharides, or polyphosphazenes. In a preferred embodiment, the pharmaceutical composition is adjuvanted with aluminium hydroxide.

In a further embodiment, the pharmaceutical composition further comprises an immunostimulatory substance, preferably selected from the group consisting of polycationic polymers, especially polycationic peptides, immunostimulatory oligodeoxynucleotides (ODNs), especially oligo $(dIdC)_{13}$ (SEQ ID NO: 32), peptides containing at least two LysLeuLys motifs, especially peptide KLKLLLLLKLK (SEQ ID NO: 33), neuroactive compounds, especially human growth hormone, aluminium hydroxide, aluminium phosphate, Freund's complete or incomplete adjuvants, or combinations thereof. Preferably, the immunostimulatory substance is a combination of either a polycationic polymer and immunostimulatory deoxynucleotides or of a peptide containing at least two LysLeuLys motifs and immunostimulatory deoxynucleotides, preferably a combination of KLKLLLLLKLK (SEQ ID NO: 33) and oligo(dIdC)$_{13}$ (SEQ ID NO: 32). More preferably, said polycationic peptide is polyarginine.

In a further embodiment, the pharmaceutical composition comprises sodium phosphate, sodium chloride, L-methionine, sucrose and Tween-20 at a pH of 6.7+/−0.2. Preferably, the pharmaceutical composition also comprises aluminium hydroxide, preferably at a concentration of 0.15%.

In one embodiment, the formulation comprises between 5 mM and 50 mM sodium phosphate, between 100 and 200 mM sodium chloride, between 5 mM and 25 mM L-Methionine, between 2.5% and 10% Sucrose, between 0.01% and 0.1% Tween 20 and between 0.1% and 0.2% (w/v) aluminium hydroxide. More preferably, the formulation comprises 10 mM sodium phosphate, 150 mM sodium chloride, 10 mM L-Methionine, 5% Sucrose, 0.05% Tween 20 and 0.15% (w/v) aluminium hydroxide at pH 6.7±0.2. Even more preferably, the formulation comprises at least one, at least two, at least three mutant OspA heterodimers according to the invention.

In one embodiment, the pharmaceutical composition comprises 3 heterodimers, preferably Lip-S1D1-S2D1 (SEQ ID NO: 186), Lip-S4D1-S3D1 (SEQ ID NO: 194) and Lip-S5D1-S6D1 (SEQ ID NO: 190). Preferably, the three heterodimers are mixed at a molar ratio of 1:2:1, 1:3:1, 1:1:2, 1:1:3, 1:2:2, 1:2:3, 1:3:2, 1:3:3, 2:1:1, 2:1:2, 2:1:3, 2:2:3, 2:2:1, 2:3:1, 2:3:2, 2:3:3, 3:1:1, 3:1:2, 3:1:3, 3:2:1, 3:2:2, 3:2:3, 3:3:1, 3:3:2, most preferably 1:1:1.

In a further embodiment, the pharmaceutical composition comprises two heterodimers, preferably Lip-S1D1-S2D1 (SEQ ID NO: 186) and Lip-S5D1-S6D1 (SEQ ID NO: 190), Lip-SID1-S2D1 (SEQ ID NO: 186) and Lip-S4D1-S3D1 (SEQ ID NO: 194) or Lip-S4D1-S3D1 (SEQ ID NO: 194) and Lip-S5D1-S6D1 (SEQ ID NO: 190) in a molar ratio of 1:2, 1:3, 2:1, 3:1, 2:3, 3:2, preferably 1:1.

In one embodiment the pharmaceutical composition or vaccine of the invention further comprises at least one additional antigen (herein referred to generically as "combination vaccine"). In a preferred embodiment, the at least one additional antigen is derived from a Borrelia species causing Lyme borreliosis. In various aspects, the at least one additional antigen is derived from another pathogen, preferably a tick-borne pathogen. In a further aspect, the pathogen causes Rocky Mountain spotted fever, Human granulocytic ehrlichiosis (HGE), Sennetsu Fever, Human Monocytic Ehrlichiosis (HME), Anaplasmosis, Boutonneuse fever, Rickettsia parkeri Rickettsiosis, Southern Tick-Associated Rash Illness (STARI), Helvetica Spotted fever, 364D Rickettsiosis, African spotted fever, Relapsing fever, Tularemia, Colorado tick fever, Tick-borne encephalitis (TBE, also known as FSME), Crimean-Congo hemorrhagic fever, Q fever, Omsk hemorrhagic fever, Kyasanur forest disease, Powassan encephalitis, Heartland virus disease or Babesiosis. In a further aspect, the disease is Japanese encephalitis.

In a further embodiment, the at least one additional antigen is derived from a vector-borne, preferably a tick-borne, pathogen selected from the group comprising Borrelia hermsii, Borrelia parkeri, Borrelia duttoni, Borrelia miyamotoi, Borrelia turicatae, Rickettsia rickettsii, Rickettsia australis, Rickettsia conori, Rickettsia helvetica, Francisella tularensis, Anaplasma phagocytophilum. Ehrlichia sennetsu, Ehrlichia chaffeensis, Coxiella burnetii and Borrelia lonestari, Tick-borne encephalitis virus (TBEV aka FSME virus), Colorado tick fever virus (CTFV), Crimean-Congo hemorrhagic fever virus (CCHFV), Omsk Hemorrhagic Fever virus (OHFV), Japanese encepalitis virus (JEV) and Babesia spp.

In another aspect, a combination vaccine of the invention comprises any vaccine composition discussed herein in combination with at least a second vaccine composition. In some aspects, the second vaccine composition protects against a vector-borne disease, preferably a tick-borne disease. In various aspects, the second vaccine composition has a seasonal immunization schedule compatible with immunization against Borrelia infection or Lyme borreliosis. In other aspects, combination vaccines are useful in the prevention of multiple diseases for use in geographical locations where these diseases are prevalent.

In one aspect, the second vaccine composition is a vaccine selected from the group consisting of a tick-borne encephalitis vaccine, a Japanese encephalitis vaccine, and a Rocky Mountain Spotted Fever vaccine. In a preferred aspect, the vaccine composition is FSME-IMMUN® (Baxter), Encepur® (Novartis Vaccines), EnceVir® (Microgen NPO) or TBE Moscow Vaccine® (Chumakov Institute of Poliomyelitis and Viral Encephalitides of Russian Academy of Medical Sciences). In another preferred aspect, the vaccine composition is IXIARO®/JESPECT® (Valneva SE), JEEV® (Biological E, Ltd.) or IMOJEV® (Sanofi Pasteur).

There is further provided a vaccine comprising the pharmaceutical composition, this vaccine may further comprise a pharmaceutically acceptable excipient. In a preferred embodiment, the excipient is L-methionine.

The invention also includes immunogenic compositions. In some aspects, an immunogenic composition of the invention comprises any of the compositions discussed herein and a pharmaceutically acceptable carrier. In various aspects, the immunogenic composition has the property of inducing production of an antibody that specifically binds an outer surface protein A (OspA) protein. In certain aspects, the immunogenic composition has the property of inducing production of an antibody that specifically binds Borrelia. In particular aspects, the immunogenic composition has the property of inducing production of an antibody that neutralizes Borrelia. In some aspects, the antibody is produced by an animal. In further aspects, the animal is a mammal. In even further aspects, the mammal is human.

The vaccine preparations containing pharmaceutical compositions of the present invention may be used to protect a mammal susceptible to Borrelia infection or treat a mammal with a Borrelia infection, by means of administering said vaccine via a systemic or mucosal route. These administrations may include injection via the intramuscular, intraperitoneal, intradermal or subcutaneous routes; or via mucosal administration to the oral/alimentary, respiratory or genitourinary tracts. Although the vaccine of the invention may be administered as a single dose, components thereof may also be co-administered together at the same time or at different times.

In one aspect of the invention is provided a vaccine kit, comprising a vial containing a pharmaceutical composition of the invention, optionally in lyophilised form, and further comprising a vial containing an adjuvant as described herein. It is envisioned that in this aspect of the invention, the adjuvant will be used to reconstitute the lyophilised immunogenic composition. In a further aspect, the pharmaceutical composition of the invention may be pre-mixed in a vial, preferably in a syringe.

A further aspect of the invention is a method of preventing or treating Borrelia infection comprising administering to the host an immunoprotective dose of the pharmaceutical composition or vaccine or kit of the invention. In one embodiment there is provided a method of preventing or treating primary and/or recurrence episodes of *Borrelia* infection comprising administering to the host an immunoprotective dose of the pharmaceutical composition or vaccine or kit of the invention.

A further aspect of the invention is a pharmaceutical composition of the invention for use in the treatment or prevention of *Borrelial* disease. In one embodiment there is provided a pharmaceutical composition for use in the treatment or prevention of *Borrelia* infection.

A further aspect of the invention is the use of the pharmaceutical composition or vaccine or kit of the invention in the manufacture of a medicament for the treatment or prevention of *Borrelia* infection. In one embodiment there is provided a pharmaceutical composition of the invention for use in the manufacture of a medicament for the treatment or prevention of *Borrelia* infection.

The invention also includes methods for inducing an immunological response in a subject. In various aspects, such methods comprise the step of administering any of the immunogenic compositions or vaccine compositions discussed herein to the subject in an amount effective to induce an immunological response. In certain aspects, the immunological response comprises production of an anti-OspA antibody.

The invention includes methods for preventing or treating a *Borrelia* infection or Lyme boreliosis in a subject. In various aspects, such methods comprise the step of administering any of the vaccine compositions discussed herein or any of the combination vaccines discussed herein to the subject in an amount effective to prevent or treat the *Borrelia* infection or Lyme borreliosis.

The invention includes uses of polypeptides, nucleic acids, antibodies, pharmaceutical compositions or vaccines of the invention for the preparation of medicaments. Other related aspects are also provided in the instant invention.

The terms "comprising", "comprise" and "comprises" herein are intended by the inventors to be optionally substitutable with the terms "consisting of", "consist of" and "consists of", respectively, in every instance. The term "comprises" means "includes". Thus, unless the context requires otherwise, the word "comprises", and variations such as "comprise" and "comprising" will be understood to imply the inclusion of a stated compound or composition (e.g., nucleic acid, polypeptide, antibody) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example".

Embodiments herein relating to "vaccine compositions" of the invention are also applicable to embodiments relating to "pharmaceutical compositions" of the invention, and vice versa.

Unless otherwise explained, all technical and scientific terms used herein have the same meaning as commonly understood by one of ordinary skill in the art to which this disclosure belongs. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a", "an", and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, may be approximate.

A preferable carrier or excipient for the polypeptides according to the present invention in their diverse embodiments, or a nucleic acid molecule according to the present invention is an immunostimulatory compound such as an adjuvant for further stimulating the immune response to the polypeptide according to the present invention or a coding nucleic acid molecule thereof.

Adjuvants which may be used in compositions of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g., oxyhydroxides), phosphates (e.g., hydroxyphosphates, orthophosphates), sulphates, etc., or mixtures of different mineral compounds, with the compounds taking any suitable form (e.g., gel, crystalline, amorphous, etc.), and with adsorption being preferred. The mineral containing compositions may also be formulated as a particle of metal salt.

A useful aluminium phosphate adjuvant is amorphous aluminium hydroxyphosphate with $PO_4/Al$ molar ratio between 0.84 and 0.92. Another useful aluminium-based adjuvant is AS04, a combination of aluminium hydroxide+monophosphoryl lipid A (MPL).

B. Oil Emulsions

Oil emulsion compositions suitable for use as adjuvants in the invention include squalene-in-water emulsions, such as MF59 (5% Squalene, 0.5% Tween 80, and 0.5% Span 85, formulated into submicron particles using a microfluidizer), AS03 (squalene, DL-α-tocopherol and Tween 80) and AF03 (squalene, Montane® 80 and Eumulgon® B1 PH). Complete Freund's adjuvant (CFA) and incomplete Freund's adjuvant (IFA) may also be used.

Useful oil-in-water emulsions typically include at least one oil and at least one surfactant, with the oil(s) and surfactant(s) being biodegradable (metabolizable) and biocompatible. The oil droplets in the emulsion are generally less than 1 μm in diameter, with these small sizes being achieved with a microfluidizer to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g., obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy) polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g., Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Preferably, substantially all (e.g. at least 90% by number) of the oil droplets have a diameter of less than 1 µm, e.g. <750 nm, <500 nm, <400 nm, <300 nm, <250 nm, <220 nm, <200 nm, or smaller. One specific useful submicron emulsion consists of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. The MF59 emulsion advantageously includes citrate ions e.g. 10 mM sodium citrate buffer.

C. Saponin Formulations

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the Quillaia saponaria Molina tree has been widely studied as adjuvant. Saponin can also be commercially obtained from *Smilax ornata* (sarsaprilla), *Gypsophilla paniculata* (brideal veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS 17, QS 18, QS21, QH-A, QH-B and QH-C. Preferably, the saponin is QS21. Saponin formulations may also comprise a sterol, such as cholesterol.

Combinations of saponins and cholesterols can be used to form unique particles called immunostimulating complexes (ISCOMs). ISCOMs typically also include a phospholipid such as phosphatidylethanolamine or phosphatidylcholine. Any known saponin can be used in ISCOMs. Preferably, the ISCOM includes one or more of QS7, QS 17, QS 18, QS21, QH-A, QH-B and QH-C. Optionally, the ISCOMS may be devoid of additional detergent.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retroviruses, Norwalk virus, Human Papilloma virus, HIV, RNA-phages, Qβ-phage (such as coat proteins), GA-phage, fr-phage, AP205 phage, and Ty (such as retrotransposon Ty protein pi).

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3 dMPL). 3 dMPL is a mixture of 3 de-O-acylated monophosphoryl lipid A with 4, 5 or 6 acylated chains. Such "small particles" of 3 dMPL are small enough to be sterile filtered through a 0.22 µm membrane. Other non-toxic LPS derivatives include monophosphoryl lipid A mimics, such as aminoalkyl glucosaminide phosphate derivatives e.g. RC-529 and the synthetic phospholipid dimer, E6020.

Lipid A derivatives include derivatives of lipid A from *Escherichia coli* such as OM-174. Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. The CpG sequence may be directed to TLR9, such as the motif GTCGTT or TTCGTT. The CpG sequence may be specific for inducing a Th1 immune response, such as a CpG-A ODN, or it may be more specific for inducing a B cell response, such a CpG-B ODN. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". A particularly useful adjuvant based around immunostimulatory oligonucleotides is known as IC31®. Thus an adjuvant used with the invention may comprise a mixture of (i) an oligonucleotide (e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising the 26-mer sequence 5'-(dIdC)$_{13}$-3' (SEQ ID NO: 32). The polycationic polymer may be a peptide comprising the 11-mer amino acid sequence KLKLLLLLKLK (SEQ ID NO: 33).

Polycationic compounds derived from natural sources include HIV-REV or HIV-TAT (derived cationic peptides, antennapedia peptides, chitosan or other derivatives of chitin) or other peptides derived from these peptides or proteins by biochemical or recombinant production. Other preferred polycationic compounds are cathelin or related or derived substances from cathelin. For example, mouse cathelin is a peptide, which has the amino acid sequence NH$_2$-RLAGLL-RKGGEKIGEKLKKIGQKIKNFFQKLVPQPE-COOH (SEQ ID NO: 31). Related or derived cathelin substances contain the whole or parts of the cathelin sequence with at least 15-20 amino acid residues. Derivations may include the substitution or modification of the natural amino acids by amino acids which are not among the 20 standard amino acids. Moreover, further cationic residues may be introduced into such cathelin molecules. These cathelin molecules are preferred to be combined with the antigen. These cathelin molecules surprisingly have turned out to be also effective as an adjuvant for an antigen without the addition of further adjuvants. It is therefore possible to use such cathelin molecules as efficient adjuvants in vaccine formulations with or without further immune activating substances.

Bacterial ADP-ribosylating toxins and detoxified derivatives thereof may be used as adjuvants in the invention. Preferably, the protein is derived from *E. coli* (*E. coli* heat labile enterotoxin "LT"), *Vibrio cholerae* (*Cholera* toxin "CT"), or *Bordetella pertussis* (*Pertussis* toxin "PT"). The use of detoxified ADP-ribosylating toxins as mucosal adjuvants and as parenteral adjuvants is known. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, LT-G192 or dmLT A useful CT mutant is CT-E29H.

F. Human Immunomodulators

Human immunomodulators suitable for use as adjuvants in the invention include cytokines such as interleukins (e.g. IL-1, IL-2, IL-4, IL-5, IL-6, IL-7, IL-12, etc.), interferons (e.g. interferon-γ), macrophage colony stimulating factor and tumor necrosis factor. A preferred immunomodulator is IL-12.

G. Bioadhesives and Mucoadhesives

Bioadhesives and mucoadhesives may also be used as adjuvants in the invention. Suitable bioadhesives include esterified hyaluronic acid microspheres or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention.

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g., a poly(α-hydroxy acid), a polyhydroxybutyric acid, a polyorthoester, a polyanhydride, a polycaprolactone, a poly(lactide-co-glycolide) etc.), wherein poly (lactide-co-glycolide) are preferred, optionally treated to have a negatively-charged surface (e.g. with SDS) or a positively-charged surface (e.g., with a cationic detergent, such as CTAB).

I. Liposomes

Examples of liposome formulations suitable for use as adjuvants are known.

J. Polyoxyethylene Ether and Polyoxyethylene Ester Formulations

Adjuvants suitable for use in the invention include polyoxyethylene ethers and polyoxyethylene esters. Such formulations further include polyoxyethylene sorbitan ester surfactants in combination with an octoxynol as well as polyoxyethylene alkyl ethers or ester surfactants in combination with at least one additional non-ionic surfactant such as an octoxynol. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-5n-glycero-3-hydroxyphosphoryloxy)-ethylamine MTP-PE).

L. Imidazoquinolone Compounds.

Examples of imidazoquinolone compounds suitable for use as adjuvants in the invention include Imiquimod and its homologues (e.g., "Resiquimod 3M").

The invention may also comprise combinations of aspects of one or more of the adjuvants identified above.

Preferably, the immunostimulatory compound in the pharmaceutical preparation according to the present invention is selected from the group of polycationic substances, especially polycationic peptides, immunostimulatory nucleic acids molecules, preferably immunostimulatory deoxynucleotides, oil-in-water or water-in-oil emulsions, MF59, aluminium salts, Freund's complete adjuvant, Freund's incomplete adjuvant, neuroactive compounds, especially human growth hormone, or combinations thereof.

The use of an aluminium hydroxide and/or aluminium phosphate adjuvant is particularly preferred, and antigens are generally adsorbed to these salts.

Also, the pharmaceutical composition in accordance with the present invention is a pharmaceutical composition which comprises at least any of the following compounds or combinations thereof: the nucleic acid molecules according to the present invention, the polypeptides according to the present invention in their diverse embodiments, the vector according to the present invention, the cells according to the present invention and the antibody according to the present invention. In connection therewith, any of these compounds may be employed in combination with a non-sterile or sterile carrier or carriers for use with cells, tissues or organisms, such as a pharmaceutical carrier suitable for administration to a subject. Such carriers may include, but are not limited to, saline, buffered saline, dextrose, water, glycerol, ethanol and combinations thereof. The formulation should suit the mode of administration.

In one embodiment, the pharmaceutical composition comprises a stabilizer. The term "stabilizer" refers to a substance or vaccine excipient which protects the immunogenic composition of the vaccine from adverse conditions, such as those which occur during heating or freezing, and/or prolongs the stability or shelf-life of the immunogenic composition in a stable and immunogenic condition or state. Examples of stabilizers include, but are not limited to, sugars, such as sucrose, lactose and mannose; sugar alcohols, such as manitol; amino acids, such as glycine or glutamic acid; and proteins, such as human serum albumin or gelatin.

The pharmaceutical compositions of the present invention may be administered in any effective, convenient manner including, for instance, administration by topical, oral, anal, vaginal, intravenous, intraperitoneal, intramuscular, subcutaneous, intranasal, intratracheal or intradermal routes, among others. In a preferred embodiment, the pharmaceutical compositions are administered subcutaneously or intramuscularly, most preferably intramuscularly.

In therapy or as a prophylactic, the active agent of the pharmaceutical composition of the present invention may be administered to an individual as an injectable composition, for example as a sterile aqueous dispersion, preferably isotonic.

Alternatively the composition, preferably the pharmaceutical composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

In a preferred embodiment the pharmaceutical composition is a vaccine composition. Preferably, such vaccine composition is conveniently in injectable form. Conventional adjuvants may be employed to enhance the immune response. A suitable unit dose for vaccination with a protein antigen is for adults between 0.02 µg and 3 µg antigen per kg body weight and for children between 0.2 µg and 10 µg antigen per kg body weight, and such dose is preferably administered 1 to 3 times at intervals of 2 to 24 weeks.

At the indicated dose range, no adverse toxicological effects are expected with the compounds of the invention, which would preclude their administration to suitable individuals.

As an additional aspect, the invention includes kits which comprise one or more pharmaceutical formulations for administration to a subject packaged in a manner which facilitates their use for administration to subjects. In a preferred embodiment, the kits comprise the formulation in a final volume of 2 mL, more preferably in a final volume of 1 mL.

In a specific embodiment, the invention includes kits for producing a single dose administration unit. The kits, in various aspects, each contain both a first container having a dried protein and a second container having an aqueous formulation. Also included within the scope of this invention are kits containing single and multi-chambered pre-filled syringes (e.g., liquid syringes and lyosyringes).

In another embodiment, such a kit includes pharmaceutical formulation described herein (e.g., a composition comprising a therapeutic protein or peptide), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (i.e., almost none).

In one aspect, the kit contains a first container having a therapeutic protein or peptide composition and a second container having a physiologically acceptable reconstitution solution for the composition. In one aspect, the pharmaceutical formulation is packaged in a unit dosage form. The kit optionally further includes a device suitable for administering the pharmaceutical formulation according to a specific route of administration. In some aspects, the kit contains a label that describes use of the pharmaceutical formulations.

The pharmaceutical composition can contain a range of different antigens. Examples of antigens are whole-killed or attenuated organisms, subfractions of these organisms, proteins, or, in their most simple form, peptides. Antigens can also be recognized by the immune system in the form of glycosylated proteins or peptides and may also be or contain polysaccharides or lipids. Short peptides can be used, since cytotoxic T-cells (CTL) recognize antigens in the form of short, usually 8-11 amino acids long, peptides in conjunction with major histocompatibility complex (MHC). B cells can recognize linear epitopes as short as 4 to 5 amino acids, as well as three-dimensional structures (conformational epitopes).

In a preferred embodiment, the pharmaceutical composition of the third aspect additionally comprises a hyperimmune serum-reactive antigen against a *Borrelia* protein or an active fragment or variant thereof, such as, e.g., the antigens, fragments and variants as described in WO 2008/031133.

According to the invention, the pharmaceutical composition according to the third aspect may be used as a medicament, particularly as a vaccine, particularly in connection with particularly a disease or diseased condition which is caused by, linked or associated with *Borrelia*.

The pharmaceutical composition of the present invention may be used as a medicament, particularly as a vaccine, particularly in connection with a disease or disease condition which is caused by, linked with or associated with *Borrelia*, more preferably any pathogenic *Borrelia* species and more preferably in a method for treating or preventing a *Borrelia* infection, particularly a *B. burgdorferi* s.s., *B. garinii, B. afzelii, B. andersoni, B. bavariensis, B. bissettii, B. valaisiana, B. lusitaniae, B. spielmanii, B. japonica, B. tanukii, B. turdi* or *B. sinica* infection, preferably a *B. burgdorferi* s.s., *B. afzelii* or *B. garinii infection.*

In connection therewith, it should be noted that the various *Borrelia* species, including *B. burgdorferi* s.l., comprise several species and strains including those disclosed herein. A disease related, caused or associated with the bacterial infection to be prevented and/or treated according to the present invention includes Lyme borreliosis (Lyme disease). Further aspects, symptoms, stages and subgroups of Lyme borreliosis as well as specific groups of patients suffering from such disease as also disclosed herein, including in the introductory part, are incorporated herein by reference. More specifically, Lyme borreliosis generally occurs in stages, with remission and exacerbations with different clinical manifestation at each stage. Early infection stage 1 consists of localized infection of the skin, followed within days or weeks by stage 2, disseminated infection, and months to years later by stage 3, persistent infection. However, the infection is variable; some patients have only localized infections of the skin, while others display only later manifestations of the illness, such as arthritis.

In a fourth aspect, the present invention relates to a method of treating or preventing a *Borrelia* infection in a subject in need thereof, comprising the step of administering to the subject a therapeutically effective amount of a pharmaceutical composition according to the third aspect.

The term "subject" is used throughout the specification to describe an animal, preferably a mammal, more preferably a human, to whom a treatment or a method according to the present invention is provided. For treatment of those infections, conditions or disease states which are specific for a specific animal such as a human patient, the term patient refers to that specific animal. Preferably, the subject is a human; however, the medical use of the composition may also include animals such as poultry including chicken, turkey, duck or goose, livestock such as horse, cow or sheep, or companion animals such as dogs or cats.

The term "effective amount" is used throughout the specification to describe an amount of the present pharmaceutical composition which may be used to induce an intended result when used in the method of the present invention. In numerous aspects of the present invention, the term effective amount is used in conjunction with the treatment or prevention. In other aspects, the term effective amount simply refers to an amount of an agent which produces a result which is seen as being beneficial or useful, including in methods according to the present invention where the treatment or prevention of a *Borrelia* infection is sought.

The term effective amount with respect to the presently described compounds and compositions is used throughout the specification to describe that amount of the compound according to the present invention which is administered to a mammalian patient, especially including a human patient, suffering from a *Borrelia*-associated disease, to reduce or inhibit a *Borrelia* infection.

In a preferred embodiment, the method of immunizing a subject according to the fourth aspect comprises the step of administering to the subject a therapeutically effective amount of a pharmaceutical composition of the third aspect of the current invention.

The method comprises inducing an immunological response in an individual through gene therapy or otherwise, by administering a polypeptide or nucleic acid according to the present invention in vivo in order to stimulate an immunological response to produce antibodies or a cell-mediated T cell response, either cytokine-producing T cells or cytotoxic T cells, to protect said individual from disease, whether or not that disease is already established within the individual.

The products of the present invention, particularly the polypeptides and nucleic acids, are preferably provided in isolated form, and may be purified to homogeneity. The term "isolated" as used herein means separated "by the hand of man" from its natural state; i.e., if it occurs in nature, it has been changed or removed from its original environment, or both. For example, a naturally-occurring nucleic acid molecule or a polypeptide naturally present in a living organism in its natural state is not "isolated", but the same nucleic acid molecule or polypeptide separated from the coexisting materials of its natural state is "isolated", as the term is employed herein. As part of or following isolation, such nucleic acid molecules can be joined to other nucleic acid molecules, such as DNA molecules, for mutagenesis, to form fusion genes, and for propagation or expression in a host, for instance. The isolated nucleic acid molecules, alone or joined to other nucleic acid molecules such as vectors, can be introduced into host cells, in culture or in whole organisms. Introduced into host cells in culture or in whole organisms, such DNA molecules still would be isolated, as the term is used herein, because they would not be in their naturally-occurring form or environment. Similarly, the nucleic acid molecules and polypeptides may occur in a composition, such as medium formulations, solutions for introduction of nucleic acid molecules or polypeptides, for example, into cells, compositions or solutions for chemical or enzymatic reactions, for instance, which are not naturally occurring compositions, and, therein remain isolated nucleic acid molecules or polypeptides within the meaning of that term as it is employed herein.

The invention is not limited to the particular methodology, protocols and reagents described herein because they may vary. Furthermore, the terminology used herein is for the purpose of describing particular embodiments only and is not intended to limit the scope of the present invention. As used herein and in the appended claims, the singular forms "a", "an", and "the" include plural reference unless the context clearly dictates otherwise. Similarly, the words "comprise", "contain" and "encompass" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, and materials are described herein.

The present invention is further illustrated by the following Figures, Tables, Examples and the Sequence listing, from which further features, embodiments and advantages may be taken. As such, the specific modifications discussed are not to be construed as limitations on the scope of the invention. It will be apparent to the person skilled in the art that various equivalents, changes, and modifications may be made without departing from the scope of the invention, and it is thus to be understood that such equivalent embodiments are to be included herein.

In connection with the present invention

FIG. 1 shows the amino acid alignment of OspA serotypes 1-6 from *Borrelia*.

FIG. 2 schematically shows the production of mutant OspA fragment heterodimers according to the current invention.

FIG. 3 schematically represents the polypeptide components of one possible pharmaceutical composition of the current invention comprising three different mutant OspA heterodimers, a "combination vaccine".

Table 1 shows the thermal stability of the folding of mutant serotype 2 OspA fragments with disulfide bond types from D1 to D5 (for nomenclature, see Table A-4) compared to the wild-type serotype 2 OspA fragment without disulfide bonds (D0).

Table 2 shows the protection of mice from *B. afzelii* (strain IS1) infection by the Tick Challenge Method following immunization with mutant serotype 2 OspA fragments with disulfide bond types D1 to D5 (for nomenclature, see Table A-4), including control groups of mice immunized with PBS, full-length OspA or the wild-type serotype 2 OspA fragment (S2D0-His).

Table 3 shows the protection of mice from *B. afzelii* (strain IS1) infection by the Tick Challenge Method following immunization with lipidated mutant serotype 2 OspA fragments with disulfide bond types D1, D3 and D4 (Lip-S2D1-His, Lip-S2D3-His and Lip-S2D4-His), including control groups of mice immunized with PBS or full-length OspA protein.

Table 4 shows the protective capacity of mutant OspA heterodimers of the invention in in vivo *Borrelia* challenge models. Mice were immunized with Lip-S1D1-S2D1-His, Lip-S4D1-S3D1-His, Lip-S4D1-S3D1 or Lip-S5D1-S6D1-His and challenged with the indicated *Borrelia* OspA serotype via Tick or Needle Challenge Method, as indicated. The control group in each experiment was immunized with Al(OH)$_3$ adjuvant alone.

Table 5 shows the protective capacity of the combination vaccine of the invention against challenge in vivo with OspA serotype 1 *Borrelia* (strain N40 in needle challenge method) and OspA serotype 2 *Borrelia* (strain IS1 in the tick challenge method). Mice were immunized with the three antigens Lip-S1D1-S2D1, Lip-S4D1-S3D1 and Lip-S5D1-S6D1 together in a 1:1:1 ratio (combination vaccine) or with the indicated control antigens and challenged with *Borrelia* via Tick or Needle Challenge Method, as indicated. The control group in each experiment was immunized with Al(OH)$_3$ adjuvant alone.

The figures and tables which may be referred to in the specification are described below in more detail.

Figure 1:
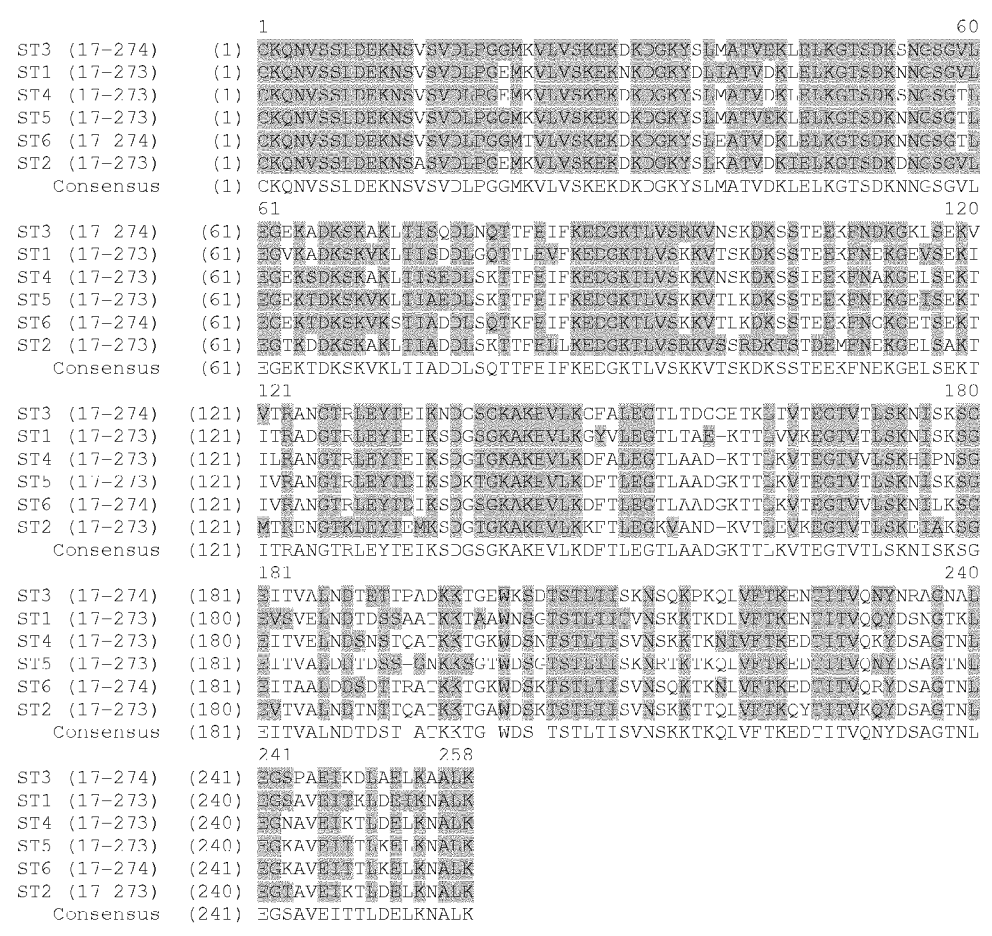

FIG. 1 Amino acid sequence alignment of OspA serotypes one through six (ST1-ST6), excluding the N-terminal lipidation signal sequence (amino acids 1-16), which is truncated during processing. The alignment illustrates that the membrane-associated N-terminal portion of the protein has a more highly-conserved amino acid sequence than the more exposed C-terminal portion. The full-length OspA sequences (excluding the N-terminal lipidation signal sequences, amino acids 1-16, which are not shown in the figure) are as follows: OspA ST3, SEQ ID NO: 21; OspA ST1, SEQ ID NO: 20; OspA ST4, SEQ ID NO: 22; OspA ST5, SEQ ID NO: 23; OspA ST6, SEQ ID NO: 24; OspA ST2, SEQ ID NO: 19.

Figure 2:
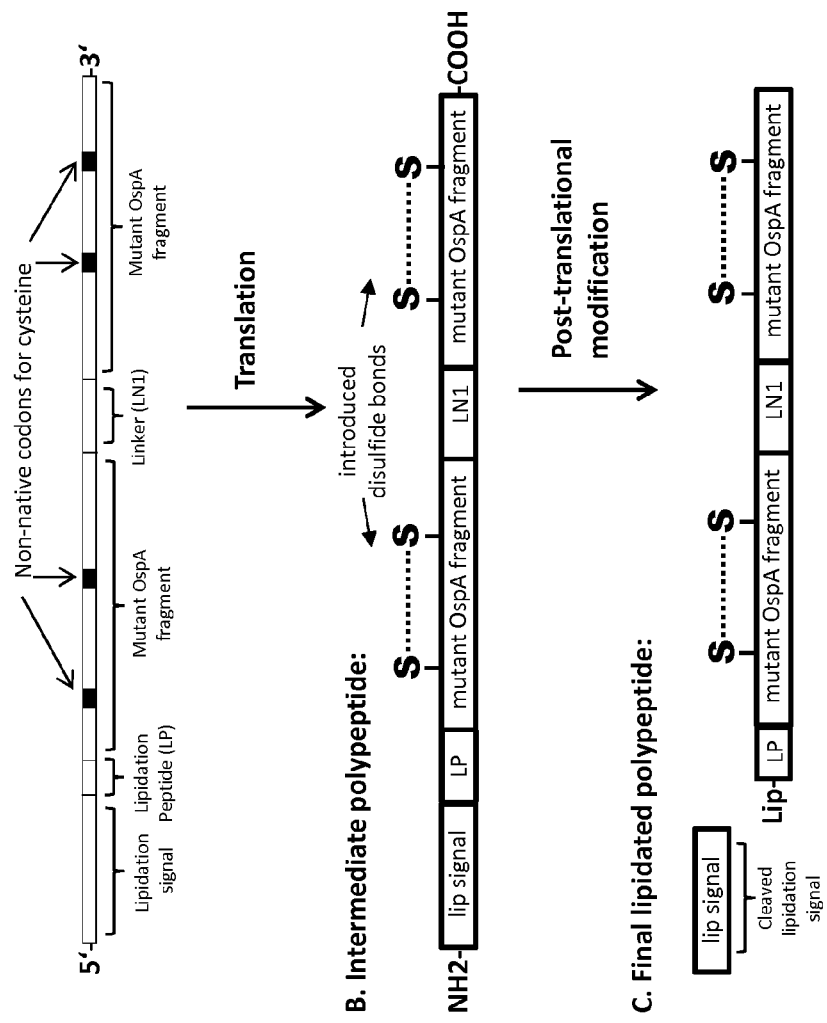

FIG. 2 Production of a mutant OspA heterodimer of the invention comprising mutant OspA C-terminal fragments from two different OspA serotypes of *Borrelia* sp. (A) Schematic representation of a nucleic acid encoding a lipidated mutant OspA heterodimer. The components, from 5' to 3', comprise the coding sequences for a lipidation signal sequence (Lip signal), a small cysteine-containing peptide for N-terminal lipidation (Lipidation peptide=LP), a mutant C-terminal fragment of OspA with two non-native cysteines, a short linker peptide (LN1), followed by a second mutant OspA C-terminal fragment with two non-native cysteines. (B) The intermediate mutant OspA heterodimer polypeptide comprises the nascent product directly following translation of the nucleic acid construct. From the N- to the C-terminus, this polypeptide consists of a lipidation signal sequence (Lip signal), a cysteine-containing peptide for lipidation (LP), a mutant OspA fragment with a non-native disulfide bond, a short linker peptide (LN1), followed by a second mutant OspA fragment with a non-native disulfide bond. (C) The final lipidated mutant OspA heterodimer polypeptide after post-translational modification. The heterodimer, from the N- to the C-terminus, consists of a short cysteine-containing peptide with the N-terminal cysteine lipidated (indicated by "Lip"), a mutant OspA fragment stabilized by a disulfide bond, a linker peptide (LN1), and a second mutant OspA fragment stabilized by a disulfide bond. The lipidation signal sequence is cleaved off during post-translational modification of the polypeptide as shown.

Figure 3:
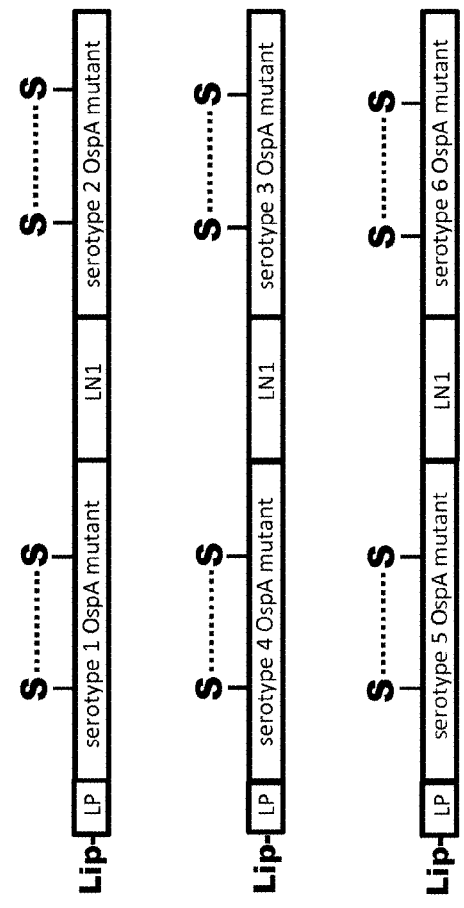

FIG. 3 An example of a preferred pharmaceutical composition according to the current invention. Three mutant OspA heterodimers, each comprising mutated OspA fragments from two different *Borrelia* OspA serotypes are present in the composition, together providing OspA antigens from six different *Borrelia* OspA serotypes. Such a pharmaceutical composition enables simultaneous immunization against six *Borrelia* serotypes.

Figure 4:
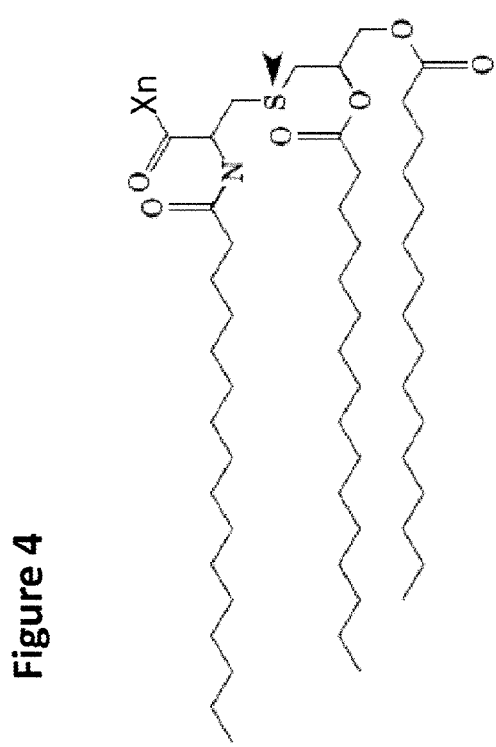
FIG. 4 shows the chemical structure of Pam$_3$Cys, an example of a fatty acid substituted cysteine, such as would be found at the N-terminus of lipidated polypeptides of the current invention.

FIG. 4 Illustration of the chemical structure of Pam$_3$Cys, an example of a fatty acid substitution of the N-terminal cysteine of full-length wild-type OspA protein as well as of lipidated mutant OspA fragment monomers and heterodimers of the invention. During post-translational modification of a full-length OspA protein or polypeptides of the invention, the N-terminal lipidation signal sequence is cleaved off and fatty acids, most commonly three palmitoyl moieties ("Pam$_3$"), are enzymatically covalently attached to the N-terminal cysteine residue (the sulfur atom, "S", is indicated by an arrow). The remaining residues of the polypeptide chain, which are located C-terminally from the Pam$_3$Cys residue, are represented by "Xn". (Modified from Bouchon, et al. (1997) Analytical Biochemistry 246: 52-61.)

Figure 5:
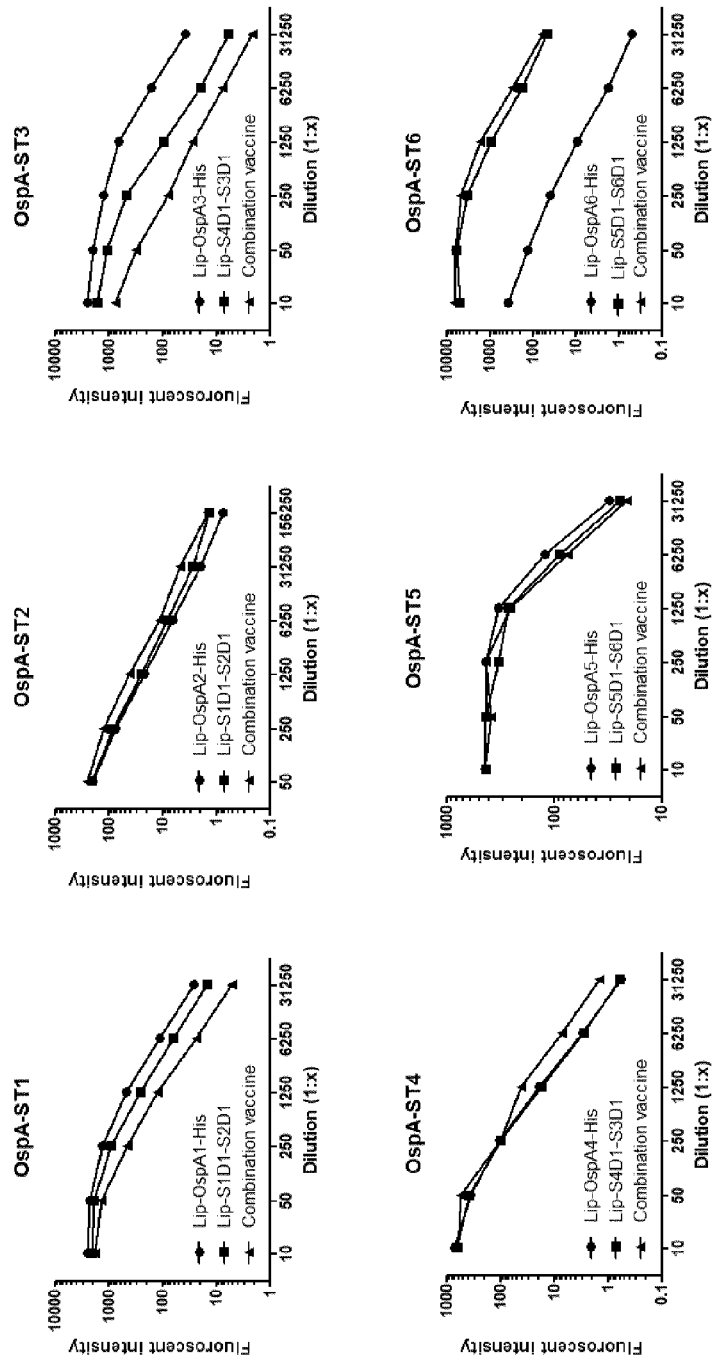
FIG. 5 shows the binding of antibodies from mice immunized with mutant OspA fragment heterodimer polypeptides of the invention to the cell surface of *Borrelia* of OspA serotypes 1-6.

FIG. 5 Binding of antibodies from immunized mice to the cell surface of *Borrelia* spirochetes. Mice were immunized three times with 1 μg each of the indicated antigens: Lipidated and His-tagged full-length OspA proteins of OspA serotypes 1-6; Lip-S1D1-S2D1, Lip-S4D1-S3D1 or Lip-S5D1-S6D1 alone, or Lip-S1D1-S2D1, Lip-S4D1-S3D1 and Lip-S5D1-S6D1 together in a 1:1:1 ratio ("combination vaccine") at two week intervals and sera were collected at one week after the last dose. Several dilutions of the sera were tested for binding to the cell surface of *Borrelia* via cell staining and flow cytometry. Fluorescent intensity values observed when staining with sera collected from control mice immunized with Al(OH)$_3$ adjuvant alone were subtracted to account for non-specific binding. (*Borrelia* used were: *B. burgdorferi*, OspA serotype 1, strain N40; *B. afzelii*, OspA serotype 2, strain "C"; *B. garinii*, OspA serotype 3, strain "D"; *B. havariensis*, OspA serotype 4, strain Fin; *B. garinii*, OspA serotype 5, strain "E"; *B. garinii*, OspA serotype 6, strain "B".)

TABLE 1

Thermal stability of non-lipidated, His-tagged *B. afzelii* K78 mutant serotype 2 OspA fragments with different placement of disulfide bonds. Mutant serotype 2 OspA fragments with different cysteine bond types (see Table A-4) were solubilized in 50 mM Tris-HCl, 150 mM NaCl (pH 8.0) and tested for thermal stability compared with the wild-type serotype 2 OspA fragment (S2D0). The presence of a disulfide bond resulted in an increased melting temperature compared to the wild-type serotype 2 OspA fragment.

| Serotype 2 OspA mutant fragment | SEQ ID NO: | Melting temperature (° C.) |
|---|---|---|
| S2D0-His* | 1 | 47.6 |
| S2D1-His | 2 | 70.4 |
| S2D2-His | 3 | 54.6 |
| S2D3-His | 4 | 58.6 |
| S2D4-His | 5 | 58.4 |
| S2D5-His | 6 | 53.8 |

*see Tables A-4 and A-5 for nomenclature.

TABLE 2

Protective capacity of decreasing doses of non-lipidated His-tagged mutant serotype 2 OspA fragments against *B. afzelii* (serotype 2) infection by the Tick Challenge Method. Five non-lipidated His-tagged mutant serotype 2 OspA fragments were tested for protective capacity at two different doses (30 μg and 5 μg) and compared with the wild-type serotype 2 OspA fragment. Groups of mice immunized with Al(OH)$_3$ adjuvant alone or with non-lipidated full-length serotype 2 OspA served as negative and positive controls, respectively. All antigens were His-tagged and non-lipidated. The data presented combine the results of several experiments performed under identical conditions.

| Immunogen | Tick challenge (OspA serotype 2: *B. afzelii*, strain IS1) | 3 × 30 μg (11 experiments) Infected/total | 3 × 5 μg (4 experiments) Infected/total |
|---|---|---|---|
| Al(OH)$_3$ adjuvant alone | Tick (OspA-ST2) | 58/62 | 20/23 |
| Full-length OspA K78-His (SEQ ID NO: 209) | Tick (OspA-ST2) | 1/72 | 1/25 |
| S2D0-His (SEQ ID NO: 1) | Tick (OspA-ST2) | 15/20 | 8/16 |
| S2D1-His (SEQ ID NO: 2) | Tick (OspA-ST2) | 1/26 | 1/25 |
| S2D2-His (SEQ ID NO: 3) | Tick (OspA-ST2) | 0/26 | 4/26 |
| S2D3-His (SEQ ID NO: 4) | Tick (OspA-ST2) | 0/34 | 1/21 |
| S2D4-His (SEQ ID NO: 5) | Tick (OspA-ST2) | 2/30 | 4/27 |
| S2D5-His (SEQ ID NO: 6) | Tick (OspA-ST2) | 5/35 | 2/11 |

TABLE 3

Protective capacity of decreasing doses of lipidated His-tagged mutant serotype 2 OspA fragments against *B. afzelii* infection by the Tick Challenge Method. Three lipidated His-tagged mutant serotype 2 OspA fragments with different disulfide bond types were tested for protective capacity at three different doses (3.0 μg, 1.0 μg and 0.3 μg). Groups of mice immunized with Al(OH)$_3$ adjuvant alone or with non-lipidated full-length serotype 2 OspA served as negative and positive controls, respectively. The data presented combine the results of several experiments performed under identical conditions.

| Immunogen | Tick challenge (OspA serotype 2: *B. afzelii*, strain IS1) | 3 × 3.0 μg (5 experiments) Infected/total | 3 × 1.0 μg (5 experiments) Infected/total | 3 × 0.3 μg (4 experiments) Infected/total |
|---|---|---|---|---|
| Al(OH)$_3$ adjuvant alone (control for all doses) | Tick (OspA-ST2) | 58/59 | — | — |
| Full-length OspA K78-His (SEQ ID NO: 209) | Tick (OspA-ST2) | 0/14 | 0/21 | 1/20 |
| Lip-S2D1-His (SEQ ID NO: 141) | Tick (OspA-ST2) | 0/17 | 5/31 | 1/29 |
| Lip-S2D3-His (SEQ ID NO: 143) | Tick (OspA-ST2) | 1/15 | 1/12 | 5/19 |
| Lip-S2D4-His (SEQ ID NO: 144) | Tick (OspA-ST2) | 0/8 | 0/25 | 0/34 |

TABLE 4

Protective capacity of mutant OspA heterodimers of the invention against in vivo Borrelia challenge via Needle or Tick Challenge Methods. Groups of mice were immunized three times at two week intervals with the indicated doses of OspA heterodimer or Al(OH)$_3$ adjuvant alone. Immunogens used were Lip-S1D1-S2D1-His (challenged with Borrelia OspA-ST1, Experiments 1-3), Lip-S1D1-S2D1-His, Lip-S4D1-S3D1-His and Lip-S5D1-S6D1-His, separately (challenged with Borrelia OspA-ST2, Experiments 4-6), Lip-S4D1-S3D1 (challenged with Borrelia OspA-ST4, Experiments 7 and 8) and Lip-S5D1-S6D1-His (challenged with Borrelia OspA-ST5, Experiments 9 and 10; challenged with Borrelia OspA-ST6, Experiments 11 and 12). Immunized mice were challenged two weeks after the last immunization via Tick or Needle Challenge Models as indicated.

| Immunogen | Dose | Needle challenge (OspA-serotype 1: B. burgdorferi s.s., strain N40) | Infected/Total Exp. 1 | Exp. 2 | Exp. 3 |
|---|---|---|---|---|---|
| Lip-S1D1-S2D1-His (SEQ ID NO: 49) | 3 × 5.0 μg | Needle (OspA-ST1) | 0/10*** | 0/9*** | 4/10** |
| Al(OH)$_3$ adjuvant alone | — | Needle (OspA-ST1) | 10/10 | 8/10 | 10/10 |

| Immunogen | Dose | Tick challenge (OspA-serotype 2: B. afzelii, strain IS1) | Exp. 4 | Exp. 5 | Exp. 6 |
|---|---|---|---|---|---|
| Lip-S1D1-S2D1-His (SEQ ID NO: 49) | 3 × 2.0 μg | Tick (OspA-ST2) | 0/10*** | 0/9*** | 0/6*** |
| Lip-S4D1-S3D1-His (SEQ ID NO: 81) | 3 × 2.0 μg | Tick (OspA-ST2) | 0/9*** | 2/7* | 0/6*** |
| Lip-S5D1-S6D1-His (SEQ ID NO: 65) | 3 × 2.0 μg | Tick (OspA-ST2) | 0/7*** | 0/9*** | 0/6*** |
| Al(OH)$_3$ adjuvant alone | — | Tick (OspA-ST2) | 9/9 | 8/8 | 7/7 |

| Immunogen | Dose | Needle challenge (OspA-serotype 4: B. bavariensis, strain Scf) | Exp. 7 | Exp. 8 | |
|---|---|---|---|---|---|
| Lip-S4D1-S3D1 (Seq ID No: 194) | 3 × 5.0 μg | Needle (OspA-ST4) | 2/10** | 1/10*** | — |
| Al(OH)$_3$ adjuvant alone | — | Needle (OspA-ST4) | 9/10 | 9/10 | — |

| Immunogen | Dose | Needle challenge (OspA-serotype 5: B. garinii) | Exp. 9 | Exp. 10 | |
|---|---|---|---|---|---|
| Lip-S5D1-S6D1-His (SEQ ID NO: 65) | 3 × 5.0 μg | Needle (OspA-ST5) | 1/10 | 2/10 | — |
| Al(OH)$_3$ adjuvant alone | — | Needle (ST5) | 6/10 | 6/10 | — |

| Immunogen | Dose | Needle challenge (OspA-serotype 6: B. garinii) | Exp. 11 | Exp. 12 | |
|---|---|---|---|---|---|
| Lip-S5D1-S6D1-His (SEQ ID NO: 65) | 3 × 5.0 μg | Needle (OspA-ST6) | 2/10** | 2/10*** | — |
| Al(OH)$_3$ adjuvant alone | — | Needle (OspA-ST6) | 9/10 | 10/10 | — |

P-value; Fisher's exact test, two tailed.
*significant (<0.05),
**highly significant (<0.01),
***extremely significant (<0.001)

TABLE 5

Protective capacity of the mutant OspA heterodimer combination vaccine of the invention against OspA serotype 1 and serotype 2 *Borrelia* challenge. Groups of mice were immunized three times with the indicated doses of immunogen or Al(OH)$_3$ adjuvant alone at two-week intervals. Immunogens used were a 1:1:1 combination of the mutant OspA heterodimers Lip-S1D1-S2D1, Lip-S4D1-S3D1 and Lip-S5D1-S6D1 (combination vaccine), Lip-S1D1-S2D1, Lip-OspA1-His and Chimeric OspA ST1/ST2. Immunized mice were challenged two weeks after the last immunization via the Tick Challenge Method (ST2, Experiments 13 and 14) or the Needle Challenge Method (ST1, Experiments 15 and 16).

| Immunogen | Dose | Tick challenge (OspA-serotype 2: *B afzelii*, strain IS1) | Infected/Total Exp. 13 | Exp. 14 |
|---|---|---|---|---|
| Lip-S1D1-S2D1 (SEQ ID NO: 186) | 3 × 5.0 μg | Tick (OspA-ST2) | 0/6*** | 0/7** |
| Combination vaccine: | | | | |
| Lip-S1D1-S2D1 (Seq ID No: 186) | 3 × 5.0 μg | Tick (OspA-ST2) | 0/9*** | 0/6** |
| Lip-S4D1-S3D1 (Seq ID No: 194) | 3 × 5.0 μg | | | |
| Lip-S5D1-S6D1 (Seq ID No: 190) | 3 × 5.0 μg | | | |
| Al(OH)$_3$ adjuvant alone | — | Tick (OspA-ST2) | 7/7 | 6/7 |

| Immunogen | Dose | Needle challenge (OspA-serotype 1: *B. burgdorferi* s.s., strain ZS7) | Exp. 15 | Exp. 16 |
|---|---|---|---|---|
| Lip-S1D1-S2D1 (Seq ID No: 186) | 3 × 1.0 μg | Needle (OspA-ST1) | 0/10*** | 0/10*** |
| Lip-OspA1-His (Seq ID No: 210) | 3 × 1.0 μg | Needle (OspA-ST1) | 0/10*** | 0/10*** |
| Chimeric OspA ST1/ST2 (Seq ID No: 212) | 3 × 1.0 μg | Needle (OspA-ST1) | 0/10*** | 0/10*** |
| Combination vaccine: | | | | |
| Lip-S1D1-S2D1 (Seq ID No: 186) | 3 × 1.0 μg | Needle (OspA-ST1) | 0/10*** | 0/10*** |
| Lip-S4D1-S3D1 (Seq ID No: 194) | 3 × 1.0 μg | | | |
| Lip-S5D1-S6D1 (Seq ID No: 190) | 3 × 1.0 μg | | | |
| Al(OH)$_3$ adjuvant alone | — | Needle (OspA-ST1) | 10/10 | 10/10 |

P-value; Fisher's exact test, two tailed.
*significant (<0.05),
**highly significant (<0.01),
***extremely significant (<0.001)

EXAMPLES

Example 1

Assessment of Thermal Stability of Mutant Serotype 2 OspA Fragments

Experimental Procedures
Thermal Stability

The melting temperatures ($T_m$) of non-lipidated mutant serotype 2 OspA fragment monomers were determined by the fluorescence-based thermal shift assay described by Pantoliano, et al. (J. Biomol Screen 6:429-440 (2001)). The fluorescent dye SYPRO® Orange protein gel stain (supplied as a 5000× concentrate in DMSO by Sigma, U.S.A.) was used to monitor protein unfolding. In each well, 7.5 μL of SYPRO® Orange (diluted 1:1000 from the stock solution) and 17.5 μL of a solution of protein (1 μg, or 2 μg) in buffer were combined. The protein samples were heated from 25° C. to 95° C. at a rate of 0.2° C./10 sec in the CFX96 Real-time Detection System (Bio-Rad, USA) and fluorescent changes were monitored. Fluorescence intensity was measured with excitation and emission wavelengths of 490 and 575 nm, respectively. The $T_m$ was determined using the Bio-Rad CFX Manager 2.0 program. The $T_m$ values of non-lipidated His-tagged serotype 2 OspA mutant fragments were measured in four different buffer systems: 50 mM Tris-HCl, 150 mM NaCl (pH 9.0); 50 mM Tris-HCl, 150 mM NaCl (pH 8.0); PBS (pH 7.4); and 25 mM HEPES, 150 mM NaCl (pH 6.5), using the non-lipidated serotype 2 OspA wild-type fragment (S2D0) as a control.

Results

In all cases, mutant serotype 2 OspA fragments with an introduced cysteine bond had higher $T_m$ than the wild-type serotype 2 OspA fragment (S2D0) (see Table 1). The $T_m$ was tested in four different buffer systems with similar results (data for proteins dissolved in 50 mM Tris-HCl, 150 mM NaCl (pH 8.0) is shown in Table 1), indicating that the stability of the proteins is similar over a wide pH range. This result lends credence to the hypothesis that the introduced disulfide bond stabilizes the OspA fragment.

Example 2

Assessment of the Protective Capacity of Non-Lipidated His-Tagged Mutant Serotype 2 OspA Fragment Monomers in the Tick Challenge Method (ST2, *B. afzelii*)

Experimental Procedures
Cloning and Expression of Recombinant Proteins

The wild-type serotype 2 OspA fragment as well as the mutant serotype 2 OspA fragments with cysteine bond types 1-5 (SEQ ID NOs: 1, 2, 3, 4, 5 and 6, respectively), were codon-optimized for *E. coli* expression by GenScript, USA. The non-lipidated mutant serotype 2 OspA fragments were C-terminally His-tagged for purification purposes. Gene fragments were cloned into the pET28b(+) vector (Novagen, USA), a vector containing a Kanamycin resistance cassette as well as a T7 promoter. The monomers were expressed in BL21 Star™ (DE3) cells (Invitrogen, USA) at 37° C. by the addition of IPTG. Cells were collected after 4 h by centrifugation and the pellet was stored at −70° C. for up to 12 months prior to further processing.

Purification of Non-Lipidated His-Tagged Wild-Type and Mutant OspA Fragment Monomer Proteins Cells were disrupted mechanically by high-pressure homogenization and the soluble fraction containing the His-tagged OspA fragments was applied to a Ni-sepharose column (Ni Sepharose™ 6 Fast Flow; GE Healthcare, United Kingdom) and the His-tagged OspA fragments were eluted on an Imidazole gradient (0-250 mM). Pooled fractions were further purified over a gel filtration column (Superdex 200, GE Healthcare) followed by a buffer exchange column (Sephadex G-25, GE Healthcare). His-tagged OspA fragment peaks were pooled on the basis of the analytical size exclusion column and reversed phase chromatography. After sterile filtration, the purified proteins were stored at −20° C. until formulation.

Immunization of Mice

Female C3H/HeN (H-$2^k$) mice were used for all studies (Harlan, Italy). Prior to each challenge, groups of five 8-week-old mice were bled via the tail vein and pre-immune sera were prepared and pooled. Five non-lipidated mutant serotype 2 OspA fragment proteins (S2D1-5, SEQ ID NOs: 2, 3, 4, 5 and 6, respectively), were tested in fifteen separate experiments. Three subcutaneous (s.c.) immunizations of 100 μL, were administered at two week intervals. Doses used were 30 and 5 μg of the respective protein, tested in 11 and 4 experiments respectively. All formulations included aluminium hydroxide (Al(OH)$_3$) at a final concentration of 0.15%. One week after the third immunization, blood was collected and hyper-immune sera were prepared. In each experiment, one group injected with PBS formulated with Al(OH)$_3$ was included as a negative control and one group of mice was immunized with S2D0, the wild-type C-terminal OspA fragment from B. afzelii strain K78 (SEQ ID NO: 1). Another group immunized with a non-lipidated full-length wild-type OspA protein from B. afzelii, strain K78 (SEQ ID NO: 209), also formulated with 0.15% Al(OH)$_3$, was included as positive control in each animal study. All animal experiments were conducted in accordance with Austrian law (BGB1 Nr. 501/1989) and approved by "Magistratsabteilung 58".

Tick Challenge of Immunized Mice and Collection of Sera and Tissues (Herein Referred to also as "Tick Challenge Method")

Tick challenge of immunized mice was done two weeks after the last immunization. In order to challenge the immunized mice with B. afzelii, the hair on the back of each mouse was removed with Veet® Cream (Reckitt Benckiser, United Kingdom) and a small ventilated container was glued to the skin with super glue (Pattex, Germany). Thereafter, one or two I. ricinus nymphs infected with B. afzelii, strain IS1, were applied per mouse, allowed to attach and feed to depletion. The feeding status was monitored daily for each individual tick and only mice where at least one fully-fed tick was collected were included in the final readout. No distinction was made between mice where one or two fully-fed ticks were collected.

Six weeks after the tick application, blood was collected by orbital bleeding and final sera were prepared and used for VlsE ELISA analysis to determine infection status. The mice were then sacrificed by cervical dislocation and one ear from each mouse was collected, DNA extracted and subjected to nested PCR analysis to identify Borrelia in tissue.

Infection Readout

Only mice where the applied tick(s) fed to completion and could be collected were included in the final readout of the experiment. The mice were sacrificed 6 weeks after tick application and organs as well as final sera were collected. The final infection readout was based on two different analyses (nested PCR targeting the 16S-23S intergenic spacer and VlsE (IR6) ELISA as described in detail below).

Nested PCR Targeting the 16S-23S Intergenic Spacer

One ear from each mouse was subjected to DNA extraction and purification using the DNeasy Blood and Tissue Kit (Qiagen, Germany) according to the manufacturer's instructions, with the following modification. Each ear was digested over night at 60° C. in recombinant Proteinase K, PCR grade (Roche, 14-22 mg/mL). The DNA was eluted in 50 μL deionized sterile water and stored at −20° C. until further analysis. As a negative control, one empty purification column was included in each DNA extraction and purification and the eluate subjected to nested PCR. All DNA extracts were screened for the presence of Borrelia DNA by a nested PCR procedure, comprising 40 cycles of 94° C. for 30 s, 56° C. for 30 s and 72° C. for 60 s using the primers; Forward 5'-GTATGTTTAGTGAGGGGGGTG-3' (SEQ ID NO: 26) and Reverse 5'-GGATCATAGCTCAG-GTGGTTAG-3' (SEQ ID NO: 27). From the reaction volume of 10 μL, 1 μL was used as template for the nested PCR reaction. The nested PCR step comprised 25 cycles of 94° C. for 30 s, 60° C. for 30 s and 72° C. for 60 s using the primers; Forward nested 5'-AGGGGGGTGAAGTCGTAACAAG-3' (SEQ ID NO: 28) and Reversed nested 5'-GTCTGA-TAAACCTGAGGTCGGA-3' (SEQ ID NO: 29). Of the final reaction volume, 5 μL was separated on a 1% agarose gel containing ethidium bromide and bands were visualized in UV-light.

In each PCR analysis, DNA purified from an in vitro grown culture of B. afzelii strain K78 was used as a positive control template. In addition, PBS was used instead of extracted DNA as negative control. Five microliters of the final product was separated on a 1% agarose gel containing ethidium bromide and bands were visualized in UV-light.

ELISA with the Invariable Region 6 (IR6) of the Variable Major Protein-Like Sequence E Protein (VlsE)

A biotinylated 25-mer peptide (MKKDDQIAAAMVL-RGMAKDGQFALK) (SEQ ID NO: 30) derived from the sequence of B. garinii strain IP90 was used for analysis (Liang F T, et al. (1999) J Immunol 163:5566-73). Streptavidin pre-coated 96-well ELISA plates (Nunc, Denmark) were coated with 100 μL/well (1 μg/mL) biotinylated peptide in PBS supplemented with 0.1% Tween 20 (PBS/0.1T). The plates were incubated overnight at 4° C. After coating with the peptide, the plates were washed once with PBS/0.1T. The plates were then blocked for one hour at room temperature (RT) with 100 μL/well of PBS+2% BSA, before being washed again with PBS/0.1T. Reactivity of post-challenge sera to the peptide was tested at 1:200, 1:400 and 1:800 dilutions in PBS+1% BSA. Plates were incubated for 90 min at RT before being washed three times with PBS/0.1T. Each well then received 50 μL of 1.3 μg/mL polyclonal rabbit anti-mouse IgG conjugated to HRP (Dako, Denmark) in PBS+1% BSA. The plates were then incubated for 1 h at RT. After three washes with PBS/0.1T, ABTS (50 μL/well) was added as substrate (Sigma-Aldrich, USA) and color was allowed to develop for 30 min. Absorbance was measured at 405 nm. All sera were tested in duplicate; negative controls included PBS instead of sera, as well as plates not coated with the peptide. Sera from mice shown to be culture positive for *B. afzelii* infection were used as positive controls.

Results

Levels of Protection in the Tick Challenge Method

High levels of protection were observed for all five stabilized OspA *B. afzelii* fragments at both of the doses tested (30 µg and 5 µg, see Table 2). The high infection rates in the PBS control group indicate that the ticks were infected with high frequency. Additionally, the positive control, non-lipidated full-length OspA from *B. afzelii* strain K78, was very protective. Together these control groups indicate the high reliability of the experimental readout.

Protection results from experiments testing 30 µg doses (11 total experiments) and 5 µg doses (4 total experiments) are summarized in Table 2. The two methods employed to verify infection, namely VlsE ELISA and nested PCR, gave virtually identical results (data not shown), demonstrating the robustness of these readout methods for assessing infection in the Tick Challenge Method.

Example 3

Assessment of the Protective Capacity of Lipidated His-Tagged Mutant Serotype 2 OspA Fragment Monomers Against In Vivo *Borrelia* Challenge Via the Tick Challenge Method (ST2, *B. afzelii*)

Experimental Procedures

Cloning and Expression of Lipidated His-Tagged Mutant OspA Fragment Proteins

The serotype 2 mutant OspA fragments with cysteine bond types 1, 3 and 4 (SEQ ID NOs: 141, 143 and 144, respectively) were modified by the addition of a lipidation signal sequence derived from OspA (SEQ ID NO: 14) and followed directly C-terminally by a CKQN peptide (SEQ ID NO: 211) to provide an N-terminal cysteine for lipidation. All mutant OspA fragments were C-terminally histidine-tagged for purification purposes. Gene fragments were cloned into the pET28b(+) vector (Novagen), a vector containing a Kanamycin resistance cassette as well as a T7 promoter. The lipidated monomers were expressed in BL21 Star™ (DE3) cells (Invitrogen) and after induction by IPTG, the growth temperature of the cells was lowered from 37° C. to 25° C. to promote efficient post-translational processing of the proteins. Cells were collected after 4 h by centrifugation and the pellet was stored at −70° C. for up to 12 months prior to further processing.

Purification of Lipidated His-Tagged Wild-Type and Mutant OspA Fragment Monomer Proteins Cells were disrupted mechanically by high-pressure homogenization and the lipidated His-tagged OspA fragment monomer polypeptides were enriched in the lipid phase by phase separation, using Triton X-114 as detergent. Subsequently, the diluted detergent phase (20 to 30 fold) was applied to a Ni-sepharose column (Ni Sepharose™ 6 Fast Flow; GE Healthcare) and the lipidated His-tagged OspA fragments were eluted by Imidazole gradient (0-250 mM) elution. Pooled fractions were further purified over a gel filtration column (Superdex 200, GE Healthcare) followed by a buffer exchange column (Sephadex G-25, GE Healthcare). Lipidated His-tagged OspA fragment peaks were pooled on the basis of the analytical size exclusion column and reversed phase chromatography. After sterile filtration, the purified proteins were stored at −20° C. until formulation.

Immunization of Mice

Three lipidated mutant OspA proteins (Lip-S2D1-His, Lip-S2D3-His and Lip-S2D4-His) were expressed and purified as described above. In vivo protection studies were performed as described in Example 2 using Al(OH)$_3$—adjuvant alone and non-lipidated full-length serotype 2 OspA as negative and positive controls, respectively. All immunogens were formulated with 0.15% Al(OH)$_3$. Mice were injected subcutaneously three times at two week intervals with formulations containing 3.0 µg, 1.0 µg or 0.3 µg antigen and challenged with *B. afzelii*-infected ticks (strain IS1) two weeks after the last immunization. Mice were sacrificed six weeks following tick challenge and infection was assessed.

Results

Levels of Protection in the Tick Challenge Method

All three lipidated mutant OspA fragments conferred very high levels of protection from *B. afzelii* challenge even at the lowest tested dose (Table 3). Infection rates in the Al(OH)$_3$—adjuvant alone immunized mice were high, indicating that the ticks were infected to a high frequency. The positive control antigen, full-length non-lipidated OspA from *B. afzelii* strain K78, was also very protective. Together, these control groups indicate the high reliability of the method of infection and thus give high credibility to the results observed following immunization with the lipidated mutant OspA fragments.

Example 4

Assessment of the Protective Capacity of Mutant OspA Heterodimers of the Invention Against In Vivo *Borrelia* Challenge Via the Needle or Tick Challenge Methods Experimental Procedures Cloning and Expression of Lipidated His-Tagged Mutant OspA Fragment Heterodimers The mutant OspA fragment monomers from *B. burgdorferi* s.s. strain B31, *B. afzelii* strain K78, *B. garinii* strain PBr, *B. bavariensis* strain PBi, *B. garinii* strain PHEi and *B. garinii* strain DK29 were codon-optimized for *E. coli* expression by GenScript, USA. The hLFA-1-like epitope (aa 164-174, SEQ ID NO: 17) of the OspA from *B. burgdorferi* s.s. strain B31 was replaced by a non-hLFA-1-like sequence NFTLEGKVAND from *B. afzelii* strain K78 (SEQ ID NO: 18). The lipidation signal sequence added to the mutant OspA fragment heterodimers was derived from the *E. coli* major outer membrane lipoprotein, Lpp, and was followed directly C-terminally by a CSS peptide to provide an N-terminal cysteine for lipidation. The mutant OspA fragment heterodimers were generated by fusing different mutant OspA fragment monomers as described above via a 21 amino acid linker sequence, originating from two separate loop regions of the N-terminal half of OspA from *B. burgdorferi* s.s. strain B31 ("LN1"; aa 65-74 and aa 42-53 with an amino acid exchange of D53S, SEQ ID NO: 184). The heterodimers were constructed with a His-tag for purification purposes. Gene fragments were cloned into the pET28b(+) vector (Novagen), a vector containing a Kanamycin resistance cassette as well as a T7 promoter. The lipoproteins of the stabilized heterodimers were expressed in BL21 Star™ (DE3) cells (Invitrogen) and after induction by IPTG, the growth temperature of the cells was lowered from 37° C. to 25° C. to promote efficient post-translational processing of the proteins. Cells were collected after 4 h by centrifugation and the pellet was stored at −70° C. for up to 12 months prior to further processing.

Purification of Lipidated His-Tagged Mutant OspA Fragment Heterodimers

Cells were disrupted mechanically by high-pressure homogenization and the lipidated His-tagged mutant OspA fragment heterodimers were enriched in the lipid phase by phase separation, using Triton X-114 as detergent. Subsequently, the diluted detergent phase (20 to 30 fold) was applied to a Ni-sepharose column (Ni Sepharose™ 6 Fast Flow; GE Healthcare) and the lipidated His-tagged OspA heterodimers were eluted by Imidazole gradient (0-250 mM) elution. Pooled fractions were further purified over a gel filtration column (Superdex 200, GE Healthcare) followed by a buffer exchange column (Sephadex G-25, GE Healthcare). The lipidated His-tagged mutant OspA heterodimer peaks were pooled on the basis of the analytical size exclusion column and reversed phase chromatography. After sterile filtration, the purified heterodimers were stored at −20° C. until formulation.

Cloning and Expression of Lipidated Non-His-Tagged Mutant OspA Fragment Heterodimers The constructs made as described as above were used for the generation of constructs without a His-tag by the introduction of a stop codon by PCR amplification. Gene fragments were cloned into the pET28b(+) vector (Merck Millipore), a vector containing a kanamycin resistance cassette as well as a T7 promoter. The lipoproteins of the stabilized heterodimers were expressed in BL21 Star™ (DE3) cells (Invitrogen) and after induction by IPTG, the growth temperature of the cells was lowered from 37° C. to 25° C. to promote efficient post-translational processing of the proteins. Cells were collected after 4 h by centrifugation and the pellet was stored at −70° C. for up to 12 months prior to further processing.

Purification of Lipidated Non-His-Tagged Mutant OspA Fragment Heterodimers

Cells were disrupted mechanically by high-pressure homogenization and the lipidated mutant OspA fragment heterodimers were enriched in the lipid phase by phase separation, using Triton X-114 as detergent. Subsequently, the diluted detergent phase was subjected to anion exchange chromatography operated in non-binding mode. The resulting flow-through was loaded on a hydroxyapatite column (Bio-Rad) and the lipidated proteins were eluted from the column by a linear salt gradient. The eluate was subjected to further purification over a DEAE-Sepharose column (GE Healthcare) in non-binding mode followed by gel filtration column (Superdex 200, GE Healthcare) for buffer exchange. The lipidated mutant OspA heterodimer peaks were pooled on the basis of the analytical size exclusion column and SDS-PAGE. After sterile filtration, the purified heterodimers were stored at −20° C. until formulation.

Immunization of Mice

Female C3H/HeN mice (Janvier, France) were used for all studies. Prior to each challenge, groups of ten 8-week-old mice were bled via the facial vein and pre-immune sera were prepared and pooled. Three subcutaneous (s.c.) immunizations of 100 μL each were administered at two week intervals. Each dose contained the amount of immunogen indicated in Table 4 (dose), formulated with aluminium hydroxide ($Al(OH)_3$) at a final concentration of 0.15%. One week after the third immunization, blood was collected from the facial vein and hyper-immune sera were prepared. In each experiment, one group immunized with $Al(OH)_3$ alone was included as a negative control. All animal experiments were conducted in accordance with Austrian law (BGB1 Nr. 501/1989) and approved by "Magistratsabteilung 58".

Tick Challenge of Immunized Mice and Collection of Sera and Tissues (Herein Referred to also as "Tick Challenge Method")

In order to challenge the immunized mice with *B. afzelii*, the hair of the back of each mouse was removed with Veet® Cream (Reckitt Benckiser) and a small ventilated container was glued to the skin with super glue (Pattex). Thereafter, one or two *I. ricinus* nymphs infected with *B. afzelii*, strain IS1, were applied per mouse, allowed to attach and feed until they were fully engorged and dropped off. The feeding status was monitored daily for each individual tick and only mice from which at least one fully-fed tick was collected were included in the final readout.

Needle Challenge of Immunized Mice with in Vitro Grown *Borrelia*

Two weeks after the last immunization, the mice were challenged s.c. with *Borrelia* diluted in 100 μL *Borrelia* growth medium (BSK II). The challenge doses were strain-dependent, the virulence of the individual strains being assessed by challenge experiments for determination of $ID_{50}$. Doses employed for needle challenge experiments ranged from 20 to 50 times the $ID_{50}$.

Sacrifice of Mice and Collection of Material

Four weeks after needle challenge with the indicated *Borrelia* spp. or six weeks after tick challenge with *B. afzelii*, mice were sacrificed by cervical dislocation. The blood was collected by orbital bleeding and final sera were prepared and used for VlsE ELISA to determine infection status. In addition, one ear from each mouse was collected, and DNA was extracted and subjected to quantitative PCR (qPCR) for identification of *Borrelia*. The final infection readout was based on two different analyses (VlsE ELISA and qPCR targeting recA).

ELISA with the Invariable Region 6 (IR6) of VlsE

A biotinylated 25-mer peptide (MKKDDQIAAAMVLRGMAKDGQFALK) derived from the sequence of *B. garinii* strain IP90 was used for the analysis (Liang F T, Alvarez A L, Gu Y, Nowling J M, Ramamoorthy R, Philipp M T. An immunodominant conserved region within the variable domain of VlsE, the variable surface antigen of *Borrelia burgdorferi*. J Immunol 1999; 163:5566-73). Streptavidin pre-coated 96-well ELISA plates (Nunc), were coated with 100 μL/well (1 μg/mL) peptide in PBS supplemented with 0.1% Tween (PBS/0.1T). The plates were incubated overnight at 4° C. After coating with the peptide, the plates were washed once with PBS/0.1T. The plates were then blocked for one hour at room temperature (RT) with 100 μL/well of PBS+2% BSA, before being washed again with PBS/0.1T. Reactivity of post-challenge sera to the peptide was tested at 1:200, 1:400 and 1:800 dilutions in PBS+1% BSA. Plates were incubated for 90 min at RT before being washed three times with PBS/0.1T. Each well then received 50 μL of 1.3 μg/mL polyclonal rabbit anti-mouse IgG conjugated to HRP (Dako) in PBS+1% BSA. The plates were then incubated for 1 h at RT. After three washes with PBS/0.1T, ABTS (50 μL/well) was added as substrate (Sigma-Aldrich) and color was allowed to develop for 30 min. Absorbance was measured at 405 nm. All sera were tested in duplicate. Negative controls included PBS instead of sera as well as plates not coated with the peptide. Sera from mice shown to be culture positive for *B. afzelii* infection were used as positive controls.

qPCR Targeting RecA

Oligonucleotide primers were designed for the recA gene in a manner that they could be used in qPCR for identification of all relevant *Borrelia* species causing Lyme borreliosis (forward: CATGCTCTTGATCCTGTTTA, reverse:

CCCATTTCTCCATCTATCTC). The recA fragment was cloned from the *B. burgdorferi* s.s. strain N40 into pET28b (+), to be used as standard in each reaction. The chromosomal DNA extracted from mouse ears was diluted 1:8 in water in order to reduce matrix effects observed with undiluted DNA. A master mix consisting of 10 µL SSoAdvanced™ SYBR® Green Supermix, 0.3 µL of each primer (10 µM), and 7.4 µL water was prepared for each experiment. Eighteen µL, of master mix was mixed with 2 µL of the diluted DNA extracted from either bladder or car in micro-titer plates and the DNA was amplified using a CFX96 real-time PCR detection system (Bio-Rad, USA). The DNA was denatured for 3 minutes at 95° C., followed by 50 cycles of 15 seconds at 95° C. and 30 seconds at 55° C. After amplification, the DNA was prepared for the melting curve analysis by denaturation for 30 seconds at 95° C. followed by 2 minutes at 55° C. The melting curve analysis was performed by 5 seconds incubation at 55° C., with a 0.5° C. increase per cycle, and 5 seconds at 95° C. On each plate, four no-template controls (NTC) were included as well as a standard curve in duplicate with template copy numbers ranging from 10 to 10,000.

Results

Lipidated mutant OspA fragment heterodimers were tested for protective capacity in twelve separate experiments. Mice were challenged with either *B. burgdorferi* s.s., strain N40, OspA serotype 1 (ST1, needle challenge) or *B. afzelii* strain IS1, OspA serotype 2 (ST2, tick challenge) in three experiments each or *B. bavariensis*, strain Scf, OspA serotype 4 (ST4, needle challenge), *B. garinii*, strain "A", OspA serotype 5 (ST5, needle challenge) or *B. garinii*, strain "B", OspA serotype 6 (ST6, needle challenge) in two experiments each. In all experiments, a group of mice immunized with Al(OH)$_3$ adjuvant alone served as a negative control group. For challenge with ticks, 1-2 ticks were applied per mouse and only mice from which at least one tick fed until fully engorged were included in the final readout. However, no distinction was made between mice from which one or two fully-fed ticks were collected. The protection data from the twelve experiments are summarized in Table 4.

The lipidated His-tagged OspA heterodimer (Lip-S1D1-S2D1-His) showed highly statistically-significant protection (Fisher's exact test, two-tailed) in all six experiments against both OspA serotype 1 and OspA serotype 2 challenge as compared to the negative control group. Surprisingly, immunization with Lip-S4D1-S3D1-His and Lip-S5D1-S6D1-His also conferred a high protective capacity against OspA serotype 2 challenge (Experiments 4-6), indicating that there can be a cross-protective effect of immunization with other serotypes of the mutant OspA fragments. Furthermore, immunization with Lip-S4D1-S3D1 conferred statistically-significant protection against needle challenge with OspA serotype 4 *Borrelia* (Experiments 7 and 8). Finally, immunization with Lip-S5D1-S6D1-His conferred protection against needle challenge with both OspA serotype 5 (Experiments 9 and 10) and OspA serotype 6 (Experiments 11 and 12). The infectious status of each mouse was determined using VlsE ELISA in combination with recA qPCR. A mouse was regarded as infected when at least one method gave a positive result.

In conclusion, immunization with mutant OspA fragment heterodimer polypeptides of the invention confers protection against all *Borrelia* serotypes tested and also may provide cross-protection in some cases.

The lipidated His-tagged OspA heterodimer (Lip-S1D1-S2D1-His) showed highly statistically-significant protection (Fisher's exact test, two-tailed) in all six experiments against both OspA serotype 1 and OspA serotype 2 challenge as compared to the negative control group. Surprisingly, immunization with Lip-S4D1-S3D1-His and Lip-S5D1-S6D1-His also conferred a high protective capacity against OspA serotype 2 challenge (Experiments 4-6), indicating that there can be a cross-protective effect of immunization with other serotypes of the mutant OspA fragments. Furthermore, immunization with Lip-S4D1-S3D1 conferred statistically-significant protection against needle challenge with OspA serotype 4 *Borrelia* (Experiments 7 and 8). Finally, immunization with Lip-S5D1-S6D1-His conferred protection against needle challenge with both OspA serotype 5 (Experiments 9 and 10) and OspA serotype 6 (Experiments 11 and 12). The infectious status of each mouse was determined using VlsE ELISA in combination with recA qPCR. A mouse was regarded as infected when at least one method gave a positive result.

In conclusion, immunization with mutant OspA fragment heterodimer polypeptides of the invention confers protection against all *Borrelia* serotypes tested and also may provide cross-protection in some cases.

Example 5

Assessment of the Protective Capacity of a 1:1:1 Combination Vaccine of the Mutant OspA Heterodimers of the Invention Against In Vivo OspA Serotype 1 and Serotype 2 *Borrelia* Challenge Via the Needle Challenge or Tick Challenge Methods Experimental Procedures Immunization of Mice Female C3H/HeN mice (Janvier, France) were used for all studies. Prior to each challenge, groups of ten 8-week-old mice were bled via the facial vein and pre-immune sera were prepared and pooled. Three s.c. immunizations of 100 µL each were administered at two week intervals. Groups of mice were immunized with the combination vaccine consisting of 1 µg each of Lip-S1D1-S2D1, Lip-S4D1-S3D1 and Lip-S5D1-S6D1. Three other OspA-based antigens were included in the challenge experiments: Lip-OspA1-His (full-length serotype 1 OspA, lipidated and his-tagged), lipidated chimeric OspA ST1/ST2* and Lip-S1D1-S2D1 alone. The negative (placebo) control was Al(OH)$_3$-adjuvant alone. All antigens were formulated in PBS with aluminium hydroxide (Al(OH)$_3$) at a final concentration of 0.15%.

*(Chimeric OspA ST1/ST2 (SEQ ID NO: 212) is an OspA chimera consisting of the first 10 amino acids of the N-terminal portion of OspB (strain B31), amino acids 11-200 of serotype 1 OspA, fused with the last 201-255 amino acids from the C-terminal portion of serotype 2 OspA and wherein the hLFA-1-like sequence of the serotype 1 OspA (146-170) is replaced with the homologous sequence from a serotype 2 OspA The serotype 2 OspA sequence is followed by two amino acids which are added because of the cloning site (XhoI) ahead of the stop codon in the vector.)

One week after the third immunization, blood was collected from the facial vein and hyper-immune sera were prepared. All animal experiments were conducted in accordance with Austrian law (BGBl Nr. 501/1989) and approved by "Magistratsabteilung 58".

Needle Challenge of Immunized Mice with in Vitro Grown *Borrelia*

Two weeks after the last immunization, the mice were challenged s.c. with *Borrelia* spirochetes diluted in 100 µL growth medium (BSKII). The challenge doses were strain-dependent, the virulence of the individual strains were assessed by challenge experiments for determination of $ID_{50}$. Doses employed for needle challenge experiments ranged from 20 to 50 times the $ID_{50}$. Four weeks after needle challenge, mice were sacrificed and blood and tissues were collected for readout methods to determine the infection status.

Tick Challenge of Immunized Mice and Collection of Sera and Tissues (Herein Referred to also as "Tick Challenge Method")

In order to challenge the immunized mice with *B. afzelii*, the hair of the back of each mouse was removed with Veet® Cream (Reckitt Benckiser, United Kingdom) and a small ventilated container was glued to the skin with super glue (Pattex, Germany). Thereafter, one or two *I. ricinus* nymphs infected with *B. afzelii*, strain IS1, were applied per mouse, allowed to attach and feed until they are fully engorged and drop off. The feeding status was monitored for each individual tick and only mice where at least one fully-fed tick was collected were included in the final readout.

Results

Lipidated mutant OspA fragment heterodimers that were not His-tagged were combined at a 1:1:1 ratio and tested for protective capacity against *Borrelia* challenge Immunized mice were challenged with *B. afzelii* (ST2, strain IS1, tick challenge) or with *B. burgdorferi* s.s. (ST1, strain ZS7, needle challenge) in two experiments each. Other OspA-based antigens included Lip-S1D1-S2D2 in all four experiments and Lip-OspA1-His and lipidated chimeric OspA ST1/ST2 in Experiments 15 and 16. A group of mice immunized with Al(OH)$_3$ adjuvant alone served as a negative control group in each experiment. For challenge with ticks, 1-2 ticks were applied per mouse and only mice from which at least one tick fed until fully engorged were included in the final readout. However, no distinction was made between mice from which one or two fully fed ticks were collected. The protection data from the four experiments are summarized in Table 5.

The combination vaccine containing three lipidated mutant OspA fragment heterodimers at a 1:1:1 ratio conferred statistically-significant protection (Fisher's exact test, two-tailed) in all four challenge experiments as compared to the negative control group. The infectious status of each mouse was determined using VlsE ELISA in combination with recA qPCR. A mouse was regarded as infected when at least one method gave a positive result.

Example 6

Binding of Antibodies from the Sera of Mice Immunized with Mutant OspA Fragment Heterodimers to the Cell Surface of *Borrelia*

Experimental Procedures
Immunization of Mice

Female C3H/HeN mice were used for all studies. Prior to each challenge, groups of twenty 8-week-old mice were bled via the facial vein and pre-immune sera were prepared and pooled. Three s.c. immunizations of 100 µL each were administered at two week intervals. Each dose contained 1 µg of each of the respective proteins: Lip-S1D1-S2D1, Lip-S4D1-S3D1 and Lip-S5D1-S6D1 (combination vaccine), or 1 µg lipidated full-length OspA protein (ST1-ST6 as indicated) or 1 µg OspA heterodimer alone (Lip-S1D1-S2D1, Lip-S4D1-S3D1 or Lip-S5D1-S6D1, as indicated) adjuvanted with aluminium hydroxide at a final concentration of 0.15%. The negative (placebo) control was Al(OH)$_3$ adjuvant alone. One week after the third immunization, blood was collected from the facial vein and hyper-immune sera were prepared. All animal experiments were conducted in accordance with Austrian law (BGB1 Nr. 501/1989) and approved by "Magistratsabteilung 58".

Flow Cytometry to Assess Binding to *Borrelia*

Spirochetes (1×10$^6$) were mixed with an equal volume of 4% paraformaldehyde and incubated for 2 hours at room temperature in a 96-well plate (Nunclon 96U, Nunc). The plate was centrifuged for 5 minutes at 2,000 g and the supernatant was discarded. Cells were washed with 150 µL HBSS with 2% BSA (HBSS-B), centrifuged as above and the supernatant was discarded. Mouse sera were heat inactivated by incubating them at 56° C. for 35 minutes. Heat-inactivated sera were diluted in HBSS-B and sterile filtered by centrifuging 4,000 g for 3 minutes using Costar spin-X centrifuge tube filters (0.22 µm, Corning, USA). Spirochetes were dissolved in 100 µL serum and incubated for 45 minutes at room temperature. The plate was centrifuged for 15 minutes at 2,000 g and the supernatant was discarded. The cells were washed once with 150 µL HBSS-B and then dissolved in 100 µL at HBSS-B.

One microliter secondary antibody (PE conjugated goat anti-mouse IgG, Beckman Coulter, USA) was added to the cells and incubated at room temperature for 45 minutes in the dark. Spirochetes were washed once with 150 µL HBSS-B and then dissolved in 200 µL HBSS containing 2.5 µM SYTO-17 DNA dye and incubated for 10 minutes at room temperature in the dark. The stained spirochetes were pelleted by centrifuging for 5 minutes at 2000 g and subsequently dissolved in 200 µL HBSS. Labelled spirochetes were measured with a FC500 (Beckman Coulter) flow cytometer, gated for SYTO-17 positive events. Values obtained with sera from the placebo-immunized group were subtracted from the values observed with sera from the heterodimer-immunized groups to control for non-specific binding.

Results

Binding of antibodies from hyperimmune mouse sera was observed in the case of different *Borreliae* expressing all six OspA serotypes, indicating that the antibodies generated in response to all of the antigens are functionally active and can bind native OspA in situ. The fluorescence intensity was linear over a large range of serum dilutions. For most OspA serotypes, the observed fluorescence intensity with heterodimer-generated sera was comparable to the fluorescence intensity seen with sera generated with lipidated full-length OspA.

Example 7

Formulation Studies

Studies regarding the formulation of the combination vaccine of the invention were carried out in order to optimize stability. Different types of buffers and stabilizers were tested at various concentrations in combination with aluminum hydroxide and antigen. An optimal formulation of 40 µg/mL each of three heterodimers (120 µg total protein), 10 mM sodium phosphate, 150 mM sodium chloride, 10 mM L-Methionine, 5% Sucrose, 0.05% Tween 20 (polysorbate 20) and 0.15% (w/v) aluminium hydroxide at pH 6.7±0.2 was determined.#

The entire contents of all of the references (including literature references, issued patents, published patent applications, and co-pending patent applications) cited throughout this application are hereby expressly incorporated by reference.

The invention claimed is:

1. A polypeptide comprising a mutant fragment of a *Borrelia* outer surface protein A (OspA), wherein said mutant OspA fragment comprises SEQ ID NO: 218, or a variant thereof, wherein said variant has at least 95% sequence identity to a wild-type serotype 5 OspA fragment defined by amino acid residues 126-273 of SEQ ID NO: 23, and wherein said variant differs from said wild-type serotype 5 OspA fragment at least by the addition of at least one disulfide bond.

2. The polypeptide according to claim 1, wherein said polypeptide comprises a heterodimer selected from the group consisting of Lip-S5D1-S6D1 (SEQ ID NO: 190), Lip-S6D1-S5D1 (SEQ ID NO: 196), S5D1-S6D4 (SEQ ID NO: 202) and S6D4-S5D1 (SEQ ID NO: 207).

3. The polypeptide according to claim 1, wherein said polypeptide consists of a heterodimer selected from the group consisting of Lip-S5D1-S6D1 (SEQ ID NO: 190), Lip-S6D1-S5D1 (SEQ ID NO: 196), S5D1-S6D4 (SEQ ID NO: 202) and S6D4-S5D1 (SEQ ID NO: 207).

4. A pharmaceutical composition comprising the polypeptide according to claim 1 and optionally a pharmaceutically acceptable carrier or excipient.

5. The pharmaceutical composition according to claim 4, wherein said excipient is L-methionine and/or aluminium hydroxide.

6. A pharmaceutical composition comprising Lip-S5D1-S6D1 (SEQ ID NO: 190) and Lip-S1D1-S2D1 (SEQ ID NO: 186) and, optionally, a pharmaceutically acceptable carrier or excipient.

7. The pharmaceutical composition according to claim 6, wherein said excipient is L-methionine and/or aluminium hydroxide.

8. A vaccine comprising Lip-S5D1-S6D1 (SEQ ID NO: 190) and Lip-S1D1-S2D1 (SEQ ID NO: 186) and, optionally, a pharmaceutically acceptable carrier or excipient.

9. The vaccine of claim 8, wherein said excipient is L-methionine and/or aluminum hydroxide.

* * * * *